US009403830B2

(12) United States Patent
Abeywardane et al.

(10) Patent No.: US 9,403,830 B2
(45) **Date of Patent: *Aug. 2, 2016**

(54) INHIBITORS OF LEUKOTRIENE PRODUCTION

(71) Applicants: Asitha Abeywardane, Danbury, CT (US); Steven Richard Brunette, New Milford, CT (US); Michael Jason Burke, Newtown, CT (US); Thomas Martin Kirrane, Jr., Middlebury, CT (US); Chuk Chui Man, Ridgefield, CT (US); Daniel Richard Marshall, Norwalk, CT (US); Anil Kumar Padyana, Oxford, CT (US); Hossein Razavi, Danbury, CT (US); Robert Sibley, North Haven, CT (US); Lana Louise Smith Keenan, Poughquag, NY (US); Roger John Snow, Danbury, CT (US); Ronald John Sorcek, Bethel, CT (US); Hidenori Takahashi, LaGrangeville, NY (US); Steven John Taylor, Southbury, CT (US); Michael Robert Turner, Danbury, CT (US); Erick Richard Roush Young, Danbury, CT (US); Qiang Zhang, Woodbury, CT (US); Yunlong Zhang, North Haven, CT (US); Renee M. Zindell, New Milford, CT (US)

(72) Inventors: Asitha Abeywardane, Danbury, CT (US); Steven Richard Brunette, New Milford, CT (US); Michael Jason Burke, Newtown, CT (US); Thomas Martin Kirrane, Jr., Middlebury, CT (US); Chuk Chui Man, Ridgefield, CT (US); Daniel Richard Marshall, Norwalk, CT (US); Anil Kumar Padyana, Oxford, CT (US); Hossein Razavi, Danbury, CT (US); Robert Sibley, North Haven, CT (US); Lana Louise Smith Keenan, Poughquag, NY (US); Roger John Snow, Danbury, CT (US); Ronald John Sorcek, Bethel, CT (US); Hidenori Takahashi, LaGrangeville, NY (US); Steven John Taylor, Southbury, CT (US); Michael Robert Turner, Danbury, CT (US); Erick Richard Roush Young, Danbury, CT (US); Qiang Zhang, Woodbury, CT (US); Yunlong Zhang, North Haven, CT (US); Renee M. Zindell, New Milford, CT (US)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 106 days.

This patent is subject to a terminal disclaimer.

(21) Appl. No.: 13/942,988

(22) Filed: Jul. 16, 2013

(65) Prior Publication Data

US 2014/0031339 A1 Jan. 30, 2014

Related U.S. Application Data

(60) Provisional application No. 61/672,504, filed on Jul. 17, 2012.

(51) Int. Cl.

| | |
|---|---|
| *C07D 487/04* | (2006.01) |
| *C07D 401/14* | (2006.01) |
| *C07D 405/14* | (2006.01) |
| *C07D 413/14* | (2006.01) |
| *C07D 401/04* | (2006.01) |
| *C07D 401/12* | (2006.01) |
| *C07D 417/14* | (2006.01) |
| *C07D 471/04* | (2006.01) |
| *C07D 471/20* | (2006.01) |
| *C07D 491/20* | (2006.01) |
| *A61K 31/454* | (2006.01) |
| *A61K 31/4545* | (2006.01) |
| *A61K 31/496* | (2006.01) |
| *A61K 31/5377* | (2006.01) |
| *A61K 31/549* | (2006.01) |
| *A61K 31/55* | (2006.01) |
| *A61K 31/551* | (2006.01) |
| *C07D 405/12* | (2006.01) |
| *C07D 497/08* | (2006.01) |
| *C07D 498/04* | (2006.01) |

(52) U.S. Cl.

CPC ............ *C07D 487/04* (2013.01); *A61K 31/454* (2013.01); *A61K 31/4545* (2013.01); *A61K 31/496* (2013.01); *A61K 31/5377* (2013.01); *A61K 31/549* (2013.01); *A61K 31/55* (2013.01); *A61K 31/551* (2013.01); *C07D 401/04* (2013.01); *C07D 401/12* (2013.01); *C07D 401/14* (2013.01); *C07D 405/12* (2013.01); *C07D 405/14* (2013.01); *C07D 413/14* (2013.01); *C07D 417/14* (2013.01); *C07D 471/04* (2013.01); *C07D 471/20* (2013.01); *C07D 491/20* (2013.01); *C07D 497/08* (2013.01); *C07D 498/04* (2013.01)

(58) Field of Classification Search

CPC ............ A61K 31/454; A61K 31/4545; A61K 31/496; A61K 31/5377; A61K 31/549; A61K 31/55; A61K 31/551; C07D 401/04; C07D 401/12; C07D 401/14; C07D 405/12; C07D 405/14; C07D 413/14; C07D 417/14; C07D 471/04; C07D 471/20; C07D 487/04; C07D 491/20; C07D 497/07; C07D 498/04; C07D 231/12; C07D 23/12; C07D 497/08

See application file for complete search history.

(56) References Cited

U.S. PATENT DOCUMENTS

| | | | |
|---|---|---|---|
| 4,918,092 | A | 4/1990 | Frenette et al. |
| 5,120,758 | A | 6/1992 | Satoh |
| 6,180,637 | B1 | 1/2001 | Schindler et al. |
| 7,098,222 | B2 | 8/2006 | Altenbach et al. |
| 7,429,665 | B2 | 9/2008 | Verhoest et al. |
| 7,674,802 | B2 | 3/2010 | Sandanayaka et al. |

| | | | |
|---|---|---|---|
| 8,551,982 | B2 | 10/2013 | Abeywardane et al. |
| 8,946,203 | B2 | 2/2015 | Abeywardane et al. |
| 2002/0132822 | A1 | 9/2002 | Noe et al. |
| 2006/0019269 | A1 | 1/2006 | Helgadottir et al. |
| 2006/0223792 | A1 | 10/2006 | Butler et al. |
| 2007/0066820 | A1 | 3/2007 | Sandanayaka et al. |
| 2007/0149544 | A1 | 6/2007 | Sandanayaka et al. |
| 2013/0196973 | A1 | 8/2013 | Abeywardane et al. |
| 2013/0236468 | A1 | 9/2013 | Bylock |
| 2013/0244996 | A1 | 9/2013 | Abeywardane et al. |
| 2014/0031339 | A1 | 1/2014 | Abeywardane et al. |

FOREIGN PATENT DOCUMENTS

| | | | |
|---|---|---|---|
| CA | 2076573 | A1 | 2/1993 |
| CA | 2280727 | A1 | 8/1998 |
| WO | 9610999 | A2 | 4/1996 |
| WO | 9611192 | A1 | 4/1996 |
| WO | 2004056369 | A1 | 7/2004 |
| WO | 2007040682 | A1 | 4/2007 |
| WO | 2008052086 | A1 | 5/2008 |
| WO | 2011032050 | A2 | 3/2011 |
| WO | 2011114220 | A1 | 9/2011 |
| WO | 2012125598 | A1 | 9/2012 |
| WO | 2013012844 | A1 | 1/2013 |
| WO | 2014014874 | A1 | 1/2014 |

OTHER PUBLICATIONS

Davies, D. R. et al., "Discovery of Leukotriene A4 Hydrolase Inhibitors Using Metabolomics Biased Fragment Crystallography+", Journal of Medicanal Chemistry, vol. 52, No. 15, Aug. 13, 2009, pp. 4694-4715.

Grice, C.A. et al., "Current Status of Leukotriene A4 Hydrolase Inhibitors". Expert Opinion on Therapeutic Patents, vol. 18, No. 12, Dec. 1, 2008, p. 1333-1350.

International Search Report and Written Opinion for PCT/US2012/028843 mailed May 7, 2012.

Minami, M. et al., "Molecular Cloning of a cDNA Coding for Human Leukotriene A4 Hydrolase". The Journal of Biological Chemistry, vol. 262, No. 29, 1987, p. 13873-13876.

Sandanayaka, V. et al., "Discovery of 4-[(2 S)-2-{[4-(4-Chlorophenoxy)phenoxy]methyl}-1-pyrrolidinyl]butanoic Acid (DG-051) as a Novel Leukotriene B4 Biosynthesis". Journal of Medicinal Chemistry, vol. 53, No. 2, Jan. 28, 2010, p. 573-585.

Sandanayaka, V. et al., "Discovery of novel leukotriene A4 hydrolase inhibitors based on piperidine and piperazine scaffolds". Bioorganice and Medicinal Chemistry Letters, Pergamon, Elsevier Science, GB, vol. 20, n0 9, May 1, 2010, pp. 2851-2854.

Thangapandian, Sundarapandian et al., "Molecular Docking and Pharacophore Filtering in the Discovery of Dual-Inhibitors for Human Leukotreine A4 Hydrolase and Leukotriene C4 Synthase", Journal of Chemical Information and Modeling, vol. 51, No. 1, Jan. 24, 2011, pp. 33-44.

U.S. Appl. No. 14/330,297, filed Jul. 14, 2014—Inhibitors of Leukotriene Production. Inventor: Asitha Abeywardane et al.

U.S. Appl. No. 14/330,307, filed Jul. 14, 2014—Inhibitors of Leukotriene Production. Inventor: Asitha Abeywardane et al.

International Search Report and Written Opinion for PCT/US2013/050624 mailed Sep. 11, 2013.

*Primary Examiner* — Sarah Pihonak

(74) *Attorney, Agent, or Firm* — Michael P. Morris; Usha R. Patel

(57) ABSTRACT

The present invention relates to compounds of formula (I):

(I)

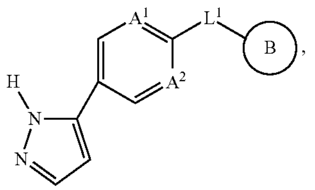

or a pharmaceutically acceptable salt thereof, wherein $A^1$, $A^2$, $L^1$ and B are as defined herein. The compounds of formula (I) are useful as inhibitors of leukotriene $A_4$ hydrolase ($LTA_4H$) and treating $LTA_4H$ related disorders. The present invention also relates to pharmaceutical compositions comprising the compounds of formula (I), methods of using these compounds in the treatment of various diseases and disorders, and processes for preparing these compounds.

15 Claims, No Drawings

INHIBITORS OF LEUKOTRIENE PRODUCTION

FIELD OF THE INVENTION

This invention relates to novel compounds that are useful as inhibitors of leukotriene $A_4$ hydrolase ($LTA_4H$) and are thus useful for treating a variety of diseases and disorders that are mediated or sustained through the activity of leukotrienes including asthma, allergy and cardiovascular diseases including atherosclerosis, myocardial infarction and stroke. This invention also relates to pharmaceutical compositions comprising these compounds, methods of using these compounds in the treatment of various diseases and disorders, to processes for preparing these compounds and intermediates useful in these processes.

BACKGROUND OF THE INVENTION

Leukotrienes (LT) are oxidized lipids that are produced by several cell types including neutrophils, mast cells, eosinophils, basophils, monocytes and macrophages. The first committed step in the intracellular synthesis of LTs involves oxidation of arachidonic acid by 5-lipoxygenase (5-LO) to leukotriene $A_4$ ($LTA_4$), a process requiring the 5-lipoxygenase-activating protein (FLAP). Leukotriene $A_4$ hydrolase ($LTA_4H$) catalyzes the hydrolysis of $LTA_4$ to produce leukotriene $B_4$ ($LTB_4$). Through the engagement of the $LTB_4$ receptors (BLT1, BLT2), $LTB_4$ stimulates an array of pro-inflammatory responses (leukocyte chemotaxis, cytokine release, etc.). The leukotriene pathway has been implicated in diseases in which inflammation is a critical component of the pathology; these include cancer, asthma, atherosclerosis, colitis, glomerularnephritis, and pain (for a review, see M. Peters-Golden and W. R. Henderson, Jr., M. D., N. Engl. J. Med., 2007, 357, 1841-1854).

BRIEF SUMMARY OF THE INVENTION

The present invention provides novel compounds which inhibit leukotriene $A_4$ hydrolase ($LTA_4H$) and are thus useful for treating a variety of diseases and disorders that are mediated or sustained through the activity of leukotrienes, including allergic, pulmonary, fibrotic, inflammatory and cardiovascular diseases and cancer.

In its broadest embodiment ("embodiment 1"), the invention relates to a compound of formula (I):

(I)

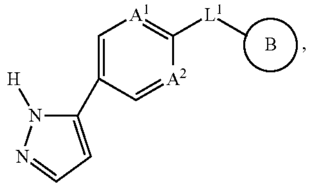

or a pharmaceutically acceptable salt thereof, wherein:

$A^1$ and $A^2$ are each independently selected from the group consisting of CH and N;

$L^1$ is a linker selected from the group consisting of —O— and —$CH_2$—;

B is a 9- or 10-membered ring selected from the group consisting of:

B-1

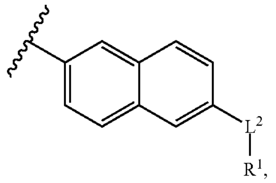

B-2

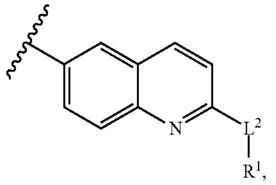

B-3

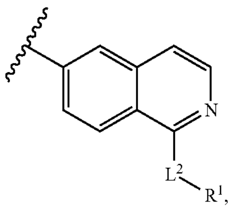

B-4

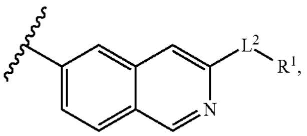

B-5

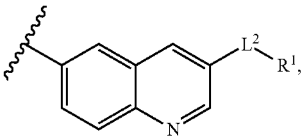

B-6

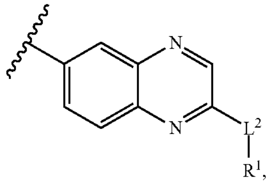

B-7

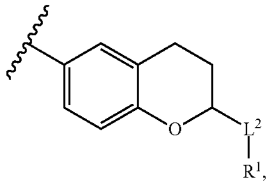

B-8

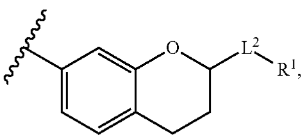

B-9

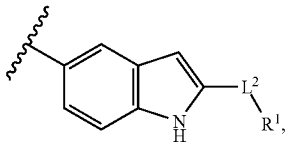

-continued

B-10

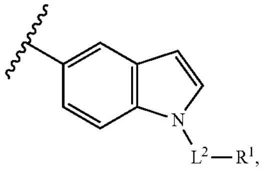

B-11

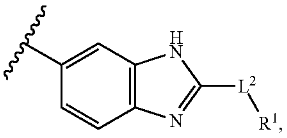

B-12

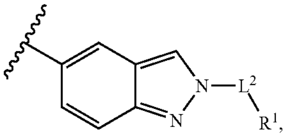

B-13

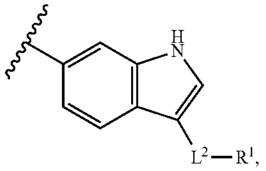

B-14

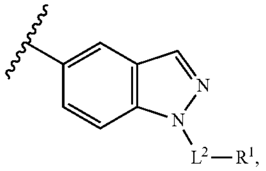

B-15

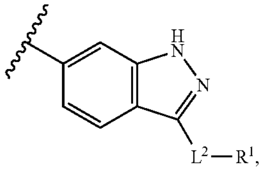

B-16

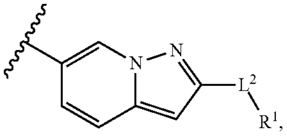

B-17

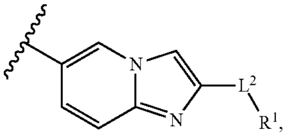

B-18

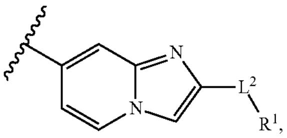

-continued

B-19

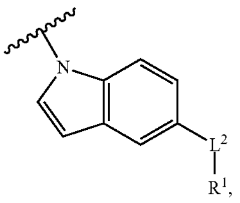

B-20

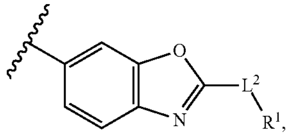

B-21

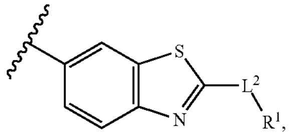

B-22

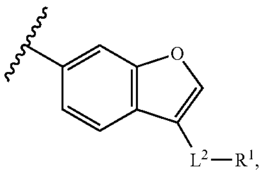

B-23

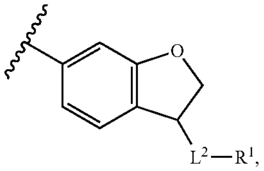

B-24

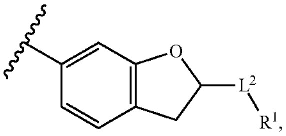

and

B-25

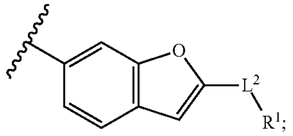

wherein each B ring may optionally be further substituted by —$(C_1$-$C_6)$alkyl;

$L^2$ is absent or a —$(CH_2)_n$— linker, wherein n is an integer selected from 1, 2 and 3, and wherein one —$(CH_2)$— moiety of said $L^2$ linker may optionally be replaced, where possible, by —O— and wherein each —$(CH_2)$— moiety of said $L^2$ linker may be substituted with one to two groups selected from the group consisting of —OH, -halo, ═O, —$(C_1$-$C_6)$alkyl, —$(C_3$-$C_6)$cycloalkyl, -(4- to 7-membered)heterocyclyl, and phenyl; wherein two —$(C_1$-$C_6)$alkyls groups, when attached to the same carbon atom of said $L^2$ linker moiety may join to form a —$(C_3$-$C_6)$cycloalkyl;

$R^1$ is selected from the group consisting of:

(a) a group of formula —$N(R^2)(R^3)$, wherein $R^2$ and $R^3$ are each independently selected from the group consisting of —H, —$(C_1$-$C_6)$alkyl, —$(C_3$-$C_6)$cycloalkyl, and -(4- to 7-membered)heterocyclyl, wherein each of said —$(C_1$-$C_6)$alkyl, —$(C_3$-$C_6)$cycloalkyl, and -(4- to 7-membered)heterocyclyl of said $R^2$ and $R^3$ may optionally be independently substituted by 1 to 3 $R^4$ groups;

$R^4$ is selected from the group consisting of halo, —OH, =O, —$(C_1$-$C_6)$alkyl, —$O(C_1$-$C_6)$alkyl, —$N(R^5)_2$, —C(O)—$R^5$, —$N(R^5)$—C(O)—$R^5$, —C(O)—$N(R^5)_2$, —$(C_3$-$C_6)$cycloalkyl optionally substituted by —C(O)—$(C_1$-$C_6)$alkyl, -(4- to 7-membered)heterocyclyl optionally substituted by —C(O)—$(C_1$-$C_6)$ alkyl, and phenyl; and each $R^5$ is independently selected from the group consisting of —H, —$(C_1$-$C_6)$alkyl, —$(C_3$-$C_6)$cycloalkyl, and -(4- to 7-membered)heterocyclyl;

(b) a 4- to 9-membered N-heterocyclic ring, wherein said 4- to 9-membered N-heterocyclic ring is optionally independently substituted by a group selected from the group consisting of (i) 1 $G^1$ group or (ii) 1 to 3 $G^2$ groups; wherein $G^1$ is selected from the group consisting of -$L^4$-$(C_1$-$C_6)$ alkyl, -$L^4$-$(C_3$-$C_6)$cycloalkyl, -$L^4$-$(C_3$-$C_6)$heterocyclyl, and -$L^4$-phenyl; wherein each of said —$(C_1$-$C_6)$ alkyl, —$(C_3$-$C_6)$cycloalkyl, -(4- to 7-membered) heterocyclyl, and phenyl substituents may optionally be individually substituted by 1 to 4 $R^6$ groups;

$L^4$ is absent or selected from the group consisting of —O—, —C(O)—, —$N(R^7)$—, —C(O)—N$(R^7)$—, —$N(R^7)$—C(O)—, and —$N(R^7)$—S$(O)_j$—;

—$R^6$ is selected from the group consisting of halo, —OH, =O, —CN, —$(C_1$-$C_6)$alkyl, —$O(C_1$-$C_6)$ alkyl, —$N(R^7)_2$, —C(O)—$R^7$, —C(O)—O—$R^7$, —$N(R^7)$—C(O)—$R^7$, —C(O)—$N(R^7)_2$, —$S(O)_j$—$R^7$, —$(C_3$-$C_6)$cycloalkyl, -(4- to 7-membered) heterocyclyl, and phenyl optionally substituted with —C(O)—O—$R^7$;

each $R^7$ is independently selected from the group consisting of —H, —$(C_1$-$C_6)$alkyl, —$(C_3$-$C_6)$cycloalkyl, and -(4- to 7-membered)heterocyclyl; and each $G^2$ is independently selected from the group consisting of -halo, —OH, =O, —CN, —$O(C_1$-$C_6)$alkyl and —$(C_1$-$C_6)$alkyl optionally substituted with —$O(C_1$-$C_6)$alkyl; or (c) a group selected from the group consisting of a tetrahydro-2H-pyranyl, —C(O)—OH and OH;

wherein j is an integer selected from 0, 1 and 2.

In a second embodiment (embodiment 2), the invention relates to a compound of embodiment 1, or a pharmaceutically acceptable salt thereof, wherein one of $A^1$ and $A^2$ is N and the other is CH.

In a third embodiment (embodiment 3), the invention relates to a compound of any one of the preceding embodiments, or a pharmaceutically acceptable salt thereof, wherein $A^2$ is N.

In a fourth embodiment (embodiment 4), the invention relates to a compound of embodiment 1, or a pharmaceutically acceptable salt thereof, wherein $A^1$ and $A^2$ are each CH.

In a fifth embodiment (embodiment 5), the invention relates to a compound of embodiment 1, or a pharmaceutically acceptable salt thereof, wherein $A^1$ and $A^2$ are each N.

In a sixth embodiment (embodiment 6), the invention relates to a compound of embodiment 1, or a pharmaceutically acceptable salt thereof, wherein ring B is selected from the group consisting of B-1, B-2, B-3, B-4, B-5 and B-6. Preferably, B is B-2.

In a seventh embodiment (embodiment 7), the invention relates to a compound of embodiment 1, or a pharmaceutically acceptable salt thereof, wherein ring B is selected from the group consisting of B-7 and B-8.

In an eight embodiment (embodiment 8), the invention relates to a compound of embodiment 1, or a pharmaceutically acceptable salt thereof, wherein ring B is selected from the group consisting of B-9, B-10, B-11, B-12, B-13, B-14, B-15, B-16, B-17, B-18 and B-19. Preferably, B is selected from the group consisting of B-11, B-12, B-14 and B-17. More preferably, B is B-11.

In a ninth embodiment (embodiment 9), the invention relates to a compound of embodiment 1, or a pharmaceutically acceptable salt thereof, wherein ring B is selected from the group consisting of B-20, B-21 B-22, B-23, B-24, and B-25. Preferably, B is selected from the group consisting of B-24 and B-25.

In a tenth embodiment (embodiment 10), the invention relates to a compound of any one of the preceding embodiments, or a pharmaceutically acceptable salt thereof, wherein $R^1$ is selected from the group consisting of a group of formula —$N(R^2)(R^3)$, wherein $R^2$ and $R^3$ are each independently selected from the group consisting of —H, —$(C_1$-$C_6)$alkyl, —$(C_3$-$C_6)$cycloalkyl, and -(4- to 7-membered)heterocyclyl, wherein each of said —$(C_1$-$C_6)$alkyl, —$(C_3$-$C_6)$cycloalkyl, and -(4- to 7-membered)heterocyclyl of said $R^2$ and $R^3$ may optionally be independently substituted by 1 to 3 $R^4$ groups;

$R^4$ is selected from the group consisting of halo, —OH, =O, —$(C_1$-$C_6)$alkyl), —$(C_1$-$C_6)$alkyl), —$N(R^5)_2$, —C(O)—$R^5$, —$N(R^5)$—C(O)—$R^5$, —C(O)—$N(R^5)_2$, —$(C_3$-$C_6)$cycloalkyl optionally substituted by —C(O)—$(C_1$-$C_6)$alkyl), -(4- to 7-membered)heterocyclyl optionally substituted by —C(O)—$(C_1$-$C_6)$alkyl), and phenyl; and each $R^5$ is independently selected from the group consisting of —H, —$(C_1$-$C_6)$alkyl, —$(C_3$-$C_6)$cycloalkyl, and -(4- to 7-membered)heterocyclyl.

In an eleventh embodiment (embodiment 11), the invention relates to a compound of any one of the preceding embodiments, or a pharmaceutically acceptable salt thereof, wherein $R^1$ is selected from the group consisting of —N(H)$((C_1$-$C_6)$alkyl), —$N((C_1$-$C_6)$alkyl$)_2$, —N(H)((4- to 7-membered)heterocyclyl) and —$N((C_1$-$C_6)$alkyl)((4- to 7-membered)heterocyclyl); wherein each of said —$(C_1$-$C_6)$alkyl groups may optionally be independently substituted by one to three groups independently selected from the group consisting of —OH, =O, —$O(C_1$-$C_6)$alkyl, —$NH_2$, -(4- to 7-membered)heterocyclyl, and phenyl.

In a twelfth embodiment (embodiment 12), the invention relates to a compound of any one of embodiments 1-10, or a pharmaceutically acceptable salt thereof, wherein $R^1$ is a 4- to 9-membered N-heterocyclic ring optionally independently substituted by a group selected from the group consisting of (i) 1 $G^1$ group as defined in embodiment 1 or (ii) 1 to 3 $G^2$ groups as defined as defined in embodiment 1.

In a thirteenth embodiment (embodiment 13), the invention relates to a compound of embodiment 12, or a pharmaceutically acceptable salt thereof, wherein said 4- to 9-membered N-heterocyclic ring is a nonaromatic 4- to 7-membered monocyclic heterocyclic radical selected from the group consisting of azetidinyl, pyrrolidinyl, tetrahydrofuranyl, oxazolidinyl, piperazinyl, piperidinyl, morpholinyl, dioxanyl, tetrahydropyranyl, thiomorpholinyl, azepanyl, 1,4-diazepanyl and 1,4-oxazepanyl; wherein each of said nonaromatic 4- to 7-membered monocyclic heterocyclic radicals is optionally substituted by a group selected from the group consisting of (i) 1 $G^1$ group as defined in embodiment 1 or (ii) 1 to 3 $G^2$ groups as defined as defined in embodiment 1.

In a fourteenth embodiment (embodiment 14), the invention relates to a compound of embodiment 12, or a pharmaceutically acceptable salt thereof, wherein said 4- to 9-membered N-heterocyclic ring is a nonaromatic 4- to 7-membered monocyclic heterocyclic radical having a spirocyclic group; wherein said nonaromatic 4- to 7-membered monocyclic heterocyclic radical having a spirocyclic group is optionally substituted by a group selected from the group consisting of (i) 1 $G^1$ group as defined in embodiment 1 or (ii) 1 to 3 $G^2$ groups as defined as defined in embodiment 1.

In a fifteenth embodiment (embodiment 15), the invention relates to a compound of embodiment 14, or a pharmaceutically acceptable salt thereof, wherein said nonaromatic 4- to 7-membered monocyclic heterocyclic radical having a spirocyclic group is selected from the group consisting of oxa-6-aza-spiro[3.4]octanane, 1,8-diaza-spiro[4.5]decan-2-onane, 2-oxa-6-aza-spiro[3.5]nonanane, 1,8-diaza-spiro[4.5]decanane, and 2-oxa-6-aza-spiro[3.3]heptanane.

In a sixteenth embodiment (embodiment 16), the invention relates to a compound of embodiment 12, or a pharmaceutically acceptable salt thereof, wherein said 4- to 9-membered N-heterocyclic ring is a nonaromatic 4- to 7-membered monocyclic heterocyclic radical fused to a 4- to 6-membered fused; wherein said nonaromatic 4- to 7-membered monocyclic heterocyclic radical fused to a 4- to 6-membered fused ring is optionally substituted by a group selected from the group consisting of (i) 1 $G^1$ group as defined in embodiment 1 or (ii) 1 to 3 $G^2$ groups as defined as defined in embodiment 1.

In a seventeenth embodiment (embodiment 17), the invention relates to a compound of embodiment 16, or a pharmaceutically acceptable salt thereof, wherein said nonaromatic 4- to 7-membered monocyclic heterocyclic radical fused to a 4- to 6-membered fused is selected from the group consisting of hexahydro-oxazolo[3,4-a]pyrazin-3-one, hexahydro-pyrrolo[1,2-a]pyrazin-6-one, and octahydro-pyrrolo[3,4-c]pyrrole.

In an eighteenth embodiment (embodiment 18), the invention relates to a compound of embodiment 12, or a pharmaceutically acceptable salt thereof, wherein said 4- to 9-membered N-heterocyclic ring is a nonaromatic 6 to 8-membered bridged N-heterobicyclic radical; wherein said nonaromatic 6 to 8-membered bridged N-heterobicyclic radical is optionally substituted by a group selected from the group consisting of (i) 1 $G^1$ group as defined in embodiment 1 or (ii) 1 to 3 $G^2$ groups as defined as defined in embodiment 1.

In an nineteenth embodiment (embodiment 19), the invention relates to a compound of embodiment 18, or a pharmaceutically acceptable salt thereof, wherein nonaromatic 6 to 8-membered bridged N-heterobicyclic radical is selected from the group consisting of 2-thia-5-aza-bicyclo[2.2.1]heptane 2,2-dioxide, 3,8-diaza-bicyclo[3.2.1]octane, 8-oxa-3-aza-bicyclo[3.2.1]octane, (endo)-(8-aza-bicyclo[3.2.1]oct-3-yl)amine, 2,5-diaza-bicyclo[2.2.1]heptane, (exo)-(8-aza-bicyclo[3.2.1]oct-3-yl)amine, 2,5-diaza-bicyclo[2.2.2]octane, 2-oxa-5-aza-bicyclo[2.2.1]heptane, and 3-aza-bicyclo[3.1.0]hexane.

In a twentieth embodiment (embodiment 20), the invention relates to a compound of embodiment 12, or a pharmaceutically acceptable salt thereof, wherein said 4- to 9-membered N-heterocyclic ring is an aromatic 6-membered heteroaryl radical selected from the group consisting of pyridine and pyrimidine; wherein each of said aromatic 6-membered heteroaryl radicals is optionally substituted by a group selected from the group consisting of (i) 1 $G^1$ group as defined in embodiment 1 or (ii) 1 to 3 $G^2$ groups as defined as defined in embodiment 1.

In a twenty-first embodiment (embodiment 21), the invention relates to a compound of embodiment 12, or a pharmaceutically acceptable salt thereof, wherein said 4- to 9-membered N-heterocyclic ring is (1R,5S)-1,2,3,4,5,6-hexahydro-1,5-methano-pyrido[1,2-a][1,5]diazocin-8-one.

In a twenty-second embodiment (embodiment 22), the invention relates to a compound of any one of embodiments 1 to 9, or a pharmaceutically acceptable salt thereof, wherein said $R^1$ group is selected from the group consisting of tetrahydro-2H-pyranyl, —C(O)—($C_1$-$C_6$)alkyl and —($C_1$-$C_6$)alkylene-OH.

DETAILED DESCRIPTION OF THE INVENTION

Definitions:

AIBN=azobisisobutyronitrile
BOC=tert-butyloxycarbonyl
BnO=benzyloxide
DCM=dichloromethane
DDQ=2,3-dichloro-5,6-dicyano-1,4-benzoquinone
DEA=diethylamine
DIBAL-H=diisobutylaluminum hydride
DIPEA=diisopropylethylamine
DMA=dimethylacetamide
DMAP=4-dimethylaminopyridine
DME=dimethyl ether
DMF=dimethylformamide
DMSO=dimethylsulfoxide
$Et_2O$=ethylether
EtOAc=ethyl acetate
EtOH=ethanol
LDA=lithium diisopropylamide
mCPBA=meta-chloroperoxybenzoic acid
MeCN=acetonitrile
MeOH=methanol
NBS=N-bromosuccinimide
PyBrop=bromo-tris-pyrrolidino phosphoniumhexafluorophosphate
SEM=2-(trimethylsilyl)ethoxymethyl
TBAF=tetra-n-butylammonium fluoride
TBTU=2-(1H-benzotriazole-1-yl)-1,1,3,3-tetramethyluronium tetrafluoroborate
TFA=trifluoroacetic acid
THF=tetrahydrofuran
TIPSO=triisopropylsiloxy It will be understood that the terms "compounds of formula (I)" and "compounds of the invention" have the same meaning unless indicated otherwise.

The following are representative compounds of the invention which were made by the general synthetic schemes, the examples, and known methods in the art.

TABLE 1

| Examples of compounds of the invention. | | |
|---|---|---|
| No. | Structure | Compound Name |
| 1 | 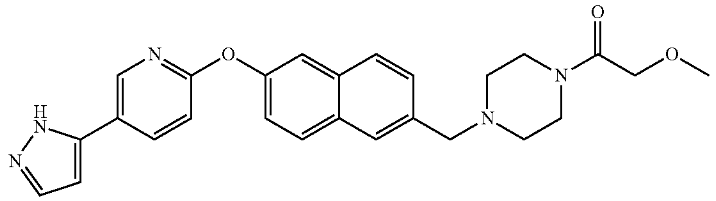 [SMILES: COCC(=O)N1CCN(Cc2ccc3cc(Oc4ccc(-c5ccn[nH]5)cn4)ccc3c2)CC1] | 2-Methoxy-1-(4-{6-[5-(2H-pyrazol-3-yl)-pyridin-2-yloxy]-naphthalen-2-ylmethyl}-piperazin-1-yl)-ethanone |
| 2 | 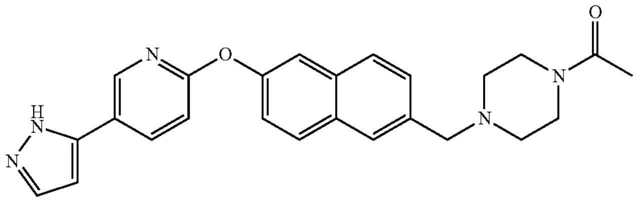 [SMILES: CC(=O)N1CCN(Cc2ccc3cc(Oc4ccc(-c5ccn[nH]5)cn4)ccc3c2)CC1] | 1-(4-{6-[5-(2H-Pyrazol-3-yl)-pyridin-2-yloxy]-naphthalen-2-ylmethyl}-piperazin-1-yl)-ethanone |
| 3 | 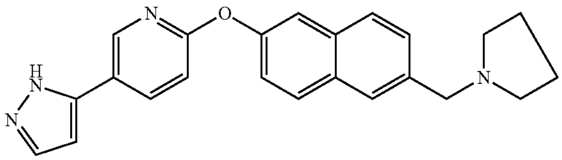 [SMILES: c1cc(-c2ccc(Oc3ccc4cc(CN5CCCC5)ccc4c3)nc2)[nH]n1] | 5-(2H-Pyrazol-3-yl)-2-(6-pyrrolidin-1-ylmethyl-naphthalen-2-yloxy)-pyridine |
| 4 | 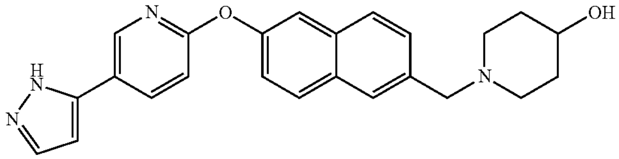 [SMILES: OC1CCN(Cc2ccc3cc(Oc4ccc(-c5ccn[nH]5)cn4)ccc3c2)CC1] | 1-{6-[5-(2H-Pyrazol-3-yl)-pyridin-2-yloxy]-naphthalen-2-ylmethyl}-piperidin-4-ol |
| 5 | 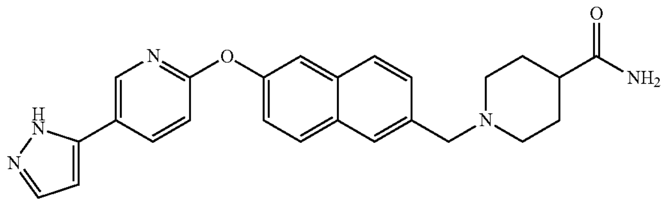 [SMILES: NC(=O)C1CCN(Cc2ccc3cc(Oc4ccc(-c5ccn[nH]5)cn4)ccc3c2)CC1] | 1-{6-[5-(2H-Pyrazol-3-yl)-pyridin-2-yloxy]-naphthalen-2-ylmethyl}-piperidine-4-carboxylic acid amide |
| 6 | 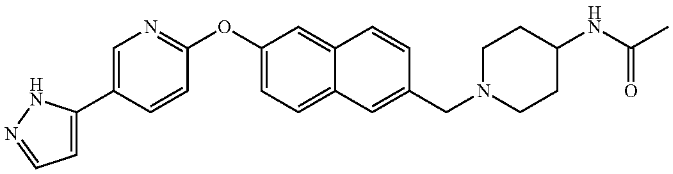 [SMILES: CC(=O)NC1CCN(Cc2ccc3cc(Oc4ccc(-c5ccn[nH]5)cn4)ccc3c2)CC1] | N-(1-{6-[5-(2H-Pyrazol-3-yl)-pyridin-2-yloxy]-naphthalen-2-ylmethyl}-piperidin-4-yl)-acetamide |
| 7 | 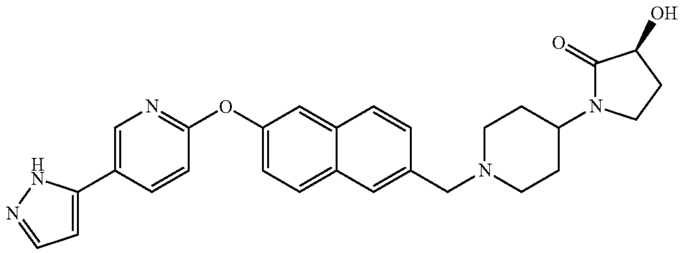 [SMILES: O=C1[C@@H](O)CCN1C1CCN(Cc2ccc3cc(Oc4ccc(-c5ccn[nH]5)cn4)ccc3c2)CC1] | (S)-3-Hydroxy-1-(1-{6-[5-(2H-pyrazol-3-yl)-pyridin-2-yloxy]-naphthalen-2-ylmethyl}-piperidin-4-yl)-pyrrolidin-2-one |

TABLE 1-continued

Examples of compounds of the invention.

| No. | Structure | Compound Name |
|---|---|---|
| 8 | 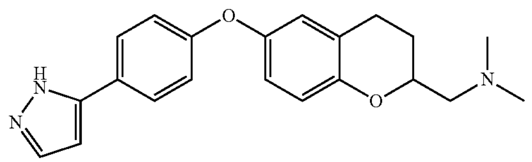 [SMILES: CN(C)CC1CCc2cc(Oc3ccc(-c4ccn[nH]4)cc3)ccc2O1] | Dimethyl-{6-[4-(2H-pyrazol-3-yl)-phenoxy]-chroman-2-ylmethyl}-amine |
| 9 | 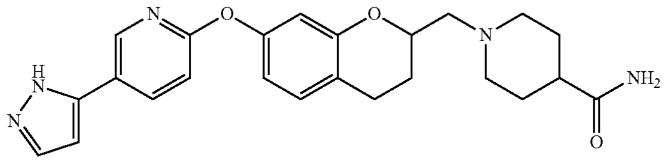 [SMILES: NC(=O)C1CCN(CC2CCc3ccc(Oc4ccc(-c5ccn[nH]5)cn4)cc3O2)CC1] | 1-{7-[5-(2H-Pyrazol-3-yl)-pyridin-2-yloxy]-chroman-2-ylmethyl}-piperidine-4-carboxylic acid amide |
| 10 | 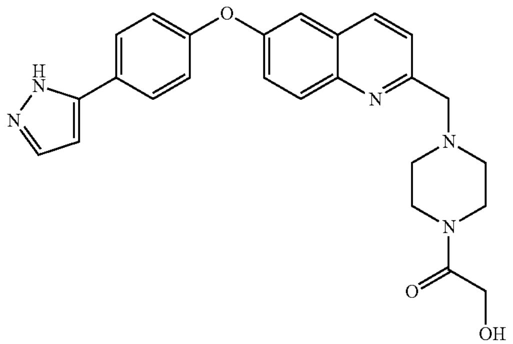 [SMILES: O=C(CO)N1CCN(Cc2ccc3cc(Oc4ccc(-c5ccn[nH]5)cc4)ccc3n2)CC1] | 2-Hydroxy-1-(4-{6-[4-(2H-pyrazol-3-yl)-phenoxy]-quinolin-2-ylmethyl}-piperazin-1-yl)-ethanone |
| 11 | 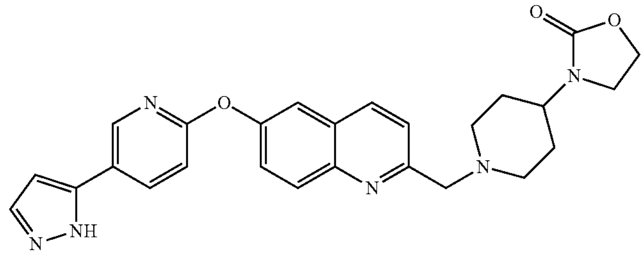 [SMILES: O=C1OCCN1C1CCN(Cc2ccc3cc(Oc4ccc(-c5ccn[nH]5)cn4)ccc3n2)CC1] | 3-(1-{6-[5-(2H-Pyrazol-3-yl)-pyridin-2-yloxy]-quinolin-2-ylmethyl}-piperidin-4-yl)-oxazolidin-2-one |
| 12 | 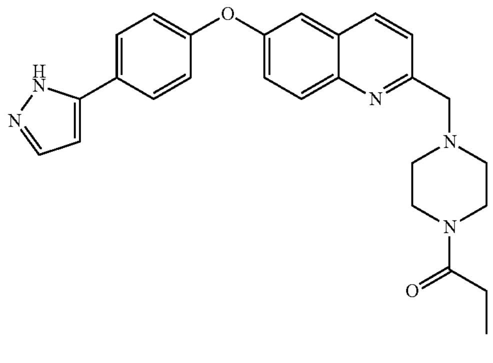 [SMILES: CCC(=O)N1CCN(Cc2ccc3cc(Oc4ccc(-c5ccn[nH]5)cc4)ccc3n2)CC1] | 1-(4-{6-[4-(2H-Pyrazol-3-yl)-phenoxy]-quinolin-2-ylmethyl}-piperazin-1-yl)-propan-1-one |

TABLE 1-continued

| Examples of compounds of the invention. | | |
|---|---|---|
| No. | Structure | Compound Name |
| 13 | 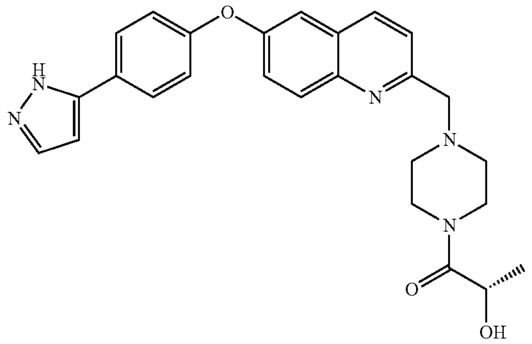 [SMILES: C[C@H](O)C(=O)N1CCN(Cc2ccc3cc(Oc4ccc(-c5ccn[nH]5)cc4)ccc3n2)CC1] | (S)-2-Hydroxy-1-(4-{6-[4-(2H-pyrazol-3-yl)-phenoxy]-quinolin-2-ylmethyl}-piperazin-1-yl)-propan-1-one |
| 14 | 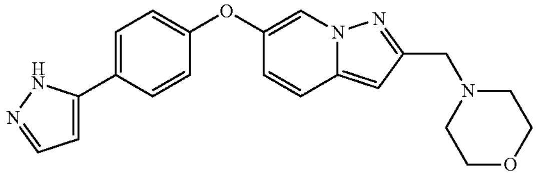 [SMILES: c1cc(-c2ccc(Oc3ccc4cc(CN5CCOCC5)nn4c3)cc2)[nH]n1] | 2-Morpholin-4-ylmethyl-6-[4-(2H-pyrazol-3-yl)-phenoxy]-pyrazolo[1,5-a] pyridine |
| 15 | 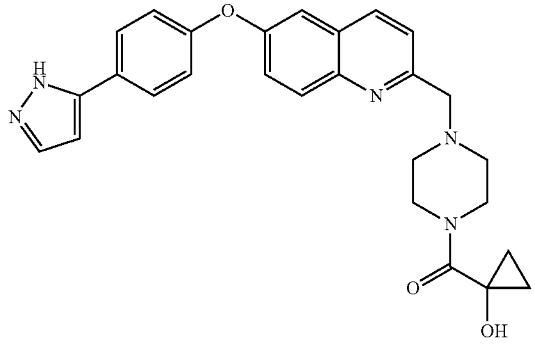 [SMILES: O=C(N1CCN(Cc2ccc3cc(Oc4ccc(-c5ccn[nH]5)cc4)ccc3n2)CC1)C1(O)CC1] | (1-Hydroxy-cyclopropyl)-(4-{6-[4-(2H-pyrazol-3-yl)-phenoxy]-quinolin-2-ylmethyl}-piperazin-1-yl)-methanone |
| 16 | 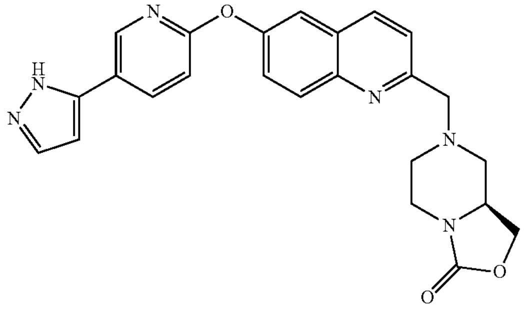 [SMILES: O=C1OC[C@@H]2CN(Cc3ccc4cc(Oc5ccc(-c6ccn[nH]6)cn5)ccc4n3)CCN12] | (S)-7-{6-[5-(2H-Pyrazol-3-yl)-pyridin-2-yloxy]-quinolin-2-ylmethyl}-hexahydro-oxazolo[3,4-a]pyrazin-3-one |
| 17 | 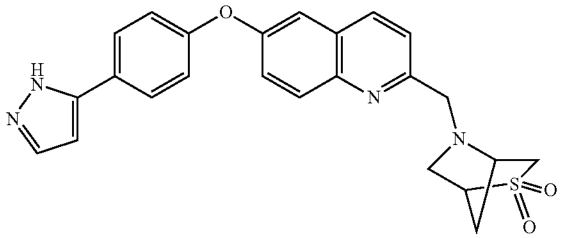 [SMILES: O=S1(=O)CC2CC1CN2Cc1ccc2cc(Oc3ccc(-c4ccn[nH]4)cc3)ccc2n1] | 2-(2,2-Dioxo-2-λ-6-thia-5-aza-bicyclo [2.2.1]hept-5-ylmethyl)-6-[4-(2H-pyrazol-3-yl)-phenoxy]-quinoline |

TABLE 1-continued

| Examples of compounds of the invention. | | |
|---|---|---|
| No. | Structure | Compound Name |
| 18 | 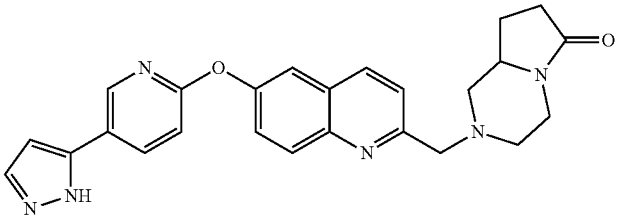 [SMILES: O=C1CCC2CN(Cc3ccc4cc(Oc5ccc(-c6ccn[nH]6)cn5)ccc4n3)CCN12] | 2-{6-[5-(2H-Pyrazol-3-yl)-pyridin-2-yloxy]-quinolin-2-ylmethyl}-hexahydro-pyrrolo[1,2-a]pyrazin-6-one |
| 19 | 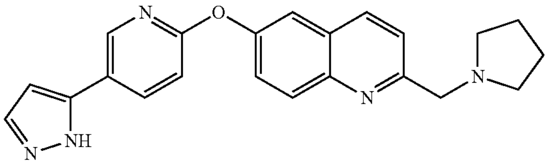 [SMILES: c1cc(-c2ccc(Oc3ccc4nc(CN5CCCC5)ccc4c3)nc2)[nH]n1] | 6-[5-(2H-Pyrazol-3-yl)-pyridin-2-yloxy]-2-pyrrolidin-1-ylmethyl-quinoline |
| 20 | 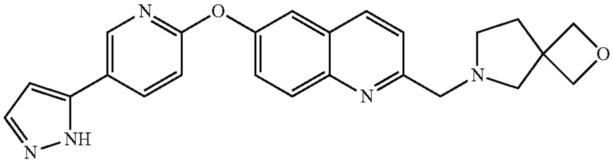 [SMILES: c1cc(-c2ccc(Oc3ccc4nc(CN5CCC6(COC6)C5)ccc4c3)nc2)[nH]n1] | 2-(2-Oxa-6-aza-spiro[3,4]oct-6-ylmethyl)-6-[5-(2H-pyrazol-3-yl)-pyridin-2-yloxy]-quinoline |
| 21 | 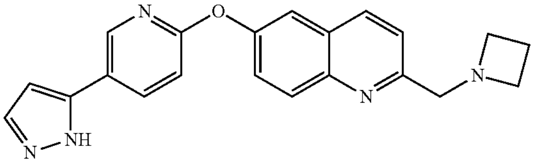 [SMILES: c1cc(-c2ccc(Oc3ccc4nc(CN5CCC5)ccc4c3)nc2)[nH]n1] | 2-Azetidin-1-ylmethyl-6-[5-(2H-pyrazol-3-yl)-pyridin-2-yloxy]-quinoline |
| 22 | 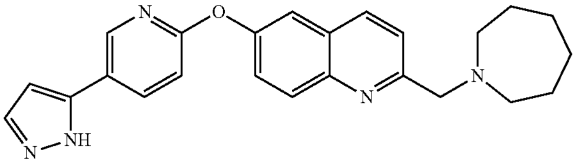 [SMILES: c1cc(-c2ccc(Oc3ccc4nc(CN5CCCCCC5)ccc4c3)nc2)[nH]n1] | 2-Azepan-1-ylmethyl-6-[5-(2H-pyrazol-3-yl)-pyridin-2-yloxy]-quinoline |
| 23 | 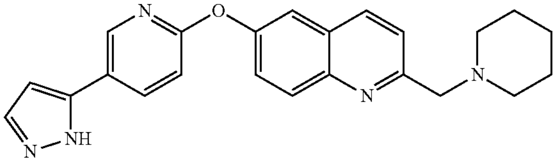 [SMILES: c1cc(-c2ccc(Oc3ccc4nc(CN5CCCCC5)ccc4c3)nc2)[nH]n1] | 2-Piperidin-1-ylmethyl-6-[5-(2H-pyrazol-3-yl)-pyridin-2-yloxy]-quinoline |
| 24 | 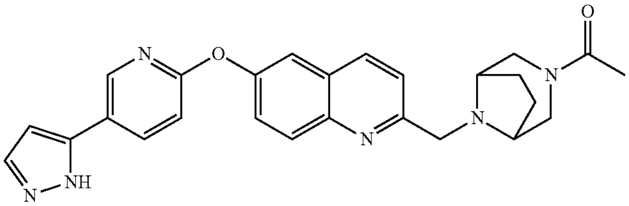 [SMILES: CC(=O)N1CC2CCC(C1)N2Cc1ccc2cc(Oc3ccc(-c4ccn[nH]4)cn3)ccc2n1] | 1-(8-{6-[5-(2H-Pyrazol-3-yl)-pyridin-2-yloxy]-quinolin-2-ylmethyl}-3,8-diaza-bicyclo[3.2.1]oct-3-yl)-ethanone |

TABLE 1-continued

| No. | Structure | Compound Name |
|---|---|---|
| Examples of compounds of the invention. | | |
| 25 | 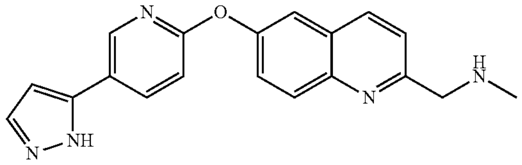 [SMILES: CNCc1ccc2cc(Oc3ccc(-c4ccn[nH]4)cn3)ccc2n1] | Methyl-{6-[5-(2H-pyrazol-3-yl)-pyridin-2-yloxy]-quinolin-2-ymethyl}-amine |
| 26 | 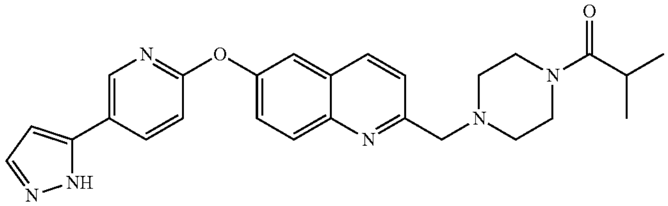 [SMILES: CC(C)C(=O)N1CCN(Cc2ccc3cc(Oc4ccc(-c5ccn[nH]5)cn4)ccc3n2)CC1] | 2-Methyl-1-(4-{6-[5-(2H-pyrazol-3-yl)-pyridin-2-yloxy]-quinolin-2-ylmethyl}-piperazin-1-yl)-propan-1-one |
| 27 | 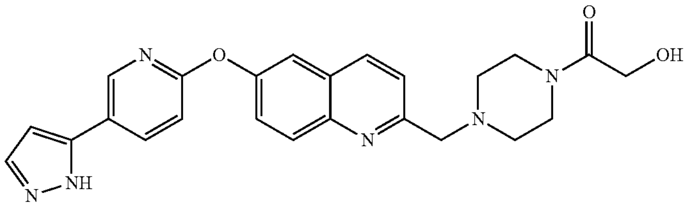 [SMILES: O=C(CO)N1CCN(Cc2ccc3cc(Oc4ccc(-c5ccn[nH]5)cn4)ccc3n2)CC1] | 2-Hydroxy-1-(4-{6-[5-(2H-pyrazol-3-yl)-pyridin-2-yloxy]-quinolin-2-ylmethyl}-piperazin-1-yl)-ethanone |
| 28 | 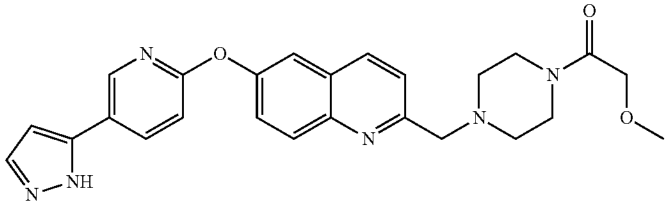 [SMILES: COCC(=O)N1CCN(Cc2ccc3cc(Oc4ccc(-c5ccn[nH]5)cn4)ccc3n2)CC1] | 2-Methoxy-1-(4-{6-[5-(2H-pyrazol-3-yl)-pyridin-2-yloxy]-quinolin-2-ylmethyl}-piperazin-1-yl)-ethanone |
| 29 | 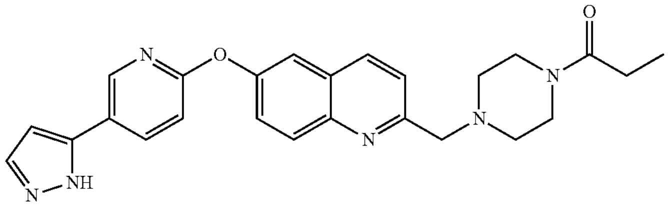 [SMILES: CCC(=O)N1CCN(Cc2ccc3cc(Oc4ccc(-c5ccn[nH]5)cn4)ccc3n2)CC1] | 1-(4-{6-[5-(2H-Pyrazol-3-yl)-pyridin-2-yloxy]-quinolin-2-ylmethyl}-piperazin-1-yl)-propan-1-one |
| 30 | 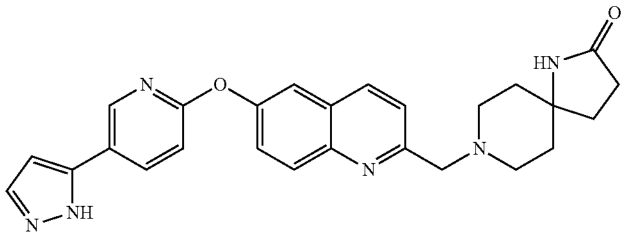 [SMILES: O=C1CCC2(CCN(Cc3ccc4cc(Oc5ccc(-c6ccn[nH]6)cn5)ccc4n3)CC2)N1] | 8-{6-[5-(2H-Pyrazol-3-yl)-pyridin-2-yloxy]-quinolin-2-ylmethyl}-1,8-diaza-spiro[4.5]decan-2-one |
| 31 | 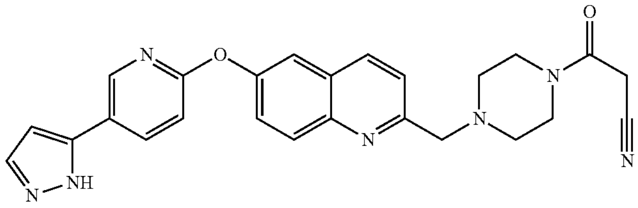 [SMILES: N#CCC(=O)N1CCN(Cc2ccc3cc(Oc4ccc(-c5ccn[nH]5)cn4)ccc3n2)CC1] | 3-Oxo-3-(4-{6-[5-(2H-pyrazol-3-yl)-pyridin-2-yloxy]-quinolin-2-ylmethyl}-piperazin-1-yl)-propionitrile |

TABLE 1-continued

Examples of compounds of the invention.

| No. | Structure | Compound Name |
| --- | --- | --- |
| 32 | 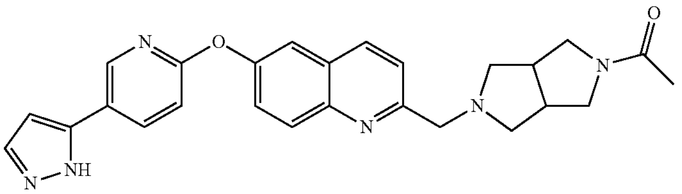 [SMILES: CC(=O)N1CC2CN(Cc3ccc4cc(Oc5ccc(-c6ccn[nH]6)cn5)ccc4n3)CC2C1] | 1-(5-{6-[5-(2H-Pyrazol-3-yl)-pyridin-2-yloxy]-quinolin-2-ylmethyl}-hexahydro-pyrrolo[3,4-c]pyrrol-2-yl)-ethanone |
| 33 | 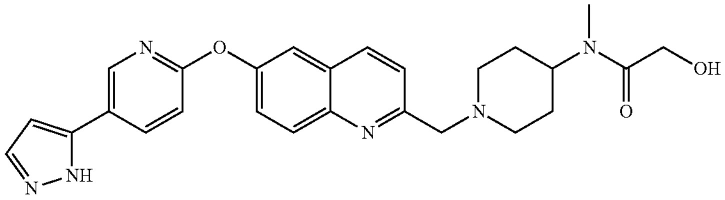 [SMILES: CN(C(=O)CO)C1CCN(Cc2ccc3cc(Oc4ccc(-c5ccn[nH]5)cn4)ccc3n2)CC1] | 2-Hydroxy-N-methyl-N-(1-{6-[5-(2H-pyrazol-3-yl)-pyridin-2-yloxy]-quinolin-2-ylmethyl}-piperidin-4-yl)-acetamide |
| 34 | 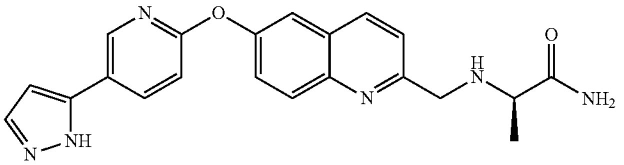 [SMILES: C[C@@H](NCc1ccc2cc(Oc3ccc(-c4ccn[nH]4)cn3)ccc2n1)C(N)=O] | (R)-2-({6-[5-(2H-Pyrazol-3-yl)-pyridin-2-yloxy]-quinolin-2-ylmethyl}-amino)-propionamide |
| 35 | 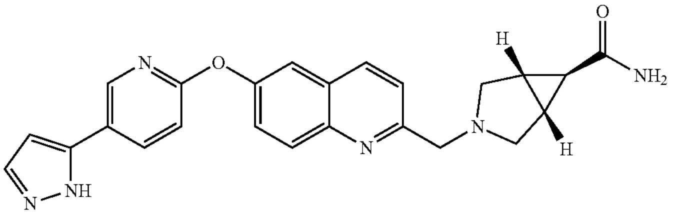 [SMILES: NC(=O)[C@H]1[C@@H]2CN(Cc3ccc4cc(Oc5ccc(-c6ccn[nH]6)cn5)ccc4n3)C[C@@H]21] | (1α,5α,6α)-3-{6-[5-(2H-Pyrazol-3-yl)-pyridin-2-yloxy]-quinolin-2-ylmethyl}-3-aza-bicyclo[3.1.0]hexane-6-carboxylic acid amide |
| 36 | 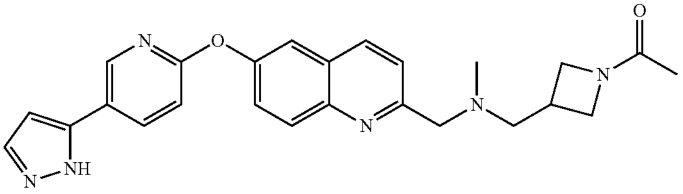 [SMILES: CC(=O)N1CC(CN(C)Cc2ccc3cc(Oc4ccc(-c5ccn[nH]5)cn4)ccc3n2)C1] | 1-{3-[(Methyl-{6-[5-(2H-pyrazol-3-yl)-pyridin-2-yloxy]-quinolin-2-ylmethyl}-amino)-methyl]-azetidin-1-yl]-ethanone |
| 37 | 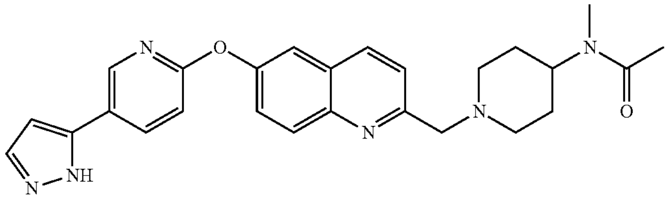 [SMILES: CC(=O)N(C)C1CCN(Cc2ccc3cc(Oc4ccc(-c5ccn[nH]5)cn4)ccc3n2)CC1] | N-Methyl-N-(1-{6-[5-(2H-pyrazol-3-yl)-pyridin-2-yloxy]-quinolin-2-ylmethyl}-piperidin-4-yl)-acetamide |
| 38 | 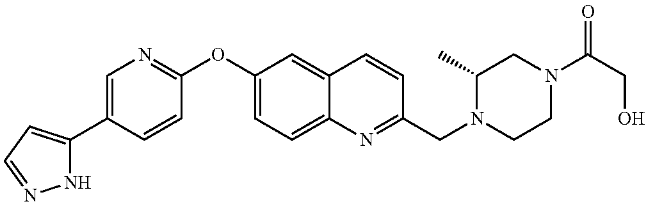 [SMILES: C[C@@H]1CN(C(=O)CO)CCN1Cc1ccc2cc(Oc3ccc(-c4ccn[nH]4)cn3)ccc2n1] | 2-Hydroxy-1-((R)-3-methyl-4-{6-[5-(2H-pyrazol-3-yl)-pyridin-2-yloxy]-quinolin-2-ylmethyl}-piperazin-1-yl)-ethanone |

TABLE 1-continued

Examples of compounds of the invention.

| No. | Structure | Compound Name |
|---|---|---|
| 39 | 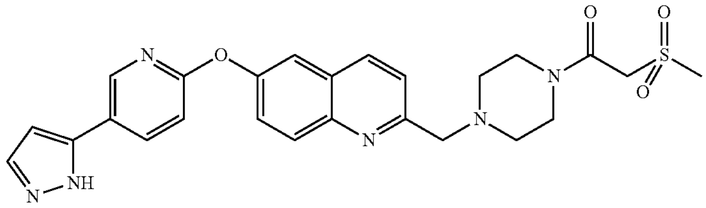 [SMILES: CS(=O)(=O)CC(=O)N1CCN(Cc2ccc3cc(Oc4ccc(-c5ccn[nH]5)cn4)ccc3n2)CC1] | 2-Methanesulfonyl-1-(4-{6-[5-(2H-pyrazol-3-yl)-pyridin-2-yloxy]-quinolin-2-ylmethyl]-piperazin-1-yl)-ethanone |
| 40 | 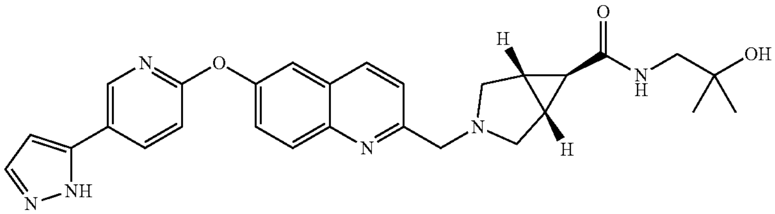 [SMILES: CC(C)(O)CNC(=O)[C@H]1[C@@H]2CN(Cc3ccc4cc(Oc5ccc(-c6ccn[nH]6)cn5)ccc4n3)C[C@@H]21] | (1α,5α,6α)-3-{6-[5-(2H-Pyrazol-3-yl)-pyridin-2-yloxy]-quinolin-2-ylmethyl}-3-aza-bicyclo[3.1.0]hexane-6-carboxylic acid (2-hydroxy-2-methyl-propyl)-amide |
| 41 | 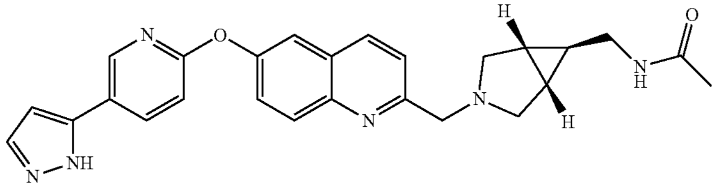 [SMILES: CC(=O)NC[C@@H]1[C@H]2CN(Cc3ccc4cc(Oc5ccc(-c6ccn[nH]6)cn5)ccc4n3)C[C@@H]12] | N-((1α,5α,6α)-3-{6-[5-(2H-Pyrazol-3-yl)-pyridin-2-yloxy]-quinolin-2-ylmethyl}-3-aza-bicyclo[3.1.0]hex-6-ylmethyl)-acetamide |
| 42 | 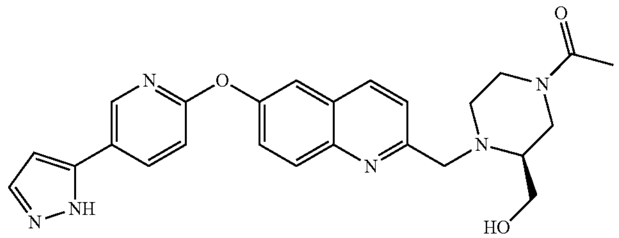 [SMILES: CC(=O)N1CCN(Cc2ccc3cc(Oc4ccc(-c5ccn[nH]5)cn4)ccc3n2)[C@H](CO)C1] | 1-((S)-3-Hydroxymethyl-4-{6-[5-(2H-pyrazol-3-yl)-pyridin-2-yloxy]-quinolin-2-ylmethyl}-piperazin-1-yl)-ethanone |
| 43 | 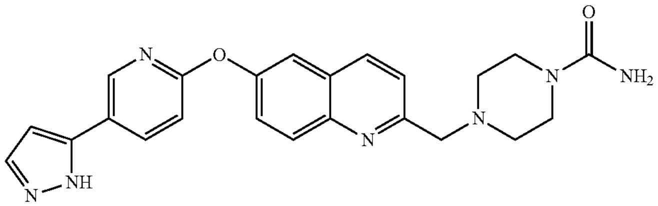 [SMILES: NC(=O)N1CCN(Cc2ccc3cc(Oc4ccc(-c5ccn[nH]5)cn4)ccc3n2)CC1] | 4-{6-[5-(2H-Pyrazol-3-yl)-pyridin-2-yloxy]-quinolin-2-ylmethyl}-piperazine-1-carboxylic acid amide |
| 44 | 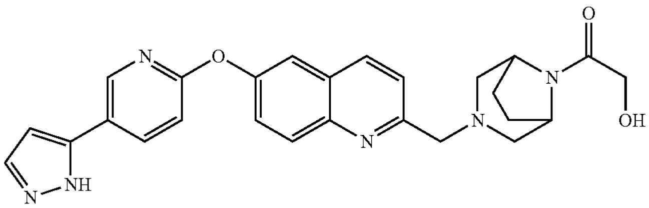 [SMILES: O=C(CO)N1C2CCC1CN(Cc1ccc3cc(Oc4ccc(-c5ccn[nH]5)cn4)ccc3n1)C2] | 2-Hydroxy-1-(3-{6-[5-(2H-pyrazol-3-yl)-pyridin-2-yloxy]-quinolin-2-ylmethyl}-3,8-diaza-bicyclo[3.2.1]oct-8-yl)-ethanone |
| 45 | 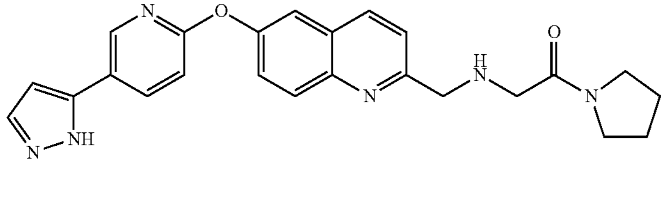 [SMILES: O=C(CNCc1ccc2cc(Oc3ccc(-c4ccn[nH]4)cn3)ccc2n1)N1CCCC1] | 2-({6-[5-(2H-Pyrazol-3-yl)-pyridin-2-yloxy]-quinolin-2-ylmethyl}-amino)-1-pyrrolidin-1-yl-ethanone |

TABLE 1-continued

| Examples of compounds of the invention. | | |
|---|---|---|
| No. | Structure | Compound Name |
| 46 | 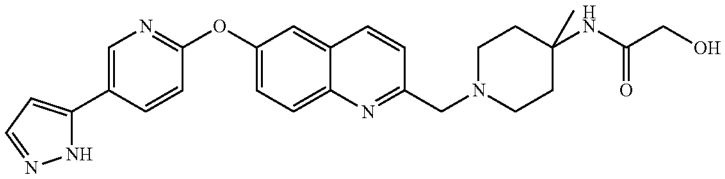 [SMILES: CC1(NC(=O)CO)CCN(Cc2ccc3cc(Oc4ccc(-c5ccn[nH]5)cn4)ccc3n2)CC1] | 2-Hydroxy-N-(4-methyl-1-{6-[5-(2H-pyrazol-3-yl)-pyridin-2-yloxy]-quinolin-2-ylmethyl}-piperidin-4-yl)-acetamide |
| 47 | 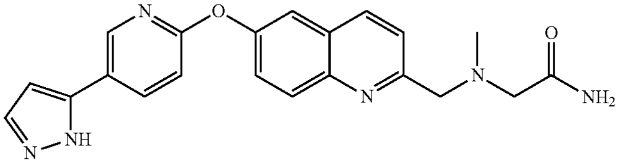 [SMILES: CN(CC(N)=O)Cc1ccc2cc(Oc3ccc(-c4ccn[nH]4)cn3)ccc2n1] | 2-(Methyl-{6-[5-(2H-pyrazol-3-yl)-pyridin-2-yloxy]-quinolin-2-ylmethyl}-amino)-acetamide |
| 48 | 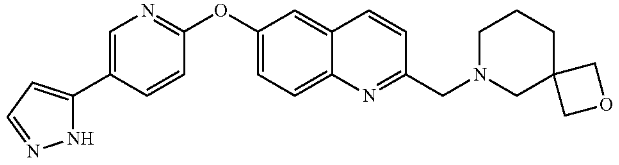 [SMILES: c1cc(-c2ccc(Oc3ccc4nc(CN5CCCC6(COC6)C5)ccc4c3)nc2)[nH]n1] | 2-(2-Oxa-6-aza-spiro[3.5]non-6-ylmethyl)-6-[5-(2H-pyrazol-3-yl)-pyridin-2-yloxy]-quinoline |
| 49 | 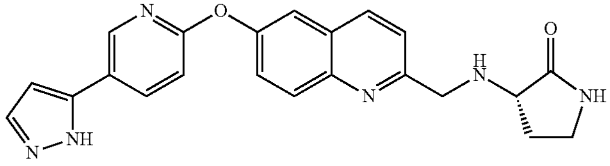 [SMILES: O=C1NCC[C@@H]1NCc1ccc2cc(Oc3ccc(-c4ccn[nH]4)cn3)ccc2n1] | (S)-3-({6-[5-(2H-Pyrazol-3-yl)-pyridin-2-yloxy]-quinolin-2-ylmethyl}-amino)-pyrrolidin-2-one |
| 50 | 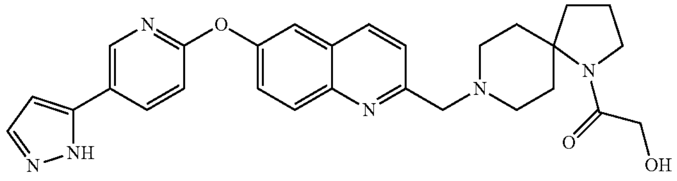 [SMILES: O=C(CO)N1CCCC12CCN(Cc1ccc3cc(Oc4ccc(-c5ccn[nH]5)cn4)ccc3n1)CC2] | 2-Hydroxy-1-(8-{6-[5-(2H-pyrazol-3-yl)-pyridin-2-yloxy]-quinolin-2-ylmethyl}-1,8-diaza-spiro[4.5]dec-1-yl)-ethanone |
| 51 | 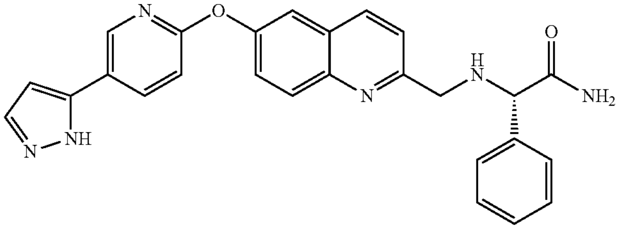 [SMILES: NC(=O)[C@@H](NCc1ccc2cc(Oc3ccc(-c4ccn[nH]4)cn3)ccc2n1)c1ccccc1] | (S)-2-Phenyl-2-({6-[5-(2H-pyrazol-3-yl)-pyridin-2-yloxy]-quinolin-2-ylmethyl}-amino)-acetamide |
| 52 | 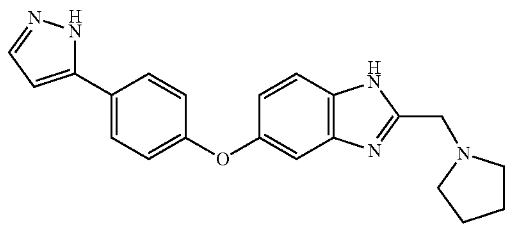 [SMILES: c1cc(-c2ccc(Oc3ccc4[nH]c(CN5CCCC5)nc4c3)cc2)[nH]n1] | 5-[4-(2H-Pyrazol-3-yl)-phenoxy]-2-pyrrolidin-1-ylmethyl-1H-benzoimidazole |

TABLE 1-continued

Examples of compounds of the invention.

| No. | Structure | Compound Name |
|---|---|---|
| 53 | 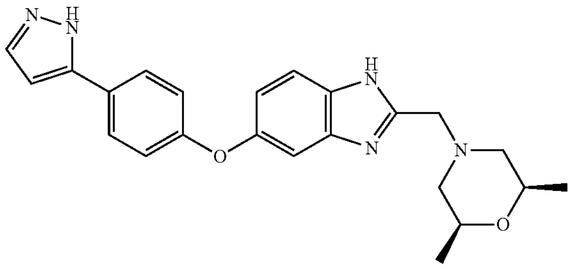 [SMILES: C[C@@H]1CN(Cc2nc3cc(Oc4ccc(-c5ccn[nH]5)cc4)ccc3[nH]2)C[C@H](C)O1] | 2-((2R,6S)-2,6-Dimethyl-morpholin-4-ylmethyl)-5-[4-(2H-pyrazol-3-yl)-phenoxy]-1H-benzoimidazole |
| 54 | 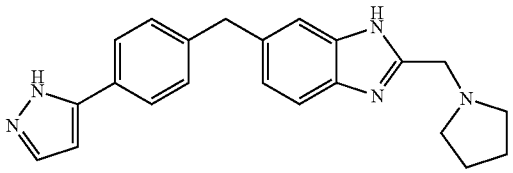 [SMILES: c1cc(-c2ccc(Cc3ccc4nc(CN5CCCC5)[nH]c4c3)cc2)[nH]n1] | 6-[4-(2H-Pyrazol-3-yl)-benzyl]-2-pyrrolidin-1-ylmethyl-1H-benzoimidazole |
| 55 | 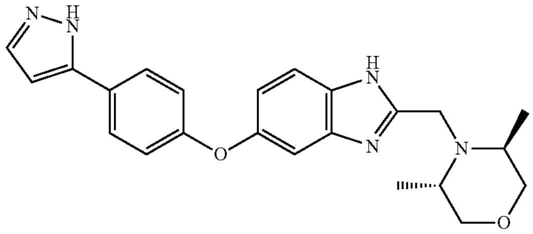 [SMILES: C[C@H]1COC[C@H](C)N1Cc1nc2cc(Oc3ccc(-c4ccn[nH]4)cc3)ccc2[nH]1] | 2-((3S,5S)-3,5-Dimethyl-morpholin-4-ylmethyl)-5-[4-(2H-pyrazol-3-yl)-phenoxy]-1H-benzoimidazole |
| 56 | 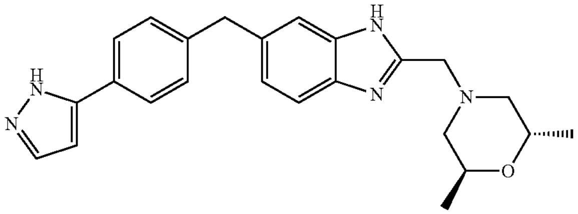 [SMILES: C[C@H]1CN(Cc2nc3ccc(Cc4ccc(-c5ccn[nH]5)cc4)cc3[nH]2)C[C@H](C)O1] | 2-((2S,6S)-2,6-Dimethyl-morpholin-4-ylmethyl)-6-[4-(2H-pyrazol-3-yl)-benzyl]-1H-benzoimidazole |
| 57 | 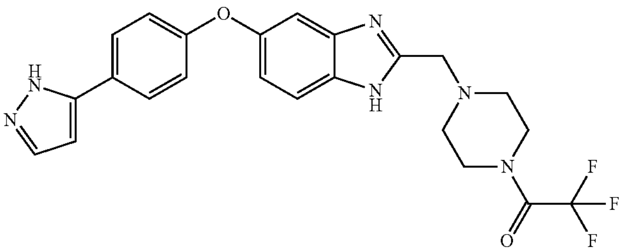 [SMILES: O=C(N1CCN(Cc2nc3cc(Oc4ccc(-c5ccn[nH]5)cc4)ccc3[nH]2)CC1)C(F)(F)F] | 2,2,2-Trifluoro-1-(4-{5-[4-(2H-pyrazol-3-yl)-phenoxy]-1H-benzoimidazol-2-ylmethyl}-piperazin-1-yl)-ethanone |
| 58 | 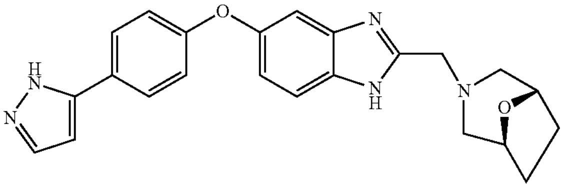 [SMILES: c1cc(-c2ccc(Oc3ccc4[nH]c(CN5C[C@@H]6CC[C@@H](C5)O6)nc4c3)cc2)[nH]n1] | (1S,5S)-3-{5-[4-(2H-Pyrazol-3-yl)-phenoxy]-1H-benzoimidazol-2-ylmethyl}-8-oxa-3-aza-bicyclo[3.2.1]octane |

TABLE 1-continued

Examples of compounds of the invention.

| No. | Structure | Compound Name |
| --- | --- | --- |
| 59 | 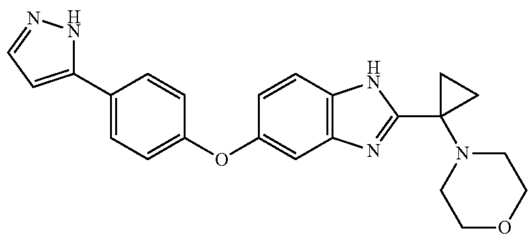 [SMILES: c1cc(-c2ccc(Oc3ccc4[nH]c(C5(N6CCOCC6)CC5)nc4c3)cc2)[nH]n1] | 2-(1-Morpholin-4-yl-cycloproyl)-5-[4-(2H-pyrazol-3-yl)-phenoxy]-1H-benzoimidazole |
| 60 | 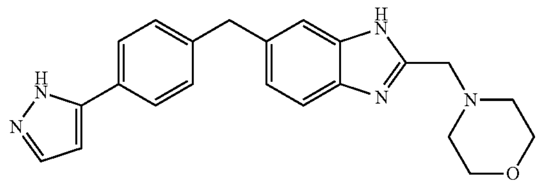 [SMILES: c1cc(-c2ccc(Cc3ccc4nc(CN5CCOCC5)[nH]c4c3)cc2)[nH]n1] | 2-Morpholin-4-ylmethyl-6-[4-(2H-pyrazol-3-yl)-benzyl]-1H-benzoimidazole |
| 61 | 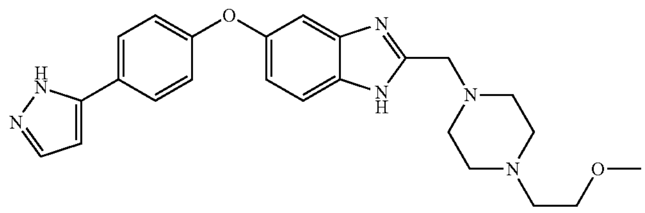 [SMILES: COCCN1CCN(Cc2nc3cc(Oc4ccc(-c5ccn[nH]5)cc4)ccc3[nH]2)CC1] | 2-[4-(2-Methoxy-ethyl)-piperazin-1-ylmethyl]-5-[4-(2H-pyrazol-3-yl)-phenoxy]-1H-benzoimidazole |
| 62 | 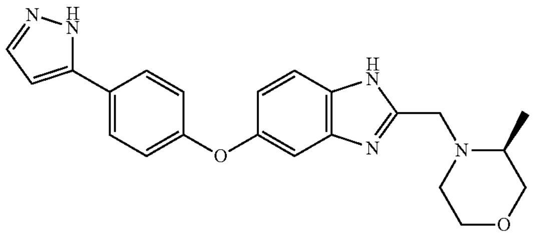 [SMILES: C[C@H]1COCCN1Cc1nc2cc(Oc3ccc(-c4ccn[nH]4)cc3)ccc2[nH]1] | 2-((S)-3-Methyl-morpholin-4-ylmethyl)-5-[4-(2H-pyrazol-3-yl)-phenoxy]-1H-benzoimidazole |
| 63 | 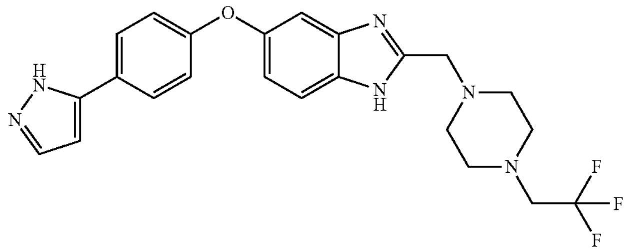 [SMILES: FC(F)(F)CN1CCN(Cc2nc3cc(Oc4ccc(-c5ccn[nH]5)cc4)ccc3[nH]2)CC1] | 5-[4-(2H-Pyrazol-3-yl)-phenoxy]-2-[4-(2,2,2-trifluoro-ethyl)-piperazin-1-ylmethyl]-1H-benzoimidazole |
| 64 | 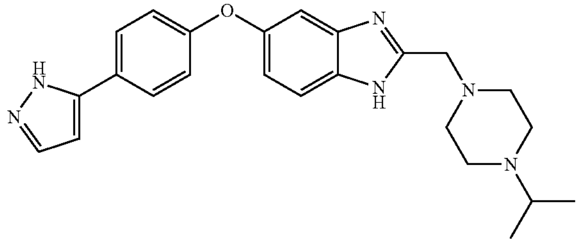 [SMILES: CC(C)N1CCN(Cc2nc3cc(Oc4ccc(-c5ccn[nH]5)cc4)ccc3[nH]2)CC1] | 2-(4-Isopropyl-piperazin-1-ylmethyl)-5-[4-(2H-pyrazol-3-yl)-phenoxy]-1H-benzoimidazole |

TABLE 1-continued

| Examples of compounds of the invention. | | |
|---|---|---|
| No. | Structure | Compound Name |
| 65 | 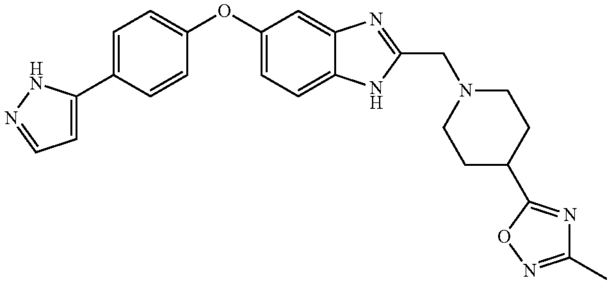 [SMILES: Cc1noc(C2CCN(Cc3nc4cc(Oc5ccc(-c6ccn[nH]6)cc5)ccc4[nH]3)CC2)n1] | 2-[4-(3-Methyl-[1,2,4]oxadiazol-5-yl)-piperidin-1-ylmethyl]-5-[4-(2H-pyrazol-3-yl)-phenoxy]-1H-benzoimidazole |
| 66 | 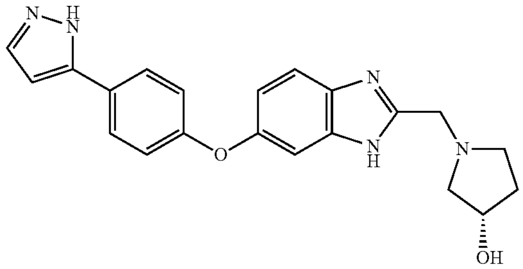 [SMILES: O[C@H]1CCN(Cc2nc3ccc(Oc4ccc(-c5ccn[nH]5)cc4)cc3[nH]2)C1] | (S)-1-{6-[4-(2H-Pyrazol-3-yl)-phenoxy]-1H-benzoimidazol-2-ylmethyl}-pyrrolidin-3-ol |
| 67 | 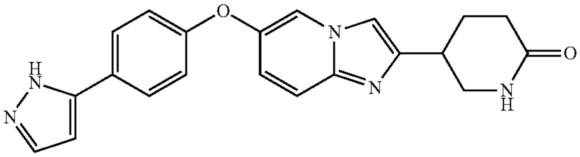 [SMILES: O=C1CCC(c2cn3cc(Oc4ccc(-c5ccn[nH]5)cc4)ccc3n2)CN1] | 5-{6-[4-(2H-Pyrazol-3-yl)-phenoxy]-imidazo[1,2-a]pyridin-2-yl}-piperidin-2-one |
| 68 | 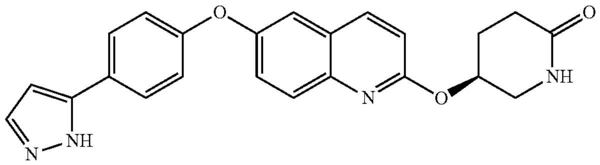 [SMILES: O=C1CC[C@H](Oc2ccc3cc(Oc4ccc(-c5ccn[nH]5)cc4)ccc3n2)CN1] | (S)-5-{6-[4-(2H-Pyrazol-3-yl)-phenoxy]-quinolin-2-yloxy}-piperidin-2-one |
| 69 | 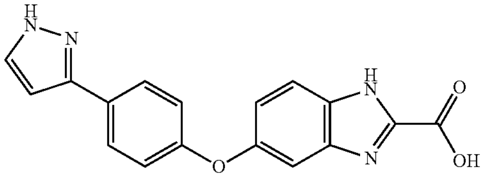 [SMILES: O=C(O)c1nc2cc(Oc3ccc(-c4cc[nH]n4)cc3)ccc2[nH]1] | 5-[4-(1H-Pyrazol-3-yl)-phenoxy]-1H-benzoimidazole-2-carboxylic acid |
| 70 | 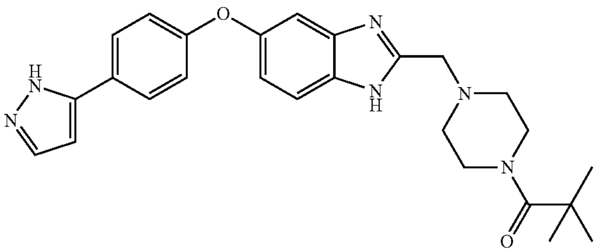 [SMILES: CC(C)(C)C(=O)N1CCN(Cc2nc3cc(Oc4ccc(-c5ccn[nH]5)cc4)ccc3[nH]2)CC1] | 2,2-Dimethyl-1-(4-{5-[4-(2H-pyrazol-3-yl)-phenoxy]-1H-benzoimidazol-2-ylmethyl}-piperazin-1-yl)-propan-1-one |

TABLE 1-continued

| Examples of compounds of the invention. | | |
|---|---|---|
| No. | Structure | Compound Name |
| 71 | 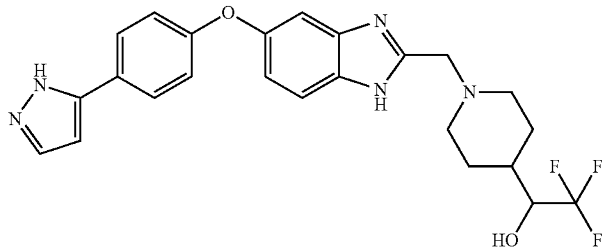 [SMILES: OC(C1CCN(Cc2nc3cc(Oc4ccc(-c5ccn[nH]5)cc4)ccc3[nH]2)CC1)C(F)(F)F] | 2,2,2-Trifluoro-1-(1-{5-[4-(2H-pyrazol-3-yl)-phenoxy]-1H-benzoimidazol-2-ylmethyl}-piperidin-4-yl)-ethanol |
| 72 | 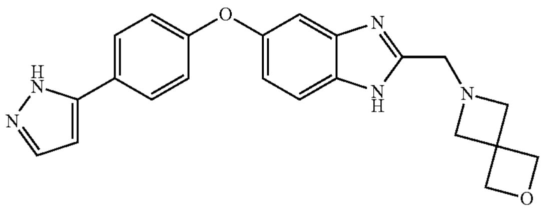 [SMILES: c1cc(-c2ccc(Oc3ccc4[nH]c(CN5CC6(COC6)C5)nc4c3)cc2)[nH]n1] | 2-(2-Oxa-6-aza-spiro[3.3]hept-6-ylmethyl)-5-[4-(2H-pyrazol-3-yl)-phenoxy]-1H-benzoimidazole |
| 73 | 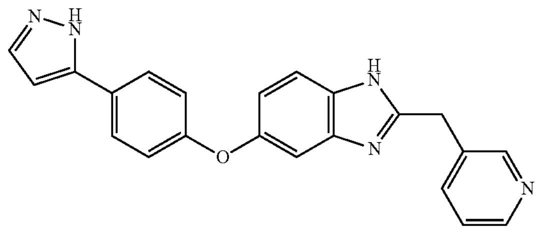 [SMILES: c1cncc(Cc2nc3cc(Oc4ccc(-c5ccn[nH]5)cc4)ccc3[nH]2)c1] | 5-[4-(2H-Pyrazol-3-yl)-phenoxy]-2-pyridin-3-ylmethyl-1H-benzoimidazole |
| 74 | 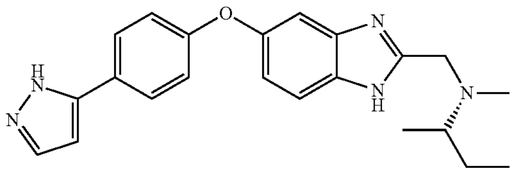 | ((S)-sec-Butyl)-methyl-{5-[4-(2H-pyrazol-3-yl)-phenoxy]-1H-benzoimidazol-2-ylmethyl}-amine |
| 75 | 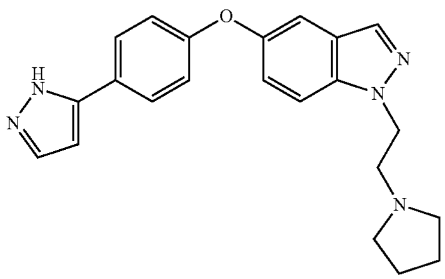 [SMILES: c1cc(-c2ccc(Oc3ccc4c(cnn4CCN4CCCC4)c3)cc2)[nH]n1] | 5-[4-(2H-Pyrazol-3-yl)-phenoxy]-1-(2-pyrrolidin-1-yl-ethyl)-1H-indazole |
| 76 | 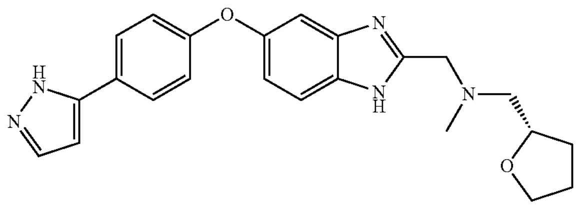 [SMILES: CN(Cc1nc2cc(Oc3ccc(-c4ccn[nH]4)cc3)ccc2[nH]1)C[C@@H]1CCCO1] | Methyl-{5-[4-(2H-pyrazol-3-yl)-phenoxy]-1H-benzoimidazol-2-ylmethyl}-[(S)-1-(tetrahydro-furan-2-yl)methyl]-amine |

TABLE 1-continued

Examples of compounds of the invention.

| No. | Structure | Compound Name |
|---|---|---|
| 77 | 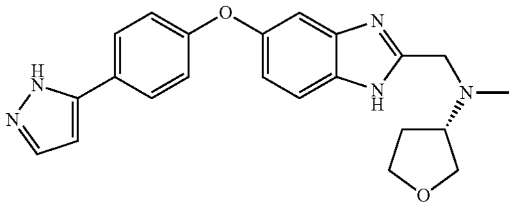 [SMILES: CN(Cc1nc2cc(Oc3ccc(-c4ccn[nH]4)cc3)ccc2[nH]1)[C@H]1CCOC1] | Methyl-{5-[4-(2H-pyrazol-3-yl)-phenoxy]-1H-benzoimidazol-2-ylmethyl}-(S)-tetrahydro-furan-3-yl-amine |
| 78 | 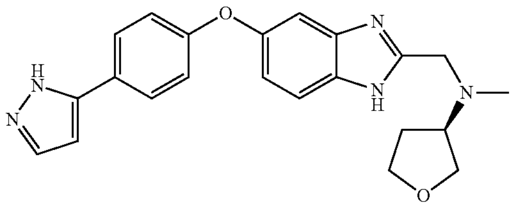 [SMILES: CN(Cc1nc2cc(Oc3ccc(-c4ccn[nH]4)cc3)ccc2[nH]1)[C@@H]1CCOC1] | Methyl-{5-[4-(2H-pyrazol-3-yl)-phenoxy]-1H-benzoimidazol-2-ylmethyl}-(R)-tetrahydro-furan-3-yl-amine |
| 79 | 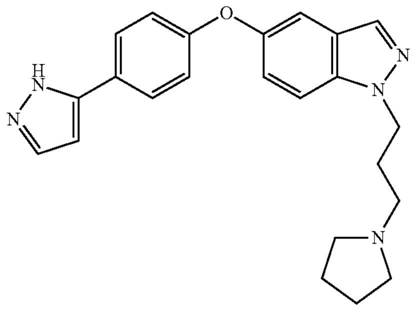 [SMILES: c1cc(-c2ccc(Oc3ccc4c(cnn4CCCN4CCCC4)c3)cc2)[nH]n1] | 5-[4-(2H-Pyrazol-3-yl)-phenoxy]-1-(3-pyrrolidin-1-yl-propyl)-1H-indazole |
| 80 | 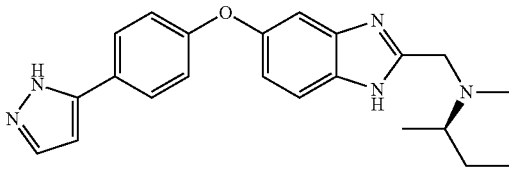 [SMILES: CC[C@@H](C)N(C)Cc1nc2cc(Oc3ccc(-c4ccn[nH]4)cc3)ccc2[nH]1] | ((R)-sec-Butyl)-methyl-{5-[4-(2H-pyrazol-3-yl)-phenoxy]-1H-benzoimidazol-2-ylmethyl}-amine |
| 81 | 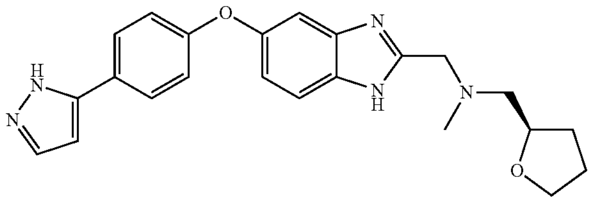 [SMILES: CN(Cc1nc2cc(Oc3ccc(-c4ccn[nH]4)cc3)ccc2[nH]1)C[C@H]1CCCO1] | Methyl-{5-[4-(2H-pyrazol-3-yl)-phenoxy]-1H-benzoimidazol-2-ylmethyl}-[(R)-1-(tetrahydro-furan-2-yl)methyl]-amine |
| 82 | 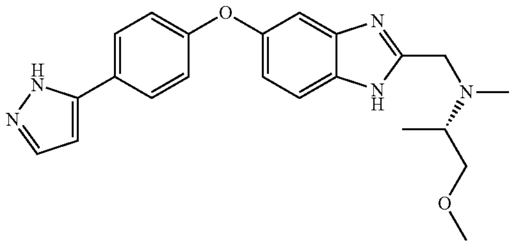 [SMILES: COC[C@H](C)N(C)Cc1nc2cc(Oc3ccc(-c4ccn[nH]4)cc3)ccc2[nH]1] | ((S)-2-Methoxy-1-methyl-ethyl)-methyl-{5-[4-(2H-pyrazol-3-yl)-phenoxy]-1H-benzoimidazol-2-ylmethyl}-amine |

TABLE 1-continued

| Examples of compounds of the invention. | | |
|---|---|---|
| No. | Structure | Compound Name |
| 83 | 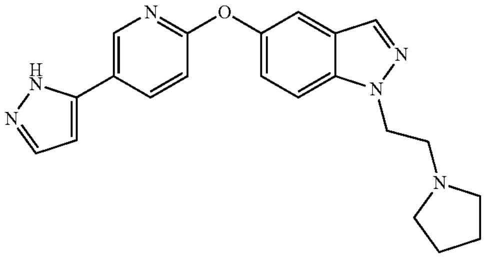 [SMILES: c1cc(-c2ccc(Oc3ccc4c(cnn4CCN4CCCC4)c3)nc2)[nH]n1] | 5-[5-(2H-Pyrazol-3-yl)-pyridin-2-yloxy]-1-(2-pyrrolidin-1-yl-ethyl)-1H-indazole |
| 84 | 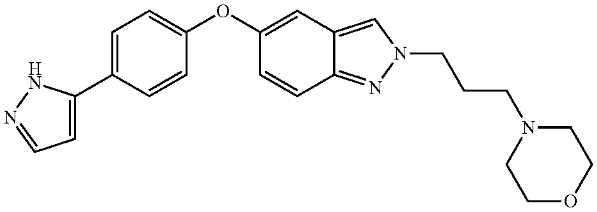 [SMILES: c1cc(-c2ccc(Oc3ccc4nn(CCCN5CCOCC5)cc4c3)cc2)[nH]n1] | 2-(3-Morpholin-4-yl-propyl)-5-[4-(2H-pyrazol-3-yl)-phenoxy]-2H-indazole |
| 85 | 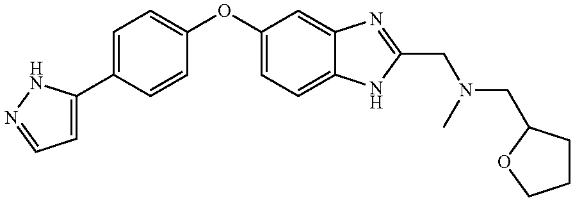 [SMILES: CN(Cc1nc2cc(Oc3ccc(-c4ccn[nH]4)cc3)ccc2[nH]1)CC1CCCO1] | Methyl-{5-[4-(2H-pyrazol-3-yl)-phenoxy]-1H-benzoimidazol-2-ylmethyl}-(tetra-hydrofuran-2-ylmethyl)-amine |
| 86 | 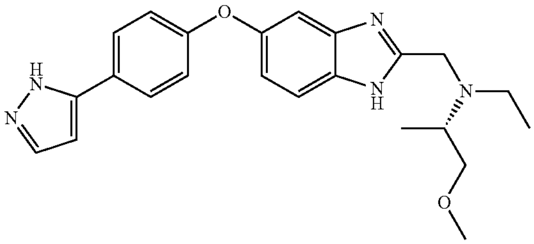 [SMILES: CCN(Cc1nc2cc(Oc3ccc(-c4ccn[nH]4)cc3)ccc2[nH]1)[C@@H](C)COC] | Ethyl-((S)-2-methoxy-1-methyl-ethyl)-{5-[4-(2H-pyrazol-3-yl)-phenoxy]-1H-benzoimidazol-2-ylmethyl}-amine |
| 87 | 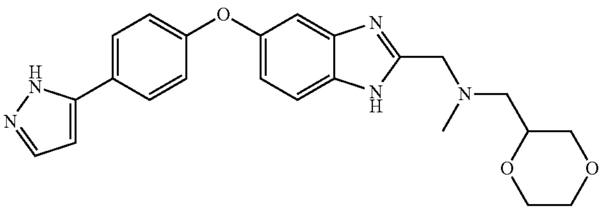 [SMILES: CN(Cc1nc2cc(Oc3ccc(-c4ccn[nH]4)cc3)ccc2[nH]1)CC1COCCO1] | [1,4]Dioxan-2-ylmethyl-methyl-{5-[4-(2H-pyrazol-3-yl)-phenoxy]-1H-benzoimidazol-2-ylmethyl}-amine |

TABLE 1-continued

| Examples of compounds of the invention. | | |
|---|---|---|
| No. | Structure | Compound Name |
| 88 | 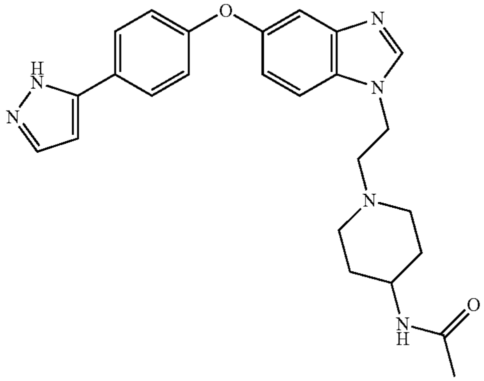 [SMILES: CC(=O)NC1CCN(CCn2cnc3cc(Oc4ccc(-c5ccn[nH]5)cc4)ccc32)CC1] | N-[1-(2-{5-[4-(2H-Pyrazol-3-yl)-phenoxy]-indazol-1-yl}-ethyl)-piperidin-4-yl}-acetamide |
| 89 | 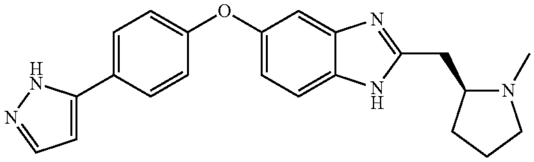 [SMILES: CN1CCC[C@H]1Cc1nc2cc(Oc3ccc(-c4ccn[nH]4)cc3)ccc2[nH]1] | 2-((S)-1-Methyl-pyrrolidin-2-ylmethyl)-5-[4-(2H-pyrazol-3-yl)-phenoxy]-1H-benzoimidazole |
| 90 | 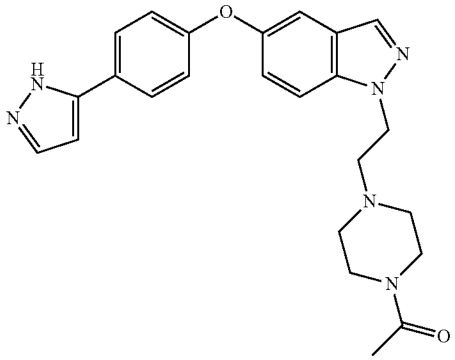 [SMILES: CC(=O)N1CCN(CCn2ncc3cc(Oc4ccc(-c5ccn[nH]5)cc4)ccc32)CC1] | 1-[4-(2-{5-[4-(2H-Pyrazol-3-yl)-phenoxy]-indazol-1-yl}-ethyl)-piperazin-1-yl]-ethanone |
| 91 | 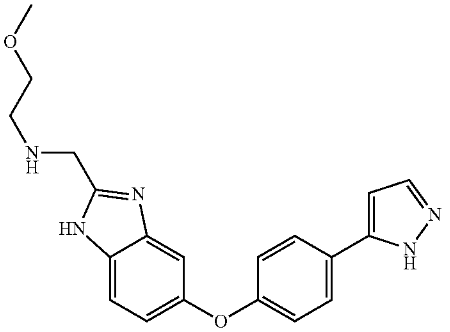 [SMILES: COCCNCc1nc2cc(Oc3ccc(-c4ccn[nH]4)cc3)ccc2[nH]1] | (2-Methoxy-ethyl)-{5-[4-(2H-pyrazol-3-yl)-phenoxy]-1H-benzoimidazol-2-ylmethyl}-amine |
| 92 | 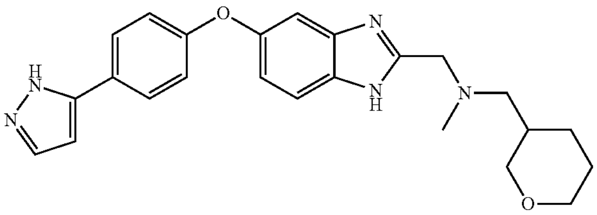 [SMILES: CN(Cc1nc2cc(Oc3ccc(-c4ccn[nH]4)cc3)ccc2[nH]1)CC1CCCOC1] | Methyl-{5-[4-(2H-pyrazol-3-yl)-phenoxy]-1H-benzoimidazol-2-ylmethyl}-(tetrahydro-pyran-3-ylmethyl)-amine |

TABLE 1-continued

| No. | Structure | Compound Name |
|---|---|---|
| | Examples of compounds of the invention. | |
| 93 | 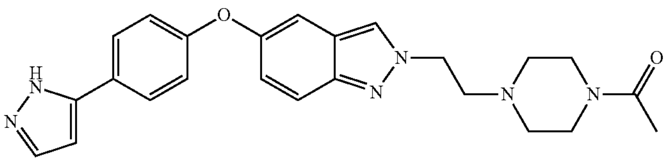 [SMILES: CC(=O)N1CCN(CCn2cc3cc(Oc4ccc(-c5ccn[nH]5)cc4)ccc3n2)CC1] | 1-[4-(2-{5-[4-(2H-Pyrazol-3-yl)-phenoxy]-indazol-2-yl}-ethyl)-piperazin-1-yl]-ethanone |
| 94 | 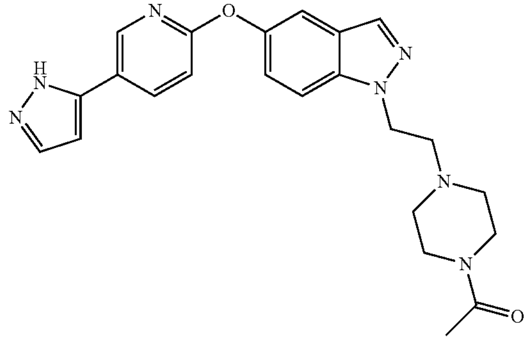 [SMILES: CC(=O)N1CCN(CCn2ncc3cc(Oc4ccc(-c5ccn[nH]5)cn4)ccc32)CC1] | 1-[4-(2-{5-[5-(2H-Pyrazol-3-yl)-pyridin-2-yloxy]-indazol-1-yl}-ethyl)-piperazin-1-yl]-ethanone |
| 95 | 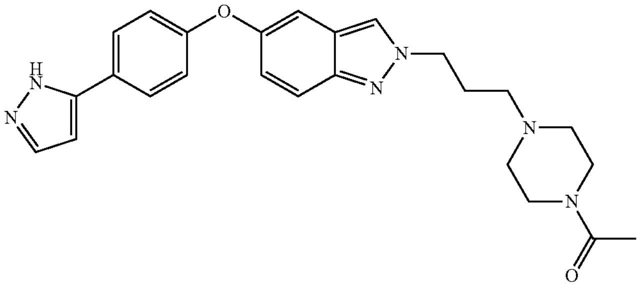 [SMILES: CC(=O)N1CCN(CCCn2cc3cc(Oc4ccc(-c5ccn[nH]5)cc4)ccc3n2)CC1] | 1-[4-(3-{5-[4-(2H-Pyrazol-3-yl)-phenoxy]-indazol-2-yl}-propyl)-piperazin-1-yl]-ethanone |
| 96 | 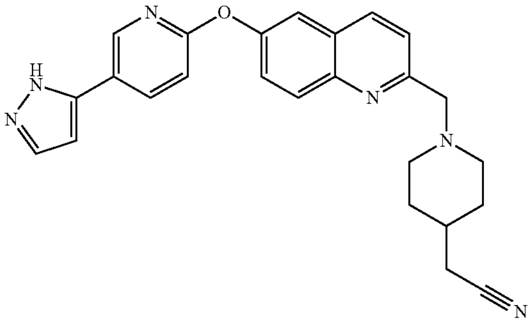 [SMILES: N#CCC1CCN(Cc2ccc3cc(Oc4ccc(-c5ccn[nH]5)cn4)ccc3n2)CC1] | (1-{6-[5-(2H-Pyrazol-3-yl)-pyridin-2-yloxy]-quinolin-2-ylmethyl}-piperidin-4-yl)-acetonitrile |
| 97 | 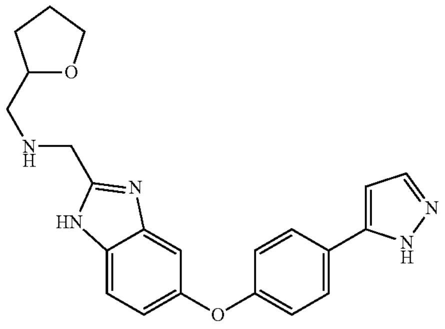 [SMILES: c1cc(-c2ccc(Oc3ccc4[nH]c(CNCC5CCCO5)nc4c3)cc2)[nH]n1] | {5-[4-(2H-Pyrazol-3-yl)-phenoxy]-1H-benzoimidazol-2-ylmethyl}-(tetrahydro-furan-2-ylmethyl)-amine |

TABLE 1-continued

Examples of compounds of the invention.

| No. | Structure | Compound Name |
|---|---|---|
| 98 | 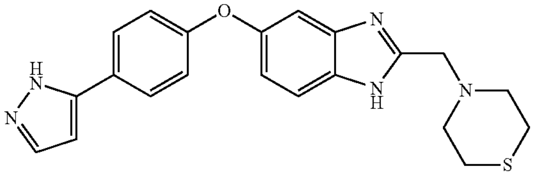 [SMILES: c1cc(-c2ccc(Oc3ccc4[nH]c(CN5CCSCC5)nc4c3)cc2)[nH]n1] | 5-[4-(2H-Pyrazol-3-yl)-phenoxy]-2-thiomorpholin-4-ylmethyl-1H-benzoimidazole |
| 99 | 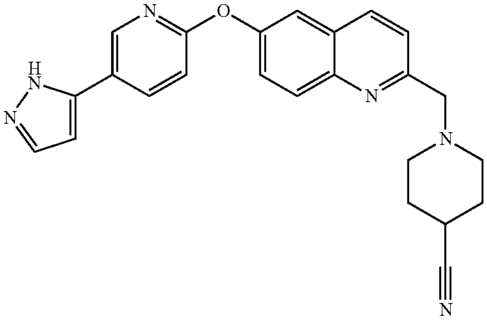 [SMILES: N#CC1CCN(Cc2ccc3cc(Oc4ccc(-c5ccn[nH]5)cn4)ccc3n2)CC1] | 1-{6-[5-(2H-Pyrazol-3-yl)-pyridin-2-yloxy]-quinolin-2-ylmethyl}-piperidine-4-carbonitrile |
| 100 | 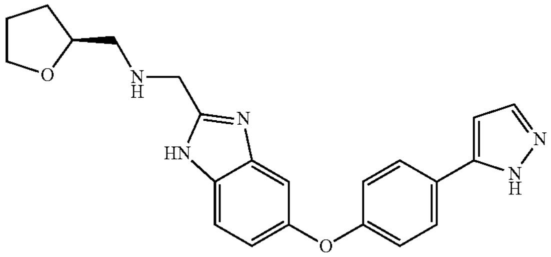 [SMILES: c1cc(-c2ccc(Oc3ccc4[nH]c(CNC[C@@H]5CCCO5)nc4c3)cc2)[nH]n1] | {5-[4-(2H-Pyrazol-3-yl)-phenoxy]-1H-benzoimidazol-2-ylmethyl}-[(S)-1-(tetrahydro-furan-2-yl)methyl]-amine |
| 101 | 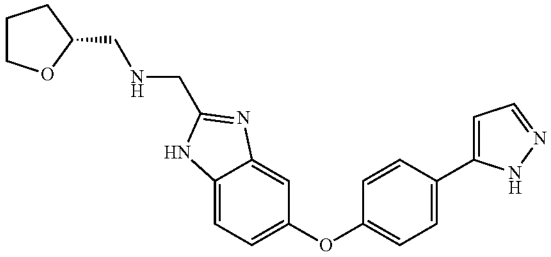 [SMILES: c1cc(-c2ccc(Oc3ccc4[nH]c(CNC[C@H]5CCCO5)nc4c3)cc2)[nH]n1] | {5-[4-(2H-Pyrazol-3-yl)-phenoxy]-1H-benzoimidazol-2-ylmethyl}-[(R)-1-(tetrahydro-furan-2-yl)methyl]-amine |
| 102 | 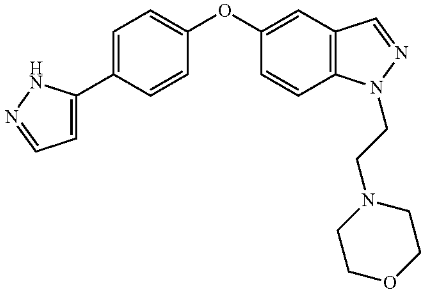 [SMILES: c1cc(-c2ccc(Oc3ccc4c(cnn4CCN4CCOCC4)c3)cc2)[nH]n1] | 1-(2-Morpholin-4-y-ethyl)-5-[4-(2H-pyrazol-3-y)-phenoxy]-1H-indazole |

TABLE 1-continued

| Examples of compounds of the invention. | | |
|---|---|---|
| No. | Structure | Compound Name |
| 103 | 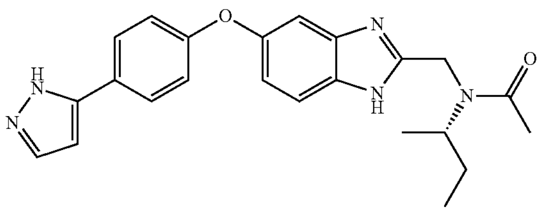 [SMILES: CC[C@H](C)N(Cc1nc2cc(Oc3ccc(-c4ccn[nH]4)cc3)ccc2[nH]1)C(C)=O] | N-((S)-sec-Butyl)-N-{5-[4-(2H-pyrazol-3-yl)-phenoxy]-1H-benzoimidazol-2-ylmethyl}-acetamide |
| 104 | 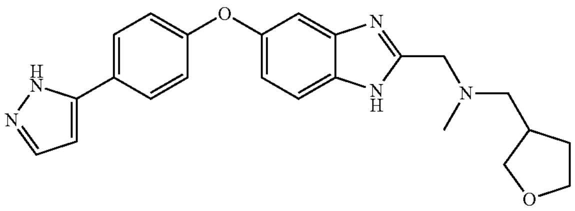 [SMILES: CN(Cc1nc2cc(Oc3ccc(-c4ccn[nH]4)cc3)ccc2[nH]1)CC1CCOC1] | Methyl-{5-[4-(2H-pyrazol-3-yl)-phenoxy]-1H-benzoimidazol-2-ylmethyl}-(tetrahydro-furan-3-ylmethyl)-amine |
| 105 | 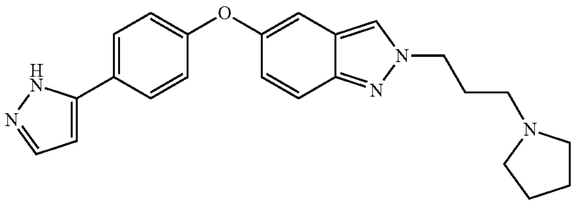 [SMILES: c1cc(-c2ccc(Oc3ccc4nn(CCCN5CCCC5)cc4c3)cc2)[nH]n1] | 5-[4-(2H-Pyrazol-3-yl)-phenoxy]-2-(3-pyrrolidin-1-yl-propyl)-2H-indazole |
| 106 | 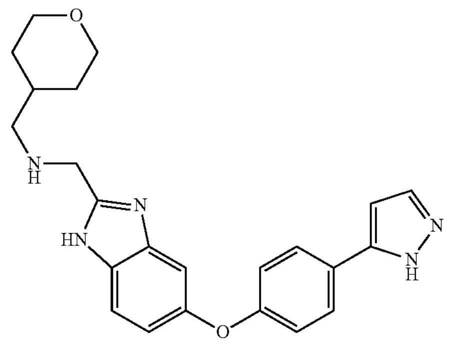 [SMILES: c1cc(-c2ccc(Oc3ccc4[nH]c(CNCC5CCOCC5)nc4c3)cc2)[nH]n1] | {5-[4-(2H-Pyrazol-3-yl)-phenoxy]-1H-benzoimidazol-2-ylmethyl}-(tetrahydro-pyran-4-ylmethyl)-amine |
| 107 | 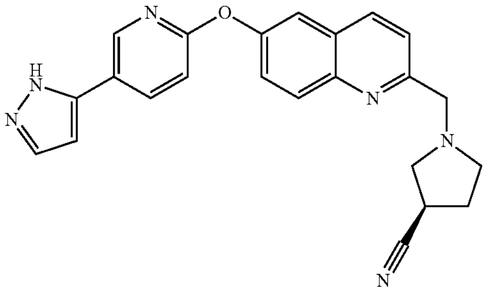 [SMILES: N#C[C@@H]1CCN(Cc2ccc3cc(Oc4ccc(-c5ccn[nH]5)cn4)ccc3n2)C1] | (R)-1-{6-[5-(2H-Pyrazol-3-yl)-pyridin-2-yloxy]-quinolin-2-ylmethyl}-pyrrolidine-3-carbonitrile |
| 108 | 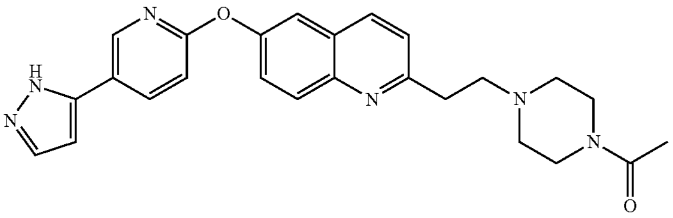 [SMILES: CC(=O)N1CCN(CCc2ccc3cc(Oc4ccc(-c5ccn[nH]5)cn4)ccc3n2)CC1] | 1-[4-(2-{6-[5-(2H-Pyrazol-3-yl)-pyridin-2-yloxy]-quinolin-2-yl}-ethyl)-piperazin-1-yl]-ethanone |

TABLE 1-continued

| Examples of compounds of the invention. | | |
|---|---|---|
| No. | Structure | Compound Name |
| 109 | 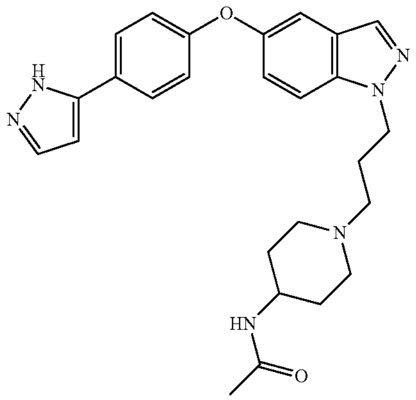 [SMILES: CC(=O)NC1CCN(CCCn2ncc3cc(Oc4ccc(-c5ccn[nH]5)cc4)ccc32)CC1] | N-[1-(3-{5-[4-(2H-Pyrazol-3-yl)-phenoxy]-indazol-1-yl}-propyl)-piperidin-4-yl]-acetamide |
| 110 | 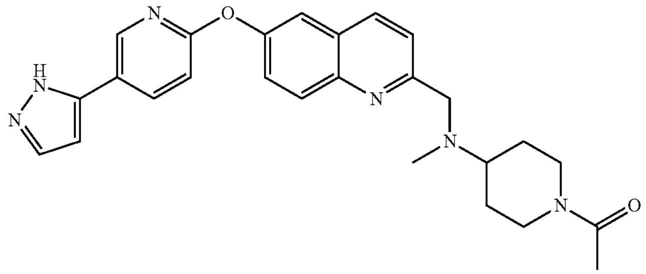 [SMILES: CC(=O)N1CCC(N(C)Cc2ccc3cc(Oc4ccc(-c5ccn[nH]5)cn4)ccc3n2)CC1] | 1-[4-(Methyl-{6-[5-(2H-Pyrazol-3-yl)-pyridin-2-yloxy]-quinolin-2-ylmethyl}-amino)-piperidin-1-yl]-ethanone |
| 111 | 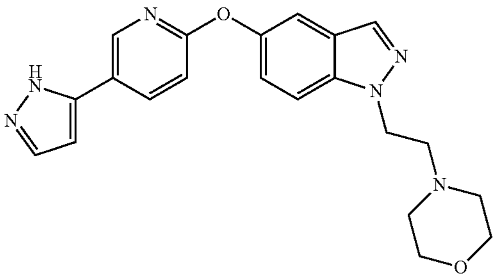 [SMILES: c1cc(-c2ccc(Oc3ccc4c(cnn4CCN4CCOCC4)c3)nc2)[nH]n1] | 1-(2-Morpholin-4-yl-ethyl)-5-[5-(2H-pyrazol-3-yl)-pyridin-2-yloxy]-1H-indazole |
| 112 | 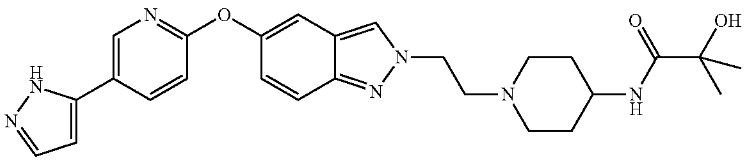 [SMILES: CC(C)(O)C(=O)NC1CCN(CCn2cc3cc(Oc4ccc(-c5ccn[nH]5)cn4)ccc3n2)CC1] | 2-Hydroxy-2-methyl-N-[1-(2-{5-[5-(2H-pyrazol-3-yl)-pyridin-2-yloxy]-indazol-2-yl}-ethyl)-piperidin-4-yl]-propionamide |
| 113 | 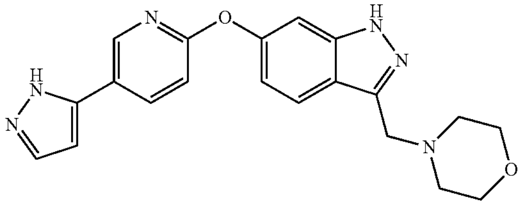 [SMILES: c1cc(-c2ccc(Oc3ccc4c(CN5CCOCC5)n[nH]c4c3)nc2)[nH]n1] | 3-Morpholin-4-ylmethyl-6-[5-(2H-pyrazol-3-yl)-pyridin-2-yloxy]-1H-indazole |

TABLE 1-continued

| Examples of compounds of the invention. | | |
|---|---|---|
| No. | Structure | Compound Name |
| 114 | 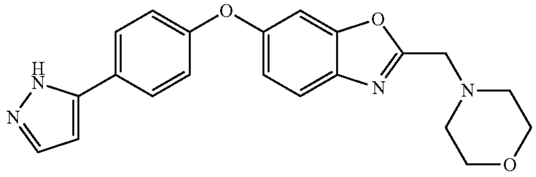 [SMILES: c1cc(-c2ccc(Oc3ccc4nc(CN5CCOCC5)oc4c3)cc2)[nH]n1] | 2-Morpholin-4-ylmethyl-6-[4-(2H-pyrazol-3-yl)-phenoxy]-benzooxazole |
| 115 | 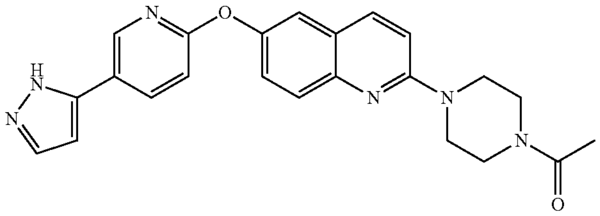 [SMILES: CC(=O)N1CCN(c2ccc3cc(Oc4ccc(-c5ccn[nH]5)cn4)ccc3n2)CC1] | 1-(4-{6-[5-(2H-Pyrazol-3-yl)-pyridin-2-yloxy]-quinolin-2-yl}-piperazin-1-yl)-ethanone |
| 116 | 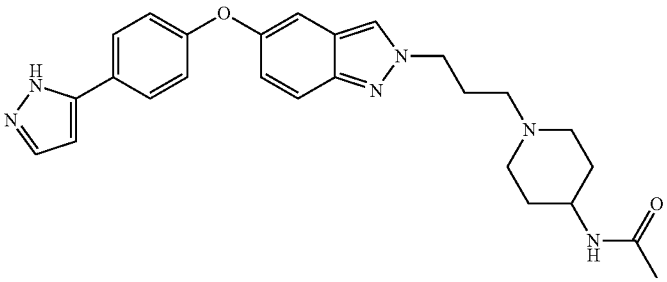 [SMILES: CC(=O)NC1CCN(CCCn2cc3cc(Oc4ccc(-c5ccn[nH]5)cc4)ccc3n2)CC1] | N-[1-(3-{5-[4-(2H-Pyrazol-3-yl)-phenoxy]-indazol-2-yl}-propyl)-piperidin-4-yl]-acetamide |
| 117 | 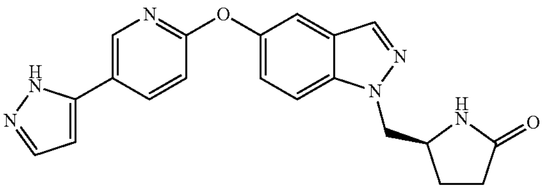 [SMILES: O=C1CC[C@@H](Cn2ncc3cc(Oc4ccc(-c5ccn[nH]5)cn4)ccc32)N1] | (S)-5-{5-[5-(2H-Pyrazol-3-yl)-pyridin-2-yloxy]-indazol-1-ylmethyl}-pyrrolidin-2-one |
| 118 | 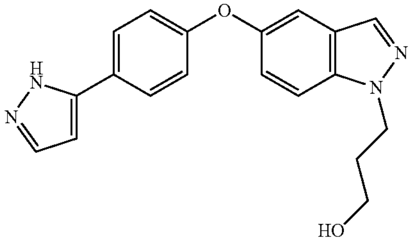 [SMILES: OCCCn1ncc2cc(Oc3ccc(-c4ccn[nH]4)cc3)ccc21] | 3-{5-[4-(2H-Pyrazol-3-yl)-phenoxy]-indazol-1-yl}-propan-1-ol |
| 119 | 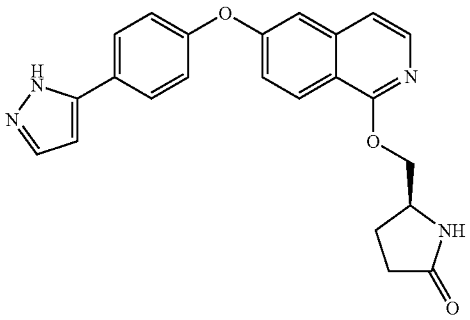 [SMILES: O=C1CC[C@@H](COc2nccc3cc(Oc4ccc(-c5ccn[nH]5)cc4)ccc23)N1] | (S)-5-{6-[4-(2H-Pyrazol-3-yl)-phenoxy]-isoquinolin-1-yloxymethyl}-pyrrolidin-2-one |

TABLE 1-continued

| Examples of compounds of the invention. | | |
|---|---|---|
| No. | Structure | Compound Name |
| 120 | 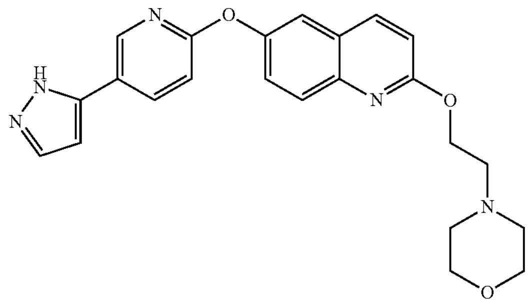 [SMILES: c1cc(-c2ccc(Oc3ccc4nc(OCCN5CCOCC5)ccc4c3)nc2)[nH]n1] | 2-(2-Morpholin-4-yl-ethoxy)-6-[5-(2H-pyrazol-3-yl)-pyridin-2-yloxy]-quinoline |
| 121 | 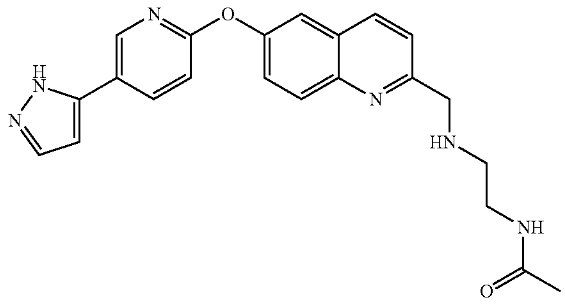 [SMILES: CC(=O)NCCNCc1ccc2cc(Oc3ccc(-c4ccn[nH]4)cn3)ccc2n1] | N-[2-({6-[5-(2H-Pyrazol-3-yl)-pyridin-2-yloxy]-quinolin-2-ylmethyl}-amino)-ethyl]-acetamide |
| 122 | 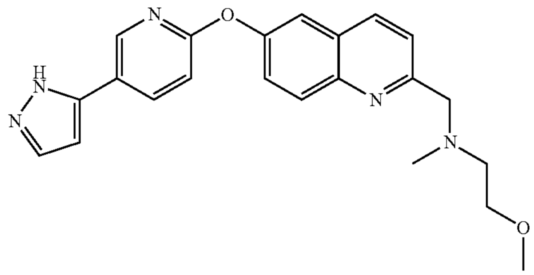 [SMILES: COCCN(C)Cc1ccc2cc(Oc3ccc(-c4ccn[nH]4)cn3)ccc2n1] | (2-Methoxy-ethyl)-methyl-{6-[5-(2H-pyrazol-3-yl)-pyridin-2-yloxy]-quinolin-2-ylmethyl}-amine |
| 123 | 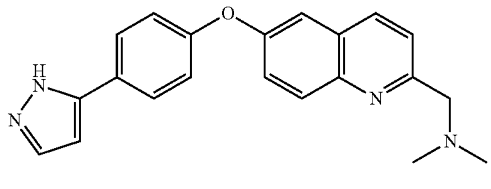 [SMILES: CN(C)Cc1ccc2cc(Oc3ccc(-c4ccn[nH]4)cc3)ccc2n1] | Dimethyl-{6-[4-(2H-pyrazol-3-yl)-phenoxy]-quinolin-2-ylmethyl}-amine |
| 124 | 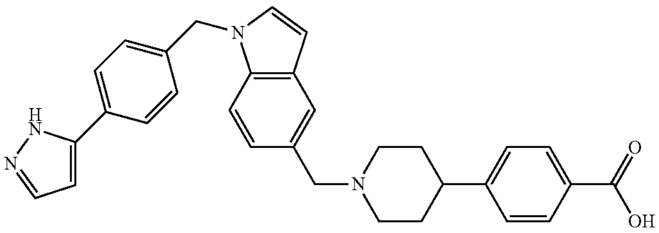 [SMILES: O=C(O)c1ccc(C2CCN(Cc3ccc4c(ccn4Cc4ccc(-c5ccn[nH]5)cc4)c3)CC2)cc1] | 4-(1-{1-[4-(2H-Pyrazol-3-yl)-benzyl]-1H-indol-5-ylmethyl}-piperidin-4-yl)-benzoic acid |

TABLE 1-continued

Examples of compounds of the invention.

| No. | Structure | Compound Name |
| --- | --- | --- |
| 125 | 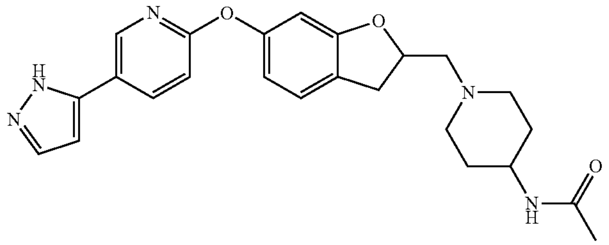 [SMILES: CC(=O)NC1CCN(CC2Cc3ccc(Oc4ccc(-c5ccn[nH]5)cn4)cc3O2)CC1] | N-(1-{6-[5-(2H-Pyrazol-3-yl)-pyridin-2-yloxy]-2,3-dihydro-benzofuran-2-ylmethyl}-piperidin-4-yl)-acetamide |
| 126 | 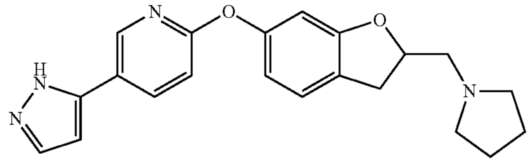 [SMILES: c1cc(-c2ccc(Oc3ccc4c(c3)OC(CN3CCCC3)C4)nc2)[nH]n1] | 5-(2H-Pyrazol-3-yl)-2-(2-pyrrolidin-1-ylmethyl-2,3-dihydro-benzofuran-6-yloxy)-pyridine |
| 127 | 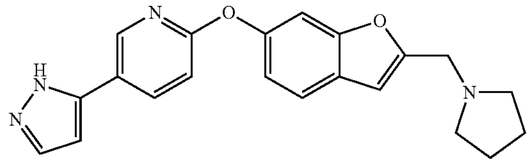 [SMILES: c1cc(-c2ccc(Oc3ccc4cc(CN5CCCC5)oc4c3)nc2)[nH]n1] | 5-(2H-Pyrazol-3-yl)-2-(2-pyrrolidin-1-ylmethyl-benzofuran-6-yloxy)-pyridine |
| 128 | 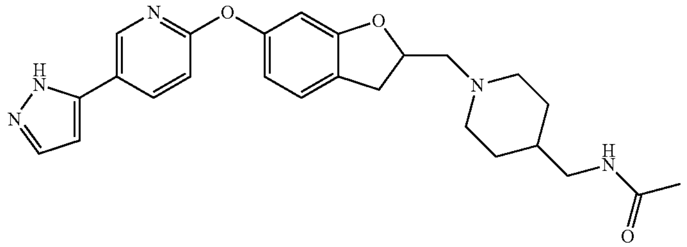 [SMILES: CC(=O)NCC1CCN(CC2Cc3ccc(Oc4ccc(-c5ccn[nH]5)cn4)cc3O2)CC1] | N-(1-{6-[5-(2H-Pyrazol-3-yl)-pyridin-2-yloxy]-2,3-dihydro-benzofuran-2-ylmethyl}-piperidin-4-ylmethyl)-acetamide |
| 129 | 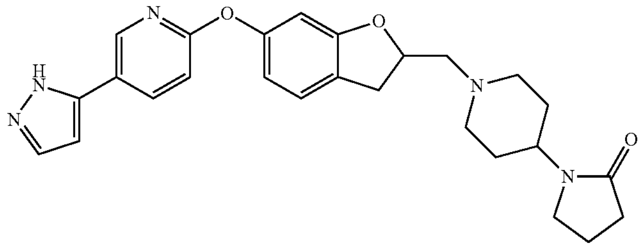 [SMILES: O=C1CCCN1C1CCN(CC2Cc3ccc(Oc4ccc(-c5ccn[nH]5)cn4)cc3O2)CC1] | 1-(1-{6-[5-(2H-Pyrazol-3-yl)-pyridin-2-yloxy]-2,3-dihydro-benzofuran-2-ylmethyl}-piperidin-4-yl)-pyrrolidin-2-one |
| 130 | 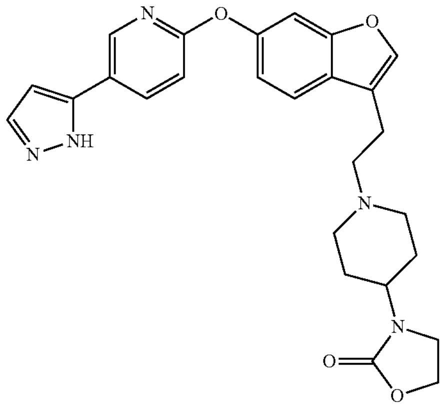 [SMILES: O=C1OCCN1C1CCN(CCc2coc3cc(Oc4ccc(-c5ccn[nH]5)cn4)ccc23)CC1] | 3-[1-(2-{6-[5-(2H-Pyrazol-3-yl)-pyridin-2-yloxy]-benzofuran-3-yl}-ethyl)-piperidin-4-yl]-oxazolidin-2-one |

TABLE 1-continued

| Examples of compounds of the invention. | | |
|---|---|---|
| No. | Structure | Compound Name |
| 131 | 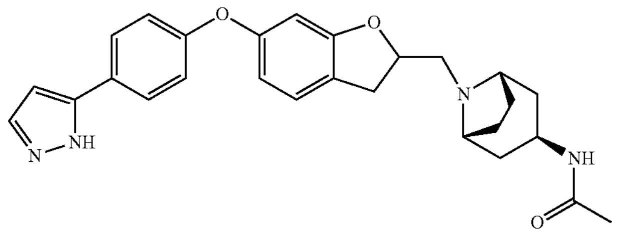 [SMILES: CC(=O)N[C@H]1C[C@H]2CC[C@@H](C1)N2CC1Cc2ccc(Oc3ccc(-c4ccn[nH]4)cc3)cc2O1] | N-((endo)-8-{6-[4-(2H-Pyrazol-3-yl)-phenoxy]-2,3-dihydro-benzofuran-2-ylmethyl}-8-aza-bicyclo[3.2.1]oct-3-yl)-acetamide |
| 132 | 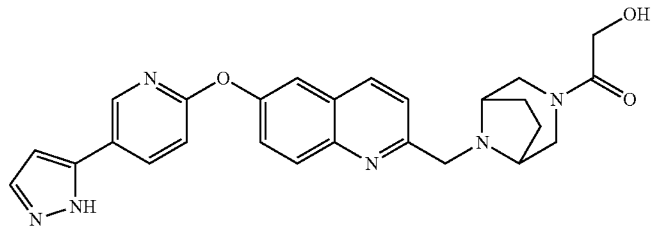 [SMILES: O=C(CO)N1CC2CCC(C1)N2Cc1ccc2cc(Oc3ccc(-c4ccn[nH]4)cn3)ccc2n1] | 2-Hydroxy-1-(8-{6-[5-(2H-pyrazol-3-yl)-pyridin-2-yloxy]-quinolin-2-ylmethyl}-3,8-diaza-bicyclo[3.2.1]oct-3-yl)-ethanone |
| 133 | 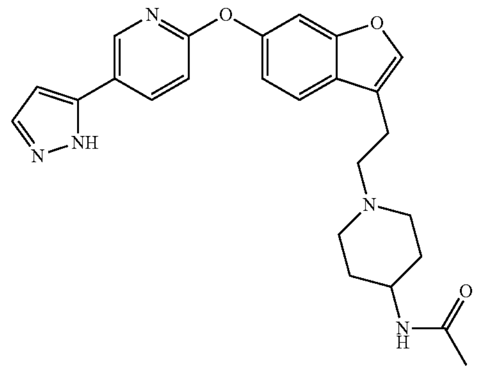 [SMILES: CC(=O)NC1CCN(CCc2coc3cc(Oc4ccc(-c5ccn[nH]5)cn4)ccc23)CC1] | N-[1-(2-{6-[5-(2H-Pyrazol-3-yl)-pyridin-2-yloxy]-benzofuran-3-yl}-ethyl)-piperidin-4-yl]-acetamide |
| 134 | 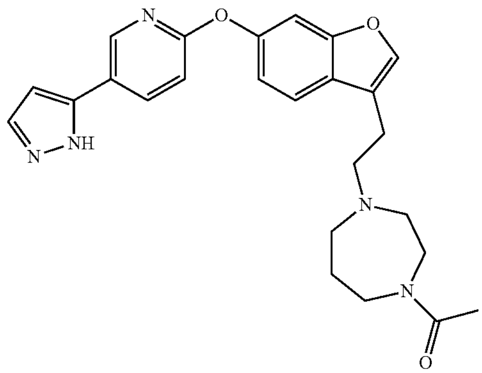 [SMILES: CC(=O)N1CCCN(CCc2coc3cc(Oc4ccc(-c5ccn[nH]5)cn4)ccc23)CC1] | 1-[4-(2-{6-[5-(2H-Pyrazol-3-yl)-pyridin-2-yloxy]-benzofuran-3-yl}-ethyl)-[1,4]diazepan-1-yl]-ethanone |

TABLE 1-continued

| Examples of compounds of the invention. | | |
|---|---|---|
| No. | Structure | Compound Name |
| 135 | 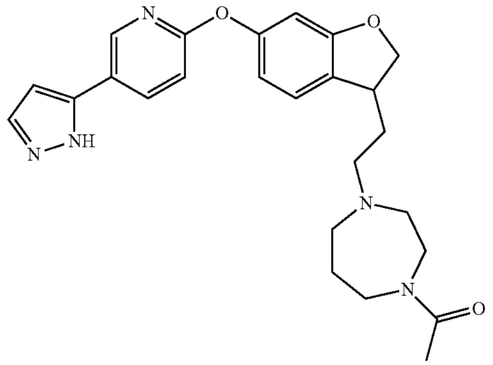 [SMILES: CC(=O)N1CCCN(CCC2COc3cc(Oc4ccc(-c5ccn[nH]5)cn4)ccc32)CC1] | 1-[4-(2-{6-[5-(2H-Pyrazol-3-yl)-pyridin-2-yloxy]-2,3-dihydro-benzofuran-3-yl}-ethyl)-[1,4]diazepan-1-yl]-ethanone |
| 136 | 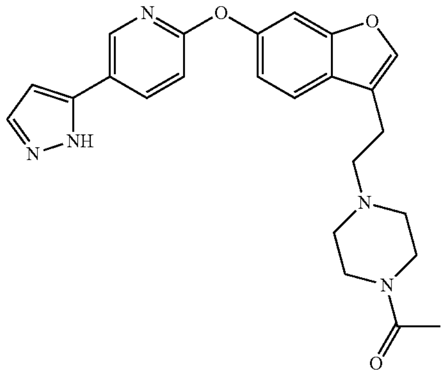 [SMILES: CC(=O)N1CCN(CCc2coc3cc(Oc4ccc(-c5ccn[nH]5)cn4)ccc23)CC1] | 1-[4-(2-{6-[5-(2H-Pyrazol-3-yl)-pyridin-2-yloxy]-benzofuran-3-yl}-ethyl)-piperazin-1-yl]-ethanone |
| 137 | 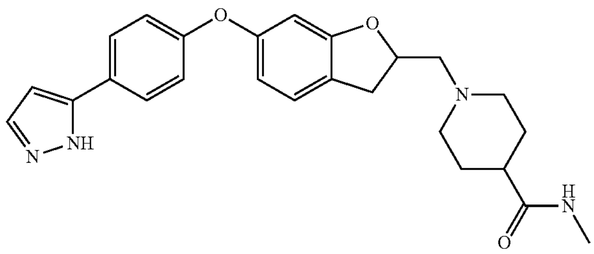 [SMILES: CNC(=O)C1CCN(CC2Cc3ccc(Oc4ccc(-c5ccn[nH]5)cc4)cc3O2)CC1] | 1-{6-[4-(2H-Pyrazol-3-yl)-phenoxy]-2,3-dihydro-benzofuran-2-ylmethyl}-piperidine-4-carboxylic acid methylamide |
| 138 | 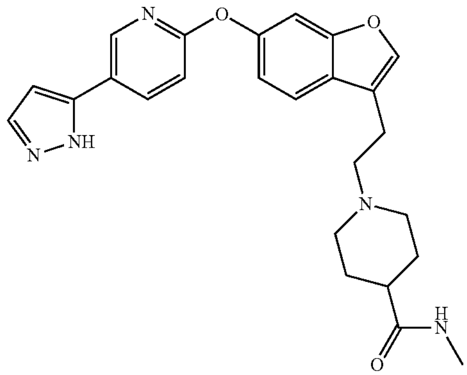 [SMILES: CNC(=O)C1CCN(CCc2coc3cc(Oc4ccc(-c5ccn[nH]5)cn4)ccc23)CC1] | 1-(2-{6-[5-(2H-Pyrazol-3-yl)-pyridin-2-yloxy]-benzofuran-3-yl}-ethyl)-piperidine-4-carboxylic acid methylamide |

TABLE 1-continued

| Examples of compounds of the invention. | | |
|---|---|---|
| No. | Structure | Compound Name |
| 139 | 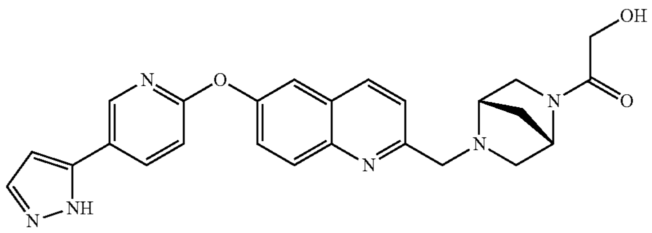 [SMILES: O=C(CO)N1C[C@@H]2C[C@H]1CN2Cc1ccc2cc(Oc3ccc(-c4ccn[nH]4)cn3)ccc2n1] | 2-Hydroxy-1-((1S,4S)-5-{6-[5-(2H-pyrazol-3-yl)-pyridin-2-yloxy]-quinolin-2-ylmethyl}-2,5-diaza-bicyclo[2.2.1]hept-2-yl)-ethanone |
| 140 | 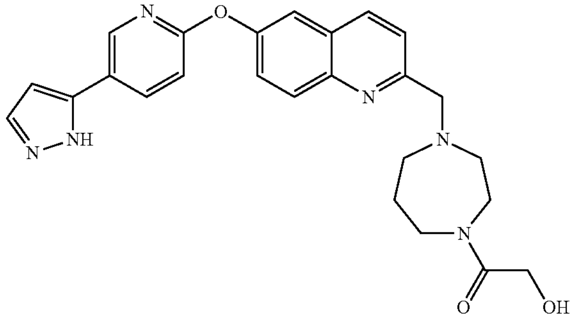 [SMILES: O=C(CO)N1CCCN(Cc2ccc3cc(Oc4ccc(-c5ccn[nH]5)cn4)ccc3n2)CC1] | 2-Hydroxy-1-(4-{6-[5-(2H-pyrazol-3-yl)-pyridin-2-yloxy]-quinolin-2-ylmethyl}-[1,4]diazepan-1-yl)-ethanone |
| 141 | 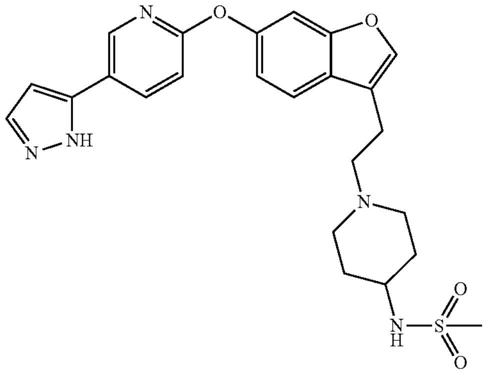 [SMILES: CS(=O)(=O)NC1CCN(CCc2coc3cc(Oc4ccc(-c5ccn[nH]5)cn4)ccc23)CC1] | N-[1-(2-{6-[5-(2H-Pyrazol-3-yl)-pyridin-2-yloxy]-benzofuran-3-yl}-ethyl)-piperidin-4-yl]-methanesulfonamide |
| 142 | 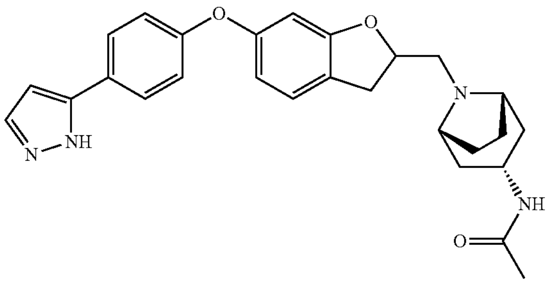 [SMILES: CC(=O)N[C@@H]1C[C@H]2CC[C@@H](C1)N2CC1Cc2ccc(Oc3ccc(-c4ccn[nH]4)cc3)cc2O1] | N-((exo)-8-{6-[4-(2H-Pyrazol-3-yl)-phenoxy]-2,3-dihydro-benzofuran-2-ylmethyl}-8-aza-bicyclo[3.2.1]oct-3-yl)-acetamide |

TABLE 1-continued

| Examples of compounds of the invention. | | |
|---|---|---|
| No. | Structure | Compound Name |
| 143 | 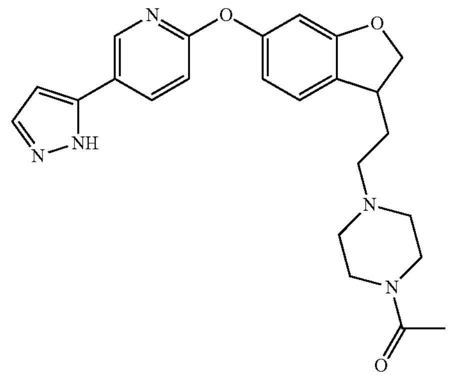 [SMILES: CC(=O)N1CCN(CCC2COc3cc(Oc4ccc(-c5ccn[nH]5)cn4)ccc32)CC1] | 1-[4-(2-{6-[5-(2H-Pyrazol-3-yl)-pyridin-2-yloxy]-2,3-dihydro-benzofuran-3-yl}-ethyl)-piperazin-1-yl]-ethanone |
| 144 | 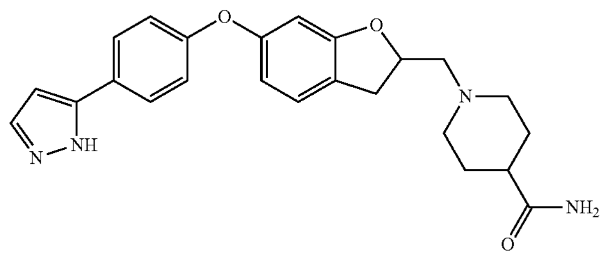 [SMILES: NC(=O)C1CCN(CC2Cc3ccc(Oc4ccc(-c5ccn[nH]5)cc4)cc3O2)CC1] | 1-{6-[4-(2H-Pyrazol-3-yl)-phenoxy]-2,3-dihydro-benzofuran-2-ylmethyl}-piperidine-4-carboxylic acid amide |
| 145 | 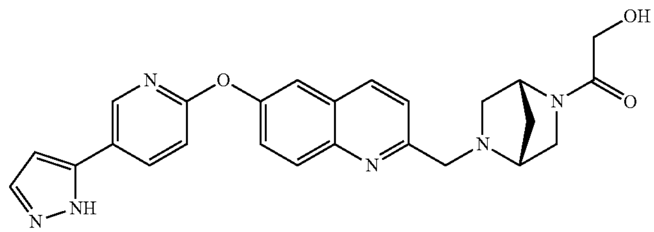 [SMILES: O=C(CO)N1C[C@H]2C[C@@H]1CN2Cc1ccc2cc(Oc3ccc(-c4ccn[nH]4)cn3)ccc2n1] | 2-Hydroxy-1-((1R,4R)-5-{6-[5-(2H-pyrazol-3-yl)-pyridin-2-yloxy]-quinolin-2-ylmethyl}-2,5-diaza-bicyclo[2.2.1] hept-2-yl)-ethanone |
| 146 | 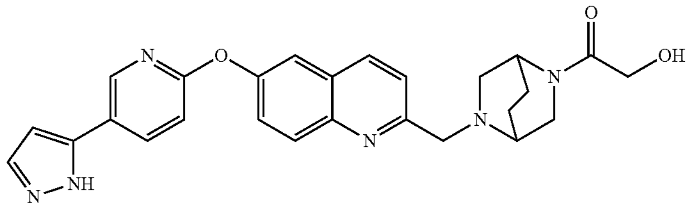 [SMILES: O=C(CO)N1CC2CCC1CN2Cc1ccc2cc(Oc3ccc(-c4ccn[nH]4)cn3)ccc2n1] | 2-Hydroxy-1-(5-{6-[5-(2H-pyrazol-3-yl)-pyridin-2-yloxy]-quinolin-2-ylmethyl}-2,5-diaza-bicyclo[2.2.2]oct-2-yl)-ethanone |
| 147 | 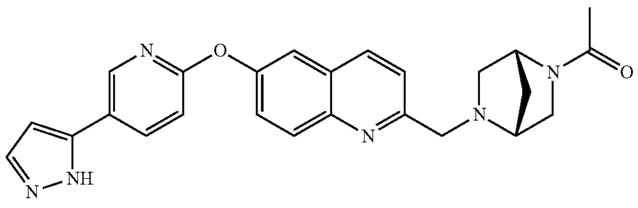 [SMILES: CC(=O)N1C[C@H]2C[C@@H]1CN2Cc1ccc2cc(Oc3ccc(-c4ccn[nH]4)cn3)ccc2n1] | 1-((1R,4R)-5-{6-[5-(2H-Pyrazol-3-yl)-pyridin-2-yloxy]-quinolin-2-ylmethyl}-2,5-diaza-bicyclo[2.2.1]hept-2-yl)-ethanone |

TABLE 1-continued

| Examples of compounds of the invention. | | |
|---|---|---|
| No. | Structure | Compound Name |
| 148 | 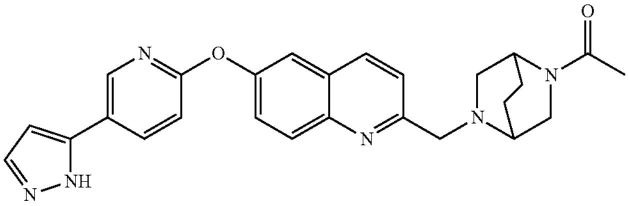 [SMILES: CC(=O)N1CC2CCC1CN2Cc1ccc2cc(Oc3ccc(-c4ccn[nH]4)cn3)ccc2n1] | 1-(5-{6-[5-(2H-Pyrazol-3-yl)-pyridin-2-yloxy]-quinolin-2-ylmethyl}-2,5-diaza-bicyclo[2.2.2]oct-2-yl)-ethanone |
| 149 | 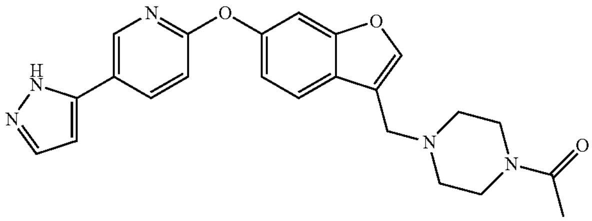 [SMILES: CC(=O)N1CCN(Cc2coc3cc(Oc4ccc(-c5ccn[nH]5)cn4)ccc23)CC1] | 1-(4-{6-[5-(2H-Pyrazol-3-yl)-pyridin-2-yloxy]-benzofuran-3-ylmethyl}-piperazin-1-yl)-ethanone |
| 150 | 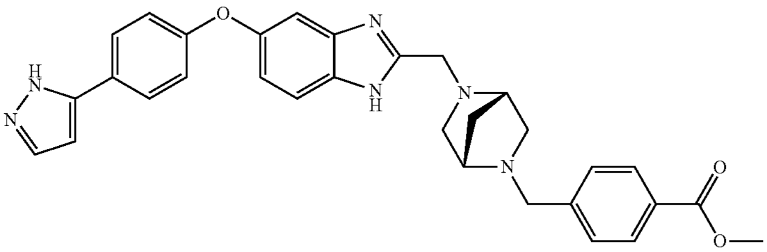 [SMILES: COC(=O)c1ccc(CN2C[C@@H]3C[C@H]2CN3Cc2nc3cc(Oc4ccc(-c5ccn[nH]5)cc4)ccc3[nH]2)cc1] | 4-((1S,4S)-5-{5-[4-(2H-Pyrazol-3-yl)-phenoxy]-1H-benzoimidazol-2-ylmethyl}-2,5-diaza-bicyclo[2.2.1]hept-2-ylmethyl)-benzoic acid methy lester |
| 151 | 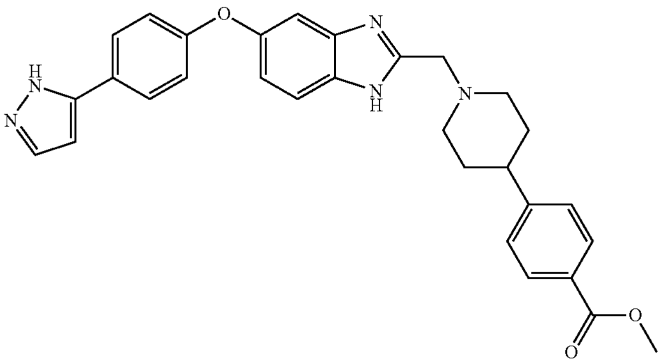 [SMILES: COC(=O)c1ccc(C2CCN(Cc3nc4cc(Oc5ccc(-c6ccn[nH]6)cc5)ccc4[nH]3)CC2)cc1] | 4-(1-{5-[4-(2H-Pyrazol-3-yl)-phenoxy]-1H-benzoimidazol-2-ylmethyl}-piperidin-4-yl)-benzoic acid methyl ester |
| 152 | 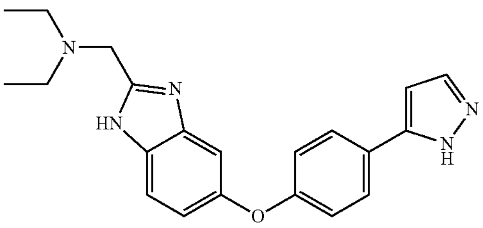 [SMILES: CCN(CC)Cc1nc2cc(Oc3ccc(-c4ccn[nH]4)cc3)ccc2[nH]1] | Diethyl-{5-[4-(2H-pyrazol-3-yl)-phenoxy]-1H-benzoimidazol-2-ylmethyl}-amine |

TABLE 1-continued

| Examples of compounds of the invention. | | |
|---|---|---|
| No. | Structure | Compound Name |
| 153 | 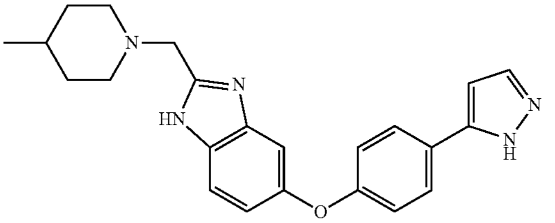 [SMILES: CC1CCN(Cc2nc3cc(Oc4ccc(-c5ccn[nH]5)cc4)ccc3[nH]2)CC1] | 2-(4-Methyl-piperidin-1-ylmethyl)-5-[4-(2H-pyrazol-3-yl)-phenoxy]-1H-benzoimidazole |
| 154 | 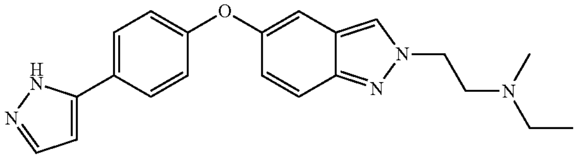 [SMILES: CCN(C)CCn1cc2cc(Oc3ccc(-c4ccn[nH]4)cc3)ccc2n1] | Ethyl-methyl-(2-{5-[4-(2H-pyrazol-3-yl)-phenoxy]-indazol-2-yl}-ethyl)-amine |
| 155 | 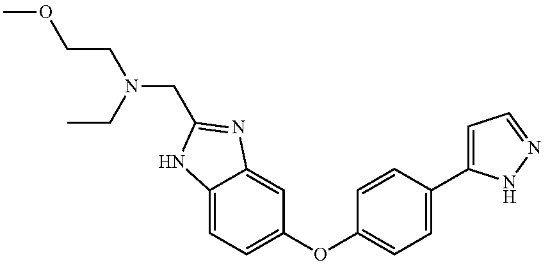 [SMILES: CCN(CCOC)Cc1nc2cc(Oc3ccc(-c4ccn[nH]4)cc3)ccc2[nH]1] | Ethyl-(2-methoxy-ethyl)-{5-[4-(2H-pyrazol-3-yl)-phenoxy]-1H-benzoimidazol-2-ylmethyl}-amine |
| 156 | 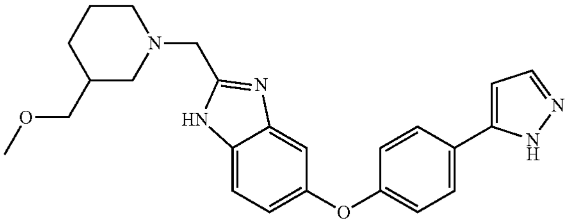 [SMILES: COCC1CCCN(Cc2nc3cc(Oc4ccc(-c5ccn[nH]5)cc4)ccc3[nH]2)C1] | 2-(3-Methoxymethyl-piperidin-1-ylmethyl)-5-[4-(2H-pyrazol-3-yl)-phenoxy]-1H-benzoimidazole |
| 157 | 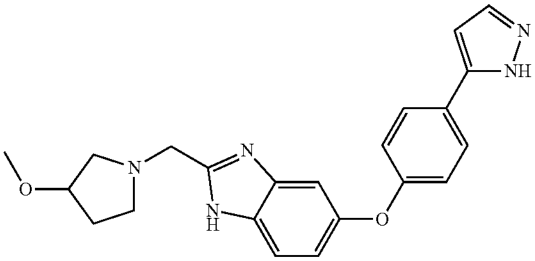 [SMILES: COC1CCN(Cc2nc3cc(Oc4ccc(-c5ccn[nH]5)cc4)ccc3[nH]2)C1] | 2-(3-Methoxy-pyrrolidin-1-ylmethyl)-5-[4-(2H-pyrazol-3-yl)-phenoxy]-1H-benzoimidazole |
| 158 | 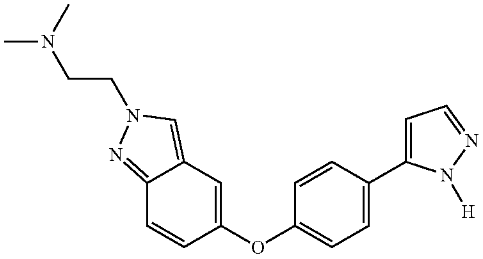 [SMILES: CN(C)CCn1cc2cc(Oc3ccc(-c4ccn[nH]4)cc3)ccc2n1] | Dimethyl-(2-{5-[4-(2H-pyrazol-3-yl)-phenoxy]-indazol-2-yl}-ethyl)-amine |

TABLE 1-continued

| Examples of compounds of the invention. | | |
|---|---|---|
| No. | Structure | Compound Name |
| 159 | 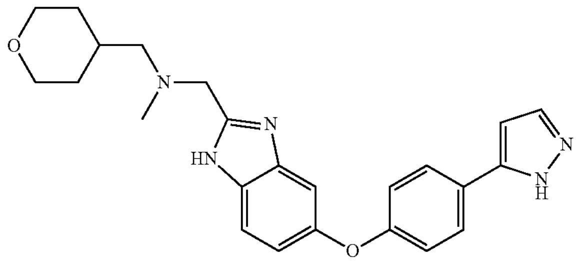 [SMILES: CN(Cc1nc2cc(Oc3ccc(-c4ccn[nH]4)cc3)ccc2[nH]1)CC1CCOCC1] | Methyl-{5-[4-(2H-pyrazol-3-yl)-phenoxy]-1H-benzoimidazol-2-ylmethyl}-(tetrahydro-pyran-4-ylmethyl)-amine |
| 160 | 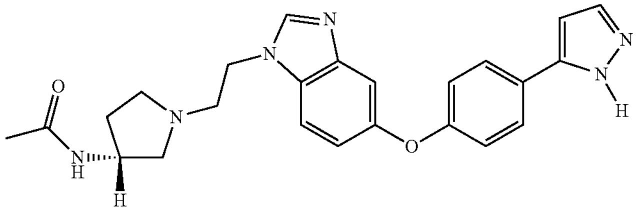 [SMILES: CC(=O)N[C@@H]1CCN(CCn2cnc3cc(Oc4ccc(-c5ccn[nH]5)cc4)ccc32)C1] | N-[(R)-1-(2-{5-[4-(2H-Pyrazol-3-yl)-phenoxy]-indazol-1-yl}-ethyl)-pyrrolidin-3-yl]-acetamide |
| 161 | 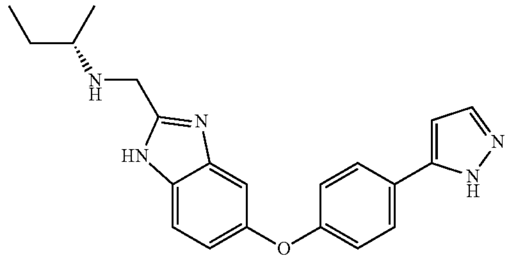 [SMILES: CC[C@H](C)NCc1nc2cc(Oc3ccc(-c4ccn[nH]4)cc3)ccc2[nH]1] | ((S)-sec-Butyl)-{5-[4-(2H-pyrazol-3-yl)-phenoxy]-1H-benzoimidazol-2-ylmethyl}-amine |
| 162 | 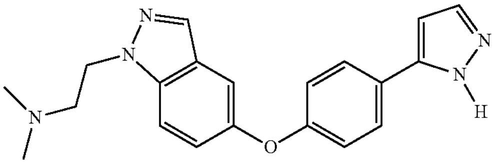 [SMILES: CN(C)CCn1ncc2cc(Oc3ccc(-c4ccn[nH]4)cc3)ccc21] | Dimethyl-(2-{5-[4-(2H-pyrazol-3-yl)-phenoxy]-indazol-1-yl}-ethyl)-amine |
| 163 | 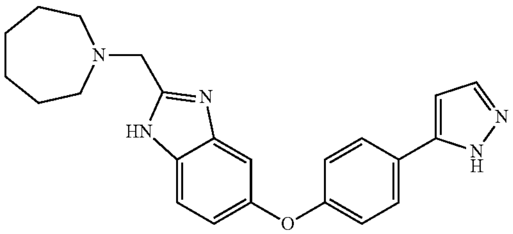 [SMILES: c1cc(-c2ccc(Oc3ccc4[nH]c(CN5CCCCCC5)nc4c3)cc2)[nH]n1] | 2-Azepan-1-ylmethyl-5-[4-(2H-pyrazol-3-yl)-phenoxy]-1H-benzoimidazole |
| 164 | 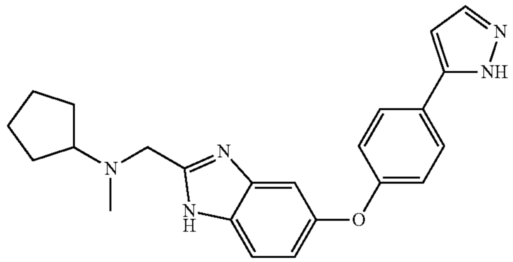 [SMILES: CN(Cc1nc2cc(Oc3ccc(-c4ccn[nH]4)cc3)ccc2[nH]1)C1CCCC1] | Cyclopentyl-methyl-{5-[4-(2H-pyrazol-3-yl)-phenoxy]-1H-benzoimidazol-2-ylmethyl}-amine |

TABLE 1-continued

| Examples of compounds of the invention. | | |
|---|---|---|
| No. | Structure | Compound Name |
| 165 | 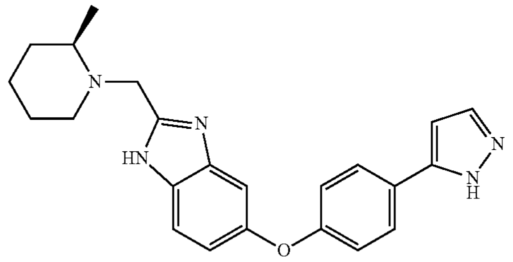 [SMILES: C[C@@H]1CCCCN1Cc1nc2cc(Oc3ccc(-c4ccn[nH]4)cc3)ccc2[nH]1] | 2-((R)-2-Methyl-piperidin-1-ylmethyl)-5-[4-(2H-pyrazol-3-yl)-phenoxy]-1H-benzoimidazole |
| 166 | 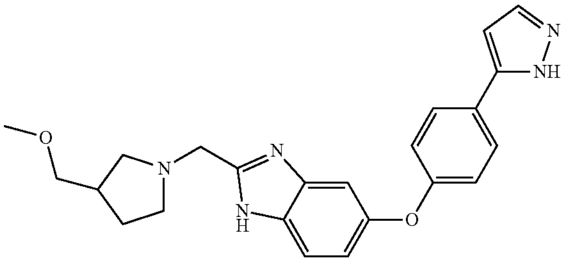 [SMILES: COCC1CCN(Cc2nc3cc(Oc4ccc(-c5ccn[nH]5)cc4)ccc3[nH]2)C1] | 2-(3-Methoxymethyl-pyrrolidin-1-ylmethyl)-5-[4-(2H-pyrazol-3-yl)-phenoxy]-1H-benzoimidazole |
| 167 | 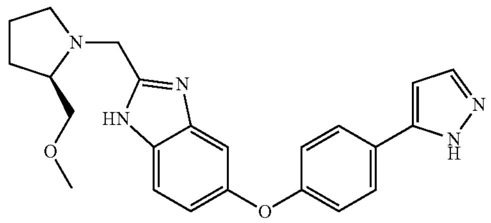 [SMILES: COC[C@H]1CCCN1Cc1nc2cc(Oc3ccc(-c4ccn[nH]4)cc3)ccc2[nH]1] | 2-((R)-2-Methoxymethyl-pyrrolidin-1-ylmethyl)-5-[4-(2H-pyrazol-3-yl)-phenoxy]-1H-benzoimidazole |
| 168 | 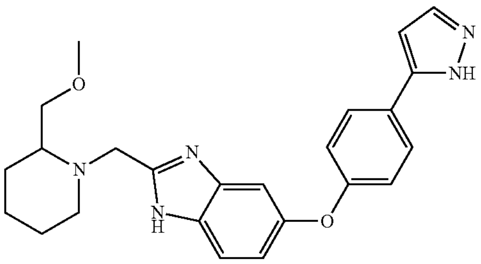 [SMILES: COCC1CCCCN1Cc1nc2cc(Oc3ccc(-c4ccn[nH]4)cc3)ccc2[nH]1] | 2-(2-Methoxymethyl-piperidin-1-ylmethyl)-5-[4-(2H-pyrazol-3-yl)-phenoxy]-1H-benzoimidazole |
| 169 | 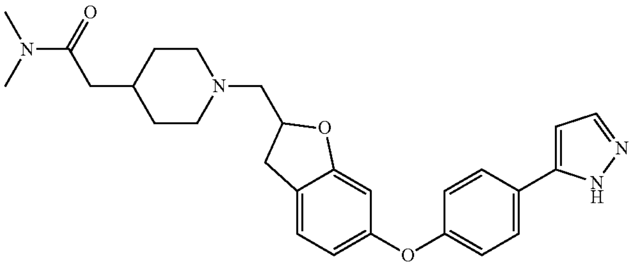 [SMILES: CN(C)C(=O)CC1CCN(CC2Cc3ccc(Oc4ccc(-c5ccn[nH]5)cc4)cc3O2)CC1] | N,N-Dimethyl-2-(1-{6-[4-(2H-pyrazol-3-yl)-phenoxy]-2,3-dihydro-benzofuran-2-ylmethyl}-piperidin-4-yl)-acetamide |

TABLE 1-continued

Examples of compounds of the invention.

| No. | Structure | Compound Name |
|---|---|---|
| 170 | 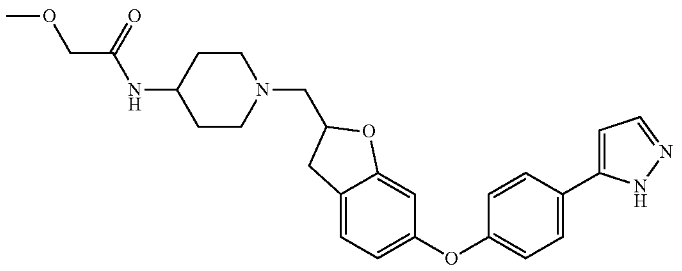 [SMILES: COCC(=O)NC1CCN(CC2Cc3ccc(Oc4ccc(-c5ccn[nH]5)cc4)cc3O2)CC1] | 2-Methoxy-N-(1-{6-[4-(2H-pyrazol-3-yl)-phenoxy]-2,3-dihydro-benzofuran-2-ylmethyl}-piperidin-4-yl)-acetamide |
| 171 | 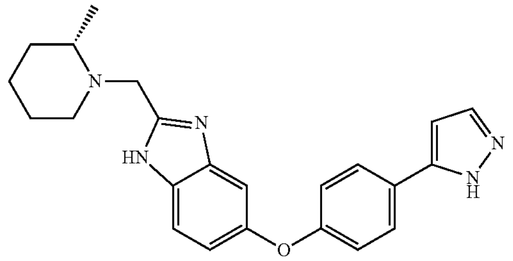 [SMILES: C[C@H]1CCCCN1Cc1nc2cc(Oc3ccc(-c4ccn[nH]4)cc3)ccc2[nH]1] | 2-((S)-2-Methyl-piperidin-1-ylmethyl)-5-[4-(2H-pyrazol-3-yl)-phenoxy]-1H-benzoimidazole |
| 172 | 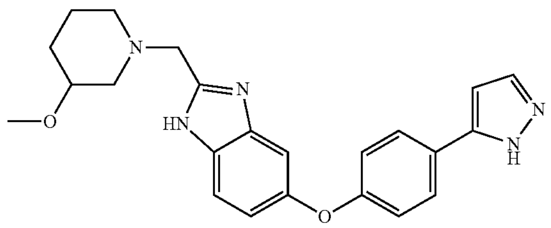 [SMILES: COC1CCCN(Cc2nc3cc(Oc4ccc(-c5ccn[nH]5)cc4)ccc3[nH]2)C1] | 2-(3-Methoxy-piperidin-1-ylmethyl)-5-[4-(2H-pyrazol-3-yl)-phenoxy]-1H-benzoimidazole |
| 173 | 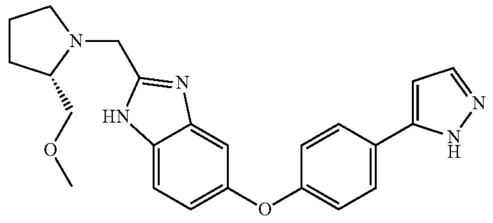 [SMILES: COC[C@@H]1CCCN1Cc1nc2cc(Oc3ccc(-c4ccn[nH]4)cc3)ccc2[nH]1] | 2-((S)-2-Methoxymethyl-pyrrolidin-1-ylmethyl)-5-[4-(2H-pyrazol-3-yl)-phenoxy]-1H-benzoimidazole |
| 174 | 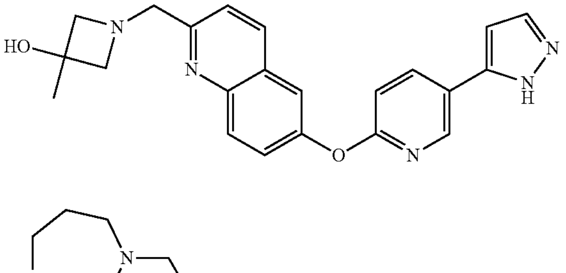 | 3-Methyl-1-{6-[5-(2H-pyrazol-3-yl)-pyridin-2-yloxy]-quinolin-2-ylmethyl}-azetidin-3-ol |
| 175 | 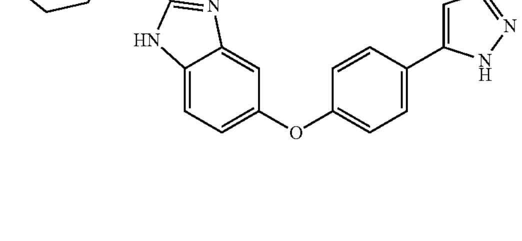 | 2-[1,4]Oxazepan-4-ylmethyl-5-[4-(2H-pyrazol-3-yl)-phenoxy]-1H-benzoimidazole |

TABLE 1-continued

| Examples of compounds of the invention. | | |
|---|---|---|
| No. | Structure | Compound Name |
| 176 | 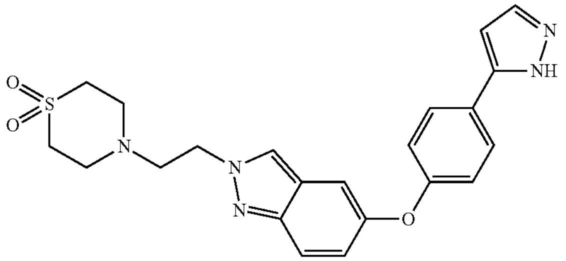 [SMILES: O=S1(=O)CCN(CCn2cc3cc(Oc4ccc(-c5ccn[nH]5)cc4)ccc3n2)CC1] | 2-[2-(1,1-Dioxo-1-λ-6-thiomorpholin-4-yl)-ethyl]-5-[4-(2H-pyrazol-3-yl)-phenoxy]-2H-indazole |
| 177 | 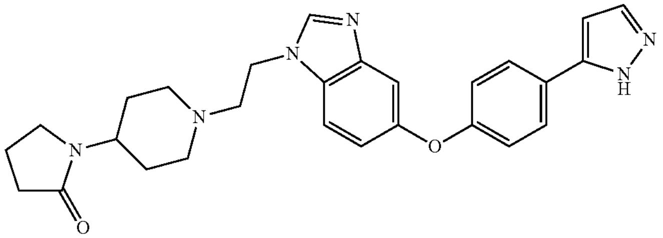 [SMILES: O=C1CCCN1C1CCN(CCn2cnc3cc(Oc4ccc(-c5ccn[nH]5)cc4)ccc32)CC1] | 1-[1-(2-{5-[4-(2H-Pyrazol-3-yl)-phenoxy]-indazol-1-yl}-ethyl)-piperidin-4-yl]-pyrrolidin-2-one |
| 178 | 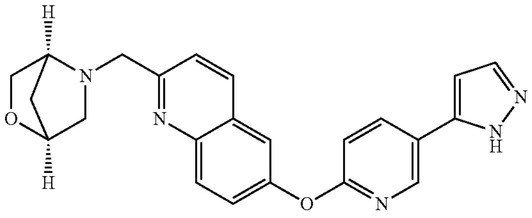 [SMILES: c1cc(-c2ccc(Oc3ccc4nc(CN5C[C@@H]6C[C@H]5CO6)ccc4c3)nc2)[nH]n1] | 2-[(1S,4S)-1-(2-Oxa-5-aza-bicyclo[2.2.1]hept-5-yl)methyl]-6-[5-(2H-pyrazol-3-yl)-pyridin-2-yloxy]-quinoline |
| 179 | 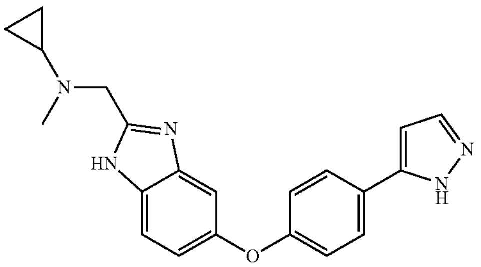 [SMILES: CN(Cc1nc2cc(Oc3ccc(-c4ccn[nH]4)cc3)ccc2[nH]1)C1CC1] | Cyclopropyl-methyl-{5-[4-(2H-pyrazol-3-yl)-phenoxy]-1H-benzoimidazol-2-ylmethyl}-amine |
| 180 | 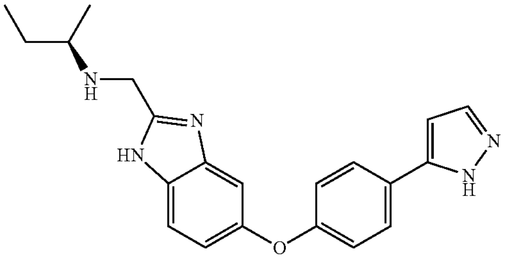 [SMILES: CC[C@@H](C)NCc1nc2cc(Oc3ccc(-c4ccn[nH]4)cc3)ccc2[nH]1] | ((R)-sec-Butyl)-{5-[4-(2H-pyrazol-3-yl)-phenoxy]-1H-benzoimidazol-2-ylmethyl}-amine |

TABLE 1-continued

| Examples of compounds of the invention. | | |
|---|---|---|
| No. | Structure | Compound Name |
| 181 | 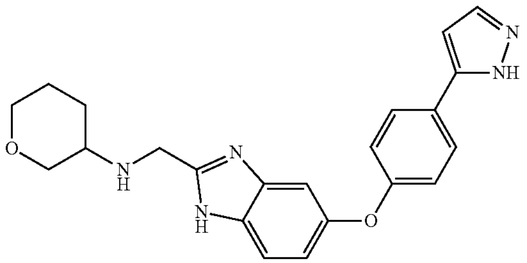 | {5-[4-(2H-Pyrazol-3-yl)-phenoxy]-1H-benzoimidazol-2-ylmethyl}-(tetrahydro-pyran-3-yl)-amine |
| 182 | 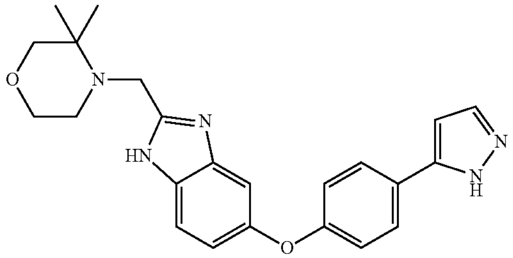 [SMILES: CC1(C)COCCN1Cc1nc2cc(Oc3ccc(-c4ccn[nH]4)cc3)ccc2[nH]1] | 2-(3,3-Dimethyl-morpholin-4-ylmethyl)-5-[4-(2H-pyrazol-3-yl)-phenoxy]-1H-benzoimidazole |
| 183 | 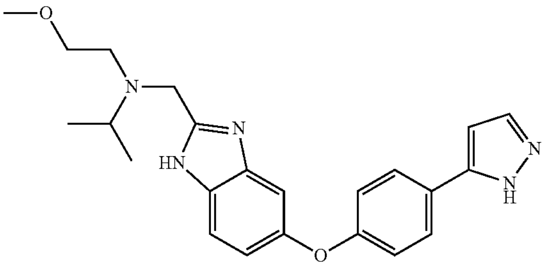 [SMILES: COCCN(Cc1nc2cc(Oc3ccc(-c4ccn[nH]4)cc3)ccc2[nH]1)C(C)C] | Isopropyl-(2-methoxy-ethyl)-{5-[4-(2H-pyrazol-3-yl)-phenoxy]-1H-benzoimidazol-2-ylmethyl}-amine |
| 184 | 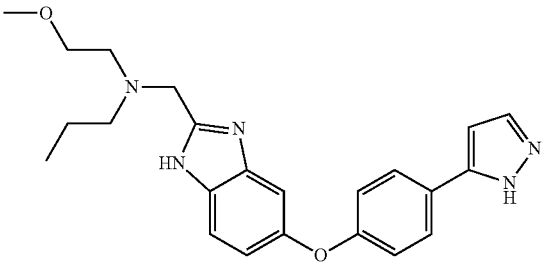 [SMILES: CCCN(CCOC)Cc1nc2cc(Oc3ccc(-c4ccn[nH]4)cc3)ccc2[nH]1] | (2-Methoxy-ethyl)-propyl-{5-[4-(2H-pyrazol-3-yl)-phenoxy]-1H-benzoimidazol-2-ylmethyl}-amine |
| 185 | 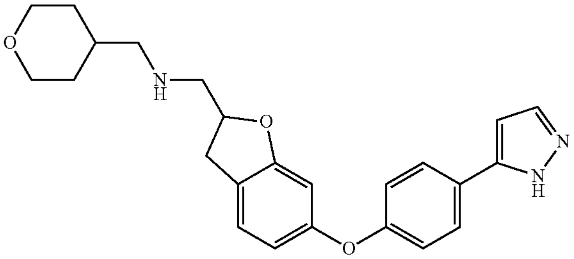 [SMILES: c1cc(-c2ccc(Oc3ccc4c(c3)OC(CNCC3CCOCC3)C4)cc2)[nH]n1] | {6-[4-(2H-Pyrazol-3-yl)-phenoxy]-2,3-dihydro-benzofuran-2-ylmethyl}-(tetrahydro-pyran-4-ylmethyl)-amine |

TABLE 1-continued

| No. | Structure | Compound Name |
|---|---|---|
| 186 | 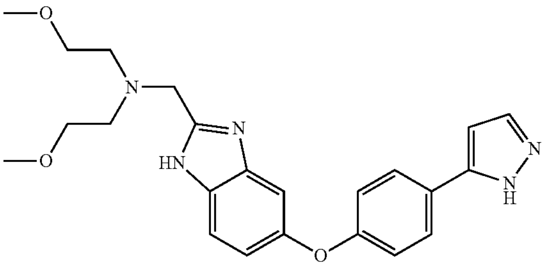 [SMILES: COCCN(CCOC)Cc1nc2cc(Oc3ccc(-c4ccn[nH]4)cc3)ccc2[nH]1] | Bis-(2-methoxy-ethyl)-{5-[4-(2H-pyrazol-3-yl)-phenoxy]-1H-benzoimidazol-2-ylmethyl}-amine |
| 187 | 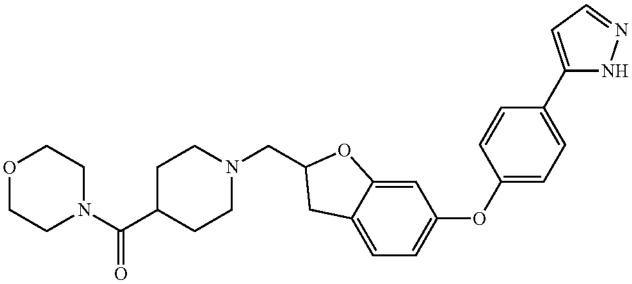 [SMILES: O=C(C1CCN(CC2Cc3ccc(Oc4ccc(-c5ccn[nH]5)cc4)cc3O2)CC1)N1CCOCC1] | Morpholin-4-yl-(1-{6-[4-(2H-pyrazol-3-yl)-phenoxy]-2,3-dihydro-benzofuran-2-ylmethyl}-piperidin-4-yl)-methanone |
| 188 | 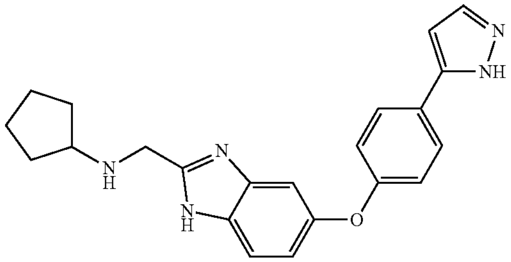 [SMILES: c1cc(-c2ccc(Oc3ccc4[nH]c(CNC5CCCC5)nc4c3)cc2)[nH]n1] | Cyclopentyl-{5-[4-(2H-pyrazol-3-yl)-phenoxy]-1H-benzoimidazol-2-ylmethyl}-amine |
| 189 | 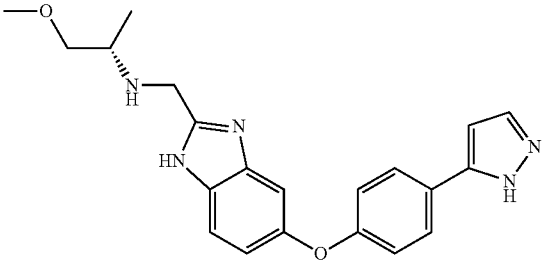 [SMILES: COC[C@H](C)NCc1nc2cc(Oc3ccc(-c4ccn[nH]4)cc3)ccc2[nH]1] | ((S)-2-Methoxy-1-methyl-ethyl)-{5-[4-(2H-pyrazol-3-yl)-phenoxy]-1H-benzoimidazol-2-ylmethyl}-amine |
| 190 | 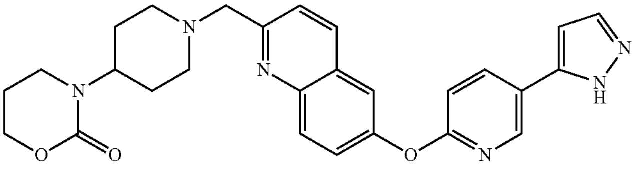 [SMILES: O=C1OCCCN1C1CCN(Cc2ccc3cc(Oc4ccc(-c5ccn[nH]5)cn4)ccc3n2)CC1] | 3-(1-{6-[5-(2H-Pyrazol-3-yl)-pyridin-2-yloxy]-quinolin-2-ylmethyl}-piperidin-4-yl)-[1,3]oxazinan-2-one |

Examples of compounds of the invention.

TABLE 1-continued

Examples of compounds of the invention.

| No. | Structure | Compound Name |
| --- | --- | --- |
| 191 | 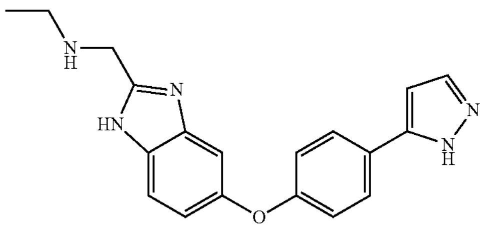 [SMILES: CCNCc1nc2cc(Oc3ccc(-c4ccn[nH]4)cc3)ccc2[nH]1] | Ethyl-{5-[4-(2H-pyrazol-3-yl)-phenoxy]-1H-benzoimidazol-2-ylmethyl}-amine |
| 192 | 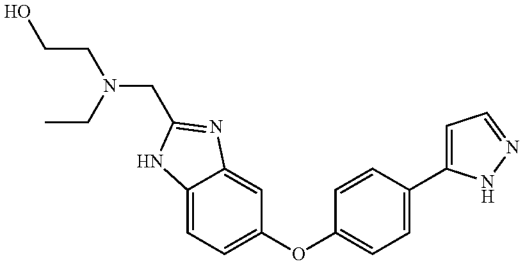 [SMILES: CCN(CCO)Cc1nc2cc(Oc3ccc(-c4ccn[nH]4)cc3)ccc2[nH]1] | 2-(Ethyl-{5-[4-(2H-pyrazol-3-yl)-phenoxy]-1H-benzoimidazol-2-ylmethyl}-amino)-ethanol |
| 193 | 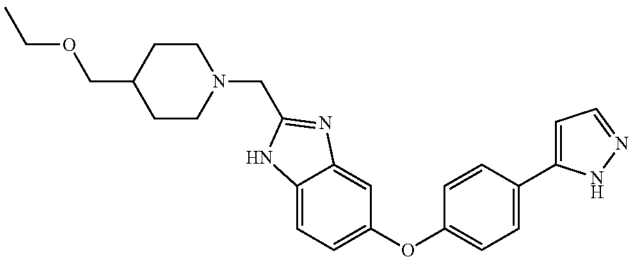 [SMILES: CCOCC1CCN(Cc2nc3cc(Oc4ccc(-c5ccn[nH]5)cc4)ccc3[nH]2)CC1] | 2-(4-Ethoxymethyl-piperidin-1-ylmethyl)-5-[4-(2H-pyrazol-3-yl)-phenoxy]-1H-benzoimidazole |
| 194 | 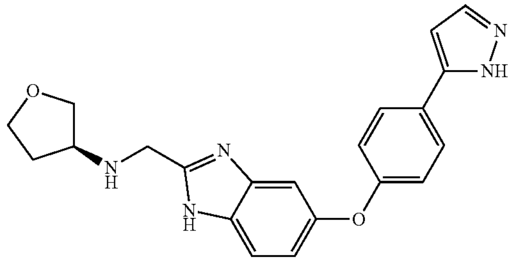 [SMILES: c1cc(-c2ccc(Oc3ccc4[nH]c(CN[C@H]5CCOC5)nc4c3)cc2)[nH]n1] | {5-[4-(2H-Pyrazol-3-yl)-phenoxy]-1H-benzoimidazol-2-ylmethyl}-(S)-tetrahydro-furan-3-yl-amine |
| 195 | 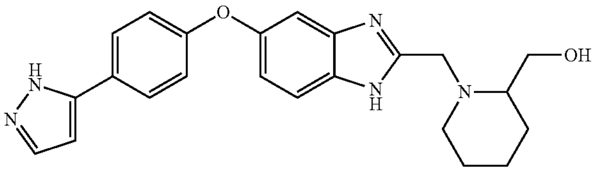 [SMILES: OCC1CCCCN1Cc1nc2cc(Oc3ccc(-c4ccn[nH]4)cc3)ccc2[nH]1] | (1-{5-[4-(2H-Pyrazol-3-yl)-phenoxy]-1H-benzoimidazol-2-ylmethyl}-piperidin-2-yl)-methanol |
| 196 | 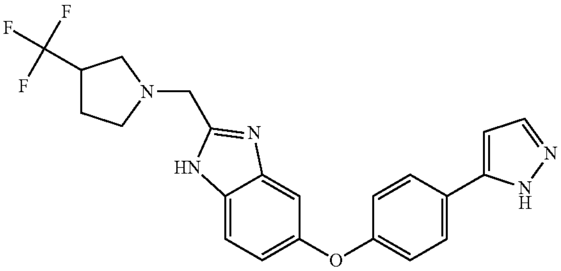 [SMILES: FC(F)(F)C1CCN(Cc2nc3cc(Oc4ccc(-c5ccn[nH]5)cc4)ccc3[nH]2)C1] | 5-[4-(2H-Pyrazol-3-yl)-phenoxy]-2-(3-trifluoromethyl-pyrrolidin-1-ylmethyl)-1H-benzoimidazole |

TABLE 1-continued

Examples of compounds of the invention.

| No. | Structure | Compound Name |
|---|---|---|
| 197 | 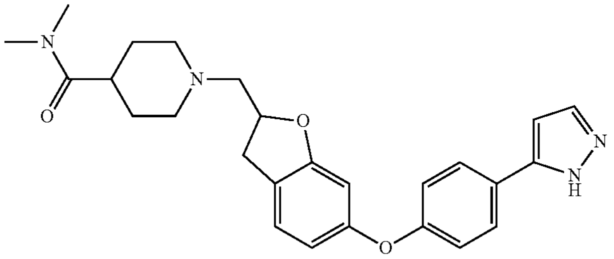 [SMILES: CN(C)C(=O)C1CCN(CC2Cc3ccc(Oc4ccc(-c5ccn[nH]5)cc4)cc3O2)CC1] | 1-{6-[4-(2H-Pyrazol-3-yl)-phenoxy]-2,3-dihydro-benzofuran-2-ylmethyl}-piperidine-4-carboxylic acid dimethylamide |
| 198 | 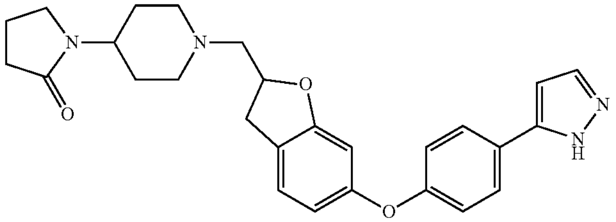 [SMILES: O=C1CCCN1C1CCN(CC2Cc3ccc(Oc4ccc(-c5ccn[nH]5)cc4)cc3O2)CC1] | 1-(1-{6-[4-(2H-Pyrazol-3-yl)-phenoxy]-2,3-dihydro-benzofuran-2-ylmethyl}-piperidin-4-yl)-pyrrolidin-2-one |
| 199 | 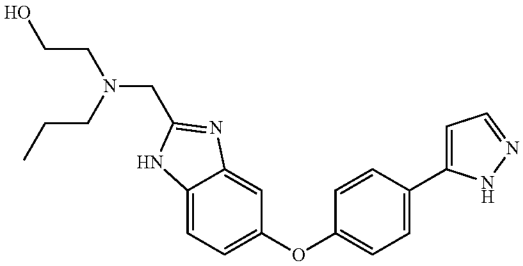 [SMILES: CCCN(CCO)Cc1nc2cc(Oc3ccc(-c4ccn[nH]4)cc3)ccc2[nH]1] | 2-(Propyl-{5-[4-(2H-pyrazol-3-yl)-phenoxy]-1H-benzoimidazol-2-ylmethyl}-amino)-ethanol |
| 200 | 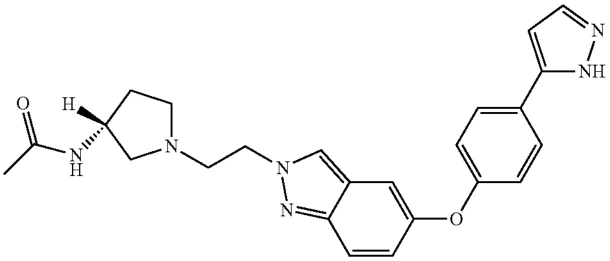 [SMILES: CC(=O)N[C@@H]1CCN(CCn2cc3cc(Oc4ccc(-c5ccn[nH]5)cc4)ccc3n2)C1] | N-[(R)-1-(2-{5-[4-(2H-Pyrazol-3-yl)-phenoxy]-indazol-2-yl}-ethyl)-pyrrolidin-3-yl]-acetamide |
| 201 | 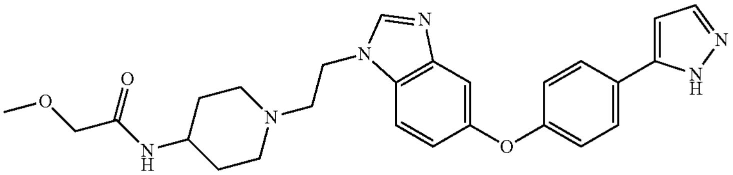 [SMILES: COCC(=O)NC1CCN(CCn2cnc3cc(Oc4ccc(-c5ccn[nH]5)cc4)ccc32)CC1] | 2-Methoxy-N-[1-(2-{5-[4-(2H-pyrazol-3-yl)-phenoxy]-indazol-1-yl}-ethyl)-piperidin-4-yl]-acetamide |
| 202 | 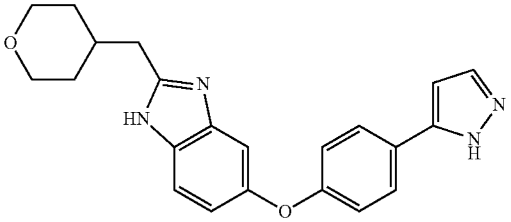 [SMILES: c1cc(-c2ccc(Oc3ccc4[nH]c(CC5CCOCC5)nc4c3)cc2)[nH]n1] | 5-[4-(2H-Pyrazol-3-yl)-phenoxy]-2-(tetrahydro-pyran-4-ylmethyl)-1H-benzoimidazole |

TABLE 1-continued

Examples of compounds of the invention.

| No. | Structure | Compound Name |
|---|---|---|
| 203 | 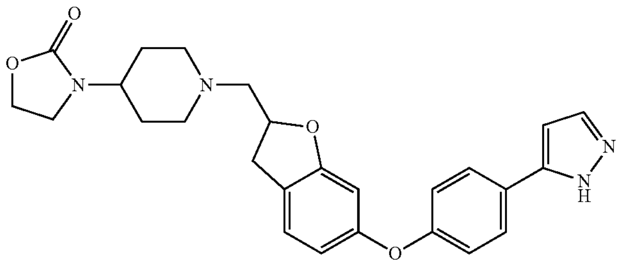 [SMILES: O=C1OCCN1C1CCN(CC2Cc3ccc(Oc4ccc(-c5ccn[nH]5)cc4)cc3O2)CC1] | 3-(1-{6-[4-(2H-Pyrazol-3-yl)-phenoxy]-2,3-dihydro-benzofuran-2-ylmethyl}-piperidin-4-yl)-oxazolidin-2-one |
| 204 | 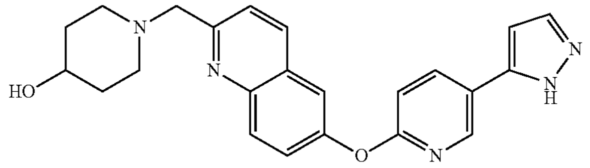 [SMILES: OC1CCN(Cc2ccc3cc(Oc4ccc(-c5ccn[nH]5)cn4)ccc3n2)CC1] | 1-{6-[5-(2H-Pyrazol-3-yl)-pyridin-2-yloxy]-quinolin-2-ylmethyl}-piperidin-4-ol |
| 205 | 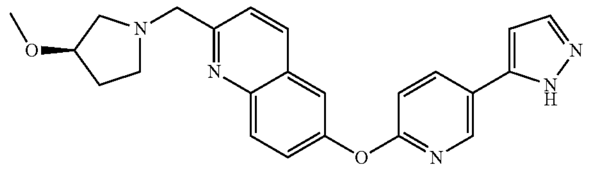 [SMILES: CO[C@@H]1CCN(Cc2ccc3cc(Oc4ccc(-c5ccn[nH]5)cn4)ccc3n2)C1] | 2-((R)-3-Methoxy-pyrrolidin-1-ylmethyl)-6-[5-(2H-pyrazol-3-yl)-pyridin-2-yloxy]-quinoline |
| 206 | 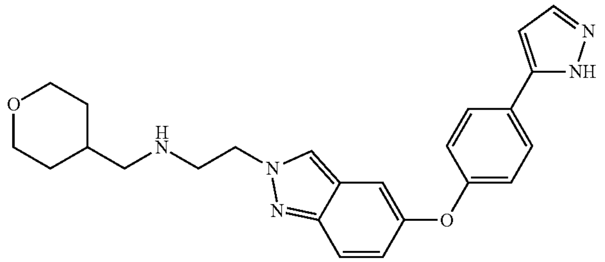 [SMILES: c1cc(-c2ccc(Oc3ccc4nn(CCNCC5CCOCC5)cc4c3)cc2)[nH]n1] | (2-{5-[4-(2H-Pyrazol-3-yl)-phenoxy]-indazol-2-yl}-ethyl)-(tetrahydro-pyran-4-ylmethyl)-amine |
| 207 | 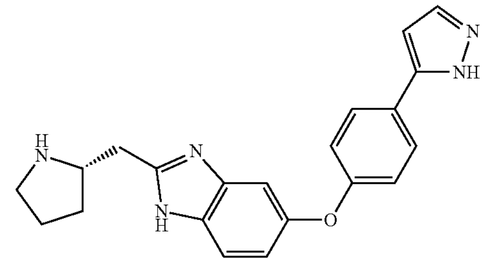 [SMILES: c1cc(-c2ccc(Oc3ccc4[nH]c(C[C@@H]5CCCN5)nc4c3)cc2)[nH]n1] | 5-[4-(2H-Pyrazol-3-yl)-phenoxy]-2-(S)-1-pyrrolidin-2-ylmethyl-1H-benzoimidazole |
| 208 | 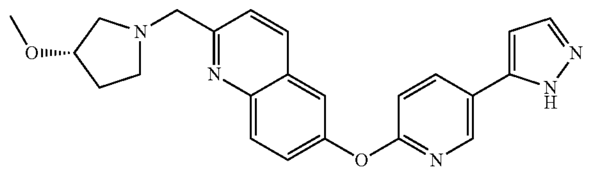 [SMILES: CO[C@H]1CCN(Cc2ccc3cc(Oc4ccc(-c5ccn[nH]5)cn4)ccc3n2)C1] | 2-((S)-3-Methoxy-pyrrolidin-1-ylmethyl)-6-[5-(2H-pyrazol-3-yl)-pyridin-2-yloxy]-quinoline |

TABLE 1-continued

| Examples of compounds of the invention. | | |
|---|---|---|
| No. | Structure | Compound Name |
| 209 | 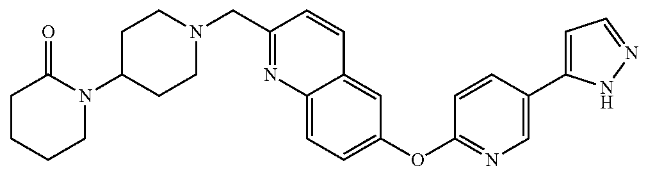 [SMILES: O=C1CCCCN1C1CCN(Cc2ccc3cc(Oc4ccc(-c5ccn[nH]5)cn4)ccc3n2)CC1] | 1'-{6-[5-(2H-Pyrazol-3-yl)-pyridin-2-yloxy]-quinolin-2-ylmethyl}-[1,4'] bipiperidinyl-2-one |
| 210 | 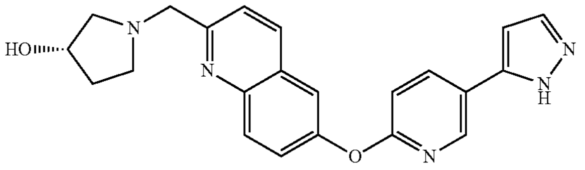 [SMILES: O[C@H]1CCN(Cc2ccc3cc(Oc4ccc(-c5ccn[nH]5)cn4)ccc3n2)C1] | (S)-1-{6-[5-(2H-Pyrazol-3-yl)-pyridin-2-yloxy]-quinolin-2-ylmethyl}-pyrrolidin-3-ol |
| 211 | 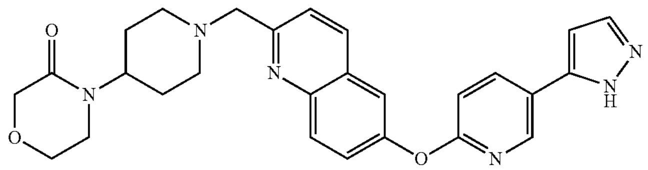 [SMILES: O=C1COCCN1C1CCN(Cc2ccc3cc(Oc4ccc(-c5ccn[nH]5)cn4)ccc3n2)CC1] | 4-(1-{6-[5-(2H-Pyrazol-3-yl)-pyridin-2-yloxy]-quinolin-2-ylmethyl}-piperidin-4-yl)-morpholin-3-one |
| 212 | 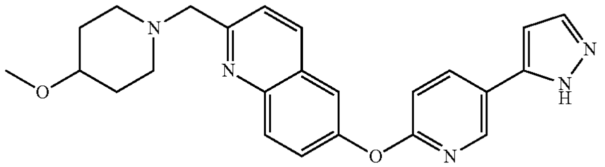 [SMILES: COC1CCN(Cc2ccc3cc(Oc4ccc(-c5ccn[nH]5)cn4)ccc3n2)CC1] | 2-(4-Methoxy-piperidin-1-ylmethyl)-6-[5-(2H-pyrazol-3-yl)-pyridin-2-yloxy]-quinoline |
| 213 | 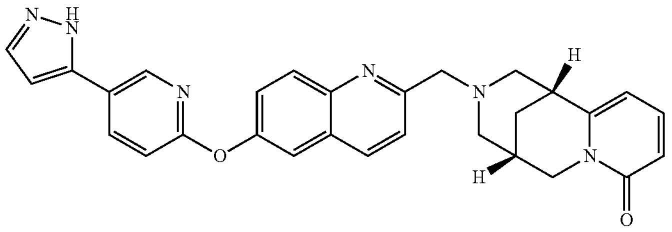 [SMILES: O=c1cccc2n1C[C@H]1C[C@@H]2CN(Cc2ccc3cc(Oc4ccc(-c5ccn[nH]5)cn4)ccc3n2)C1] | (1R,5S)-3-{6-[5-(2H-Pyrazol-3-yl)-pyridin-2-yloxy]-quinolin-2-ylmethyl}-1,2,3,4,5,6-hexahydro-1,5-methano-pyrido[1,2-a][1,5]diazocin-8-one |
| 214 | 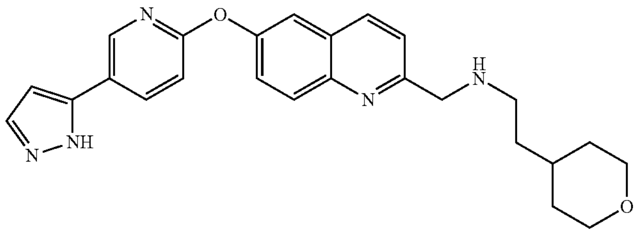 [SMILES: c1cc(-c2ccc(Oc3ccc4nc(CNCCC5CCOCC5)ccc4c3)nc2)[nH]n1] | {6-[5-(2H-Pyrazol-3-yl)-pyridin-2-yloxy]-quinolin-2-ylmethyl}-[2-(tetrahydro-pyran-4-yl)-ethyl]-amine |
| 215 | 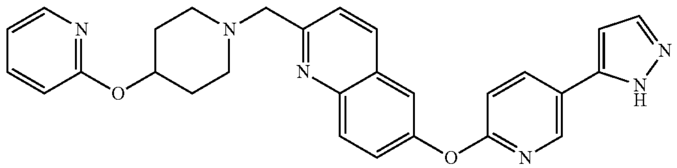 [SMILES: c1ccc(OC2CCN(Cc3ccc4cc(Oc5ccc(-c6ccn[nH]6)cn5)ccc4n3)CC2)nc1] | 6-[5-(2H-Pyrazol-3-yl)-pyridin-2-yloxy]-2-[4-(pyridin-2-yloxy)-piperidin-1-ylmethyl]-quinoline |

TABLE 1-continued

Examples of compounds of the invention.

| No. | Structure | Compound Name |
|---|---|---|
| 216 | 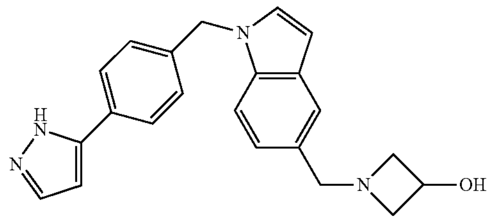 [SMILES: OC1CN(Cc2ccc3c(ccn3Cc3ccc(-c4ccn[nH]4)cc3)c2)C1] | 1-{1-[4-(2H-Pyrazol-3-yl)-benzyl]-1H-indol-5-ylmethyl}-azetidin-3-ol |
| 217 | 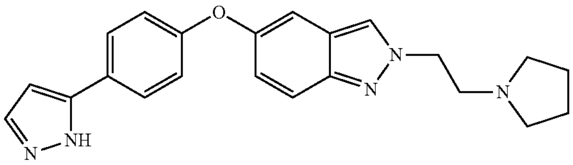 [SMILES: c1cc(-c2ccc(Oc3ccc4nn(CCN5CCCC5)cc4c3)cc2)[nH]n1] | 5-[4-(2H-Pyrazol-3-yl)-phenoxy]-2-(2-pyrrolidin-1-yl-ethyl)-2H-indazole |
| 218 | 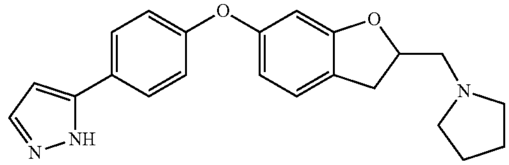 [SMILES: c1cc(-c2ccc(Oc3ccc4c(c3)OC(CN3CCCC3)C4)cc2)[nH]n1] | 5-[4-(2-Pyrrolidin-1-ylmethyl-2,3-dihydro-benzofuran-6-yloxy)-phenyl]-1H-pyrazole |
| 219 | 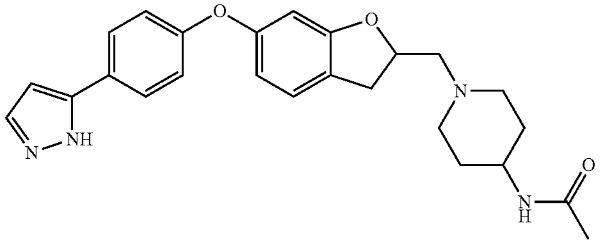 [SMILES: CC(=O)NC1CCN(CC2Cc3ccc(Oc4ccc(-c5ccn[nH]5)cc4)cc3O2)CC1] | N-(1-{6-[4-(2H-Pyrazol-3-yl)-phenoxy]-2,3-dihydro-benzofuran-2-ylmethyl}-piperidin-4-yl)-acetamide |
| 220 | 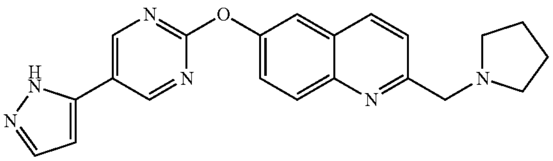 [SMILES: c1cc(-c2cnc(Oc3ccc4nc(CN5CCCC5)ccc4c3)nc2)[nH]n1] | 6-[5-(2H-Pyrazol-3-yl)-pyrimidin-2-yloxy]-2-pyrrolidin-1-ylmethyl-quinoline |
| 221 | 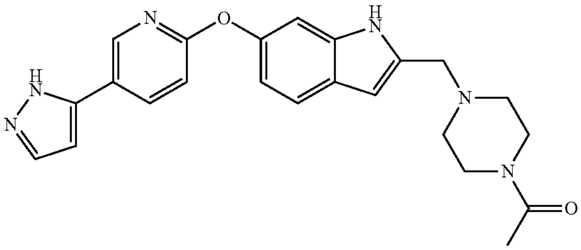 [SMILES: CC(=O)N1CCN(Cc2cc3ccc(Oc4ccc(-c5ccn[nH]5)cn4)cc3[nH]2)CC1] | 1-(4-{6-[5-(2H-Pyrazol-3-yl)-pyridin-2-yloxy]-1H-indol-2-ylmethyl}-piperazin-1-yl)-ethanone |

TABLE 1-continued

| Examples of compounds of the invention. | | |
|---|---|---|
| No. | Structure | Compound Name |
| 222 | 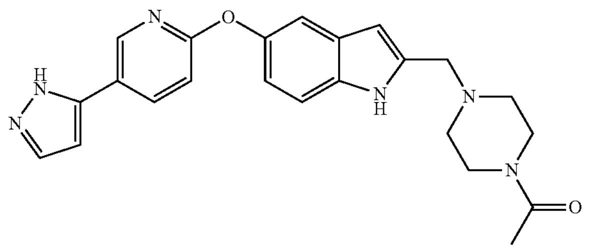 [SMILES: CC(=O)N1CCN(Cc2cc3cc(Oc4ccc(-c5ccn[nH]5)cn4)ccc3[nH]2)CC1] | 1-(4-{5-[5-(2H-Pyrazol-3-yl)-pyridin-2-yloxy]-1H-indol-2-ylmethyl}-piperazin-1-yl)-ethanone |
| 223 | 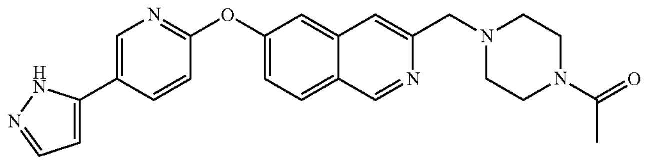 [SMILES: CC(=O)N1CCN(Cc2cc3cc(Oc4ccc(-c5ccn[nH]5)cn4)ccc3cn2)CC1] | 1-(4-{6-[5-(2H-Pyrazol-3-yl)-pyridin-2-yloxy]-isoquinolin-3-ylmethyl}-piperazin-1-yl)-ethanone |
| 224 | 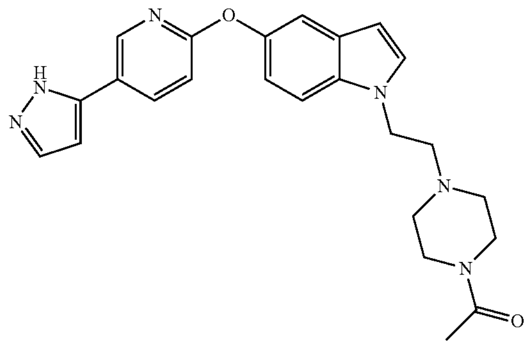 | 1-[4-(2-{5-[5-(2H-Pyrazol-3-yl)-pyridin-2-yloxy]-indol-1-yl}-ethyl)-piperazin-1-yl]-ethanone |
| 225 | 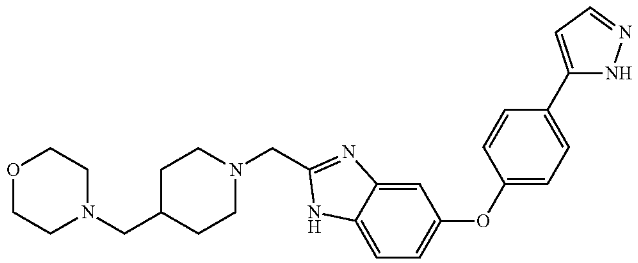 [SMILES: c1cc(-c2ccc(Oc3ccc4[nH]c(CN5CCC(CN6CCOCC6)CC5)nc4c3)cc2)[nH]n1] | 2-(4-Morpholin-4-ylmethyl-piperidin-1-ylmethyl)-5-[4-(2H-pyrazol-3-yl)-phenoxy]-1H-benzoimidazole |
| 226 | 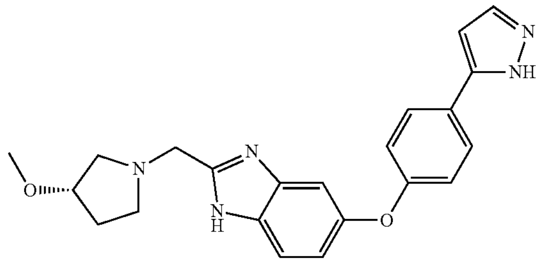 [SMILES: CO[C@H]1CCN(Cc2nc3cc(Oc4ccc(-c5ccn[nH]5)cc4)ccc3[nH]2)C1] | 2-((S)-3-Methoxy-pyrrolidin-1-ylmethyl)-5-[4-(2H-pyrazol-3-yl)-phenoxy]-1H-benzoimidazole |

TABLE 1-continued

| Examples of compounds of the invention. | | |
|---|---|---|
| No. | Structure | Compound Name |
| 227 | 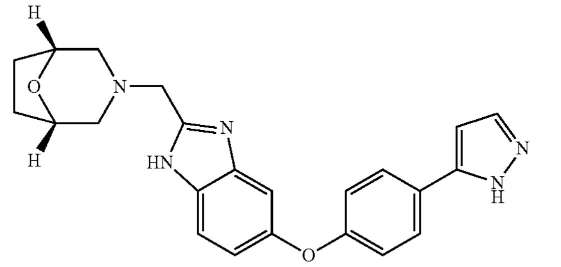 [SMILES: c1cc(-c2ccc(Oc3ccc4[nH]c(CN5C[C@H]6CC[C@@H](C5)O6)nc4c3)cc2)[nH]n1] | 3-{5-[4-(2H-Pyrazol-3-yl)-phenoxy]-1H-benzoimidazol-2-ylmethyl}-8-oxa-3-aza-bicyclo[3.2.1]octane |
| 228 | 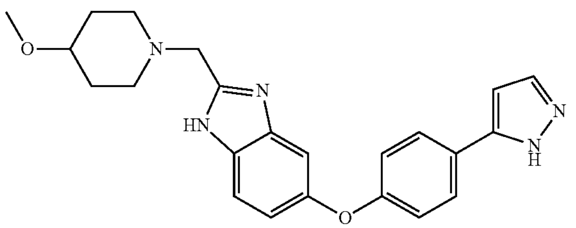 [SMILES: COC1CCN(Cc2nc3cc(Oc4ccc(-c5ccn[nH]5)cc4)ccc3[nH]2)CC1] | 2-(4-Methoxy-piperidin-1-ylmethyl)-5-[4-(2H-pyrazol-3-yl)-phenoxy]-1H-benzoimidazole |
| 229 | 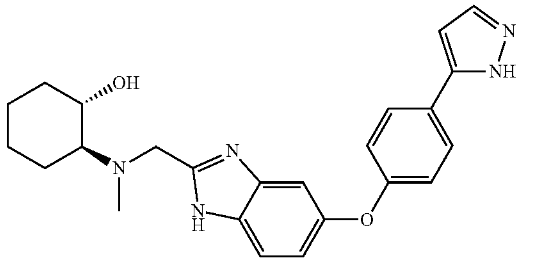 [SMILES: CN(Cc1nc2cc(Oc3ccc(-c4ccn[nH]4)cc3)ccc2[nH]1)[C@H]1CCCC[C@@H]1O] | (1S,2S)-2-(Methyl-{5-[4-(2H-pyrazol-3-yl)-phenoxy]-1H-benzoimidazol-2-ylmethyl}-amino)-cyclohexanol |
| 230 | 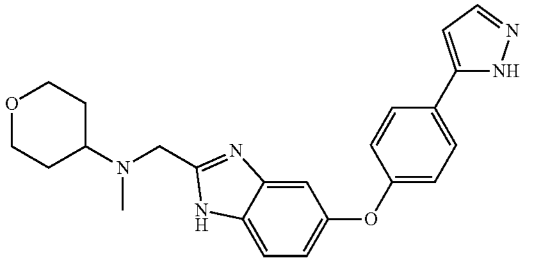 [SMILES: CN(Cc1nc2cc(Oc3ccc(-c4ccn[nH]4)cc3)ccc2[nH]1)C1CCOCC1] | Methyl-{5-[4-(2H-pyrazol-3-yl)-phenoxy]-1H-benzoimidazol-2-ylmethyl}-(tetrahydro-pyran-4-yl)-amine |
| 231 | 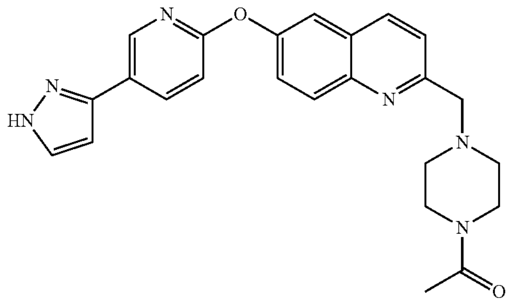 [SMILES: CC(=O)N1CCN(Cc2ccc3cc(Oc4ccc(-c5cc[nH]n5)cn4)ccc3n2)CC1] | 1-(4-{6-[5-(1H-Pyrazol-3-yl)-pyridin-2-yloxy]-quinolin-2-ylmethyl}-piperazin-1-yl)-ethanone |

TABLE 1-continued

| Examples of compounds of the invention. | | |
|---|---|---|
| No. | Structure | Compound Name |
| 232 | 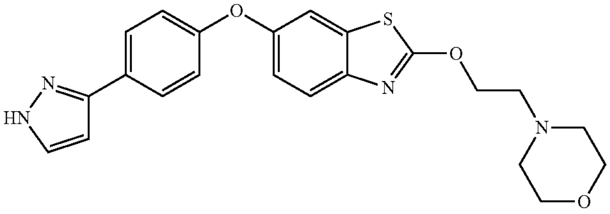 [SMILES: c1cc(-c2ccc(Oc3ccc4nc(OCCN5CCOCC5)sc4c3)cc2)n[nH]1] | 2-(2-Morpholin-4-yl-ethoxy)-6-[4-(1H-pyrazol-3-yl)-phenoxy]-benzothiazole |
| 233 | 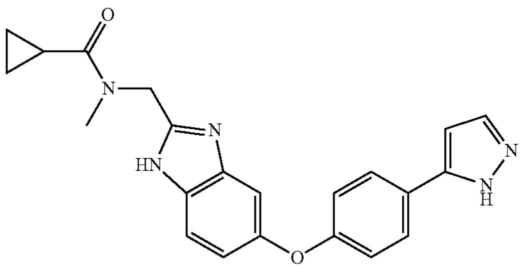 [SMILES: CN(Cc1nc2cc(Oc3ccc(-c4ccn[nH]4)cc3)ccc2[nH]1)C(=O)C1CC1] | Cyclopropanecarboxylic acid methyl-{5-[4-(2H-pyrazol-3-yl)-phenoxy]-1H-benzoimidazol-2-ylmethyl}-amide |
| 234 | 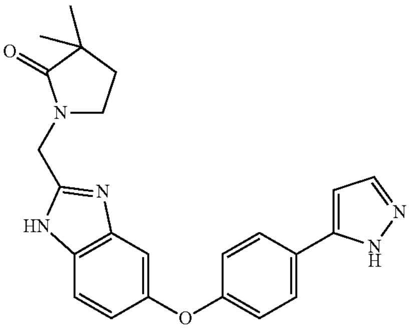 [SMILES: CC1(C)CCN(Cc2nc3cc(Oc4ccc(-c5ccn[nH]5)cc4)ccc3[nH]2)C1=O] | 3,3-Dimethyl-1-{5-[4-(2H-pyrazol-3-yl)-phenoxy]-1H-benzoimidazol-2-ylmethyl}-pyrrolidin-2-one |
| 235 | 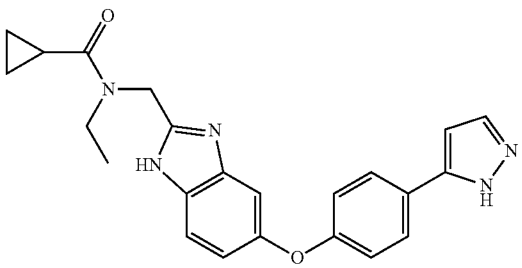 [SMILES: CCN(Cc1nc2cc(Oc3ccc(-c4ccn[nH]4)cc3)ccc2[nH]1)C(=O)C1CC1] | Cyclopropanecarboxylic acid ethyl-{5-[4-(2H-pyrazol-3-yl)-phenoxy]-1H-benzoimidazol-2-ylmethyl}-amide |
| 236 | 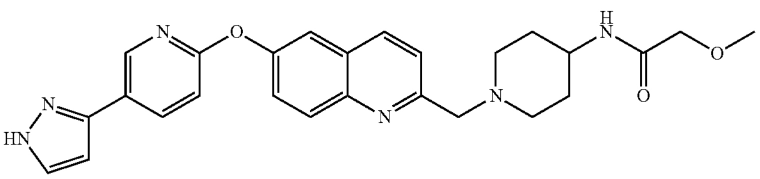 [SMILES: COCC(=O)NC1CCN(Cc2ccc3cc(Oc4ccc(-c5cc[nH]n5)cn4)ccc3n2)CC1] | 2-Methoxy-N-(1-{6-[5-(1H-pyrazol-3-yl)-pyridin-2-yloxy]-quinolin-2-ylmethyl}-piperidin-4-yl)-acetamide |
| 237 | 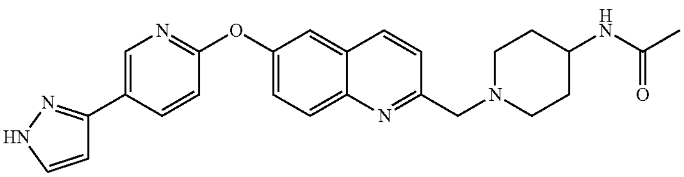 [SMILES: CC(=O)NC1CCN(Cc2ccc3cc(Oc4ccc(-c5cc[nH]n5)cn4)ccc3n2)CC1] | N-(1-{6-[5-(1H-Pyrazol-3-yl)-pyridin-2-yloxy]-quinolin-2-ylmethyl}-piperidin-4-yl)-acetamide |

TABLE 1-continued

| Examples of compounds of the invention. | | |
|---|---|---|
| No. | Structure | Compound Name |
| 238 | 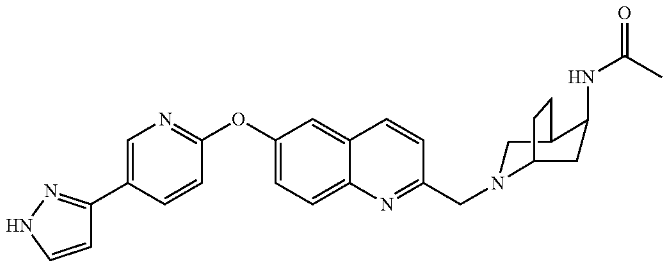 [SMILES: CC(=O)NC1CC2CCC1CN2Cc1ccc2cc(Oc3ccc(-c4cc[nH]n4)cn3)ccc2n1] | N-((endo)-8-{6-[5-(1H-Pyrazol-3-yl)-pyridin-2-yloxy]-quinolin-2-ylmethyl}-8-aza-bicyclo[3.2.1]oct-3-yl)-acetamide |
| 239 | 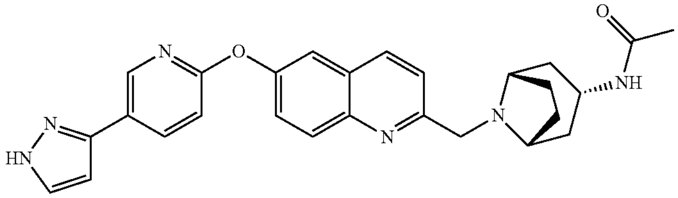 [SMILES: CC(=O)N[C@@H]1C[C@H]2CC[C@@H](C1)N2Cc1ccc2cc(Oc3ccc(-c4cc[nH]n4)cn3)ccc2n1] | N-((exo)-8-{6-[5-(1H-Pyrazol-3-yl)-pyridin-2-yloxy]-quinolin-2-ylmethyl}-8-aza-bicyclo[3.2.1]oct-3-yl)-acetamide |
| 240 | 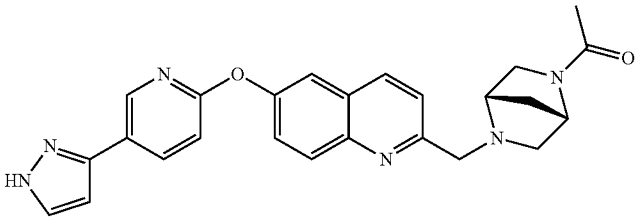 [SMILES: CC(=O)N1C[C@@H]2C[C@H]1CN2Cc1ccc2cc(Oc3ccc(-c4cc[nH]n4)cn3)ccc2n1] | 1-((S)-5-{6-[5-(1H-Pyrazol-3-yl)-pyridin-2-yloxy]-quinolin-2-ylmethyl}-2,5-diaza-bicyclo[2.2.1]hept-2-yl)-ethanone |
| 241 | 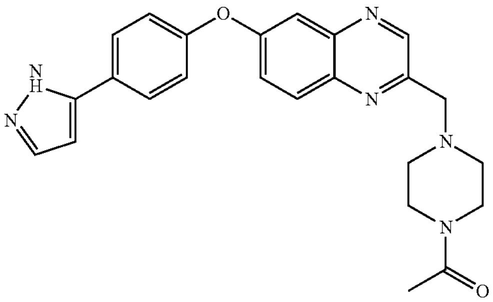 [SMILES: CC(=O)N1CCN(Cc2cnc3cc(Oc4ccc(-c5ccn[nH]5)cc4)ccc3n2)CC1] | 1-(4-{6-[4-(2H-Pyrazol-3-yl)-phenoxy]-quinoxalin-2-ylmethyl}-piperazin-1-yl)-ethanone |
| 242 | 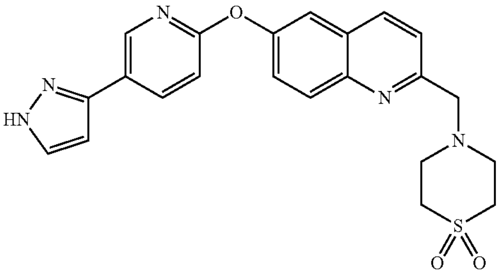 [SMILES: O=S1(=O)CCN(Cc2ccc3cc(Oc4ccc(-c5cc[nH]n5)cn4)ccc3n2)CC1] | 2-(1,1-Dioxo-1-λ-6-thiomorpholin-4-ylmethyl)-6-[5-(1H-pyrazol-3-yl)-pyridin-2-yloxy]-quinoline |
| 243 | 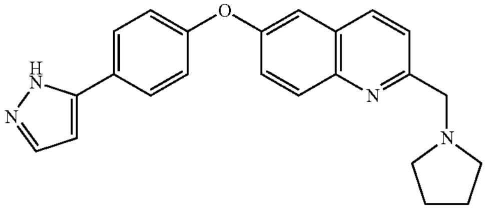 [SMILES: c1cc(-c2ccc(Oc3ccc4nc(CN5CCCC5)ccc4c3)cc2)[nH]n1] | 6-[4-(2H-Pyrazol-3-yl)-phenoxy]-2-pyrrolidin-1-ylmethyl-quinoline |

TABLE 1-continued

| No. | Structure | Compound Name |
| --- | --- | --- |
| Examples of compounds of the invention. | | |
| 244 | 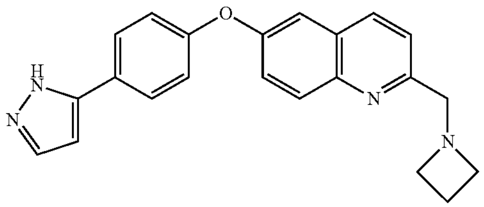 [SMILES: c1cc(-c2ccc(Oc3ccc4nc(CN5CCC5)ccc4c3)cc2)[nH]n1] | 2-Azetidin-1-ylmethyl-6-[4-(2H-pyrazol-3-yl)-phenoxy]-quinoline |
| 245 | 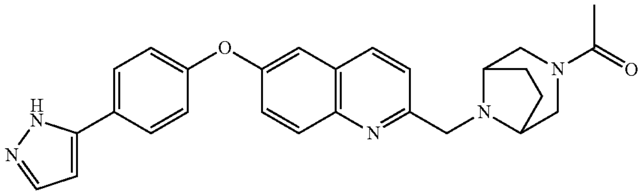 [SMILES: CC(=O)N1CC2CCC(C1)N2Cc1ccc2cc(Oc3ccc(-c4ccn[nH]4)cc3)ccc2n1] | 1-(8-{6-[4-(2H-Pyrazol-3-yl)-phenoxy]-quinolin-2-ylmethyl}-3,8-diaza-bicyclo[3.2.1]oct-3-yl)-ethanone |
| 246 | 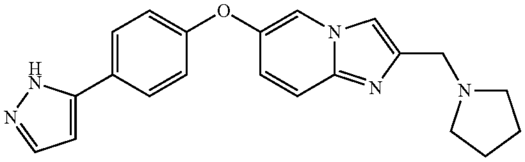 [SMILES: c1cc(-c2ccc(Oc3ccc4nc(CN5CCCC5)cn4c3)cc2)[nH]n1] | 6-[4-(2H-Pyrazol-3-yl)-phenoxy]-2-pyrrolidin-1-ylmethyl-imidazo[1,2-a]pyridine |
| 247 | 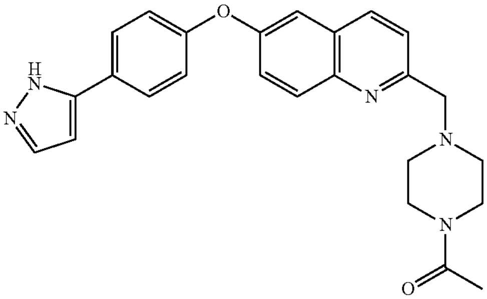 [SMILES: CC(=O)N1CCN(Cc2ccc3cc(Oc4ccc(-c5ccn[nH]5)cc4)ccc3n2)CC1] | 1-(4-{6-[4-(2H-Pyrazol-3-yl)-phenoxy]-quinolin-2-ylmethyl}-piperazin-1-yl)-ethanone |
| 248 | 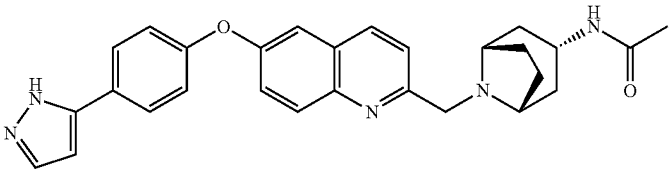 [SMILES: CC(=O)N[C@@H]1C[C@H]2CC[C@@H](C1)N2Cc1ccc2cc(Oc3ccc(-c4ccn[nH]4)cc3)ccc2n1] | N-((exo)-8-{6-[4-(2H-Pyrazol-3-yl)-phenoxy]-quinolin-2-ylmethyl}-8-aza-bicyclo[3.2.1]oct-3-yl)-acetamide |
| 249 | 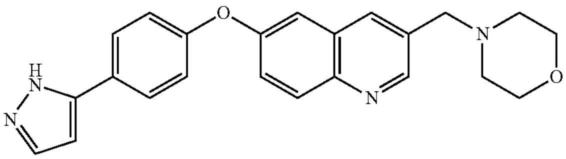 [SMILES: c1cc(-c2ccc(Oc3ccc4ncc(CN5CCOCC5)cc4c3)cc2)[nH]n1] | 3-Morpholin-4-ylmethyl-6-[4-(2H-pyrazol-3-yl)-phenoxy]-quinoline |
| 250 | 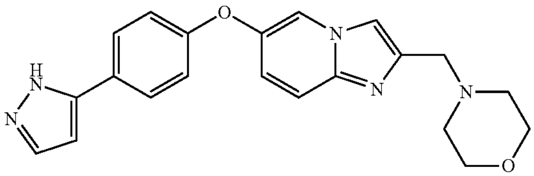 [SMILES: c1cc(-c2ccc(Oc3ccc4nc(CN5CCOCC5)cn4c3)cc2)[nH]n1] | 2-Morpholin-4-ylmethyl-6-[4-(2H-pyrazol-3-yl)-phenoxy]-imidazo[1.2-a]pyridine |

TABLE 1-continued

| No. | Structure | Compound Name |
|---|---|---|
| 251 | 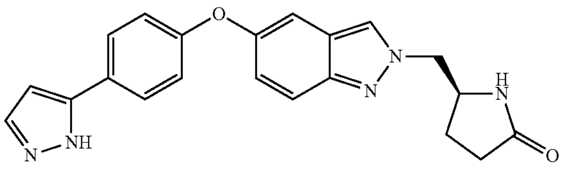 [SMILES: O=C1CC[C@@H](Cn2cc3cc(Oc4ccc(-c5ccn[nH]5)cc4)ccc3n2)N1] | (S)-5-{5-[4-(2H-Pyrazol-3-yl)-phenoxy]-indazol-2-ylmethyl}-pyrrolidin-2-one |
| 252 | 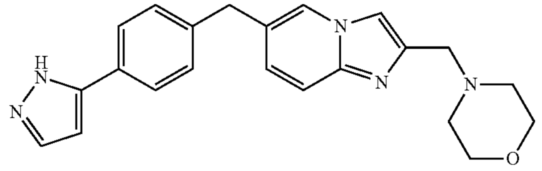 [SMILES: c1cc(-c2ccc(Cc3ccc4nc(CN5CCOCC5)cn4c3)cc2)[nH]n1] | 2-Morpholin-4-ylmethyl-6-[4-(2H-pyrazol-3-yl)-benzyl]-imidazo[1,2-a]pyridine |
| 253 | 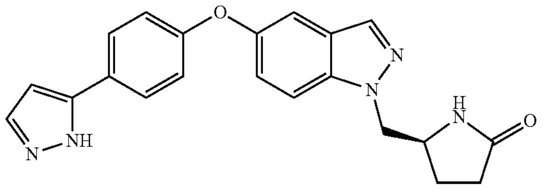 [SMILES: O=C1CC[C@@H](Cn2ncc3cc(Oc4ccc(-c5ccn[nH]5)cc4)ccc32)N1] | (S)-5-{5-[4-(2H-Pyrazol-3-yl)-phenoxy]-indazol-1-ylmethyl}-pyrrolidin-2-one |
| 254 | 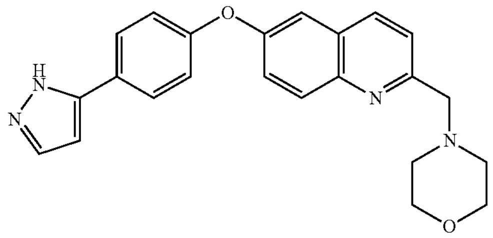 [SMILES: c1cc(-c2ccc(Oc3ccc4nc(CN5CCOCC5)ccc4c3)cc2)[nH]n1] | 2-Morpholin-4-ylmethyl-6-[4-(2H-pyrazol-3-yl)-phenoxy]-quinoline |
| 255 | 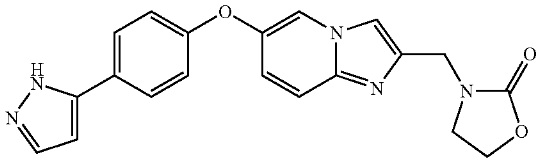 [SMILES: O=C1OCCN1Cc1cn2cc(Oc3ccc(-c4ccn[nH]4)cc3)ccc2n1] | 3-{6-[4-(2H-Pyrazol-3-yl)-phenoxy]-imidazo[1,2-a]pyridin-2-ylmethyl}-oxazolidin-2-one |
| 256 | 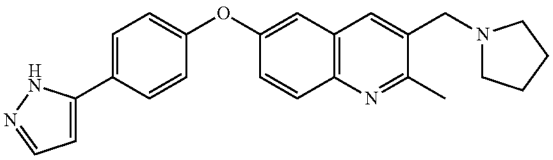 [SMILES: Cc1nc2ccc(Oc3ccc(-c4ccn[nH]4)cc3)cc2cc1CN1CCCC1] | 2-Methyl-6-[4-(2H-pyrazol-3-yl)-phenoxy]-3-pyrrolidin-1-ylmethyl-quinoline |
| 257 | 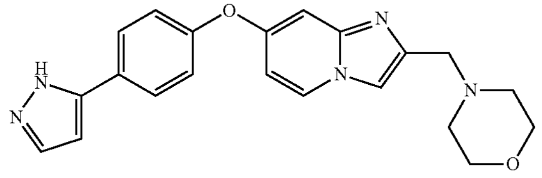 [SMILES: c1cc(-c2ccc(Oc3ccn4cc(CN5CCOCC5)nc4c3)cc2)[nH]n1] | 2-Morpholin-4-ylmethyl-7-[4-(2H-pyrazol-3-yl)-phenoxy]-imidazo[1,2-a]pyridine |
| 258 | 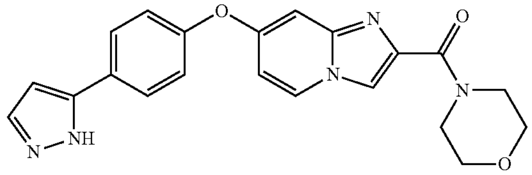 [SMILES: O=C(c1cn2ccc(Oc3ccc(-c4ccn[nH]4)cc3)cc2n1)N1CCOCC1] | Morpholin-4-yl-{7-[4-(2H-pyrazol-3-yl)-phenoxy]-imidazo[1,2-a]pyridin-2-yl}-methanone |

Examples of compounds of the invention.

TABLE 1-continued

Examples of compounds of the invention.

| No. | Structure | Compound Name |
|---|---|---|
| 259 | 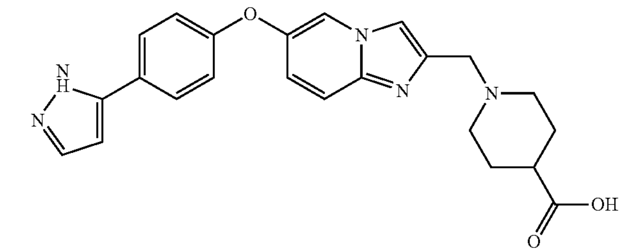 [SMILES: O=C(O)C1CCN(Cc2cn3cc(Oc4ccc(-c5ccn[nH]5)cc4)ccc3n2)CC1] | 1-{6-[4-(2H-Pyrazol-3-yl)-phenoxy]-imidazo[1,2-a]pyridin-2-ylmethyl}-piperidine-4-carboxylic acid |
| 260 | 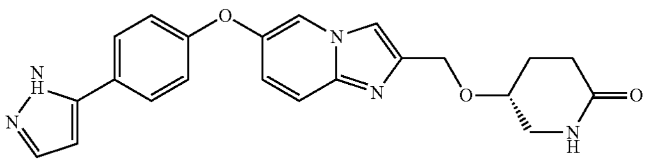 [SMILES: O=C1CC[C@@H](OCc2cn3cc(Oc4ccc(-c5ccn[nH]5)cc4)ccc3n2)CN1] | (R)-5-{6-[4-(2H-Pyrazol-3-yl)-phenoxy]-imidazo[1,2-a]pyridin-2-ylmethoxy}-piperidin-2-one |

In a further embodiment, the invention relates to any one of the compounds depicted in Table 1, and pharmaceutically acceptable salts thereof.

In another embodiment, the invention relates to a compound selected from the group consisting of:

2-Methoxy-1-(4-{6-[5-(2H-pyrazol-3-yl)-pyridin-2-yloxy]-naphthalen-2-ylmethyl}-piperazin-1-yl)-ethanone;
1-(4-{6-[5-(2H-Pyrazol-3-yl)-pyridin-2-yloxy]-naphthalen-2-ylmethyl}-piperazin-1-yl)-ethanone;
1-{6-[5-(2H-Pyrazol-3-yl)-pyridin-2-yloxy]-naphthalen-2-ylmethyl}-piperidin-4-ol;
1-{6-[5-(2H-Pyrazol-3-yl)-pyridin-2-yloxy]-naphthalen-2-ylmethyl}-piperidine-4-carboxylic acid amide;
N-(1-{6-[5-(2H-Pyrazol-3-yl)-pyridin-2-yloxy]-naphthalen-2-ylmethyl}-piperidin-4-yl)-acetamide;
(S)-3-Hydroxy-1-(1-{6-[5-(2H-pyrazol-3-yl)-pyridin-2-yloxy]-naphthalen-2-ylmethyl}-piperidin-4-yl)-pyrrolidin-2-one;
3-(1-{6-[5-(2H-Pyrazol-3-yl)-pyridin-2-yloxy]-quinolin-2-ylmethyl}-piperidin-4-yl)-oxazolidin-2-one;
1-(8-{6-[5-(2H-Pyrazol-3-yl)-pyridin-2-yloxy]-quinolin-2-ylmethyl}-3,8-diaza-bicyclo[3.2.1]oct-3-yl)-ethanone;
2-Methyl-1-(4-{6-[5-(2H-pyrazol-3-yl)-pyridin-2-yloxy]-quinolin-2-ylmethyl}-piperazin-1-yl)-propan-1-one;
2-Hydroxy-1-(4-{6-[5-(2H-pyrazol-3-yl)-pyridin-2-yloxy]-quinolin-2-ylmethyl}-piperazin-1-yl)-ethanone;
2-Methoxy-1-(4-{6-[5-(2H-pyrazol-3-yl)-pyridin-2-yloxy]-quinolin-2-ylmethyl}-piperazin-1-yl)-ethanone;
1-(4-{6-[5-(2H-Pyrazol-3-yl)-pyridin-2-yloxy]-quinolin-2-ylmethyl}-piperazin-1-yl)-propan-1-one;
8-{6-[5-(2H-Pyrazol-3-yl)-pyridin-2-yloxy]-quinolin-2-ylmethyl}-1,8-diaza-spiro[4.5]decan-2-one;
3-Oxo-3-(4-{6-[5-(2H-pyrazol-3-yl)-pyridin-2-yloxy]-quinolin-2-ylmethyl}-piperazin-1-yl)-propionitrile;
2-Hydroxy-N-methyl-N-(1-{6-[5-(2H-pyrazol-3-yl)-pyridin-2-yloxy]-quinolin-2-ylmethyl}-piperidin-4-yl)-acetamide;
2-((S)-3-Methyl-morpholin-4-ylmethyl)-5-[4-(2H-pyrazol-3-yl)-phenoxy]-1H-benzoimidazole;
5-[5-(2H-Pyrazol-3-yl)-pyridin-2-yloxy]-1-(2-pyrrolidin-1-yl-ethyl)-1H-indazole;
(2-Methoxy-ethyl)-{5-[4-(2H-pyrazol-3-yl)-phenoxy]-1H-benzoimidazol-2-ylmethyl}-amine;
1-[4-(2-{5-[5-(2H-Pyrazol-3-yl)-pyridin-2-yloxy]-indazol-1-yl}-ethyl)-piperazin-1-yl]-ethanone;
(1-{6-[5-(2H-Pyrazol-3-yl)-pyridin-2-yloxy]-quinolin-2-ylmethyl}-piperidin-4-yl)-acetonitrile;
1-{6-[5-(2H-Pyrazol-3-yl)-pyridin-2-yloxy]-quinolin-2-ylmethyl}-piperidine-4-carbonitrile;
1-[4-(2-[6-[5-(2H-Pyrazol-3-yl)-pyridin-2-yloxy]-quinolin-2-yl]-ethyl)-piperazin-1-yl]-ethanone;
1-[4-(Methyl-{6-[5-(2H-pyrazol-3-yl)-pyridin-2-yloxy]-quinolin-2-ylmethyl}-amino)-piperidin-1-yl]-ethanone;
4-(1-{1-[4-(2H-Pyrazol-3-yl)-benzyl]-1H-indol-5-ylmethyl}-piperidin-4-yl)-benzoic acid;
N-(1-{6-[5-(2H-Pyrazol-3-yl)-pyridin-2-yloxy]-2,3-dihydro-benzofuran-2-ylmethyl}-piperidin-4-yl)-acetamide;
N-(1-{6-[5-(2H-Pyrazol-3-yl)-pyridin-2-yloxy]-2,3-dihydro-benzofuran-2-ylmethyl}-piperidin-4-ylmethyl)-acetamide;
1-(1-[6-[5-(2H-Pyrazol-3-yl)-pyridin-2-yloxy]-2,3-dihydro-benzofuran-2-ylmethyl]-piperidin-4-yl)-pyrrolidin-2-one;
2-Hydroxy-1-(8-[6-[5-(2H-pyrazol-3-yl)-pyridin-2-yloxy]-quinolin-2-ylmethyl]-3,8-diaza-bicyclo[3.2.1]oct-3-yl)-ethanone;
N-[1-(2-[6-[5-(2H-Pyrazol-3-yl)-pyridin-2-yloxy]-benzofuran-3-yl]-ethyl)-piperidin-4-yl]-acetamide;
1-[4-(2-[6-[5-(2H-Pyrazol-3-yl)-pyridin-2-yloxy]-2,3-dihydro-benzofuran-3-yl]-ethyl)-[1,4]diazepan-1-yl]-ethanone;
1-[4-(2-{6-[5-(2H-Pyrazol-3-yl)-pyridin-2-yloxy]-benzofuran-3-yl}-ethyl)-piperazin-1-yl]-ethanone;
2-Hydroxy-1-((1S,4S)-5-{6-[5-(2H-pyrazol-3-yl)-pyridin-2-yloxy]-quinolin-2-ylmethyl}-2,5-diaza-bicyclo[2.2.1]hept-2-yl)-ethanone;
2-Hydroxy-1-(4-{6-[5-(2H-pyrazol-3-yl)-pyridin-2-yloxy]-quinolin-2-ylmethyl}-[1,4]diazepan-1-yl)-ethanone;
1-(4-{6-[5-(2H-Pyrazol-3-yl)-pyridin-2-yloxy]-benzofuran-3-ylmethyl}-piperazin-1-yl)-ethanone;
3-Methyl-1-{6-[5-(2H-pyrazol-3-yl)-pyridin-2-yloxy]-quinolin-2-ylmethyl}-azetidin-3-ol;
2-[(1S,4S)-1-(2-Oxa-5-aza-bicyclo[2.2.1]hept-5-yl)methyl]-6-[5-(2H-pyrazol-3-yl)-pyridin-2-yloxy]-quinoline;

{5-[4-(2H-Pyrazol-3-yl)-phenoxy]-1H-benzoimidazol-2-yl-methyl}-(S)-tetrahydro-furan-3-yl-amine;

1-{6-[5-(2H-Pyrazol-3-yl)-pyridin-2-yloxy]-quinolin-2-yl-methyl}-piperidin-4-ol;

(S)-1-{6-[5-(2H-Pyrazol-3-yl)-pyridin-2-yloxy]-quinolin-2-ylmethyl}-pyrrolidin-3-ol;

2-(4-Methoxy-piperidin-1-ylmethyl)-6-[5-(2H-pyrazol-3-yl)-pyridin-2-yloxy]-quinoline 1-(4-{6-[5-(2H-Pyrazol-3-yl)-pyridin-2-yloxy]-1H-indol-2-ylmethyl}-piperazin-1-yl)-ethanone;

1-(4-{6-[5-(2H-Pyrazol-3-yl)-pyridin-2-yloxy]-isoquinolin-3-ylmethyl}-piperazin-1-yl)-ethanone; and 1-(4-{6-[5-(1H-Pyrazol-3-yl)-pyridin-2-yloxy]-quinolin-2-ylmethyl}-piperazin-1-yl)-ethanone;

and pharmaceutically acceptable salts thereof.

All terms as used herein in this specification, unless otherwise stated, shall be understood in their ordinary meaning as known in the art. Other more specific definitions are as follows:

Unless otherwise defined, the phrases "compound of formula (I)s," "compounds of formula (I)," "compound of the invention" and "compounds of the invention" refer to the compounds described in any one of the embodiments above.

The term "$(C_1-C_6)$alkyl" refers to branched and unbranched alkyl groups having from 1 to 6 carbon atoms. Examples of —$(C_1-C_6)$alkyls include methyl, ethyl, n-propyl, isopropyl, n-butyl, sec-butyl, isobutyl, tert-butyl, n-pentane, iso-pentyl, neopentyl, n-hexane, iso-hexanes (e.g., 2-methylpentyl, 3-methylpentyl, 2,3-dimethylbutyl, and 2,2-dimethylbutyl). It will be understood that any chemically feasible carbon atom of the $(C_1-C_6)$alkyl group can be the point of attachment to another group or moiety.

The term "$(C_3-C_6)$cycloalkyl" refers to a nonaromatic 3- to 6-membered monocyclic carbocyclic radical. Examples of "$(C_3-C_6)$cycloalkyls" include cyclopropyl, cyclobutyl, cyclohexyl, cyclopentyl and cyclohexyl.

As used herein, the term "$(C_6-C_{10})$aryl" refers to an aromatic hydrocarbon rings containing from six to ten carbon ring and includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

As used herein, the term "4- to 9-membered N-heterocycle" includes stable nonaromatic 4- to 7-membered monocyclic heterocyclic radicals containing one N atom and optionally containing 1-3 additional heteroatoms independently selected from N, O and S, stable nonaromatic 7- to 8-membered bridged heterobicyclic radicals containing one N atom and optionally containing 1-3 additional heteroatoms independently selected from N, O and S, and aromatic 6-membered heteroaryl radicals containing 1-3 N atoms. The 4 to 9-membered N-heterocycle consists of carbon atoms, at least one nitrogen atom, and optionally one to three additional hetero-ring atoms selected from nitrogen, oxygen and sulfur. It will be understood that when a 4- to 9-membered N-heterocycle contains a S ring atom, such S ring atom can be present in the ring in its divalent, tetravalent, or hexavalent form, i.e., —S—, —S(O)— or —$S(O)_2$—. The term 4- to 9-membered N-heterocycle also includes compounds in which the substituents on two adjacent ring atoms join to form a 4- to 6-membered fused ring, and/or the substituents on the same ring atom join to form a 4- to 6-membered spirocyclic ring. It will be understood that any 4- to 6-membered fused ring or 4- to 6-membered spirocyclic ring may contain one to three additional ring hetero atoms selected from nitrogen, oxygen and sulfur, and said fused and spirocyclic rings may be further substituted by $G^1$ and $G^2$ groups (as defined above). The heterocycle may be either saturated or partially unsaturated. Non-limiting examples of stable nonaromatic 4- to 7-membered monocyclic heterocyclic radicals include azetidinyl, tetrahyropyrrolidinyl, tetrahydrofuranyl, oxazolidinyl, piperazinyl, piperidinyl, morpholinyl, dioxanyl, tetrahydropyranyl, thiomorpholinyl, azepanyl, 1,4-diazepanyl and 1,4-oxazepanyl. Non-limiting examples of stable nonaromatic 4- to 7-membered monocyclic heterocyclic radicals having a spirocyclic group include 2-oxa-6-aza-spiro[3.4]octanane, 1,8-diaza-spiro[4.5]decan-2-onane, 2-oxa-6-aza-spiro[3.5]nonanane, 1,8-diaza-spiro[4.5]decanane, and 2-oxa-6-aza-spiro[3.3]heptanane. Non-limiting examples of stable nonaromatic 4- to 7-membered monocyclic heterocyclic radicals fused to a 4- to 6-membered fused ring include hexahydro-oxazolo[3,4-a]pyrazin-3-one, hexahydro-pyrrolo[1,2-a]pyrazin-6-one, and octahydro-pyrrolo[3,4-c]pyrrole. Non-limiting examples of stable nonaromatic 6 to 8-membered bridged N-heterobicyclic radicals include 2-thia-5-aza-bicyclo[2.2.1]heptane 2,2-dioxide, 3,8-diaza-bicyclo[3.2.1]octane, 8-oxa-3-aza-bicyclo[3.2.1]octane, (endo)-(8-aza-bicyclo[3.2.1]oct-3-yl)amine, 2,5-diaza-bicyclo[2.2.1]heptane' (exo)-(8-aza-bicyclo[3.2.1]oct-3-yl)amine, 2,5-diaza-bicyclo[2.2.2]octane, 2-oxa-5-aza-bicyclo[2.2.1]heptane, and 3-aza-bicyclo[3.1.0]hexanel. Non-limiting examples of aromatic 6-membered heteroaryl radicals include pyridine and pyrimidine. A non-limiting example of a 4- to 9-membered N-heterocycle containing both a nonaromatic 4- to 7-membered monocyclic N-heterocyclic portion, a stable nonaromatic 7- to 8-membered bridged N-heterobicyclic and a fused ring is (1R,5S)-1,2,3,4,5,6-hexahydro-1,5-methano-pyrido[1,2-a][1,5]diazocin-8-one.

As used herein, the term "4- to 7-membered heterocycle" refers to stable nonaromatic 4- to 7-membered monocyclic heterocyclic radicals and stable aromatic 5- to 6-membered monocyclic heterocyclic radicals (or "5 to 6-membered heteroaryl"). The 4- to 7-membered heterocycle consists of carbon atoms and one or more, preferably from one to four heteroatoms chosen from nitrogen, oxygen and sulfur. The nonaromatic 4- to 7-membered monocyclic heterocyclic may be either saturated, partially unsaturated, or aromatic. Non-limiting examples of nonaromatic 4- to 7 membered monocyclic heterocyclic radicals include tetrahydrofuranyl, azetidinyl, oxazolidinyl tetrahydropyrrolidinyl, pyranyl, tetrahydropyranyl, dioxanyl, thiomorpholinyl, thiomorpholinyl, morpholinyl, piperidinyl, piperazinyl, 1,3-oxazinanyl and azepinyl. The 5- to 6-membered heteroaryl consists of carbon atoms and one or more, preferably from one to three heteroatoms chosen from nitrogen, oxygen and sulfur. Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. It will be understood that when a 4- to 7-membered heterocycle contains a S ring atom, such S ring atom can be present in the ring in its divalent, tetravalent, or hexavalent form, i.e., —S—, —S(O)— or —$S(O)_2$—.

Each aryl or heteroaryl unless otherwise specified includes it's partially or fully hydrogenated derivatives. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

The term "heteroatom" as used herein shall be understood to mean atoms other than carbon such as O, N, and S.

The term "halo" or "halogen" refers to fluoro, chloro, bromo or iodo.

The symbol

means point of attachment of a group R to a moiety.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

The compounds of the invention are only those which are contemplated to be 'chemically stable' as will be appreciated by those skilled in the art. For example, a compound which would have a 'dangling valency', or a 'carbanion' is not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1$-$C_4)$alkyl$)^{4+}$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

General Synthetic Methods

The compounds of the invention may be prepared by the examples presented below, and methods known to those of ordinary skill in the art and reported in the chemical literature. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section.

EXAMPLES

General Methods:

Unless noted otherwise, all reactions are run at ambient temperature (about 25° C.), under inert atmosphere (e.g., Argon, $N_2$), and under anhydrous conditions. All compounds are characterized by at least one of the following methods: $^{1}H$ NMR, HPLC, HPLC-MS, and melting point.

Typically, reaction progress is monitored by thin layer chromatography (TLC) or HPLC-MS. Intermediates and products are purified using at least one of the following methods:

Flash chromatography on silica gel,

Recrystallization,

Chiral HPLC using a 20×500 mm Chiralpak AD-H column, or 20×500 mm Chiralpak OD-H column, and eluting with an isocratic mixture of isopropanol in heptanes with 0.1% diethylamine (DEA) at 7.5 mL/min, 20×250 mm Chiralcel OD-H column, and eluting with an isocratic mixture of isopropanol in heptanes at 7.5 mL/min, Super Critical Fluid (SCF) Chiral HPLC using a 3.0×25.0 cm RegisPack column, eluting with an isocratic mixture of MeOH, isopropylamine (IPA), and super critical carbon dioxide at 125 bar; 80 mL/min, and/or Reversed phase HPLC using a C18 semi-preparative column eluting with a gradient of MeCN+0.1% TFA/$H_2O$+0.1% TFA, or MeCN+0.1% formic acid/$H_2O$+0.1% formic acid.

The reported MS data is for observed $[M+H]^+$. For bromine containing compounds, the $[M+H]^+$ is either reported for one or both of the bromine isotopes (i.e., $^{79}Br$ and $^{81}Br$).

Compounds of the invention are characterized using LC/MS/MS with electron spray ionization (ESI). The LC method includes the following parameters:

Injection volume: 5 uL

Mobile Phases: 0.1% Formic Acid in Water (A) and 0.1% Formic Acid in Acetonitrile (B) (HPLC grade)

Left and Right Temperature: 35° C.

Run Time: 4 min

Column: Thermo Scientific, Aquasil C18, 50×2.1 mm, 5μ, part number 77505-052130, or equivalent LC Pump Gradient:

| Total Time (min) | Flow Rate (uL/min) | % A | % B |
|---|---|---|---|
| 0 | 500 | 90.0 | 10.0 |
| 0.5 | 500 | 90.0 | 10.0 |
| 1.5 | 500 | 1.0 | 99.0 |
| 2.5 | 500 | 1.0 | 99.0 |
| 3.0 | 500 | 90.0 | 10.0 |
| 4.0 | 500 | 90.0 | 10.0 |

Synthesis of Intermediates

Intermediate A: Preparation of 2-Chloro-5-[2-(2-trimethylsilanyl-ethoxymethyl)-2H-pyrazol-3-yl]-pyridine (A)

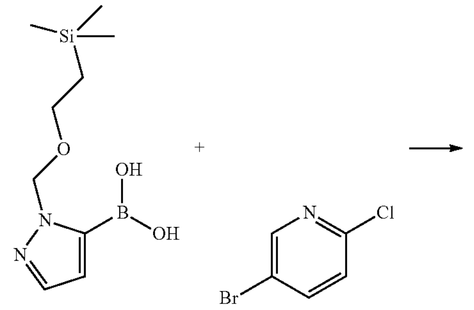

A-1 A-2

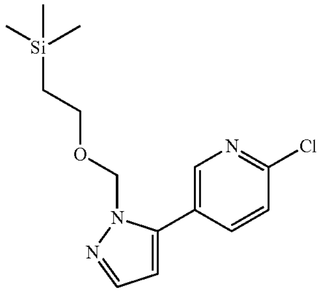

A

To a mixture of A-1 (16.0 g, 83.1 mmol) and A-2 (24.1 g, 99.6 mmol) in THF (200 mL) is added an aqueous solution of $Na_2CO_3$ (26.0 g, 100 mL of water). The mixture is sparged with Ar for 30 min Next, tetrakis(triphenylphosphine)palladium(0) (1.92 g, 1.66 mmol) is added and the resultant mixture is heated at 76° C. for 16 h. The mixture is diluted with water (400 mL) and extracted with EtOAc (2×150 mL). Phases are separated, and the aqueous layer is extracted with EtOAc (100 mL). The combined organic layers are washed with brine (150 mL), dried over $Na_2SO_4$, filtered and concentrated. The residue is purified on $SiO_2$ (0-40% EtOAc in heptane) to give the title product (A).

Intermediate B: Preparation of 4-[2-(2-Trimethylsilanyl-ethoxymethyl)-2H-pyrazol-3-yl]-phenol (B)

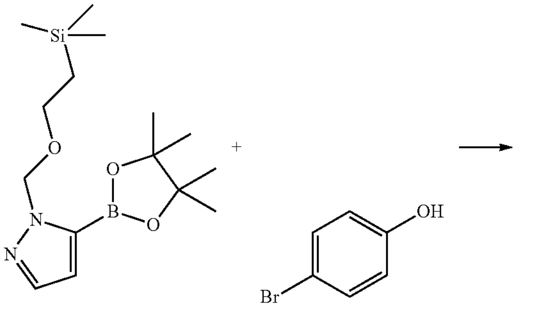

B-1 B-2

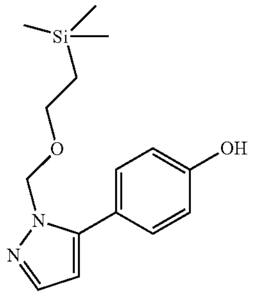

B

A suspension of B-1 (5.6 g, 17 mmol), B-2 (2.5 g, 14 mmol), Tetrakis(triphenylphosphine)palladium(0) (1.6 g, 1.4 mmol) in a mixture of DME (75 mL) and aqueous $Na_2CO_3$ (2 N, 22 mL) is evacuated and purged thrice with argon, and heated at 100° C. for 16 hours. Upon cooling, the reaction is diluted with EtOAc, washed with water, brine and dried over $Na_2SO_4$, filtered and concentrated. The residue is purified on $SiO_2$ (10-60% EtOAc in heptane) to give the title product (B).

Intermediate C: Preparation of 6-{5-[2-(2-Trimethyl-silanyl-ethoxymethyl)-2H-pyrazol-3-yl]-pyridin-2-yloxy}-naphthalene-2-carbaldehyde (C)

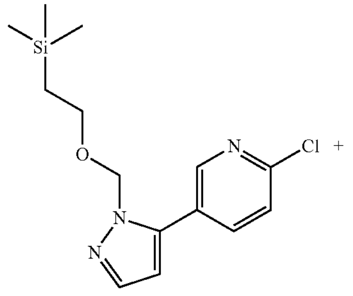

A

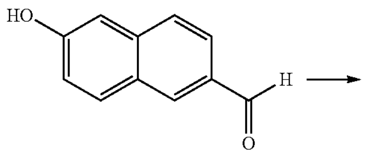

C-1

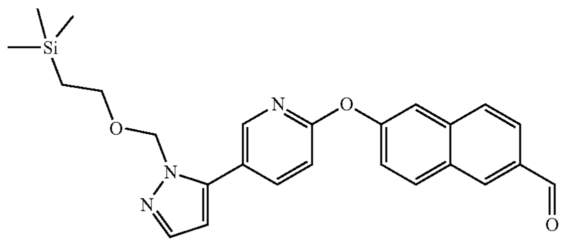

C

A mixture of A (1.90 g, 6.132 mmol), C-1 (1.00 g, 6.132 mmol) and $K_2CO_3$ (1.20 g, 9.20 mmol) in DMF (10 mL) is stirred at 120° C. After 2 days, the mixture is poured into water and thrice extracted with EtOAc. The combined organic extracts are washed with water and brine, dried over $Na_2SO_4$, filtered and concentrated. The residue is purified by flash chromatography (0-40% EtOAc/heptane) to give the title product (C). MS (ES+): m/z 446.2 $[M+H]^+$ Intermediate D: Preparation of 6-{5-[2-(2-Trimethyl-silanyl-ethoxymethyl)-2H-pyrazol-3-yl]-pyridin-2-yloxy}-quinoline-2-carbaldehyde (D)

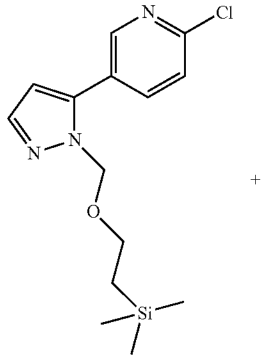

A

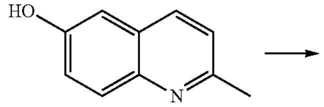

D-2

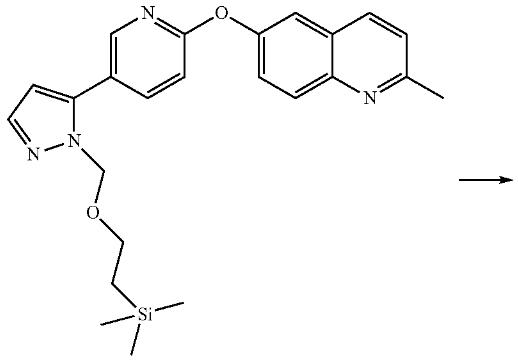

D-3

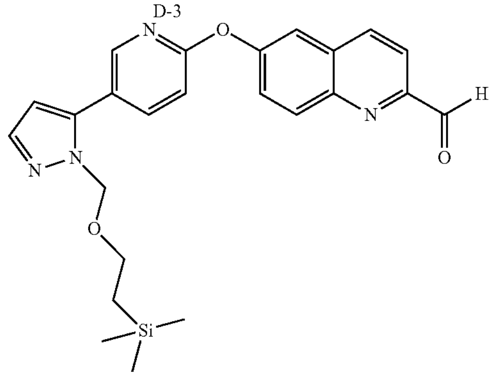

D

A solution of A (31.0 g, 100 mmol) and D-2 (17.5 g, 110 mmol) in DMSO (300 mL) is treated with potassium carbonate (69.0 g, 500 mmol) and the mixture is sparged with argon for 5 minutes. The reaction is warmed to 130° C. under an Ar atmosphere overnight. After cooling to room temperature, the mixture is poured into water (1000 mL), neutralized to pH 7 with aqueous 1N HCl and is extracted with EtOAc (3×300 mL). The extracts are combined, washed with water (4×300 mL) and brine (300 mL), dried over $Na_2SO_4$, filtered and concentrated. The residue is dissolved in a minimum amount of DCM, treated with activated charcoal, filtered through Diatomaceous earth, and concentrated to afford the crude intermediate D-3.

Selenium dioxide (11.4 g, 103 mmol) is added to a solution of D-3 (37.0 g, 85.5 mmol) in 1,4-dioxane (300 mL). The reaction is then warmed to 100° C. for 3.5 h, cooled to ambient temperature, filtered through Diatomaceous earth, and concentrated. The residue is dissolved in dichloromethane (300 mL) and passed though Diatomaceous earth, and concentrated. The residue is passed through a bed of silica gel (400 g), eluting with a gradient of 0-40% EtOAc in heptanes (10% increase in gradient every 1 L, and holding at 40% until product eluted). The fractions containing the product are pooled and concentrated. The residue is triturated with heptanes and the resultant solid is filtered to afford the title compound (D).

Intermediate E: Preparation of (6-{4-[2-(2-Trimethylsilanyl-ethoxymethyl)-2H-pyrazol-3-yl]-phenoxy}-quinolin-2-yl)-methanol (E)

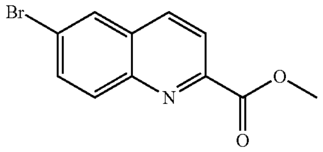

E-1

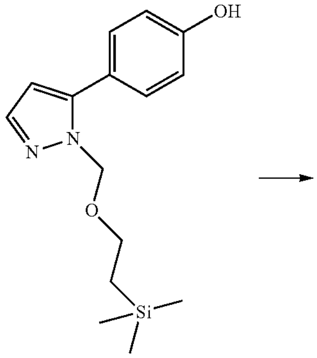

B

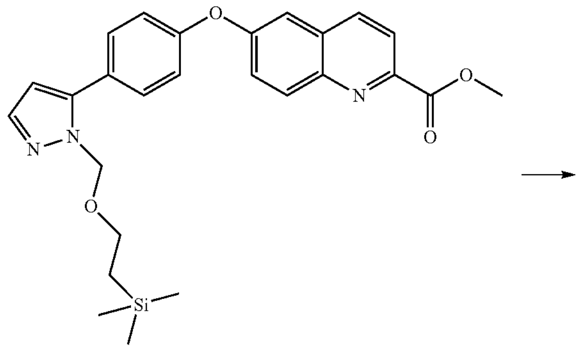

E-2

-continued

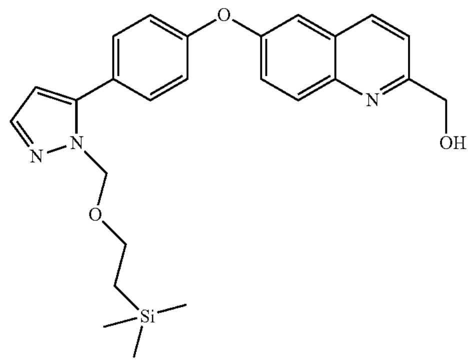

E

Compound E-2 is synthesized from intermediates E-1 (1032 mg, 3.88 mmol) and B (1.183 g, 4.07 mmol) according to procedure described for the synthesis of 258-3 from 258-2 and intermediate B.

The title product (E) is synthesized from intermediate E-2 (322 mg, 0.68 mmol) according to procedure described for the synthesis of intermediate AU from AU-3.

Intermediate F: Preparation of 2-(piperazin-1-ylmethyl)-6-[4-(1H-pyrazol-5-yl)phenoxy]quinoline (F)

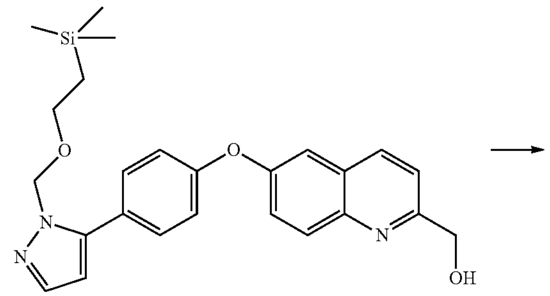

E

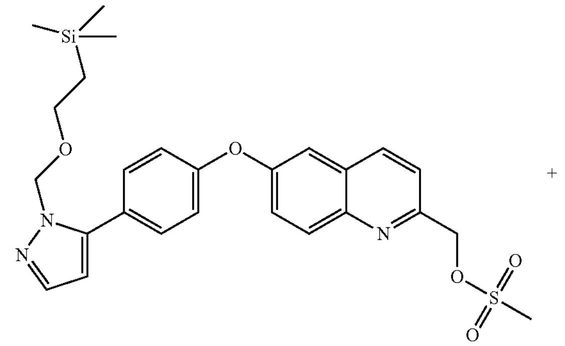

F-1

-continued

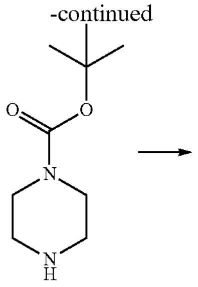

F-2

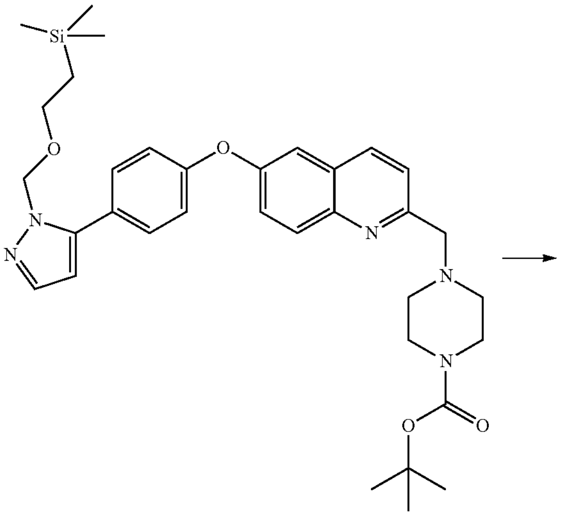

F-3

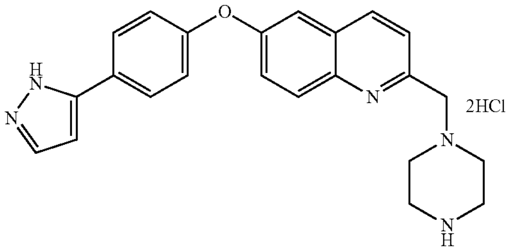

F

A stirred solution of E (1.00 g, 2.23 mmol) in DCM (2.00 mL) is treated with methanesulfonyl chloride (0.208 mL, 2.68 mmol), and triethylamine (0.374 mL, 2.68 mmol). After 2 h, the volatiles are removed under vacuum to provide the crude intermediate F-1, which is redissolved in DCM (2.00 mL), and treated with F-2 (0.998 g, 5.36 mmol). After stirring for 18 h, the mixture is concentrated and the resultant residue is purified using silica gel flash chromatography (15-60% EtOAc in heptane) to afford intermediate F-3.

A stirred solution of F-3 (0.301 g, 0.490 mmol) in methanol (0.250 mL) is treated with a to solution of HCl in dioxane (4N, 5.00 mL). After 12 h, the mixture is concentrated to afford the title compound (F), as a dihydrochloride salt.

Intermediate G: Preparation of 2,2-dioxo-2-λ-6-thia-5-azabicyclo[2.2.1]heptane (G)

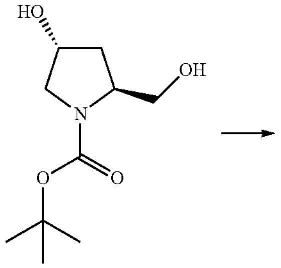

G-1

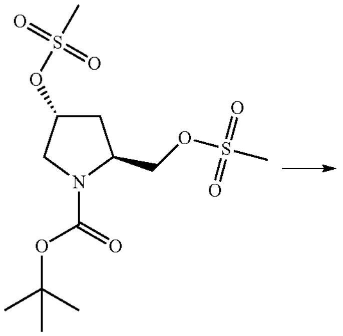

G-2

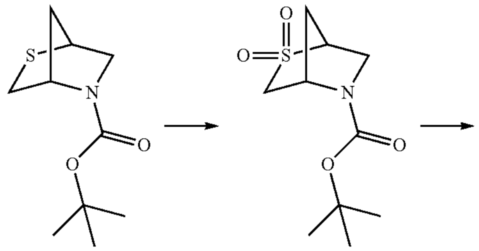

G-3 G-4

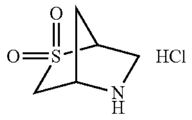

G

A solution of G-1 (5.00 g, 23.0 mmol) in DCM (10.0 mL) is treated with triethylamine (8.02 mL, 575 mmol) and cooled in an ice bath. The resultant mixture is treated with methanesulfonyl chloride (3.93 mL, 505 mmol) and warmed to 25° C. over 4 h. The volatiles are removed in vacuo, the resultant residue is redissolved in EtOAc (100 mL) and poured into saturated aqueous $NH_4Cl$ (150 mL). The aqueous phase is separated and extracted with EtOAc (2×100 mL). The organic layers are combined, dried over $Na_2SO_4$, decanted and concentrated. The resultant residue is purified using silica gel flash chromatography (20-100% EtOAc in Heptane) to afford intermediate G-2.

A solution of G-2 (7.93 g, 21.2 mmol) in DMSO (15 mL) is treated with sodium sulfide.$9H_2O$ (5.36 g, 22.3 mmol) and heated to 110° C. for 1 h. The reaction is cooled to 25° C. and diluted with $H_2O$ (100 mL) and EtOAc (100 mL). The aqueous phase is separated and extracted with EtOAc (2×100 mL). The organic layers are combined, dried over $Na_2SO_4$, decanted and concentrated. The resultant residue is purified using silica gel flash chromatography (0-5% MeOH in DCM) to afford the intermediate G-3.

A stirred solution of G-3 (1.00 g, 4.64 mmol) in DCM (10 mL) is treated with 3-chloroperbenzoic acid (2.65 g, 11.8 mmol). After 48 h, the reaction is quenched with aqueous NaOH (1N, 50 mL). The aqueous phase is separated and extracted with DCM (2×50 mL). The organic layers are combined and washed with $H_2O$ (200 mL), brine (200 mL), dried over $Na_2SO_4$, decanted and concentrated to afford the crude intermediate G-4.

G-4 (0.066 g, 0.27 mmol) is dissolved in a solution of HCl in Dioxane (4N, 2 mL). After 2 h, the volatiles are removed in vacuo to afford the title product (G), as the hydrochloride salt.

Intermediate H: Preparation of 2-methoxy-1-piperazin-1-yl-ethanone (H)

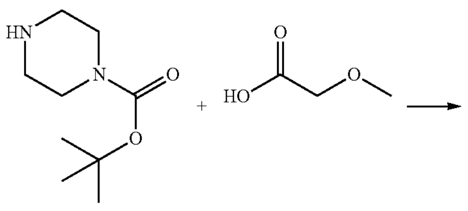

F-2 H-1

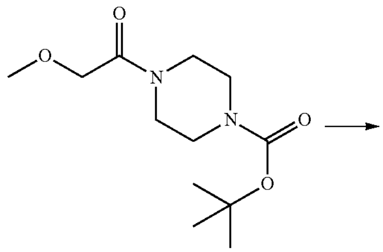

H-2

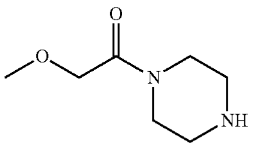

H

A stirred solution of H-1 (100 μL, 1.25 mmol) in MeCN (10 mL) is treated with TBTU (400 mg, 1.25 mmol). After 20 minutes, F-2 (0.190 g, 1.00 mmol) is added and the mixture is stirred overnight. The reaction is poured into dilute aqueous $Na_2CO_3$, and extracted with DCM (3×5 mL). The combined extracts are dried over $Na_2SO_4$, filtered and concentrated. The residue is dissolved in DCM and passed through a MP-tosic acid cartridge, and concentrated to afford H-2.

A stirred solution of H-2 (0.100 g, 0.380 mmol) in 1,4-dioxane (4 mL) is treated with a solution of HCl in 1,4-dioxane (4M, 1 mL). After 72 h, the reaction is concentrated, redissolved in wet MeOH, passed through a PS—$HCO_3$ cartridge, and concentrated to afford the title product (H).

Intermediate I: Preparation of 2-methanesulfonyl-1-piperazin-1-yl-ethanone (I)

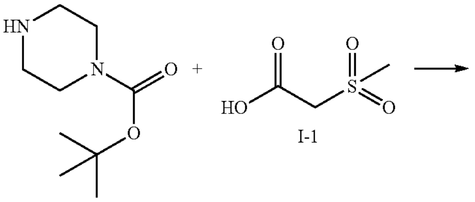

I-1

F-2

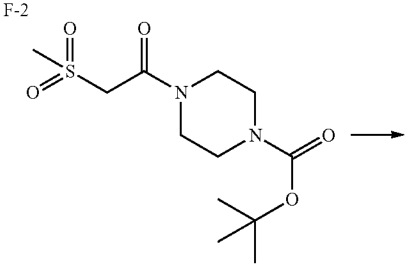

I-2

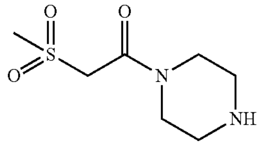

I

The title product (I) is synthesized from Intermediates F-2 (0.190 g, 1.00 mmol) and I-1 (0.170 g, 1.20 mmol) according to the procedure described for the synthesis of intermediate H.

Intermediate J: Preparation of 3-oxo-3-piperazin-1-yl-propionitrile (J)

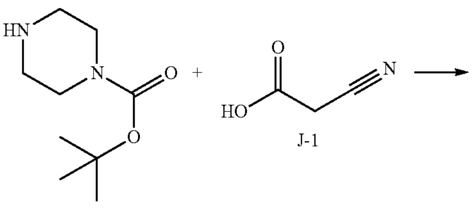

J-1

F-2

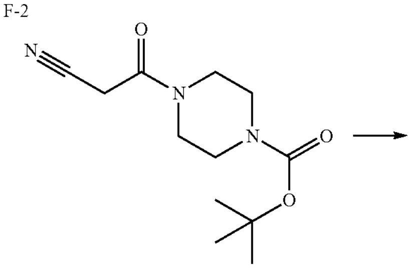

J-2

-continued

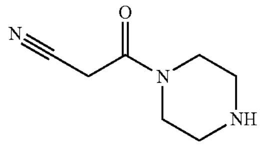

J

The title product (J) is synthesized from Intermediates F-2 (0.190 g, 1.00 mmol) and J-1 (0.170 g, 1.20 mmol) according to the procedure described for the synthesis of intermediate H.

Intermediate K: Preparation of 1,8-Diaza-spiro[4.5]decan-2-one (K)

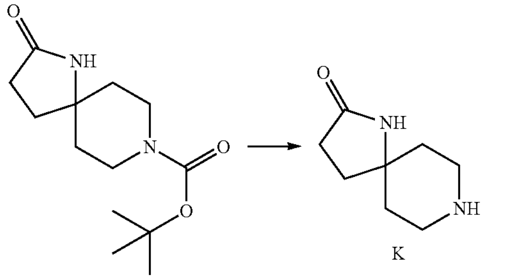

K-1

K

To a stirred solution of K-1 (0.25 g, 0.98 mmol) in 1,4-dioxane (5 mL) is added a solution of HCl in 1,4-dioxane (4M, 2.5 mL). After 72 h, the reaction is diluted with $Et_2O$, and the mixture is filtered under an inert atmosphere. The filter cake is dissolved in MeOH, passed though a PS—$HCO_3$ cartridge, and concentrated to afford the title product (K).

Intermediate L: Preparation of 4-{4-[2-(2-Trimethyl-silanyl-ethoxymethyl)-2H-pyrazol-3-yl]-phenoxy}-benzene-1,2-diamine (L)

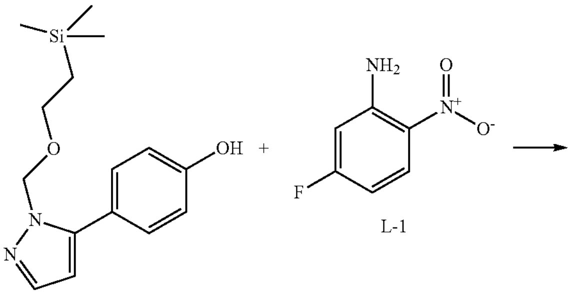

B

L-1

-continued

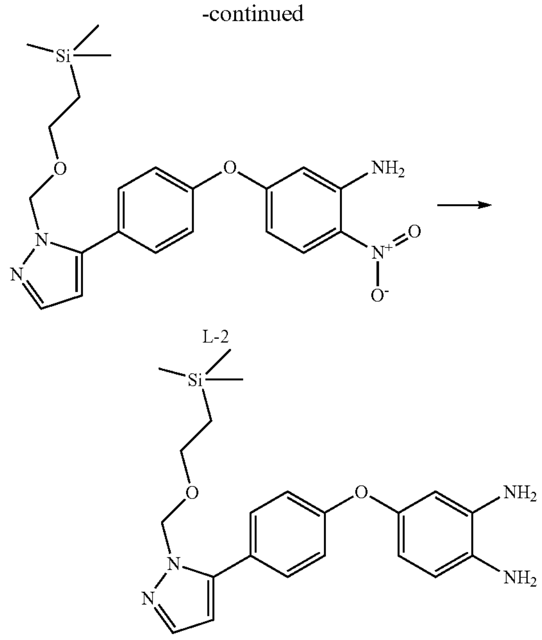

L-2

L

A solution of B (1.00 g, 3.44 mmol) in DMF (4 mL) is treated with cesium carbonate at ambient temperature. After 20 min, L-1 (597 mg, 3.44 mmol) is added and the mixture is stirred at 70° C. for 16 h. The mixture is diluted with EtOAc (20 mL), and is washed with water (5 mL). Phases are separated; the organic layer is washed with brine (5 mL), dried over $Na_2SO_4$, filtered and concentrated. The residue is purified by flash chromatography (10-50% EtOAc in Heptane) to give L-2.

A mixture of L-2 (600 mg, 1.41 mmol), 10% Pd on carbon (149 mg), and ammonium format (887 mg, 14.1 mmol) in ethanol (10 mL) is stirred under an atmosphere of $H_2$ at ambient temperature. After 16 h, the mixture is filtered though a pad of Diatomaceous earth and concentrated. The residue is purified by flash chromatography (1-6% MeOH with 7N ammonia in DCM) to give the title product (L).

Intermediate M: Preparation of 4-{4-[2-(2-Trimethylsilanyl-ethoxymethyl)-2H-pyrazol-3-yl]-benzyl}-benzene-1,2-diamine (M)

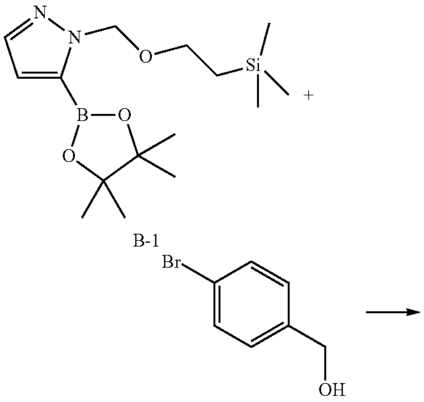

B-1

M-1

-continued

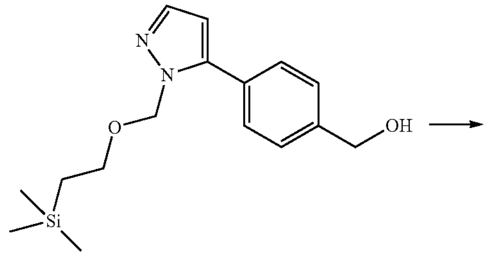

M-2

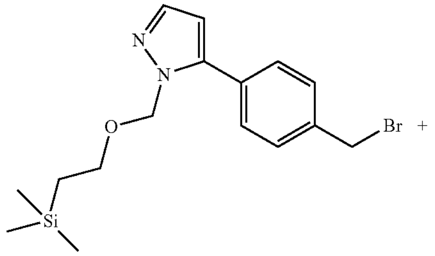

M-3

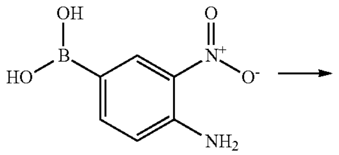

M-4

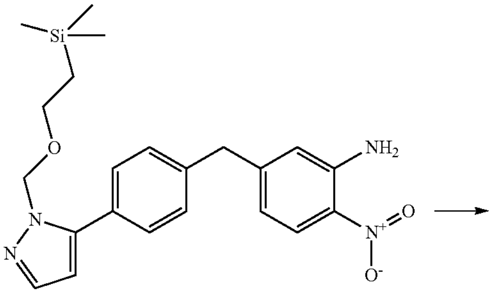

M-5

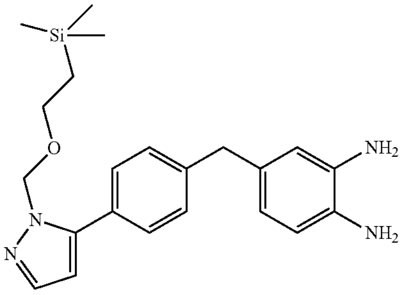

M

To a stirred solution of M-1 (1.00 g, 5.35 mmol) in DME (20 mL) is added Tetrakis(triphenylphosphine)palladium(0) (309 mg, 0.27 mmol). After 10 min, B-1 (1.60 g, 6.42 mmol) and aqueous solution of $Na_2CO_3$ (2M, 8.01 mL) are added; the mixture is sparged with Ar and heated to 100° C. in a microwave for 20 min Upon cooling to ambient temperature, the reaction mixture is diluted with EtOAc (20 mL) and washed with water (10 mL). The organic layer is dried over $Na_2SO_4$, filtered and concentrated. The resultant residue is purified by flash chromatography (10-80% EtOAc in Heptane) to yield M-2.

To a solution of M-2 (1.28 g, 4.20 mmol) in DCM (50 mL) is added PS-triphenylphosphine (3 mmol/g polymer-supported, 4.20 g, 12.6 mmol) and carbon tetra bromide (4.18 g, 12.6 mmol). The reaction is stirred for 1 h at ambient temperature, filtered and concentrated. The residue is purified by flask chromatography (10-40% EtOAc in Heptane) to give M-3.

To a degassed solution of M-3 (1.10 g, 2.99 mmol), M-4 (654 mg, 3.59 mmol) and bromo(N-succinimidyl)bis(triphenylphosphine)palladium(II) (121 mg, 0.150 mmol) in DME (12 mL) is added aqueous solution of $Na_2CO_3$ (2M, 4.49 mL). The mixture is heated to 80° C. in microwave for 1 h, cooled to ambient temperature, diluted with EtOAc (20 mL) and washed with water (10 mL). The organic layer is washed with brine (10 mL), dried over $Na_2SO_4$, filtered and concentrated. The resultant residue is purified by flash chromatography (5-60% EtOAc in heptane) to give M-5.

A solution of M-5 (1.17 g, 2.75 mmol) in MeOH (25 mL) is heated to 70° C. Ammonia formate (1.74 g, 27.6 mmol) is added, followed by careful addition of zinc (900 mg, 13.8 mmol). The mixture is heated to reflux for 10 min, cooled to ambient temperature, filtered through a pad of Diatomaceous earth, and concentrated. The residue is purified by flash chromatography (1-6% MeOH containing 10% $NH_4OH$/DCM) to give the title product (M).

Intermediate N: Preparation of 5-[4-(2H-pyrazol-3-yl)-phenoxy]-1H-benzoimidazole-2-carbaldehyde (N)

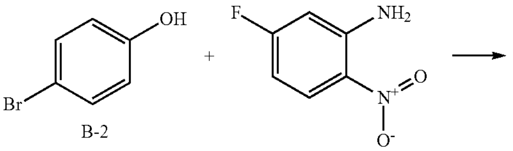

B-2

L-1

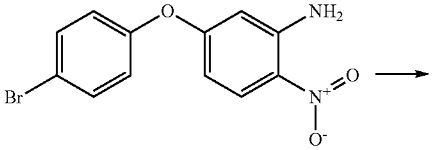

N-1

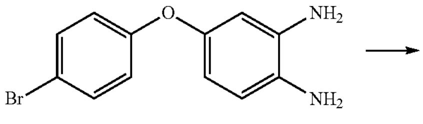

N-2

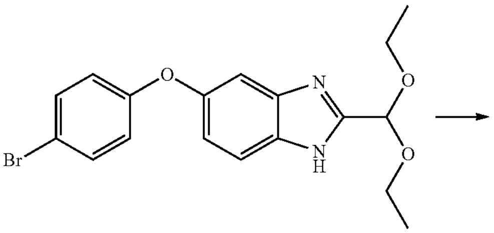

N-3

-continued

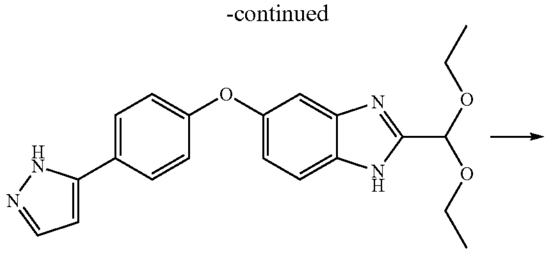

N-4

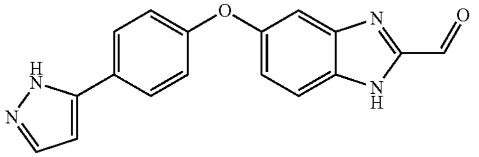

N

A mixture of B-2 (11.1 g, 64.2 mmol), L-1 (10.0 g, 64.1 mmol), and $K_2CO_3$ (22.3 g, 161 mmol) in DMSO (50 mL) is heated at 70° C. for 16 h. The reaction mixture is cooled to ambient temperature, poured into ice-water (300 mL) and stirred for 1 h. The resultant solids are filtered to give N-1.

A mixture of N-1 (6.40 g, 20.7 mmol), ammonium formate (13.5 g, 214 mmol), and Zinc (4.00 g, 61.2 mmol) in MeOH (50 mL) is heated at 70° C. for 3 h. The reaction mixture is cooled to ambient temperature, filtered through a pad of Diatomaceous earth, and concentrated. The residue is purified by flash chromatography (0-7.5% MeOH containing 10% $NH_4OH$/DCM) to give N-2.

Intermediate N-2 (3.40 g, 12.2 mmol) and ethyl diethyloxyacetate (2.80 mL, 15.7 mmol) are slowly added to a solution of NaOEt (freshly prepared from 700 mg of Na and 100 mL of EtOH). The resultant mixture is heated to reflux for 16 h, cooled to ambient temperature, diluted with DCM (100 mL), washed with $H_2O$ (2×75 mL), dried over $Na_2SO_4$, filtered, and concentrated. The residue is purified by flash chromatography (0-100% EtOAc in heptane) to give N-3.

An aqueous solution of $K_3PO_4$ (1M, 1.0 mL) is added to a mixture of 1H-pyrazole-5-boronic acid (55.0 mg, 0.490 mmol), N-3 (100 mg, 0.260 mmol), and $PdCl_2$(dppf) (40 mg, 0.050 mmol) in a solution of DME:$H_2O$:EtOH (7:3:2; 3.0 mL). The mixture is heated at 100° C. in a microwave for 30 min, cooled to ambient temperature, diluted with EtOAc (50 mL), and washed with $H_2O$ (50 mL). The organic layer is dried over $Na_2SO_4$, filtered and concentrated. The residue is purified by flash chromatography (1-10% MeOH containing 10% $NH_4OH$/DCM) to give N-4.

A mixture of N-4 (1.78 g, 4.70 mmol) in aqueous $H_2SO_4$ (1M, 20.0 mL) is heated at 100° C. for 1 h. Upon cooling to ambient temperature, the pH of the reaction is adjusted to 8 with a solution of saturated aqueous $Na_2CO_3$. The resultant mixture is filtered to give the title product (N).

Intermediates O and P: Preparation of ((2R,6R)-2,6-Dimethyl-morpholin-4-yl)-acetic acid (O) and ((2R, 6S)-2,6-Dimethyl-morpholin-4-yl)-acetic acid (P)

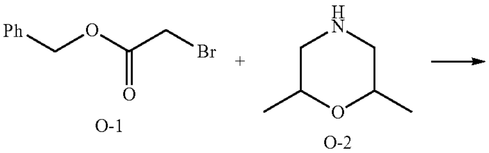

O-1

O-2

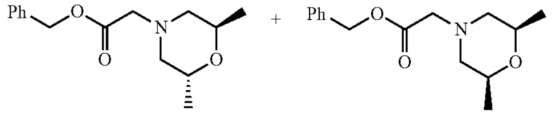

O-3

O-4

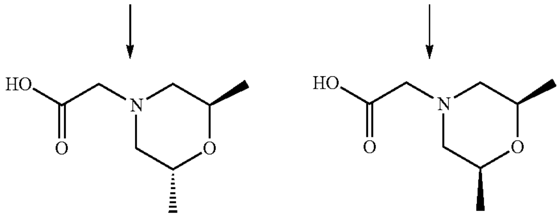

O

P

A solution of O-2 (422 mg, 3.67 mmol) in MeCN (6 mL) is treated with $K_2CO_3$ (1.05 g, 7.64 mmol) and O-1 (500 μL, 3.05 mmol). The mixture is stirred at 50° C. for 16 h, cooled to ambient temperature and filtered. The solid is washed with MeCN (20 mL). The combined organic layers are concentrated and the residue is purified by chromatography (10-50% EtOAc in Heptane) to give O-3 and O-4.

A mixture of O-4 (594 mg, 2.26 mmol) and 10% Pd on carbon (190 mg, 0.180 mmol) in MeOH (15 mL) are stirred under an atmosphere of $H_2$ for 2 h. The mixture is filtered though a pad of Diatomaceous earth, the pad is washed with MeOH (20 mL), and the combined filtrates are concentrated to yield the title product (P).

The title product O is synthesized from O-3 according to the procedure described for the synthesis of P from O-4.

The following intermediates are synthesized from their corresponding amine reagents according to the procedure described for the synthesis of intermediate P. In general, chiral HPLC is utilized for the isolation of a desired enantiomer.

| Intermediate | Name | Structure | Amine Reagent |
| --- | --- | --- | --- |
| Q | Pyrrolidin-1-yl acetic acid | 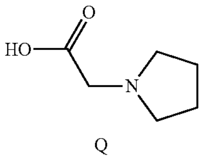 Q | 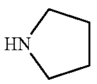 Q-1 |

-continued

| Intermediate | Name | Structure | Amine Reagent |
|---|---|---|---|
| R | ((3S,5S)-3,5-Dimethyl-morpholin-4-yl)-acetic acid | 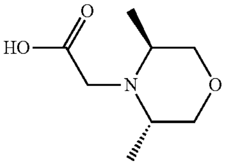 R | 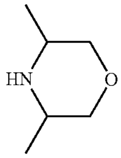 R-1 |
| S | ((S)-3-Methyl-morpholin-4-yl)-acetic acid | 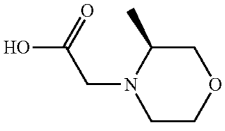 S | 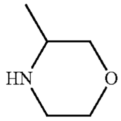 S-1 |

Intermediate T: Preparation of 5-[4-[2-(2-trimethylsilylethoxymethyl)pyrazol-3-yl]phenoxy]pyridin-2-amine (T)

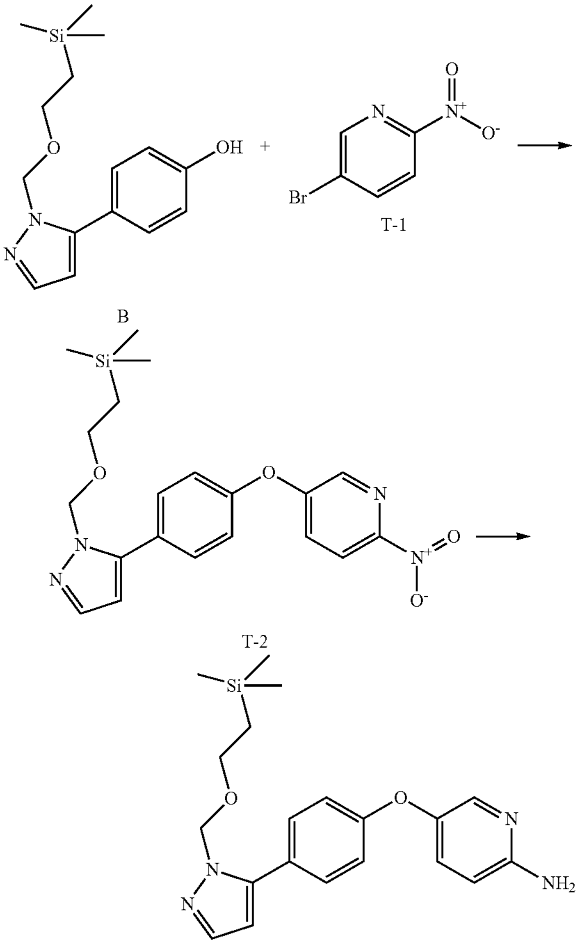

B T-1 T-2 T

To a stirred solution of intermediate B (2.00 g, 6.89 mmol) in DMF (15 mL) is added cesium carbonate (4.50 g, 13.8 mmol). After 20 min, T-1 (1.50 g, 7.58 mmol) is added and the mixture is stirred at 60° C. for 2 h. The mixture is diluted with EtOAc (50 mL) and washed with water (2×10 mL). The organic layer is dried over $Na_2SO_4$, filtered and concentrated. The residue is purified by flash chromatography (0-50% EtOAc in heptane) to give T-2.

A solution of T-2 (1.87 g, 4.53 mmol) in MeOH (45 mL) is treated with Pd (10% on carbon, 200 mg). The mixture is stirred under an atmosphere of $H_2$ for 3 h, flittered and concentrated. The residue is purified by flash chromatography (0-6% MeOH in DCM) to give title product (T).

Intermediate U: Preparation of 5-(2-chloroacetyl)piperidin-2-one (U)

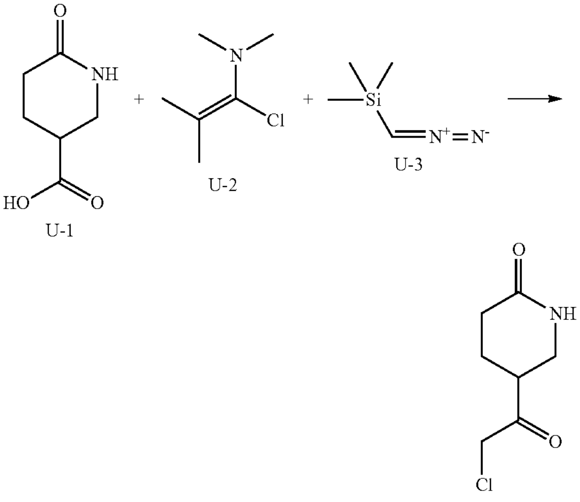

U-1 U-2 U-3 U

To a suspension of U-1 (500 mg, 3.49 mmol) in DCM (16 mL) is added U-2 (1.46 g, 10.48 mmol). The mixture is stirred at ambient temperature for 30 min, concentrated, suspended in toluene (10 mL), and concentrated. The resulting residue is dissolved in MeCN (8 mL), U-3 (2M solution in ether, 8.73 mL) is added and the mixture is stirred at ambient temperature for 30 min. The reaction mixture is cooled to 0° C. and HCl (4M solution in dioxane, 5.24 mL) is added. The resultant solution is stirred at 0° C. for 10 min, neutralized with saturated aqueous $NaHCO_3$ to pH 7, and extracted with EtOAc (20 mL). The organic layer is dried over $Na_2SO_4$, filtered and concentrated to afford the title product (U).

Intermediate V: Preparation of (5S)-5-[(6-bromo-2-quinolyl)oxy]piperidin-2-one (V)

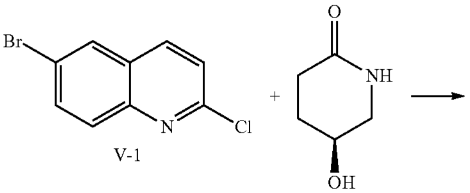

V-1 V-2

-continued

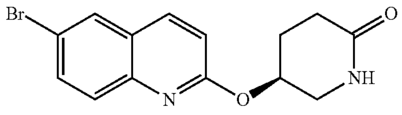

V

To a solution of V-2 (114 mg, 0.990 mmol) in DMF (4 mL) is added NaOt-Bu (158 mg, 1.65 mmol) at 0° C. The mixture is stirred at ambient temperature for 30 min, V-1 (200 mg, 0.830 mmol) is added, and the resultant mixture is heated in a microwave at 100° C. for 20 min. The reaction is diluted with water (4 mL) and extracted with EtOAc (3×20 mL). The combined organic layers are concentrated, and treated with MeOH (2 mL). The mixture is filtered; the precipitate is washed with ether (10 mL), and purified by reverse phase HPLC eluting with 30-95% MeCN in water (+0.1% TFA) to give the title product (V).

Intermediate W: Preparation of 2,2,2-trifluoro-1-(4-piperidyl)ethanol (W)

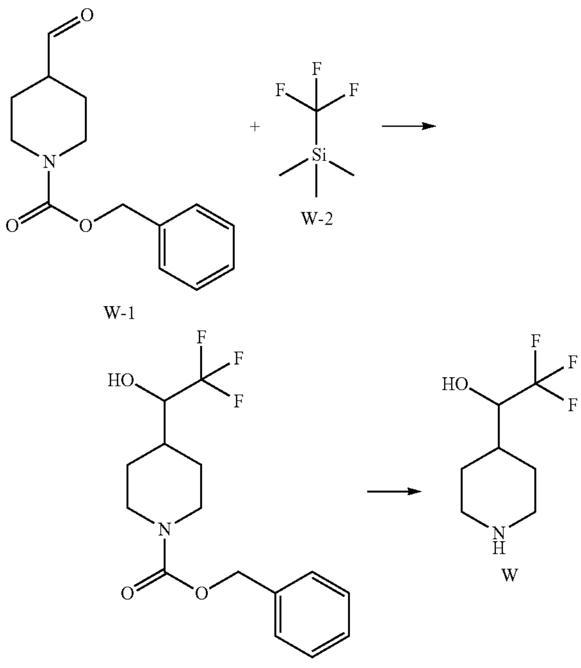

W-1 W-2 W-3 W

To a solution of W-1 (200 mg, 2.02 mmol) in DMF (2 mL) is added W-2 (862 mg, 6.07 mmol). The mixture is cooled to −25° C., and 1,3-bis(1-adamantyl)imidazol-2-ylidene (3.4 mg, 0.010 mmol) is added. The resultant mixture is warmed up to ambient temperature and stirred for 1 h. The reaction is treated with 2N HCl in dioxane (2 mL), stirred for 1 h, neutralized with 5M NaOH and concentrated. The residue is purified by reverse phase HPLC eluting with 10-90% MeCN in water (+0.1% TFA) to give intermediate W-3.

A mixture of W-3 (524 mg, 1.65 mmol) and 10% Pd on carbon (200 mg) in MeOH (16 mL) is stirred under an atmosphere of $H_2$ for 15 h. The mixture is filtered through a pad of Diatomaceous earth, and the pad is washed with MeOH (20 mL). The filtrate is concentrated to give the title product (W).

Intermediate X: Preparation of 1-[4-(2H-pyrazol-3-yl)-benzyl]-1H-indole-5-carbaldehyde (X)

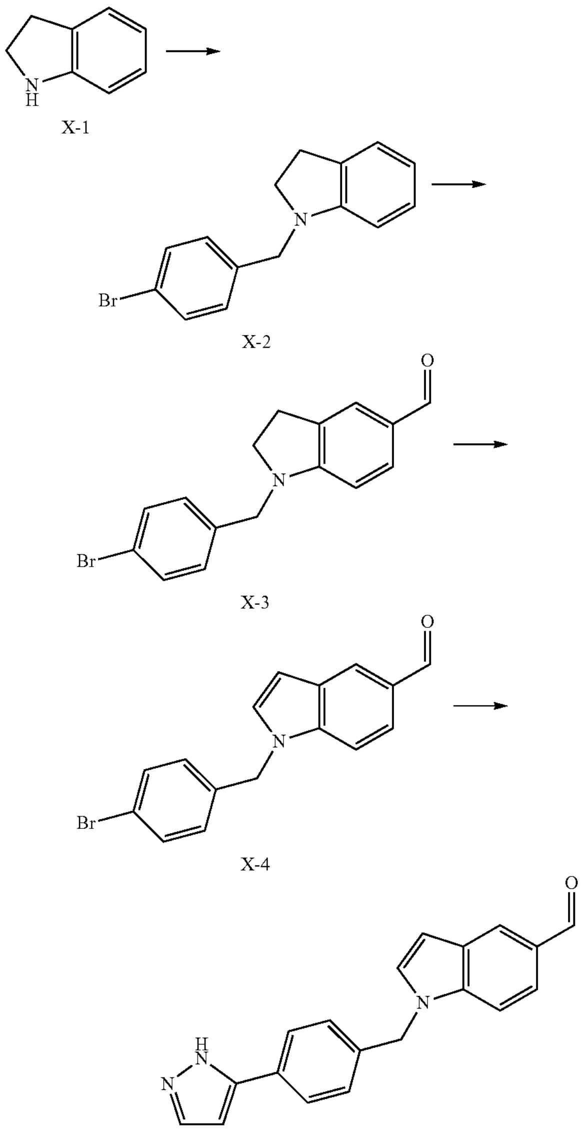

X-1 X-2 X-3 X-4 X

To a solution of X-1 (3.00 mL, 26.9 mmol) in MeOH (50 mL) is added $K_2CO_3$ (4.10 g, 29.5 mmol) and benzyl bromide (8.10 g, 32.2 mmol). The reaction mixture is heated at reflux for 3 h, cooled to room temperature and is stirred for 16 h. The mixture is filtered through a pad of Diatomaceous earth. The pad is washed with DCM (50 mL) and concentrated. The resultant residue is triturated with DCM. The filtrates is concentrated, and the residue is purified by flash chromatography (0-8% EtOAc in heptanes) to give X-2.

To a solution of trichloroethylene (60 mL) and DMF (9.20 mL, 119 mmol) is added $POCl_3$ (3.70 mL, 39.5 mmol) dropwise at ambient temperature. After stirring for 5 min, a solution of the X-2 (7.2 g, 24.9 mmol) in trichloroethylene (20 mL) is added, and the mixture is heated at 80° C. for 3 h. Upon cooling to ambient temperature, a solution of sodium acetate (15 g) in $H_2O$ (50 mL) is added, and the resultant mixture is stirred for 16 h. Phases are separated, and the aqueous layer is extracted with DCM (125 mL). The combined organic layers are dried over $Na_2SO_4$, filtered, and concentrated. The residue is purified by flash chromatography ($SiO_2$, 10-40% EtOAc in heptane) to give X-3.

To a suspension of DDQ (186 mg, 0.82 mmol) in DCM (10 mL) at 0° C. is added a solution of the X-3 (200 mg, 0.633 mmol) in DCM (1 mL). The mixture is stirred at 0° C. for 30 min, filtered, and the filter pad is washed with DCM (5 mL). The combined organic layers are washed with aqueous solution of $K_2CO_3$ (2×5 mL), $H_2O$ (5 mL) and brine (5 mL), dried over $Na_2SO_4$, and concentrated. The residue is purified by flash chromatography (0-100% EtOAc in heptane) to give X-4.

To a mixture of the A-4 (30 mg, 0.10 mmol), 1H-pyrazole-5-boronic acid (10 mg, 0.15 mmol), and $PdCl_2$(dppf) (8 mg, 0.1 mmol) in a solution of DME/$H_2O$/EtOH (1.8 mL; 7:3:2) is added aqueous solution of $K_3PO_4$ (1.0M, 110 μL). The reaction mixture is heated in a microwave at 110° C. for 15 min, diluted with $H_2O$ (2 mL) and EtOAc (8 mL), and filtered. Phases are separated and the aqueous layer is extracted with EtOAc (5 mL). The combined organic layers are washed with brine (3 mL), dried over $Na_2SO_4$, filtered and concentrated. The residue is purified by flash chromatography (0-100% EtOAc in heptane) to give the title product (X).

Intermediate Y: Preparation of 2-(5-{4-[2-(2-trimethylsilanyl-ethoxymethyl)-2H-pyrazol-3-yl]-phenoxy}indazol-1-yl)-ethanol (Y)

To a stirred solution of Y-1 (5.00 g, 25.4 mmol) in DMF (10 mL) is added $K_2CO_3$ (7.00 g, 50.6 mmol) and methyl bromoacetate (2.75 mL, 30.0 mmol). The reaction mixture is stirred at ambient temperature for 16 h, diluted with EtOAc (100 mL), washed with $H_2O$ (2×100 mL), dried over $Na_2SO_4$, filtered and concentrated. The residue is purified by flash chromatography (0-50% EtOAc in heptane) to give Y-2 and Y-3.

To a stirred solution of Y-2 (1.00 g, 3.70 mmol) in THF (15 mL) at 0° C. is added $LiAlH_4$ (160 mg, 4.00 mmol). The reaction mixture is stirred at 0° C. for 1 h, sequentially quenched with $H_2O$ (160 mL), aqueous NaOH (1M, 160 mL), and $H_2O$ (480 mL). The mixture is stirred at ambient temperature for 1 h, filtered through a pad of Diatomaceous earth and concentrated. The residue is purified by flash chromatography (0-100% EtOAc in heptane) to give Y-4.

A mixture of B (850 mg, 2.93 mmol), Y-4 (700 mg, 2.90 mmol), picolinic acid (80.0 mg, 0.650 mmol), and potassium phosphate (1.25 g, 5.89 mmol) in DMSO (7.5 mL) is sparged with $N_2$ for 5 min, and treated with CuI (60.0 mg, 0.320 mmol). The mixture is heated at 100° C. for 16 h, cooled to ambient temperature, diluted with EtOAc (100 mL), and filtered through a pad of Diatomaceous earth. The organic layer is washed with $H_2O$ (2×75 mL), dried over $Na_2SO_4$, filtered

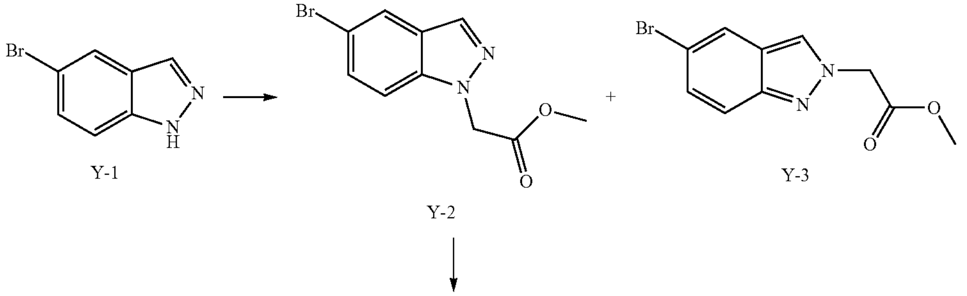

Y-1 Y-2 Y-3

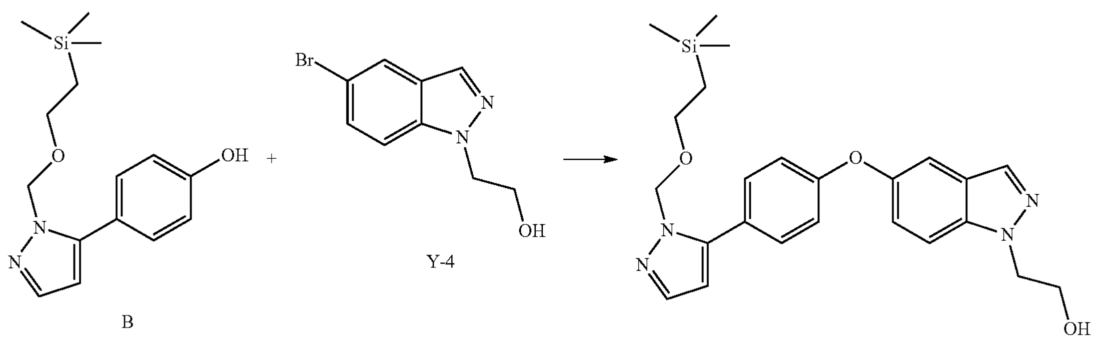

B Y-4 Y and concentrated. The residue is purified by flash chromatography (0-50% EtOAc in heptane) to give the title product (Y).

Intermediate Z: Preparation of 2-(5-{4-[2-(2-trimethylsilanyl-ethoxymethyl)-2H-pyrazol-3-yl]-phenoxy}-indazol-2-yl)-ethanol (Z)

Z

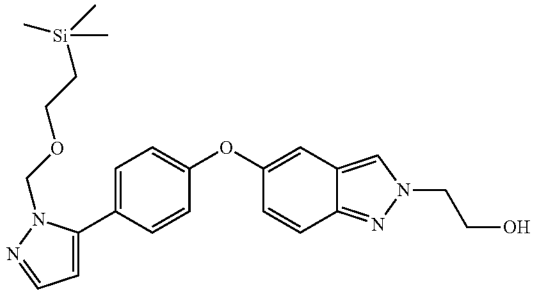

The titled compound (Z) is synthesized from intermediate Y-3 according to the procedure described for the synthesis of intermediate Y.

Intermediate AA: Preparation of 3-(5-{4-[2-(2-trimethylsilanyl-ethoxymethyl)-2H-pyrazol-3-yl]-phenoxy}-indazol-1-yl)-propan-1-ol (AA)

AA

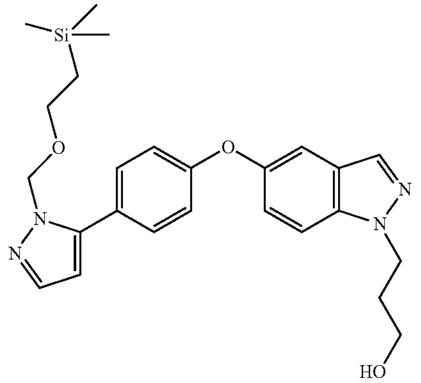

The titled compound AA is synthesized from intermediate Y-1 and 3-bromo-propionic acid methyl ester according to the procedure described for the synthesis of intermediate Y.

Intermediate AB: Preparation of 3-(5-{4-[2-(2-trimethylsilanyl-ethoxymethyl)-2H-pyrazol-3-yl]-phenoxy}-indazol-2-yl)-propan-1-ol (AB)

AB

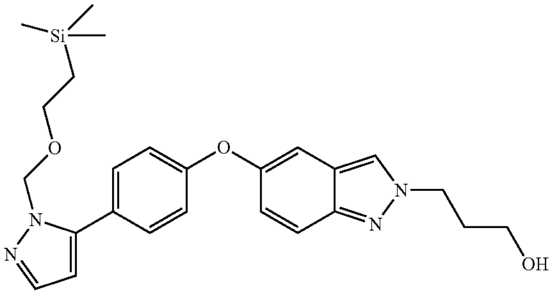

The titled compound AB is synthesized from intermediate Y-1 and 3-bromo-propionic acid methyl ester according to the procedure described for the synthesis of intermediate Y.

Intermediates AC and AD: Preparation of (5-{5-[2-(2-trimethylsilanyl-ethoxymethyl)-2H-pyrazol-3-yl]-pyridin-2-yloxy}-indazol-1-yl)-acetic acid methyl ester (AC) and (5-{5-[2-(2-trimethylsilanyl-ethoxymethyl)-2H-pyrazol-3-yl]-pyridin-2-yloxy}-indazol-2-yl)-acetic acid methyl ester (AD)

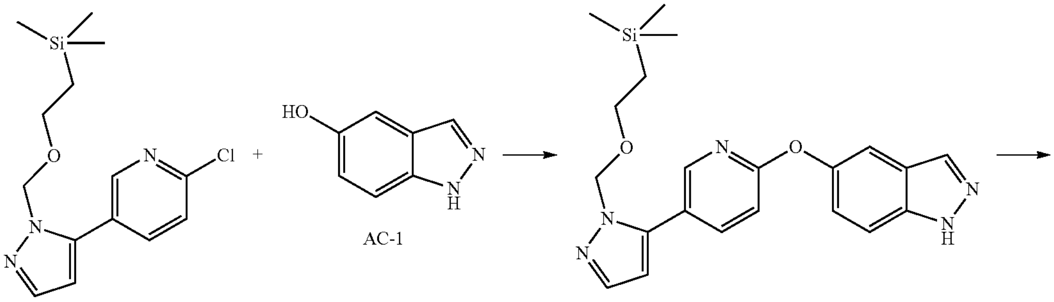

A AC-1 AC-2

-continued

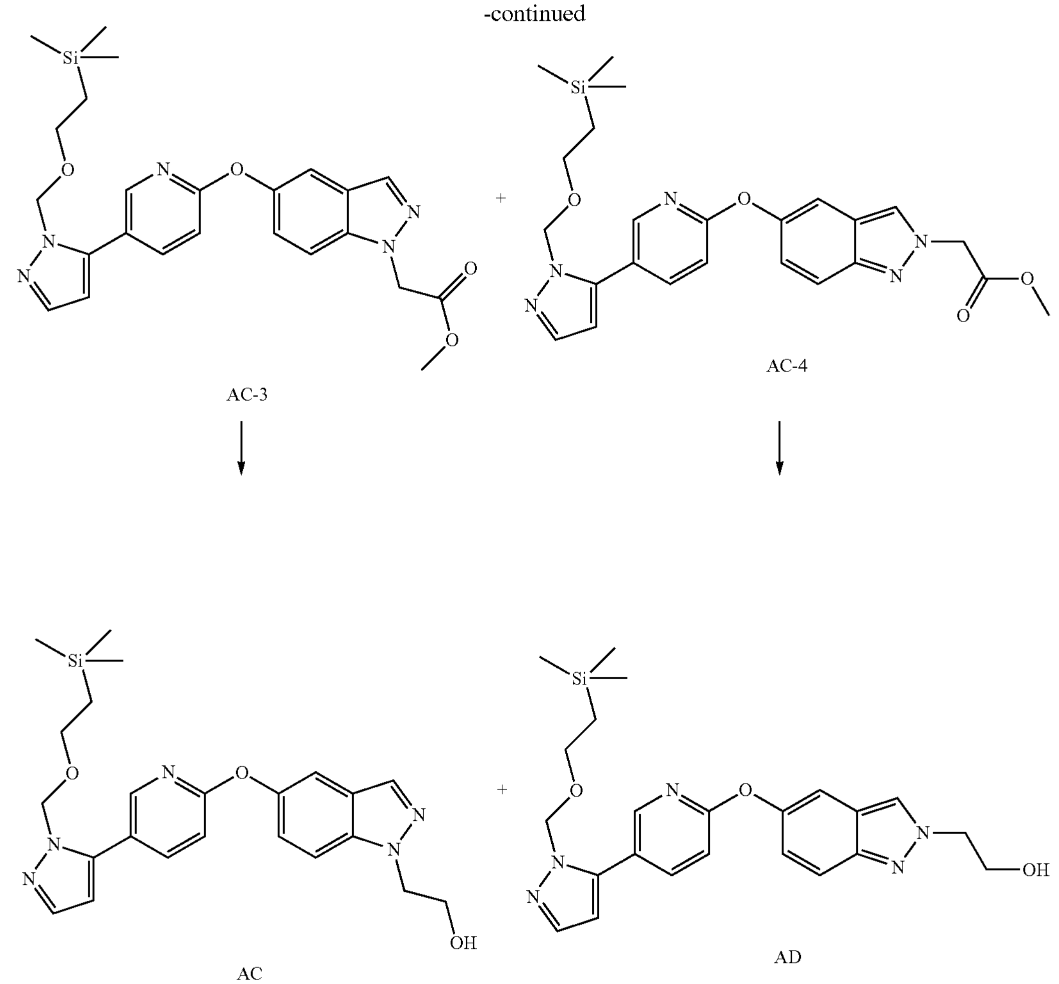

AC-3 AC-4 AC AD

A mixture of A (2.00 g, 6.45 mmol), AC-1 (900 mg, 6.70 mmol), $K_2CO_3$ (2.00 g, 14.5 mmol) in DMSO (15.0 mL) is heated at 150° C. for 3 h. The reaction is cooled to ambient temperature, diluted with EtOAc (50 mL), washed with $H_2O$ (2×50 mL), dried over $Na_2SO_4$, filtered and concentrated. The residue is purified by flash chromatography (0-100% EtOAc in heptane) to give AC-2.

To a stirred solution of AC-2 (1.00 g, 2.50 mmol) in DMF (10 mL) is added $K_2CO_3$ (700 mg, 6.10 mmol) and methyl bromoacetate (300 μL, 3.30 mmol). The reaction mixture is stirred at ambient temperature for 16 h, diluted with EtOAc (100 mL), washed with $H_2O$ (2×100 mL), dried over $Na_2SO_4$ and concentrated. The residue is purified by flash chromatography (0-50% EtOAc in heptane) to give AC-3 and AC-4.

The title compounds AC and AD are synthesized from intermediates AC-3 and AC-4, respectively, according to the procedure described for the synthesis of intermediate Y-4 from Y-2.

Intermediate AE: Preparation of Methanesulfonic acid 6-{5-[2-(2-trimethylsilanyl-ethoxymethyl)-2H-pyrazol-3-yl]-pyridin-2-yloxy}-2,3-dihydro-benzofuran-2-ylmethyl ester (AE)

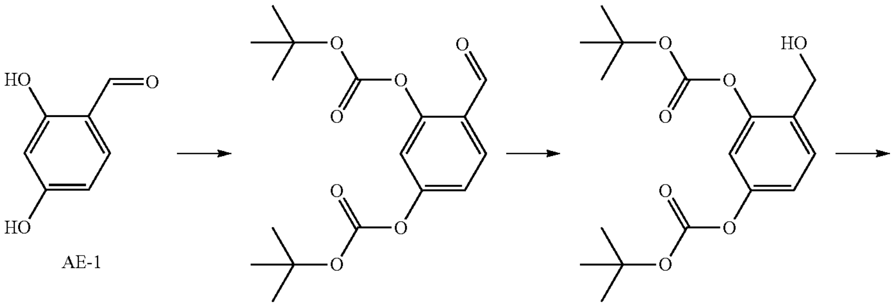

AE-1 AE-2 AE-3

-continued

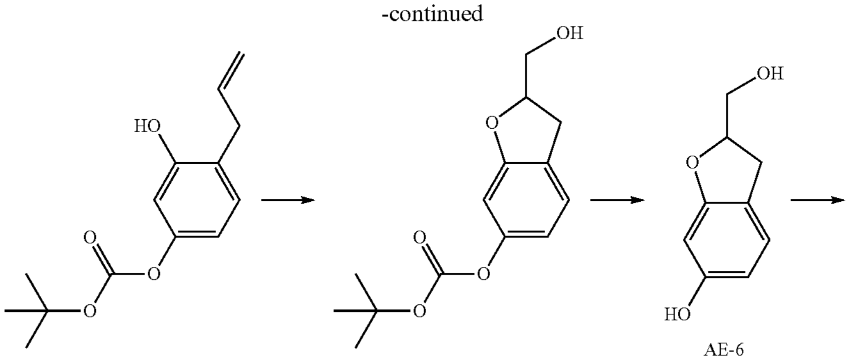

AE-4 AE-5 AE-6

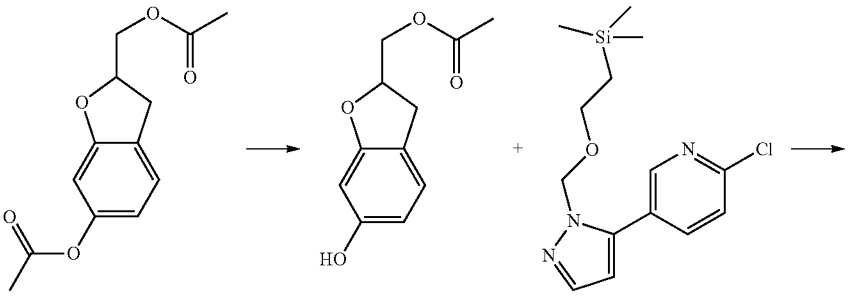

AE-7 AE-8 A

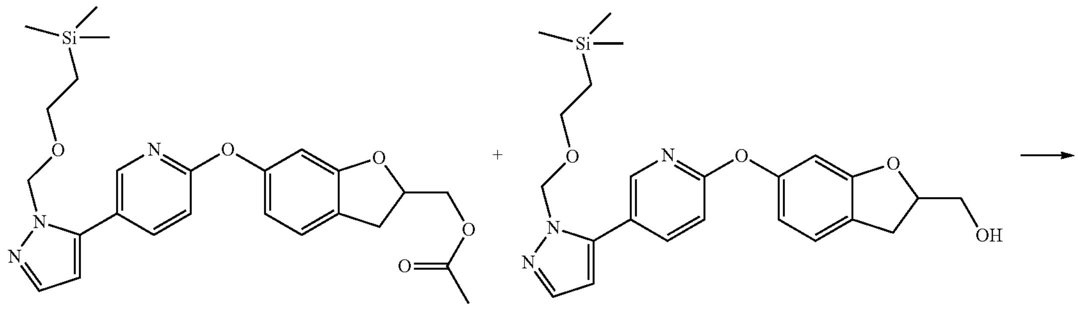

AE-9 AE-10

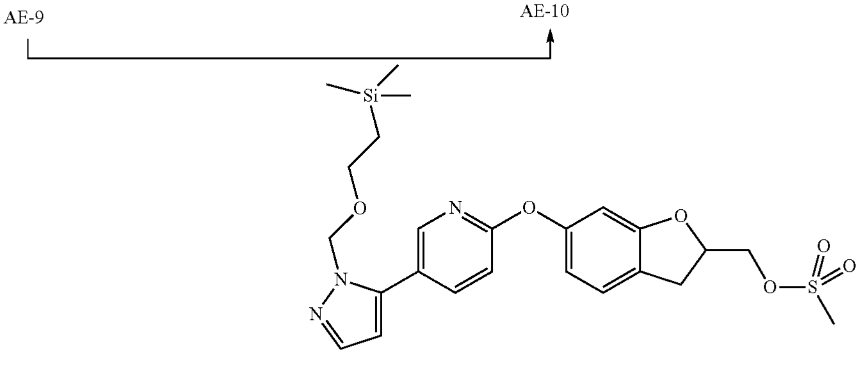

AE

To a solution of AE-1 (10.0 g, 72.4 mmol) in dry THF (100 mL) is added BOC anhydride (33.2 g, 152 mmol), DIPEA (30.0 mL, 160 mmol) and DMAP (7 mmol). The mixture is stirred overnight, diluted with EtOAc (700 mL), washed with saturated aqueous $NH_4Cl$ (2×500 mL), $H_2O$ (2×500 mL) and brine (500 mL), dried over $MgSO_4$, filtered and concentrated to give AE-2.

To a solution of AE-2 (24.0 g, 70.9 mmol) in THF (500 mL) at 4° C. is added $BH_3$.DMS (7.31 mL, 77.0 mmol). The mixture is stirred for 3 h and warmed to ambient temperature, placed in a water bath and quenched with 0.1 M HCl. The mixture is diluted with $Et_2O$ (500 mL), washed with water (2×200 mL), and brine (200 mL), dried over $MgSO_4$, filtered and concentrated. The residue is purified on a $SiO_2$ column (0-25% EtOAc in heptane) to afford AE-3.

To vinylMgBr (140 mL, 1.0 M in THF) at 4° C. is added AE-3 (15.4 g, 45.2 mmol) in $Et_2O$ (200 mL+100 ML rinse). The mixture is warmed slowly to ambient temperature and stirred for 3 h, quenched with 0.1 M HCl (100 mL), and diluted with $Et_2O$ (500 mL). Phases are separated, and the organic layer is washed with $H_2O$ (500 mL). The aqueous phase is extracted with $Et_2O$ (200 mL). The combined organic layers are washed with brine (500 mL), dried over $MgSO_4$, filtered and concentrated. The residue is purified on a $SiO_2$ column (0-25% EtOAc in heptane) to give AE-4.

To a stirred solution of AE-4 (11.3 g, 45.3 mmol) in DCM (200 ML) is added mCPBA (77%, 10.3 g, 46.2 mmol). The solution is stirred at ambient temperature for 5 h, diluted with EtOAc (400 mL), and sequentially washed with 10% Sodium sulfite (50 mL) and saturated aqueous $K_2CO_3$ (300 mL). The organic layer is dried over $MgSO_4$, filtered and concentrated. The residue is re-dissolved DCM (1 L), and treated with $SiO_2$ (500 mL). The mixture is stirred overnight and filtered. The $SiO_2$ pad is washed with DCM (1.5 L) and EtOAc (3 L). The filtrates are concentrated separately. The residue from DCM wash is purified on a $SiO_2$ column (0-50% EtOAc in heptane). The desired fractions are pooled and combined with the residue from EtOAc wash to give AE-5.

To a solution of AE-5 (9.40 g, 35.3 mmol) in MeOH (150 mL) is added $K_2CO_3$ (9.0 g). The mixture is stirred for 1 h and concentrated. The residue is treated with $H_2O$ (200 mL), neutralized with AcOH, and extracted with EtOAc (2×400 mL). The combined organic layers are washed with brine (200 mL), dried over $MgSO_4$, filtered and concentrated to give AE-6.

To a solution of AE-6 (5.94 g, 35.7 mmol) in DCM (250 mL) at 4° C. is added DIPEA (13 mL, 75.8 mmol) and acetyl chloride (7.85 g, 100 mmol). The mixture is stirred for 16 h, concentrated and diluted with EtOAc (500 mL). The organic phase is washed with saturated aqueous $NaHCO_3$ (3×100 mL), saturated aqueous $NH_4Cl$ (2×100 mL), and brine (200 mL), dried over $MgSO_4$, filtered and concentrated to give AE-7.

To a solution of AE-7 (8.90 g, 35.6 mmol) in a 4:1 mixture of $MeOH/H_2O$ (100 mL) is to added $NH_4OAc$ (20 g). The mixture is stirred for 16 h, additional $NH_4OAc$ (20 g) is added and the mixture is heated at 50° C. for 3 h. The mixture is concentrated; the resultant residue is dissolved in $H_2O$ (200 mL) and extracted with EtOAc (2×200 mL). The combined organic extracts are washed with brine (300 mL), dried over $MgSO_4$, filtered and concentrated to give AE-8.

A mixture of AE-8 (6.78 g, 32.6 mmol), A (20.2 g, 65.1 mmol) and $K_2CO_3$ (22.5 g, 163 mmol) in DMSO (100 mL) is heated in a sealed flask at 160° C. for 4 h. The reaction mixture is cooled to ambient temperature, diluted with EtOAc (500 mL) and washed with $H_2O$ (2×400 mL). The aqueous phase is extracted with EtOAc (500 mL). The organic extracts are combined and washed with brine (600 mL), dried over $MgSO_4$, filtered and concentrated. The residue is purified on a $SiO_2$ column (0-50% EtOAc in heptane) to give AE-9 and AE-10.

To a solution of AE-9 (10.1 g, 20.9 mmol) in a 1:5 mixture of $H_2O$/MeOH (100 mL) is added solid $K_2CO_3$ (10.0 g), and the resultant mixture is stirred at 50° C. for 2 h. The reaction is cooled to ambient temperature and concentrated. The residue is suspended in $H_2O$ (300 mL), treated with AcOH until gas evolution ceased and extracted with EtOAc (2×500 mL). The combined organic layers are washed with brine (500 mL), dried over MgSO4, filtered and concentrated to give AE-10.

To a solution of AE-10 (262 mg, 0.600 mmol) in DCM (10 ML) is added DIPEA (0.440 mL, 2.40 mmol) and methanesulfonyl chloride (0.120 mL, 1.50 mmol). The mixture is stirred for 2 h at ambient temperature, diluted with EtOAc (50 mL), and quenched with saturated aqueous $NH_4Cl$ (20 mL). Phases are separated and the organic layer is washed with saturated aqueous $K_2CO_3$ (2×20 mL) and brine (20 mL), dried over MgSO4, filtered and concentrated to give the title product (AE).

Intermediate AF: Preparation of 6-{5-[2-(2-Trimethylsilanyl-ethoxymethyl)-21'-pyrazol-3-yl]-pyridin-2-yloxy}-benzofuran-3-carbaldehyde (AF)

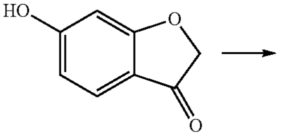

AF-1

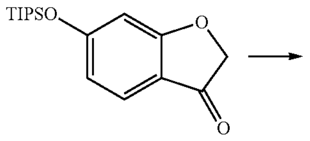

AF-2

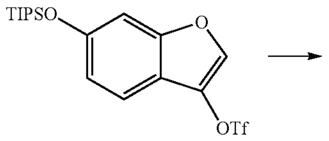

AF-3

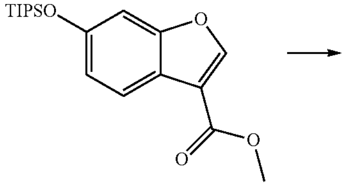

AF-4

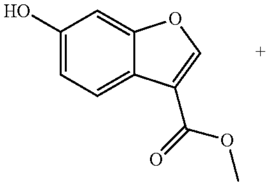

AF-5

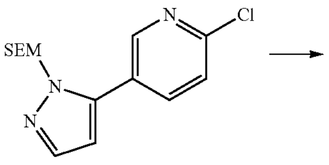

A

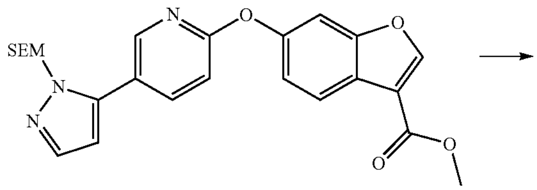

AF-6

-continued

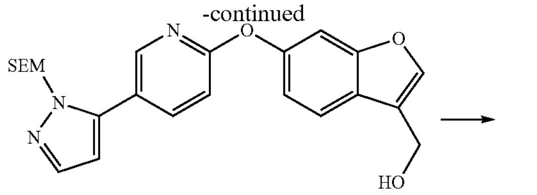

AF-7

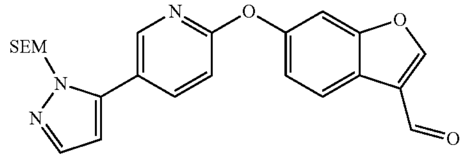

AF

To a solution of AF-1 (10.2 g, 65.7 mmol) and 1H-imidazole (10.8 g, 157 mmol) in DMF (80 mL) is added chlorotriisopropylsilane (17.4 mL, 78.9 mmol) and the reaction is stirred at ambient temperature for 2 h. The reaction is diluted with EtOAc (400 mL) and washed with water (400 mL) and brine (200 mL). The aqueous layers are extracted with EtOAc (400 mL), and the combined organic layers are dried over $Na_2SO_4$, filtered and concentrated. The residue is purified by silica gel chromatography (0-25% EtOAc in heptane) to afford AF-2.

To a solution of AF-2 (1.00 g, 3.17 mmol) in DCM (20 mL) at 0° C. is added 2,6-lutidine (0.405 mL, 3.48 mmol) and trifluoromethanesulfonic anhydride (0.582 mL, 3.48 mmol) over 2 min. The stirred mixture is warmed to ambient temperature over 45 min, cooled to 0° C., quenched with saturated aqueous $NH_4Cl$ (50 mL) and extracted with EtOAc (2×50 mL). The combined organic layers are dried over $Na_2SO_4$ and concentrated. The crude is purified by silica gel chromatography (100% heptane) to give AF-3.

To a mixture of AF-3 (100 mg, 0.228 mmol) in DMF (2 mL) was added $Mo(CO)_6$ (61 mg, 0.23 mmol) and trans-di-mu-acetobis[2-(di-O-tolylphosphino)benzyl]dipalladium(II) (Hermann's Catalyst, 22 mg, 0.023 mmol). The reaction is heated at 100° C. in a microwave for 15 min, cooled to ambient temperature, quenched with 1M HCl (20 mL) and extracted with EtOAc (2×20 mL). The combined organic layers are dried over $Na_2SO_4$ and concentrated. The crude is purified by prep-TLC (10% EtOAc in heptane) to give AF-4.

To a stirred solution of AF-4 (110 mg, 0.316 mmol) in THF (5 mL) at ambient temperature is added TBAF (1.0M in THF, 0.325 mL). After 24 h, the reaction is quenched with water (40 mL) and extracted with EtOAc (3×50 mL). The combined organic layers are dried over $Na_2SO_4$ and concentrated to give AF-5.

A mixture of AF-5 (51.0 mg, 0.260 mmol), A (107 mg, 0.335 mmol), and $K_2CO_3$ (108 mg, 0.772 mmol) in DMSO (2 mL) is heated at 150° C. for 3 h. The reaction is quenched with water (50 mL) and is extracted with EtOAc (3×50 mL). The combined organic layers are washed with brine (30 mL), dried over $Na_2SO_4$, filtered and concentrated. The residue is purified by silica gel chromatography (0-30% EtOAc in heptane) to give AF-6.

To a solution of AF-6 (41.0 mg, 0.0870 mmol) in THF (5 mL) at −25° C. is added lithium aluminum hydride (1M in THF, 0.436 mL). The mixture is warmed to ambient temperature over 1 h. LCMS indicates presence of starting material. The mixture is cooled to −25° C. and more lithium aluminum hydride (1M in THF, 0.218 mL) is added. The reaction stirred at ambient temperature for 1 h, quenched with saturated solution of Rochelle salt (75 mL) and extracted with EtOAc (2×100 mL). The combined organic layers are washed with brine (50 mL) and dried over $Na_2SO_4$, filtered and concentrated. The residue is purified by silica gel chromatography (0-55% EtOAc in heptane) to afford AF-7.

To a solution of AF-7 (3.36 g, 7.45 mmol) in DCM (125 mL) at 0° C. is added Dess-Martin Periodinane (3.60 g, 8.23 mmol). After 1 h at 0° C., more Dess-Martin Periodinane (7.20 g, 16.5 mmol) is added, the reaction is warmed to ambient temperature and stirred 1 h. The reaction is cooled to −10° C., quenched with saturated aqueous $NaHCO_3$ (500 mL) and stirred for 30 min. The mixture is extracted with EtOAc (3×500 mL). The combined organic layers are washed with brine (150 mL), dried over $Na_2SO_4$, filtered and concentrated. The residue is suspended in DCM and filtered. The filtrate is purified by silica gel chromatography (0-50% EtOAc in heptane). The resultant residue is dissolved in EtOAc (20 mL), treated with heptane (150 mL), concentrated to 100 mL and filtered to give the title product (AF).

Intermediate AG: Preparation of 6-{4-[2-(2-Trimethylsilanyl-ethoxymethyl)-2H-pyrazol-3-yl]-phenoxy}-2,3-dihydro-benzofuran-2-carbaldehyde (AG)

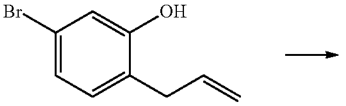

AG-1

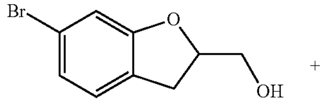

AG-2

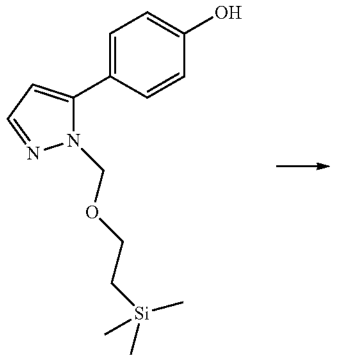

B

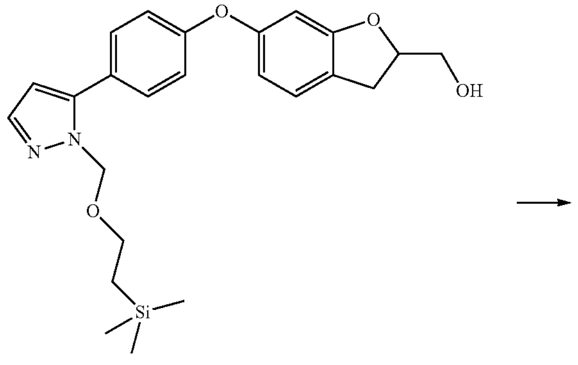

AG-3

-continued

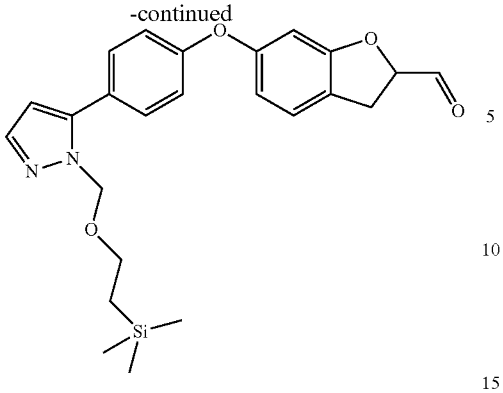

AG

Intermediate AG-1 is prepared according to the method described by Minutolo et al. *J. Med. Chem.* 2008, 51, 1344-1351.

To a stirred solution of the AG-1 (2.00 g, 9.39 mmol) in DCM (40 mL) is added mCPBA (77%, 6.31 g, 28.2 mmol). The solution is stirred at ambient temperature for 5 h. The solution is diluted with DCM (100 mL) and washed with a 1:1 mixture of 10% aqueous sodium sulfite and saturated aqueous $NaHCO_3$ (100 mL). The organic layer is dried over $MgSO_4$, filtered and concentrated. The resulting residue is dissolved in MeOH (100 mL), treated with $K_2CO_3$ (3.24 g, 2.50 mmol), and stirred for 16 h. The mixture is concentrated, and the residue is partitioned between EtOAc and water. The aqueous layer is acidified to with 1M HCl and extracted with EtOAc. The combined organic layers are dried over MgSO4, filtered and concentrated. The residue is purified on $SiO_2$ (15-100% EtOAc in heptane) to give AG-2.

A mixture of B (0.634 g, 2.18 mmol), AG-2 (0.500 g, 2.18 mmol), CuI (41.6 mg, 0.218 mmol), 2-picolinic acid (53.7 mg, 0.437 mmol) and potassium phosphate (0.927 g, 4.37 mmol) in DMSO (10 mL) is sparged with Ar for 20 min, and heated at 110° C. for 42 h. The mixture is cooled to ambient temperature, diluted with EtOAc (100 mL) and washed with saturated aqueous $NH_4Cl$ (100 mL), saturated aqueous NaHCO3 (100 mL), and brine (100 mL). The organic layer is dried over $MgSO_4$, filtered and concentrated. The mixture is purified on $SiO_2$ (10-70% EtOAc in heptane). The residue is triturated with ether to give AG-3.

To a stirred solution of oxalyl chloride (516 mL, 5.92 mmol) in DCM (25 mL) at −78° C. is added a solution of DMSO (840 mL, 11.8 mmol) in DCM (5 mL). After 30 minutes, a solution of AG-3 (1.30 g, 2.96 mmol) in DCM (10 mL) is added. After 15 min, NEt3 (2.48 mL, 17.8 mmol) is added and the reaction is allowed to slowly warm to ambient temperature. The reaction is diluted with DCM (50 mL) and quenched with water (50 mL). The organic layer is washed with water (5×10 mL) and brine (50 mL), dried over $MgSO_4$, filtered and concentrated to give the title product (AG).

Intermediate AH: Preparation of 2-Chloro-5-[2-(2-trimethylsilanyl-ethoxymethyl)-2H-pyrazol-3-yl]-pyrimidine (AH)

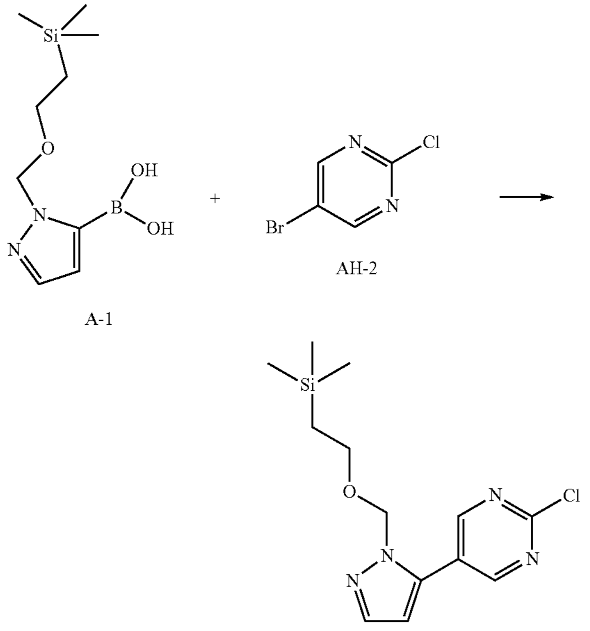

A-1 AH-2 AH

The title product (AH) is synthesized from A-1 and AH-2 according to the procedure described for the synthesis of intermediate A from A-1 and A-2.

Intermediate AI: Preparation of 6-{4-[2-(2-Trimethylsilanyl-ethoxymethyl)-2H-pyrazol-3-yl]-phenoxy}-quinoxaline-2-carbaldehyde (AI)

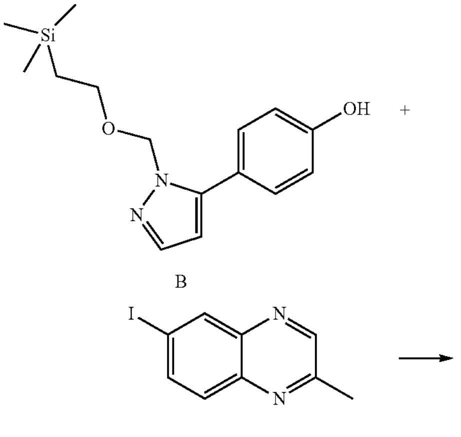

B

AI-1

-continued

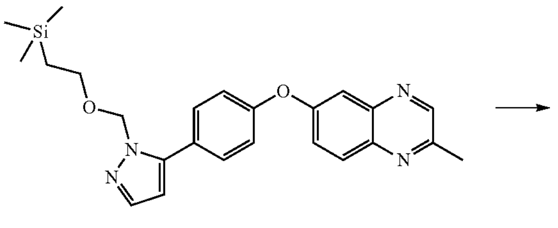

AI-2

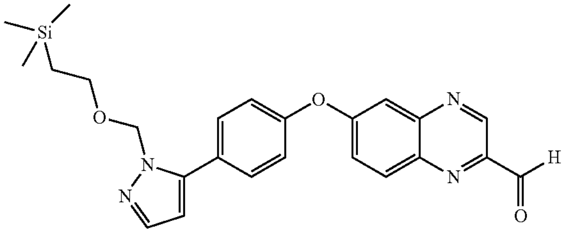

AI

A mixture of B (0.200 g, 0.689 mmol), AI-1 (0.186 g, 0.689 mmol), picolinic acid (0.0620 g, 0.504 mmol) and potassium phosphate (0.424 g, 2.00 mmol) in DMSO (5 mL) is sparged with Ar. Next, CuI (0.045 g, 0.236 mmol) is added, and the mixture is heated at 120° C. overnight. The crude reaction mixture is purified by flash chromatography (0-50% EtOAc in heptane) to give AI-2.

The title product AI is synthesized from AI-2 according to the procedure described for the synthesis of intermediate D from D-3.

Intermediate AJ: Preparation of (3,3-Dimethyl-2-oxo-pyrrolidin-1-yl)-acetic acid (AJ)

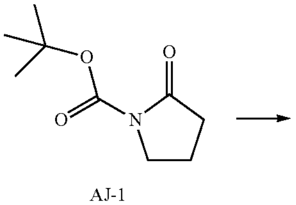

AJ-1

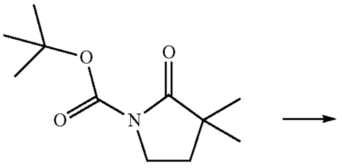

AJ-2

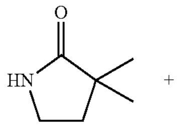

AJ-3

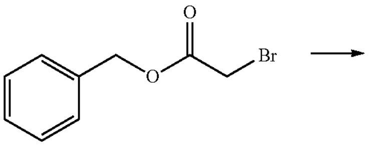

AJ-4

-continued

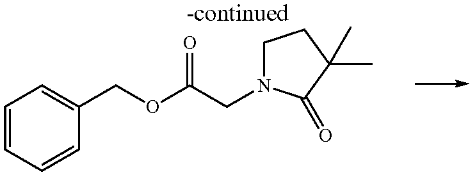

AJ-5

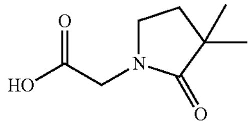

AJ

To a solution of AJ-1 (1.000 g, 5.00 mmol) in THF (100 mL) at −20° C. is added lithium bis-trimethylsilyl amide (1M in THF, 14 ml). After 1 h, MeI (0.873 mL, 14.00 mmol) is added, and the mixture is warmed to ambient temperature overnight. The mixture is quenched with water (100 ml), and extracted with EtOAc (500 mL). The organic layer is concentrated, and the residue is purified by flash chromatography (0-50% EtOAc in heptane) to give AJ-2.

To a solution of AJ-2 (0.700 g, 3.28 mmol) in DCM (50 mL) is added HO/Dioxane (4 M, 5 ml). The mixture is stirred overnight, and concentrated to give AJ-3.

To a stirred solution of AJ-3 (0.500 g, 4.42 mmol) in DMF (100 mL) is added NaH (0.177 g, 4.42 mmol). After 1 h, AJ-4 (1.00 mL, 4.42 mmol) is added and the mixture is stirred overnight. The mixture is quenched with water (100 ml) and extracted with EtOAc (100 mL). The organic layer is concentrated, and the residue is purified by flash chromatography (0-50% EtOAc in heptane) to give AJ-5.

To a solution of AJ-5 (0.100 g, 0.383 mmol) in MeOH (10 mL) is added 10% Pd/C (50.0 mg). The mixture is stirred under an atmosphere of H2 overnight. The mixture is filtered through a pad of Diatomaceous earth, and the pad is washed with MeOH (20 mL). The filtrate is concentrated to give the title product (AJ).

Intermediate AK: Preparation of (endo)-N-(8-Aza-bicyclo[3.2.1]oct-3-yl)-acetamide (AK)

AK

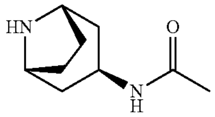

The title product (AK) is prepared according to the procedure described in WO2009/126806A2.

Intermediate AL: Preparation of Acetic acid 2-(3,8-diaza-bicyclo[3.2.1]oct-3-yl)-2-oxo-ethyl ester.TFA (AL)

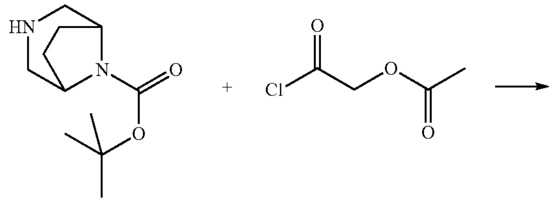

AL-1

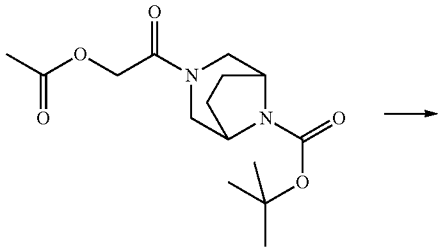

AL-3

-continued

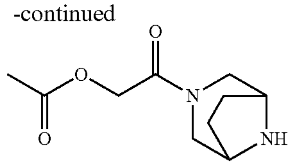

TFA

AL

To a chilled solution of AL-1 (200 mg, 0.942 mmol) in DCM (5 mL) is added AL-2 (110 μL, 1.04 mmol) followed by DIPEA (200 μL, 1.13 mmol). After 72 h, the reaction is poured into water (20 mL) and extracted with DCM (20 mL). The organic layer is dried over $MgSO_4$, filtered and concentrated. The residue is purified on $SiO_2$ (0-50% EtOAc in heptane) to afford AL-3.

To a stirred solution of the AL-3 (287 mg, 0.919 mmol) in DCM (2.0 mL) is added TFA (2.0 mL). After 80 h, the reaction is concentrated to give the title product (AL).

The following intermediates are synthesized from the appropriate amine reagent according to the procedure described for the synthesis of Intermediate AL. For the syntheses of intermediates AQ and AR, acetic anhydride is used instead of AL-2.

| Intermediate | Name | Structure | Amine Reagent |
|---|---|---|---|
| AM | Acetic acid (1S,4S)-2-2,5-diaza-bicyclo[2.2.1]hept-2-yl-2-oxo-ethyl ester•TFA | 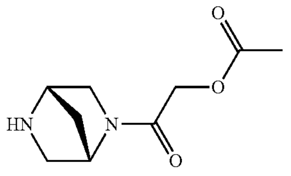 TFA | 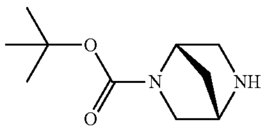 |
| AN | Acetic acid 2-[1,4]diazepan-1-yl-2-oxo-ethyl ester•TFA | 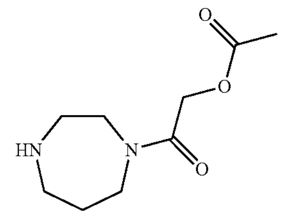 TFA | 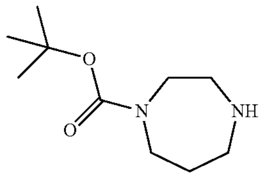 |
| AO | Acetic acid (1R,4R)-2-2,5-diaza-bicyclo[2.2.1]hept-2-yl-2-oxo-ethyl ester•TFA | 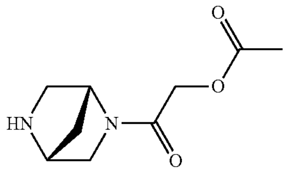 TFA | 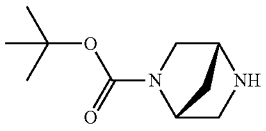 |

-continued
| Intermediate | Name | Structure | Amine Reagent |
|---|---|---|---|
| AP | Acetic acid 2-(2,5-diaza-bicyclo[2.2.2]oct-2-yl)-2-oxo-ethyl ester•TFA | 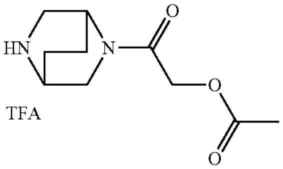 TFA | 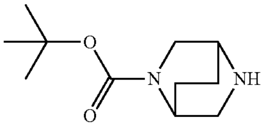 |
| AQ | (1R,4R)-1-(2,5-Diaza-bicyclo[2.2.1]hept-2-yl)-ethanone•TFA | 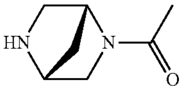 TFA | 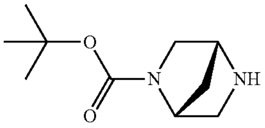 |
| AR | 1-(2,5-Diaza-bicyclo[2.2.2]oct-2-yl)-ethanone•TFA | 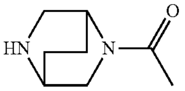 TFA | 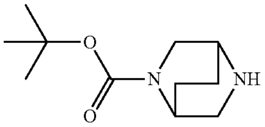 |
Intermediate AS: Preparation of (6-{5-[2-(2-Trimethylsilanyl-ethoxymethyl)-2H-pyrazol-3-yl]-pyridin-2-yloxy}-benzofuran-3-yl)-acetaldehyde (AS)
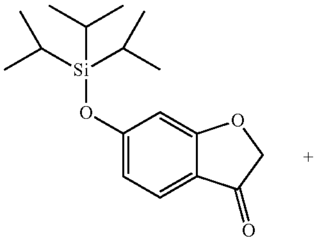
AF-2
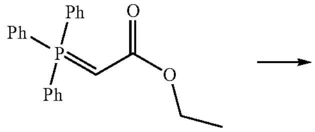
AS-1
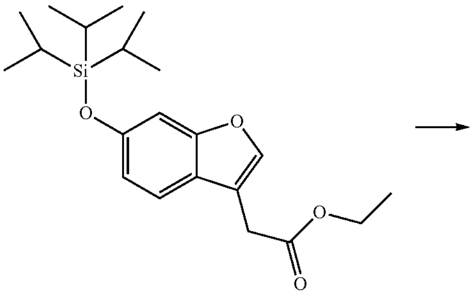
AS-2
-continued
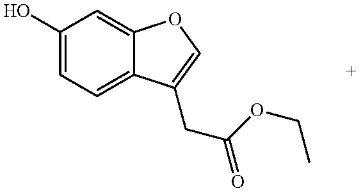
AS-3
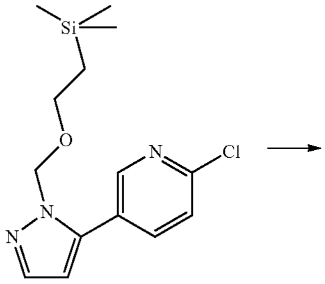
A
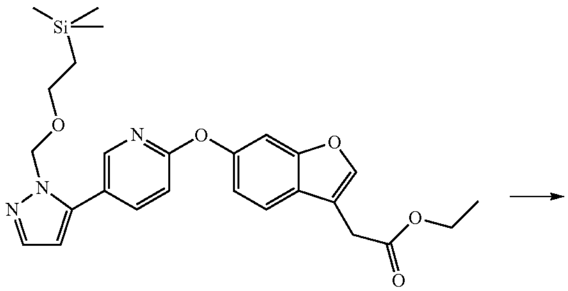
AS-4

-continued

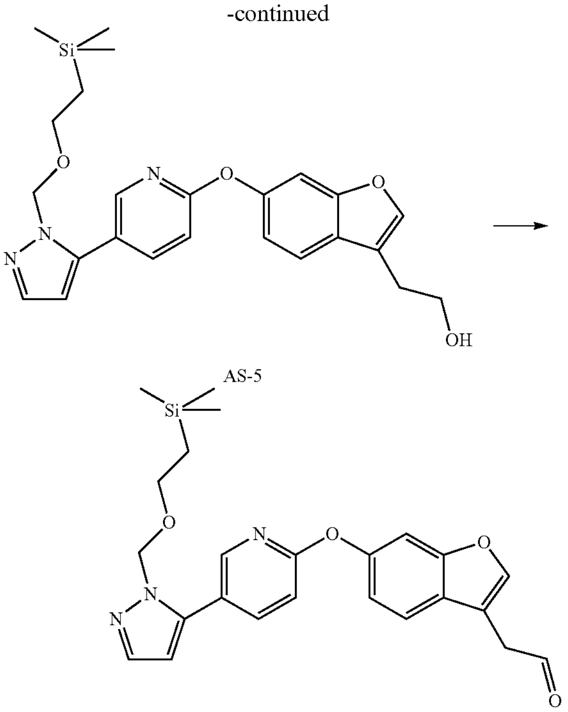

AS-5

AS

To a solution of AF-2 (1.00 g, 3.26 mmol) in toluene (40 mL) is added AS-1 (4.55 g, 13.0 mmol). The resultant solution is stirred at 110° C. After 78 h, the mixture is concentrated and purified on $SiO_2$ (0-30% EtOAc in heptane) to give AS-2.

To a solution of AS-2 (300 mg, 0.797 mmol) in THF (3 mL) is added TBAF (797 mL, 0.797 mmol) at ambient temperature. After 30 min, the mixture is poured into a mixture of EtOAc (100 mL) and water (100 mL). Phases are separated and the aqueous layer is extracted with EtOAc (3×30 mL). The combined organic layers are washed with water (100 mL), brine (100 mL), dried over $MgSO_4$, filtered and concentrated. The mixture is purified on $SiO_2$ (0-30% EtOAc in heptane) to give AS-3.

Compound AS-4 is synthesized from AS-3 (787 mg, 3.57 mmol) and intermediate A (1.44 g, 4.65 mmol) according to the procedure described for the synthesis AF-6 from AF-5 and intermediate A.

A solution of AS-4 (1.20 g, 2.43 mmol) in anhydrous THF (20 mL) is cooled to 0° C., and treated with DIBAL-H (1.5M in toluene, 1.78 mL). The mixture is stirred at 0° C. for 1 h, and warmed to ambient temperature. After 22 h, the mixture is cooled to 0° C., quenched with EtOAc (350 mL) water (100 mL), and saturated aqueous Rochelle's salt solution (200 mL) while insuring that the internal temperature stayed below 10° C. The resultant mixture is stirred at ambient temperature for 6 h. Phases are separated, and the aqueous layer is extracted with EtOAc (2×50 mL). The combined organic layers are washed with $NaHCO_3$ (100 mL) and brine (100 mL), dried over $MgSO_4$, filtered and concentrated. The residue is purified on $SiO_2$ (0-70% EtOAc in heptane) to provide AS-5.

To a 0° C. solution of AS-5 (600 mg, 1.33 mmol) in anhydrous DCM (20 mL) is added Dess-Martin periodinane (592 mg, 1.40 mmol). The mixture is stirred at 0° C. for 30 min, quenched with saturated aqueous $NaHCO_3$ (20 mL), and stirred for 20 min at ambient temperature. The resultant mixture is extracted with EtOAc (3×50 mL). The combined organic layers are washed with saturated aqueous $NaHCO_3$ (50 mL) and brine (50 mL), dried over $MgSO_4$, filtered and concentrated. The mixture is purified on $SiO_2$ (0-50% EtOAc in heptane) to yield the title product (AS).

Intermediate AT: Preparation of (6-{5-[2-(2-Trimethylsilanyl-ethoxymethyl)-2H-pyrazol-3-yl]-pyridin-2-yloxy}-2,3-dihydro-benzofuran-3-yl)-acetaldehyde (AT)

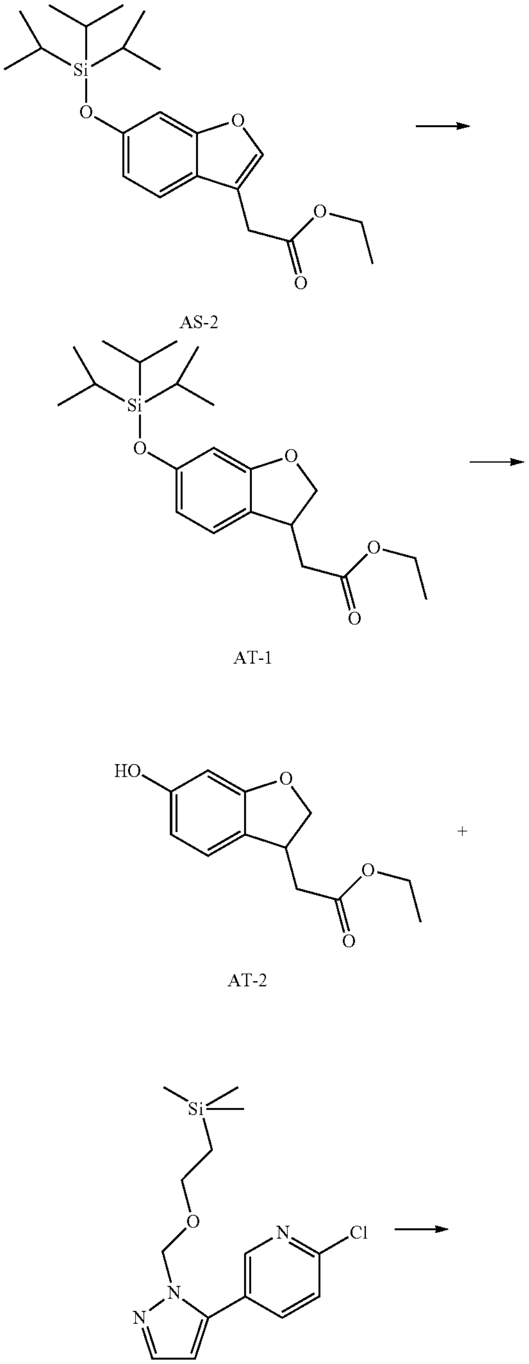

AS-2

AT-1

AT-2

+

A

-continued

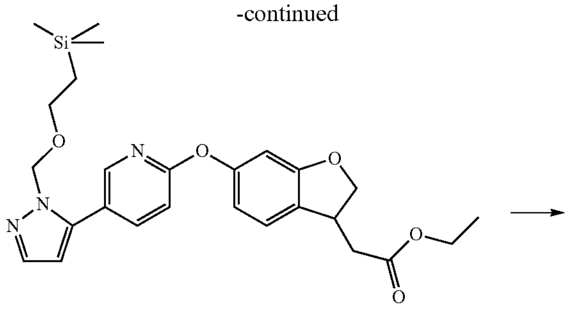

AT-3

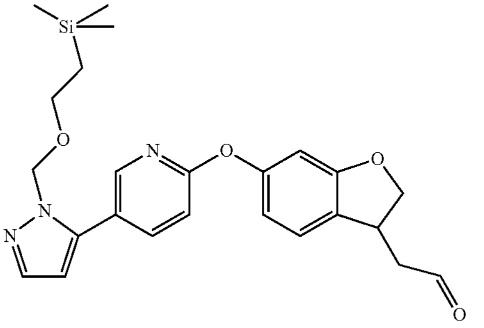

AT

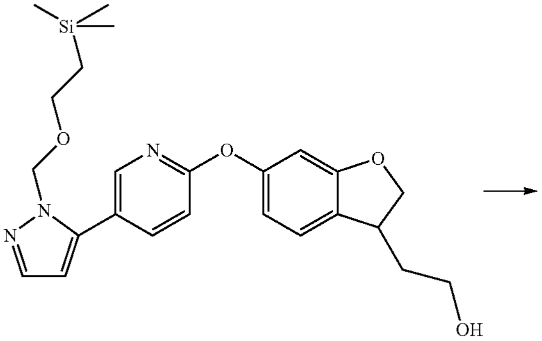

AT-4

A mixture of AS-2 (350 mg, 0.929 mmol) and 10% Pd/C (50 mg) in EtOAc (50 ml) is stirred under an atmosphere of $H_2$. After 4 h, the mixture is filtered through a pad of Diatomaceous earth and concentrated to give AT-1.

The title product (AT) is synthesized from AT-1 according to procedures described for the synthesis of intermediate AS from AS-2.

Intermediate AU: Preparation of (6-{4-[2-(2-Trimethylsilanyl-ethoxymethyl)-2H-pyrazol-3-yl]-phenoxy}-imidazo[1,2-a]pyridin-2-yl)-methanol (AU)

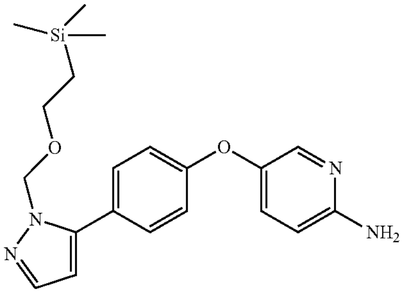

T

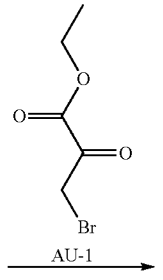

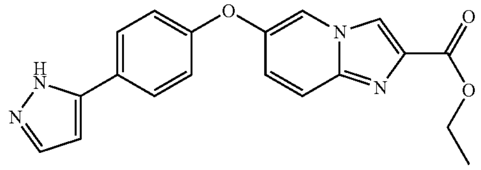

AU-2

+

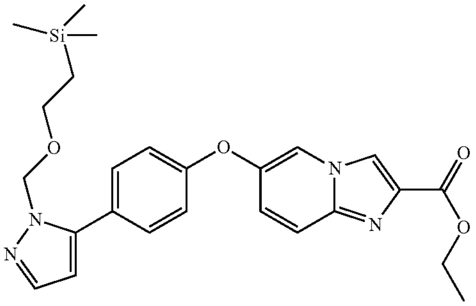

AU-3

-continued

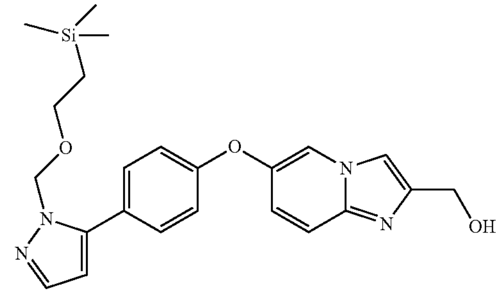

AU

To a solution of T (1.11 mg, 2.91 mmol) in THF (25 ml) is added AU-1 (0.43 ml, 3.4 mmol). The mixture is heated at 60° C. for 4 h, cooled to ambient temperature, washed with saturated aqueous $NaHCO_3$ and brine, and concentrated. The residue is purified on $SiO_2$ (0-10% MeOH in DCM) to give AU-2 and AU-3.

A solution of AU-3 (355 mg, 0.740 mmol) in THF (10 ml) is treated with LAH (43 mg, 1.1 mmol). The mixture is stirred at ambient temperature for 3 h, treated with $Na_2SO_4.10H_2O$, stirred for 15 min, and filtered. The filtrate is concentrated and purified on $SiO_2$ (0-10% MeOH in DCM) to give the title product (AU).

Intermediates AV and AW: Preparation of (S)-5-(5-Bromo-indazol-1-ylmethyl)-pyrrolidin-2-one (AV) and (S)-5-(5-Bromo-indazol-2-ylmethyl)-pyrrolidin-2-one

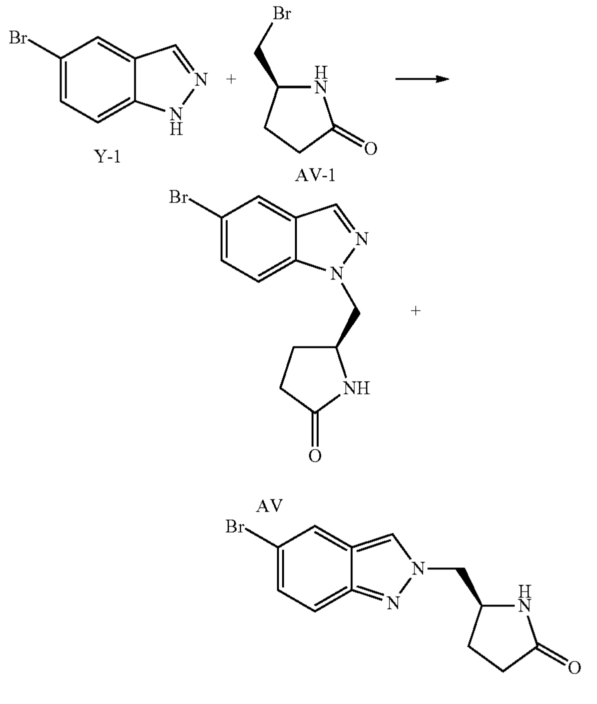

Y-1 AV-1 AV AW

A mixture of Y-1 (0.700 g, 3.55 mmol) and NaH (60% in oi-1,142 mg, 3.55 mmol) in DMF (5 ml) is stirred for 15 min, AV-1 (3.91 mmol) is added, and the resultant mixture is heated in a microwave at 120° C. for 11 h. The reaction mixture is diluted with water and extracted with EtOAc. The organic layer is dried over $Na_2SO_4$, filtered and concentrated. The residue is purified on $SiO_2$ (0-15% MeOH containing 1% $NH_4OH$/DCM) to afford intermediates AV and AW.

Preparation of [(1α,5α,6α)-3-aza-bicyclo[3.1.0]hexane]-6-carboxylic acid ethyl ester (AX)

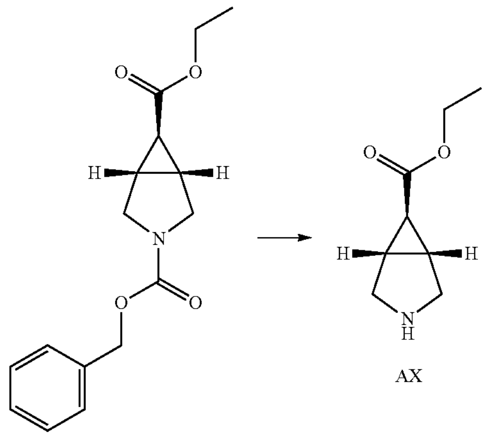

AX-1 AX

Intermediate AX-1 can be synthesized according to the procedure described in WO2010/116328.

To a solution of AX-1 (700 mg, 2.42 mmol) in MeOH (5 mL) is added 5% Pd/C (52 mg) and the mixture stirred under $H_2$ at room temperature. After 18 h, the mixture is evacuated and purged with Argon, filtered through a pad of Diatomaceous earth filter aid, and concentrated to give the title product (AX).

Intermediate AY: Preparation of 2-Hydroxy-1-piperazin-1-yl-ethanone (AY)

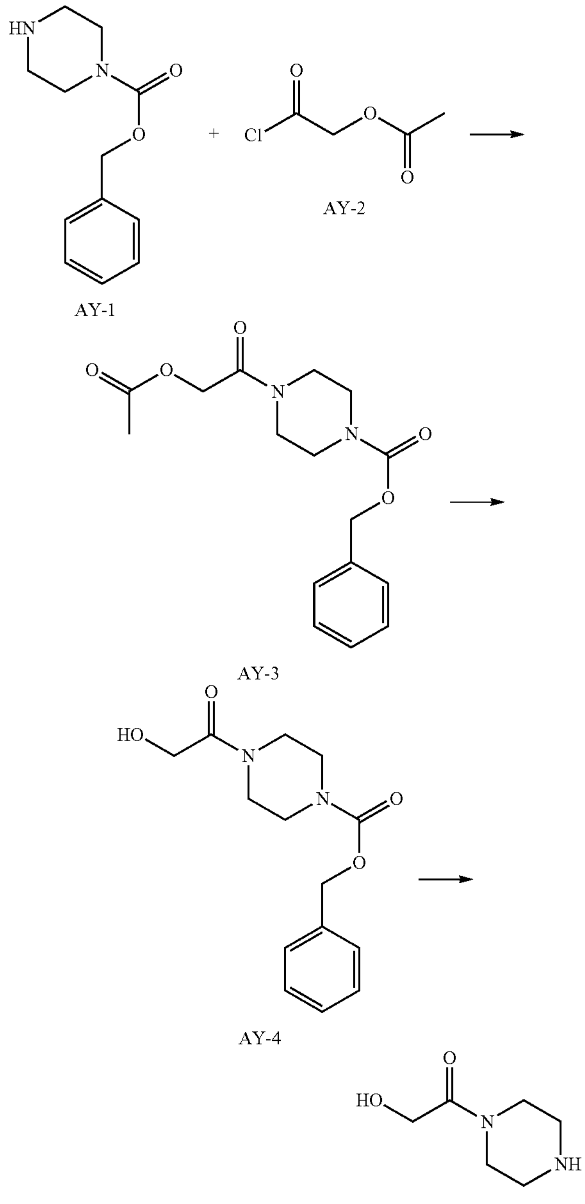

AY-1 AY-2 AY-3 AY-4 AY

To a solution of AY-1 (21.8 g, 98.9 mmol) and triethylamine (31.7 mL, 220 mmol) in MeCN (200 mL) at 0° C. is added AY-2 (15.0 g, 110 mmol). The resultant mixture is warmed to ambient temperature, stirred for 30 min, poured into ice water, and extracted with EtOAc (200 mL). The organic layer is extracted with saturated aqueous $NaHCO_3$ (100 mL) and brine (100 mL), dried over $Na_2SO_4$, filtered and concentrated to afford AY-3.

To a solution of AY-3 (33.2 g, 104 mmol) in a mixture of dioxane (100 mL) and water (50 mL) is added LiOH (10.9 g, 259 mmol). The resultant mixture is stirred for 2 h, neutralized with concentrated HCL, and extracted with EtOAc (2×200 mL). The organic layer is dried over $Na_2SO_4$, filtered and concentrated. The residue is purified on $SiO_2$ (0-75% EtOAc in DCM) to give AY-4.

To a solution of AY-4 (12.5 g, 44.9 mmol) in EtOH (200 mL) is added 10% Pd/C (4.78 g). The mixture is stirred for 4 h under an atmosphere of $H_2$, filtered through a pad of Diatomaceous earth, and concentrated to give the title product (AY).

Syntheses of Compounds of Formula I

Methods of making the compounds of the invention are described in detail below. Mass spectral data for the compounds of the invention are found in Table 2.

Example 1

Preparation of 2-Methoxy-1-(4-{6-[5-(2H-pyrazol-3-yl)-pyridin-2-yloxy]-naphthalen-2-ylmethyl}-piperazin-1-yl)-ethanone (1)

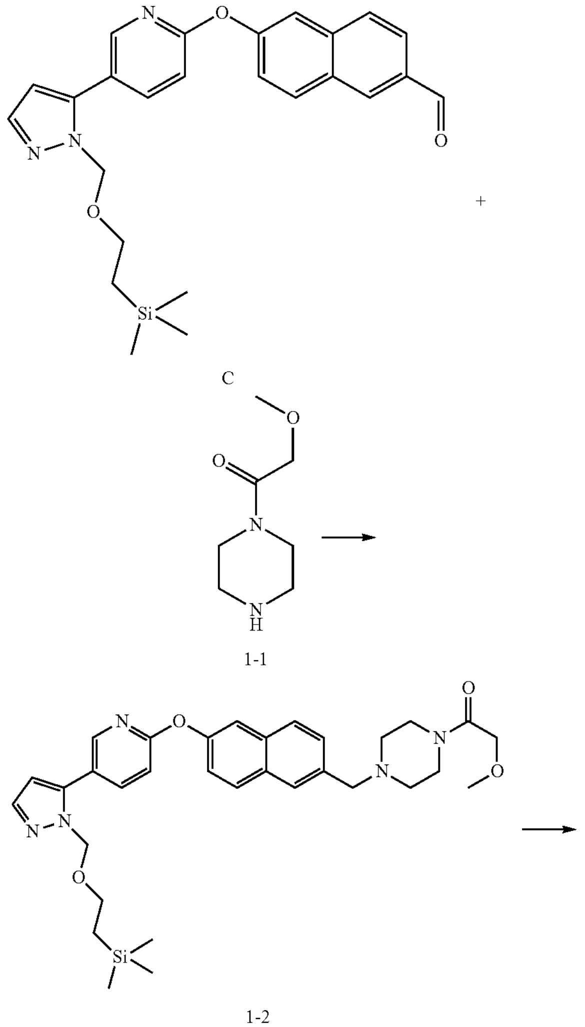

\+

1-1

1-2

-continued

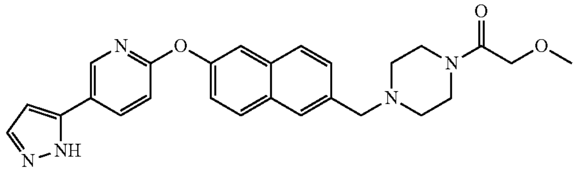

1

A solution of intermediates C (30.0 mg, 0.0670 mmol) and 1-1 (13.8 mg, 0.0880 mmol) in DCM (2 mL) is treated with sodiumtriacetoxyborohydride (21.4 mg, 0.101 mmol). The resultant mixture is stirred at ambient temperature for 24 h and concentrated. The residue is purified by reverse phase HPLC eluting with 0-65% MeCN in water (+0.1% TFA) to give the intermediate 1-2. MS (ES+): m/z 588.7 $[M+H]^+$ To 1-2 (30.0 mg, 0.0470 mmol) is added a solution of TFA/DCM (2 mL, 1:1). The mixture is stirred for 2 h and concentrated. The residue is purified by reversed phase HPLC eluting with 0-65% MeCN in water (+0.1% TFA). Fractions containing the desired product are combined and concentrated. The residue is dissolved in DCM and washed with saturated aqueous $NaHCO_3$. The organic layer is dried over $Na_2SO_4$, filtered and concentrated to give the title product (1).

The following examples are synthesized using intermediate C and the appropriate amine reagent according to the procedure described for the synthesis of Example 1.

| Ex. | Compound Name | Amine Reagent |
|---|---|---|
| 3 | 5-(2H-Pyrazol-3-yl)-2-(6-pyrrolidin-1-ylmethyl-naphthalen-2-yloxy)-pyridine | 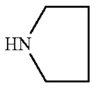 |
| 5 | 1-{6-[5-(2H-Pyrazol-3-yl)-pyridin-2-yloxy]-naphthalen-2-ylmethyl}-piperidine-4-carboxylic acid amide | 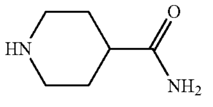 |
| 6 | N-(1-{6-[5-(2H-Pyrazol-3-yl)-pyridin-2-yloxy]-naphthalen-2-ylmethyl}-piperidin-4-yl)-acetamide | 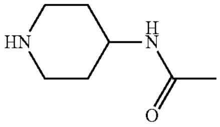 |
| 7 | (S)-3-Hydroxy-1-(1-{6-[5-(2H-pyrazol-3-yl)-pyridin-2-yloxy]-naphthalen-2-ylmethyl}-piperidin-4-yl)-pyrrolidin-2-one | 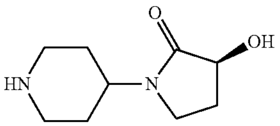 [SMILES: O=C1[C@@H](O)CCN1C1CCNCC1] |

Example 2

Preparation of 1-(4-{6-[5-(2H-Pyrazol-3-yl)-pyridin-2-yloxy]-naphthalen-2-ylmethyl}-piperazin-1-yl)-ethanone (2)

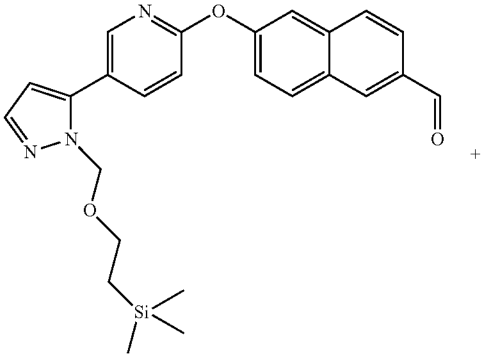

C

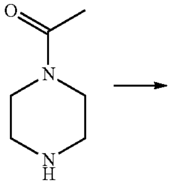

2-1

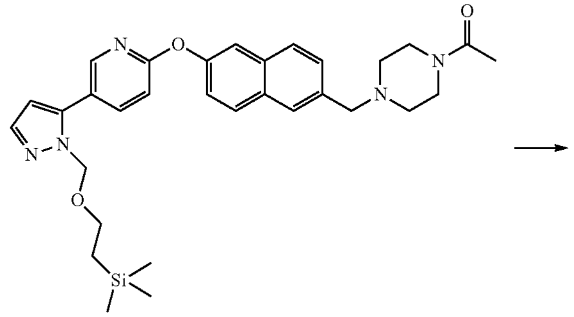

2-2

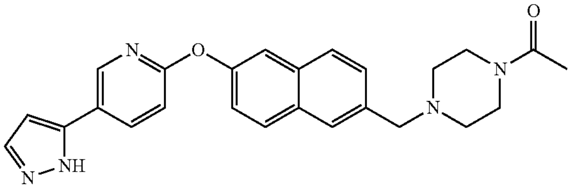

2

To a solution of intermediate C (200 mg, 0.449 mmol) and 2-1 (97.8 mg, 0.763 mmol) in DCM (2.0 mL) is added sodium triacetoxyborohydride (152 mg, 0.718 mmol), and the resultant mixture is stirred at ambient temperature. After 24 h, the reaction mixture is diluted with DCM and extracted with saturated aqueous $NaHCO_3$. Phases are separated and the organic layer is dried over $Na_2SO_4$, filtered and concentrated to give 2-2.

To compound 2-2 (195 mg, 0.350 mmol) is added a mixture of TFA in DCM (2 mL, 1:1). The resultant mixture is stirred for 2 h at ambient temperature, and concentrated. The residue is purified by reverse phase prep HPLC eluting with 0-50% MeCN in water (+0.1% TFA). The desired fractions are pooled, concentrated, dissolved in DCM, extracted with saturated aqueous $NaHCO_3$, dried over $Na_2SO_4$, filtered and concentrated to give the title product (2).

Example 4

Preparation of 1-{6-[5-(2H-Pyrazol-3-yl)-pyridin-2-yloxy]-naphthalen-2-ylmethyl}-piperidin-4-ol (4)

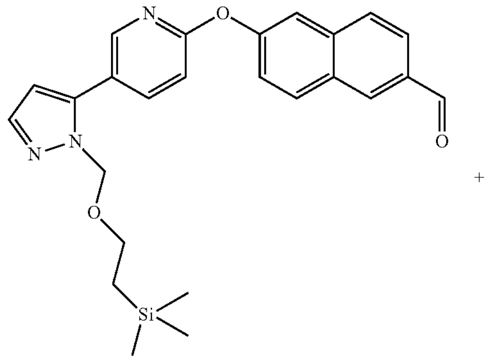

C

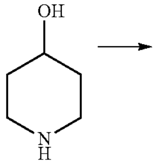

41

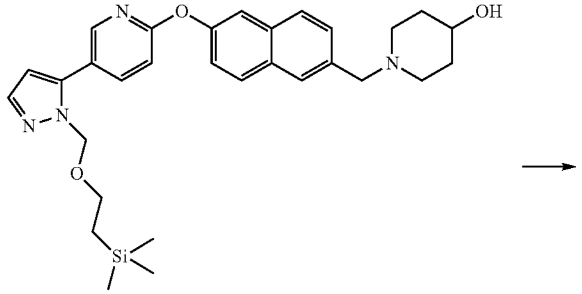

4-2

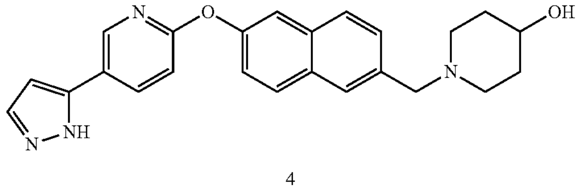

4

To a stirred solution of intermediate C (200 mg, 0.449 mmol) and 4-1 (77.2 mg, 0.763 mmol) in DCM (2.0 mL) is added sodium triacetoxyborohydride (152 mg, 0.718 mmol). After 24 h at ambient temperature, the mixture is diluted with DCM and extracted with saturated aqueous $NaHCO_3$. The organic layer is dried over $Na_2SO_4$, filtered and concentrated to afford 4-2.

To 4-2 (197 mg, 0.371 mmol) is added a mixture of TFA and DCM (2 mL, 1:1). After stirring for 2 h at ambient temperature, the reaction mixture is concentrated and purified by reverse phase prep HPLC eluting with 0-60% MeCN in water (+0.1% TFA). The desired fractions are pooled and concentrated. The residue is dissolved in DCM, extracted with saturated aqueous $NaHCO_3$, dried over $Na_2SO_4$, filtered and concentrated to give the title product (4).

Example 8

Preparation of dimethyl-{6-[4-(2H-pyrazol-3-yl)-phenoxy]-chroman-2-ylmethyl}-amine (8)

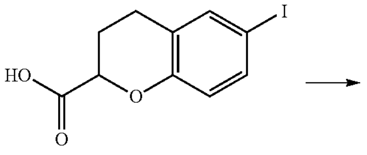

8-1

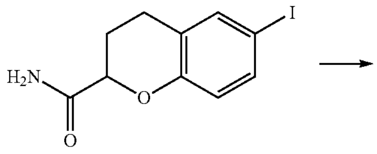

8-2

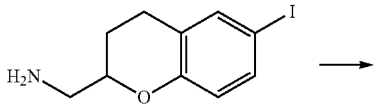

8-3

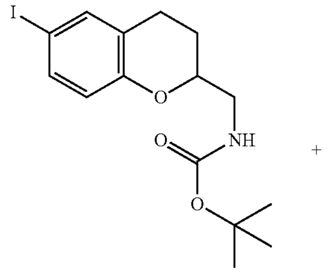

8-4

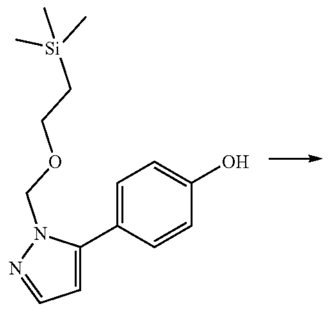

B

-continued

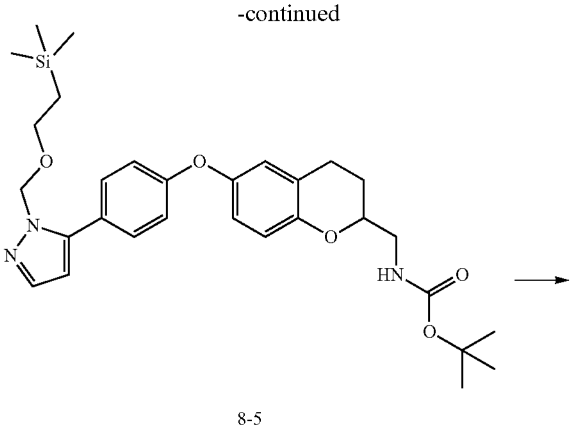

8-5

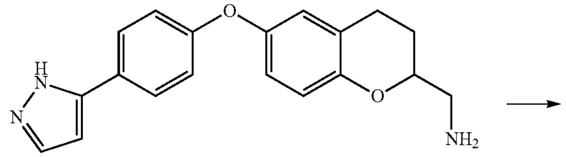

8-6

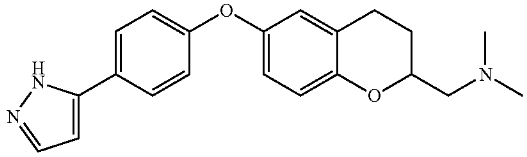

8

To a solution of 8-1(8.90 g, 29.5 mmol) in DMF (100 mL) is added CDI (5.70 g, 35.4 mmol). After stirring for 1.5 h at ambient temperature, ammonium acetate (5.30 g, 88.4 mmol) is added, and the mixture is stirred overnight. The reaction is poured into water and the resultant precipitate is filtered and air dried to give the intermediate 8-2. MS (ES+): m/z 304.1 $[M+H]^+$ To a solution of 8-2 (4.70 g, 15.5 mmol) in THF (165 mL) is added a solution of borane.dimethylsulfide complex in THF (2M, 38.8 mL). The reaction mixture is heated to reflux for 3 h, cooled to ambient temperature, and quenched with EtOH followed by 2N to HCl. The stirred mixture is warmed to reflux for 1 hour, made basic with 1N NaOH, concentrated and thrice extracted with EtOAc. The combined organic extracts are washed with brine, dried over $Na_2SO_4$ filtered and concentrated to give the crude intermediate 8-3. MS (ES+): m/z 289.9 $[M+H]^+$ A solution of 8-3 (4.40 g, 15.2 mmol), Boc anhydride (4.00 g, 18.5 mmol), and the Hunig's base (3.40 mL, 18.5 mmol) in THF (75 mL) is stirred at ambient temperature overnight. The mixture is concentrated, and partitioned between EtOAc and water. The organic layer is washed with saturated aqueous $NaHCO_3$ and brine, dried over $Na_2SO_4$, filtered and concentrated. The residue is purified by flash chromatography (0-80% EtOAc in hexane) to give the intermediate 8-4. MS (ES+): m/z 389.9 $[M+H]^+$ A mixture of 8-4 (300 mg, 1.03 mmol), B (402 mg, 1.03 mmol), dimethylamino-acetic acid (31.9 mg, 0.310 mmol), CuI (19.6 mg, 0.103 mmol) and cesium carbonate (336 mg, 1.03 mmol) in DMSO (3 mL) is sparged with $N_2$ for 10 min, and the resultant mixture is heated at 130° C. After 30 min, the mixture is cooled to the ambient temperature, diluted with EtOAc and filtered through a pad of Diatomaceous earth. The filtrate is washed with water, dried over $Na_2SO_4$, filtered and concentrated. The residue is purified by flash chromatography (0-40% EtOAc in heptane) to give the intermediate 8-5. MS (ES+): m/z 552.7 $[M+H]^+$ To 8-5 (125.0 mg, 0.227 mmol) is added a solution of TFA/DCM (4 mL, 1:1). The mixture is stirred for 2 h and concentrated. The residue is purified by reverse phase HPLC eluting with 0-50% MeCN in water (+0.1% TFA). Fractions containing the desired product are combined and concentrated. The residue is dissolved in DCM and washed with saturated aqueous $NaHCO_3$. The organic layer is dried over $Na_2SO_4$, filtered and concentrated to give the intermediate 8-6. MS (ES+): m/z 322.5 $[M+H]^+$ A solution of 8-6 (20.0 mg, 0.0620 mmol) and formaldehyde (19.2 mL, 0.311 mmol) in THF (1 mL) is stirred for 10 min at ambient temperature. Sodiumtriacetoxyborohydride (69.4 mg, 0.311 mmol) is added and the mixture is stirred at ambient temperature. After 24 h, the mixture is quenched with methanol and concentrated. The residue is purified by reverse phase HPLC eluting with 0-60% MeCN in water (+0.1% TFA). Fractions containing the desired product are combined and concentrated. The residue is dissolved in DCM and washed with saturated aqueous $NaHCO_3$. The organic layer is dried over $Na_2SO_4$, filtered and concentrated to give the title product (8). MS (ES+): m/z 350.6 $[M+H]^+$.

Example 9

Preparation of 1-{7-[5-(2H-Pyrazol-3-yl)-pyridin-2-yloxy]-chroman-2-ylmethyl}-piperidine-4-carboxylic acid amide (9)

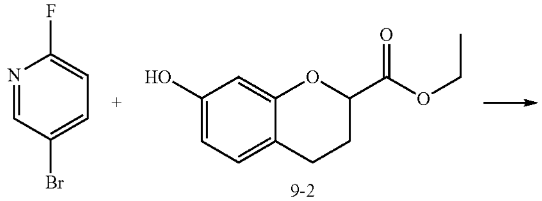

9-1 9-2

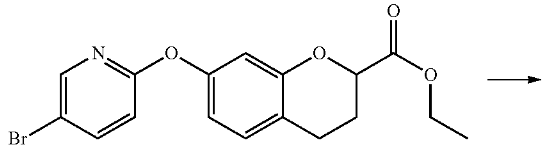

9-3

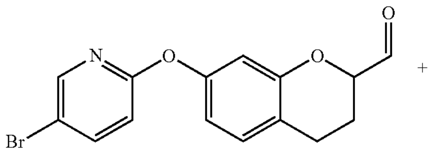

9-4

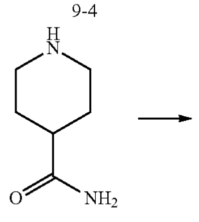

9-5

-continued

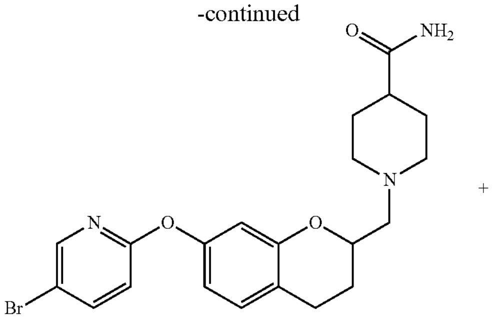

9-6

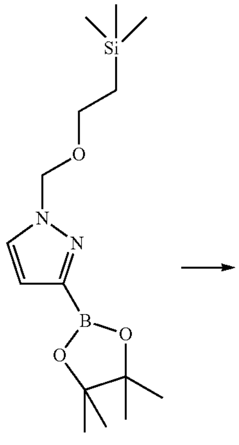

9-7

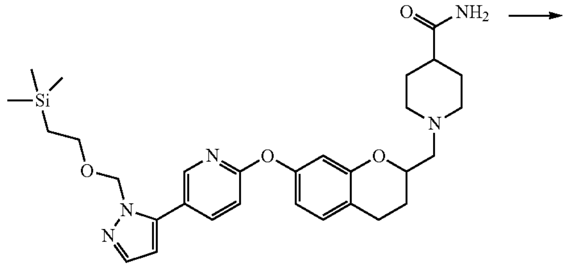

9-8

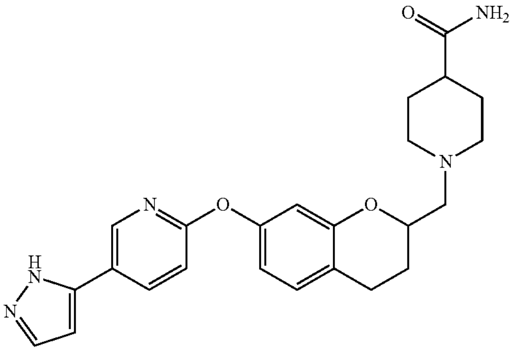

9

A mixture of 9-1 (1.50 g, 8.52 mmol), 9-2 (0.900 g, 4.26 mmol) and $K_2HCO_3$ (1.70 g, 12.8 mmol) in DMF (12 mL) is heated at 120° C. After 6 h, the mixture is cooled to ambient temperature, poured into water and extracted twice with EtOAc. The combined organic layers are washed with water, dried over $Na_2SO_4$, filtered and concentrated. The residue is purified by flash chromatography (0-50% EtOAc in heptane) to give the intermediate 9-3. MS (ES+): m/z 379.7 $[M+H]^+$ A solution of 9-3 (1.00 g, 2.64 mmol) in THF (12 mL) under an Ar atmosphere is treated with a solution of DIBAL in toluene (1 M, 2.6 mL) at −78° C. The mixture is stirred for 2 to h, quenched with a saturated aqueous solution of potassium sodium tartrate (6 mL), and stirred for 24 h. The mixture is diluted with EtOAc and extracted. The organic layer is dried over $Na_2SO_4$, filtered and concentrated to give the crude intermediate 9-4. MS (ES+): m/z 334.3 $[M+H]^+$ A solution of 9-4 (150 mg, 0.449 mmol) and 9-5 (80.5 mg, 0.628 mmol) in DCM (2 mL) is treated with sodiumtriacetoxyborohydride (150.0 mg, 0.672 mmol). The mixture is stirred for 4 h at ambient temperature and concentrated. The residue is purified by reverse phase HPLC eluting with 0-60% MeCN in water (+0.1% TFA). Fractions containing the desired product are combined and concentrated. The residue is dissolved in DCM and washed with saturated aqueous $NaHCO_3$. The organic layer is dried over $Na_2SO_4$, filtered and concentrated to give the intermediate 9-6. MS (ES+): m/z 448.5 $[M+H]^+$ To a mixture of 9-6 (145 mg, 0.325 mmol), 9-7 (166.4 mg, 0.513 mmol), and bis(di-tert-butyl(4-dimethylaminophenyl) phosphine)dichloropalladium (II) (28.8 mg, 0.041 mmol) in DME (1 mL) is added aqueous solution of $Na_2CO_3$ (2M, 347 mL). The reaction mixture is sparged with $N_2$, and heated at 120° C. for 15 min. The mixture is diluted with EtOAc and filtered through a pad of Diatomaceous earth. The filtrate is dried over $Na_2SO_4$, filtered and concentrated. The residue is purified by reverse phase HPLC eluting with 0-60% MeCN in water (+0.1% TFA). Fractions containing the desired product are combined and concentrated. The residue is dissolved in DCM and washed with saturated aqueous $NaHCO_3$. The organic layer is dried over $Na_2SO_4$, filtered and concentrated to give the intermediate 9-8. MS (ES+): m/z 564.7 $[M+H]^+$ Intermediate 9-8 (141.0 mg, 0.250 mmol) is stirred in a solution of TFA/DCM (2 mL, 1:1) for 2 h. The mixture is concentrated and the resultant residue is purified by reversed phase HPLC eluting with 0-65% MeCN in water (+0.1% TFA). Fractions containing the desired product are combined and concentrated. The residue is dissolved in DCM and washed with saturated aqueous $NaHCO_3$. The organic layer is dried over $Na_2SO_4$, filtered and concentrated to give the title product (9).

Example 10

Preparation of 2-hydroxy-1-(4-{6-[4-(2H-pyrazol-3-yl)-phenoxy]-quinolin-2-ylmethyl}-piperazin-1-yl)-ethanone (10)

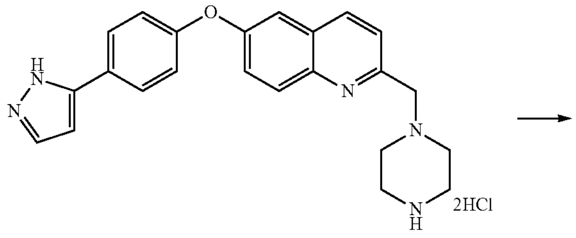

F

-continued

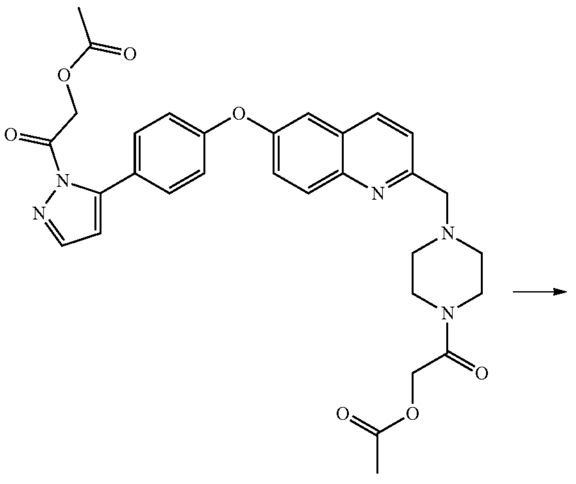

10-1

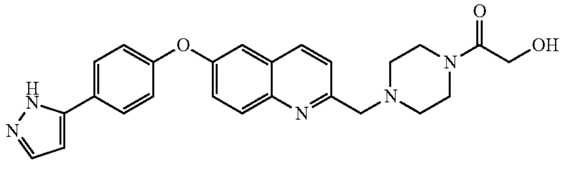

10

A stirred suspension of intermediate F (50.0 mg, 0.110 mmol) in DCM (2.00 mL) is treated with acetoxyacetyl chloride (14.7 µL, 0.140 mmol) and triethylamine (61.0 mL, 0.440 mmol). After 2 h, the volatiles are removed in vacuo to afford the crude intermediate 10-1.

A stirred solution of 10-1 (64.4 mg, 0.110 mmol) in THF (4.00 mL) and MeOH (1.00 mL) is treated with a solution of LiOH (27.3 mg, 0.550 mmol) in $H_2O$ (1.00 mL). After 3 h, the volatiles are removed, and the resultant residue is purified using silica gel flash chromatography (0-10% MeOH in DCM) to afford the title compound (10).

Example 11

Preparation of 3-(1-{6-[5-(2H-pyrazol-3-yl)-pyridin-2-yloxy]-quinolin-2-ylmethyl}-piperidin-4-yl)-oxazolidin-2-one (11)

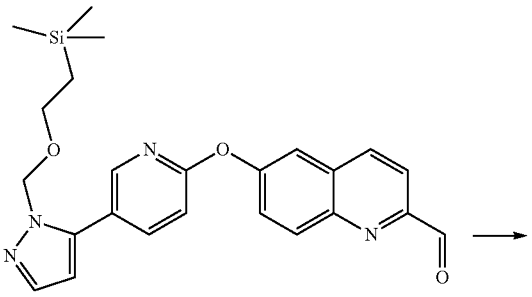

D

-continued

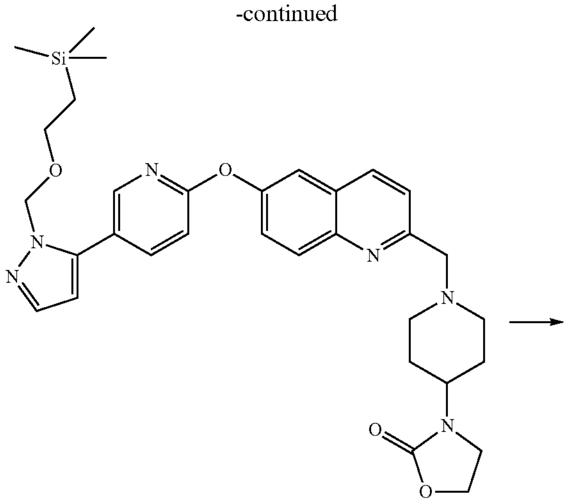

11-1

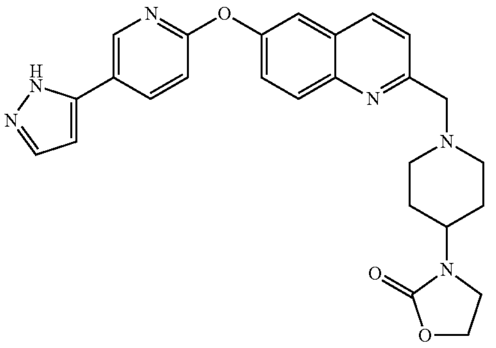

11

A stirred solution of D (0.100 g, 0.224 mmol) and 3-(4-piperidyl)oxazolidin-2-one (95.3 mg, 0.560 mmol) in $CH_3CN$ (2.00 mL) is treated with sodium triacetoxyborohydride (94.9 mg, 0.448 mmol). After 24 h, the reaction is quenched with MeOH (1.00 mL), stirred for 15 min, and concentrated. The resultant residue is purified using reverse phase HPLC to afford the intermediate 11-1 as the trifluoroacetate salt.

A suspension of 11-1 (0.149 g, 0.208 mmol) in $H_2O$ (1.00 mL) is treated with aqueous HCl (1N, 0.417 mL), and heated to 80° C. After 4 h, the reaction is cooled to 25° C., neutralized with aqueous NaOH (1N, 0.417 mL), and extracted with DCM (3×5 mL). The combined organic layers are dried over $Na_2SO_4$, decanted and concentrated. The resultant residue is purified using silica gel flash chromatography (5-10% MeOH in DCM) to afford the title compound (II).

Example 12

Preparation of 1-(4-{6-[4-(2H-pyrazol-3-yl)-phenoxy]-quinolin-2-ylmethyl}-piperazin-1-yl)-propan-1-one (12)

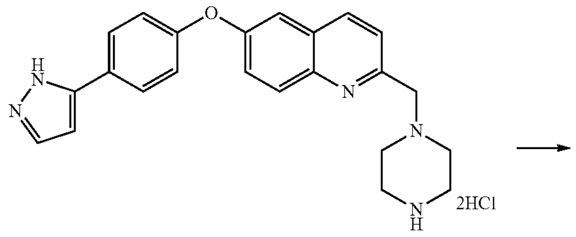

F

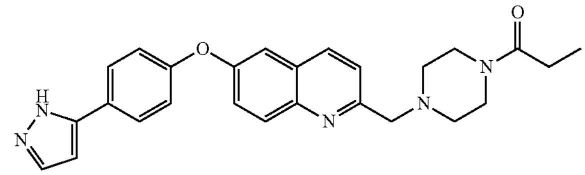

12

The title product (12) is prepared from intermediate F (40.0 mg, 0.087 mmol) and propionyl chloride (9.5 μL, 0.11 mmol) according to the procedure described for the synthesis of Example 10.

Example 13

Preparation of (S)-2-hydroxy-1-(4-{6-[4-(2H-pyrazol-3-yl)-phenoxy]-quinolin-2-ylmethyl}-piperazin-1-yl)-propan-1-one (13)

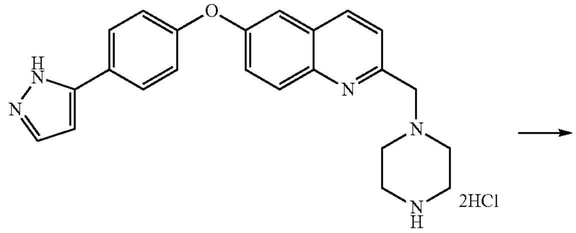

F

-continued

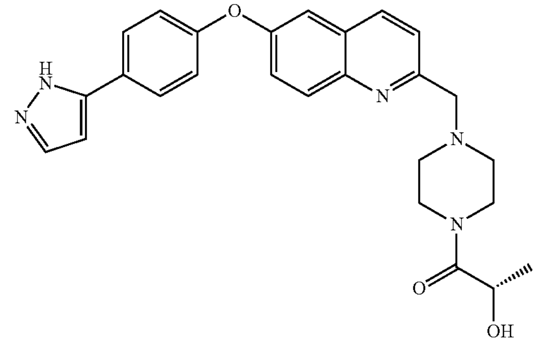

13

A stirred suspension of intermediate F (35.0 mg, 0.076 mmol) in DCM (2.00 mL) is treated with L-(+)-lactic acid (17.2 mg, 0.191 mmol), triethylamine (53 mL, 0.382 mmol) and TBTU (30.7 mg, 0.095 mmol). After 72 h, the mixture is concentrated and purified using silica gel flash chromatography (0-10% MeOH in DCM) to afford the title compound (13).

Example 14

Preparation of 2-morpholin-4-ylmethyl-6-[4-(2H-pyrazol-3-yl)-phenoxy]-pyrazolo[1,5-a]pyridine (14)

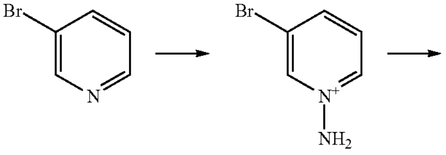

14-1

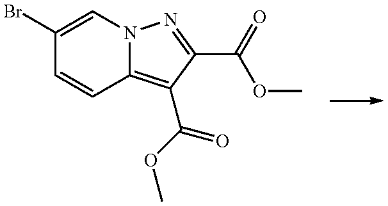

14-2

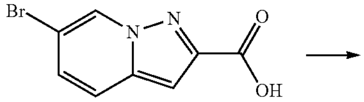

14-3

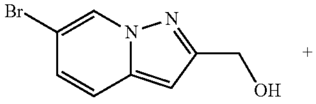

14-4

-continued

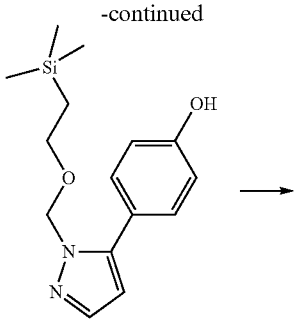

B

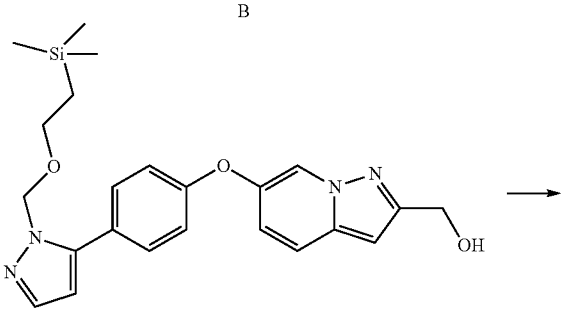

14-5

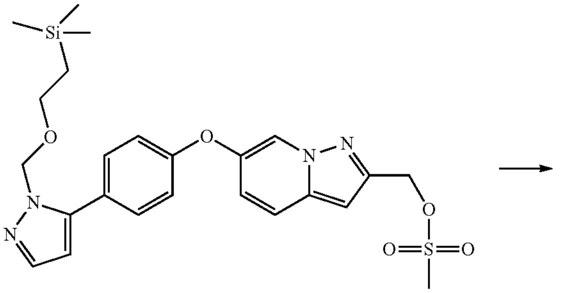

14-6

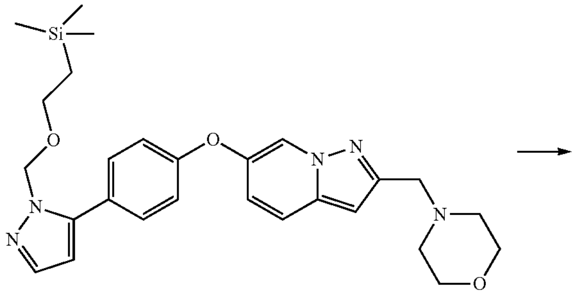

14-5

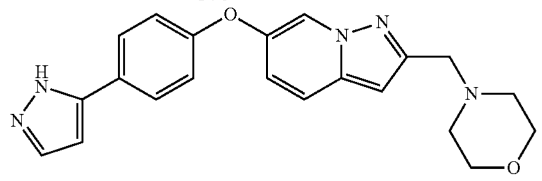

14

A solution of hydroxylamine-O-sulfonic acid (22.0 g, 195 mmol) is dissolved in cold $H_2O$ (12.0 mL). To this solution is added 3-bromopyridine (30.8 g, 190 mmol) and the mixture is heated to 90° C. for 30 min. The reaction is cooled to 25° C., and potassium carbonate (26.9 g, 195 mmol) is added with stirring. The water is removed in vacuo and the resultant residue is suspended in EtOH (100 mL), sonicated and filtered. To the filtrate is added hydroiodic acid (27.9 g, 204 mmol). The resultant solids are collected, dried and used without further purification.

The stirred solution of the crude 14-1 (8.77 g, 50.4 mmol) in DMF (100 mL) is added dimethyl acetylenedicarboxylate (6.50 g, 52.9 mmol). After 2 h, the reaction is diluted with $H_2O$ (150 mL) and poured into a mixture of EtOAC:$Et_2O$ (250 mL, 1:1). The aqueous phase is separated and extracted with EtOAc/$Et_2O$ (1:1, 2×100 mL). The organic layers are combined, washed with brine, dried over $Na_2SO_4$, decanted and concentrated. The crude is purified using silica gel flash chromatography (10-50% EtOAc in Heptane) to afford 14-2.

A solution of 14-2 (0.600 g, 1.92 mmol) in $H_2SO_4$:$H_2O$ (20 mL, 1:1) is heated to 80° C. for 8 h. The reaction is cooled to 25° C. and the pH is adjusted to pH 2 with NaOH (5N). The resultant solid is filtered to afford 14-3.

A stirred solution of 14-3 (0.405 g, 1.68 mmol) in THF (15 mL) is treated with $BH_3$.THF (1M, 8.40 mL). After 18 h, the reaction is quenched with aqueous NaOH (1N, 5 mL) and extracted with EtOAc (100 mL). The organic phase is washed with brine (2×50 mL), dried over $Na_2SO_4$, decanted and concentrated to afford 14-4.

A mixture of 14-4 (0.250 g, 1.10 mmol), B (0.351 g, 1.21 mmol), CuI (0.021 g, 0.11 mmol), pyridine-2-carboxylic acid (0.0271 g, 0.22 mmol) and potassium phosphate (0.467 g, 2.20 mmol) in degassed DMSO (10 mL) is heated to 140° C. for 24 h. The reaction is cooled to 25° C. and concentrated. The resultant residue is resuspended in EtOAc (15 mL) and poured into $H_2O$ (25 mL). The aqueous phase is separated and extracted with EtOAc (2×25 mL). The combined organic layers are washed with brine (2×50 mL), dried over $Na_2SO_4$, decanted and concentrated. The resultant residue is purified using silica gel flash chromatography (20-75% EtOAc in Heptane) to afford 14-5.

A stirred solution of 14-5 (0.067 g, 0.15 mmol) in DCM (3.00 mL) is treated with methanesulfonyl chloride (0.018 mL, 0.23 mmol) and triethylamine (0.032 mL, 0.023 mmol). After 4 h, the reaction is directly purified using silica gel flash chromatography (20-75% EtOAc in Heptane) to afford 14-6.

A stirred solution 14-6 (0.051 g, 0.10 mmol) in DCM (2.00 mL) is treated with morpholine (0.043 mL, 0.50 mmol). After 24 h, the mixture is concentrated and the resultant residue is purified using silica gel flash chromatography (20-75% EtOAc in Heptane) to afford 14-7.

A solution of 14-7 (0.045 g, 0.090 mmol) in 1,4-dioxane (1.00 mL) is treated with HCl in dioxane (4N, 2.00 mL) and aged for 6 h. The mixture is concentrated and the resultant residue is redissolved EtOAc (25 mL) and poured into 10% aqueous $NaHCO_3$ (50 mL). The aqueous phase is separated and extracted with EtOAc (2×25 mL). The combined organic layers are dried over $Na_2SO_4$, decanted and concentrated. The resultant residue is purified using silica gel flash chromatography (0-10% MeOH in DCM) to afford the title compound 14.

Example 15

Preparation of (1-hydroxy-cyclopropyl)-(4-{6-[4-(2H-pyrazol-3-yl)-phenoxy]-quinolin-2-ylmethyl}-piperazin-1-yl)-methanone (15)

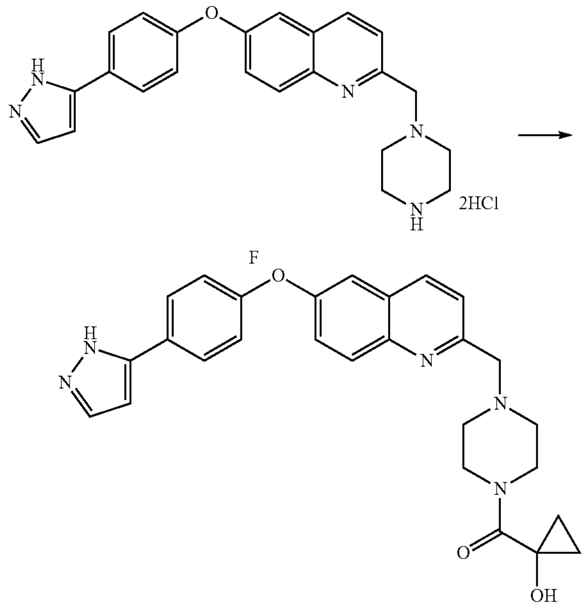

15

The title compound 15 is synthesized from intermediate F (35 mg, 0.076 mmol), and 1-hydroxy-1-cyclopropanecarboxylic acid (19 mg, 0.19 mmol) according to the procedure described for the synthesis of compound 13.

Example 16

Preparation of (S)-7-{6-[5-(2H-pyrazol-3-yl)-pyridin-2-yloxy]-quinolin-2-ylmethyl}-hexahydro-oxazolo[3,4-a]pyrazin-3-one (16)

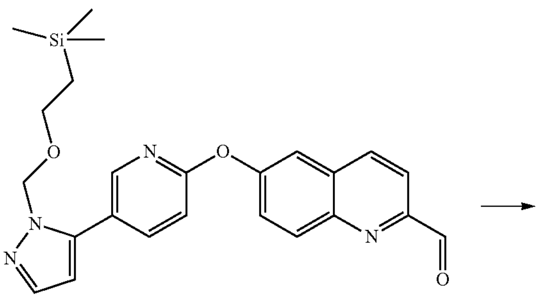

D

-continued

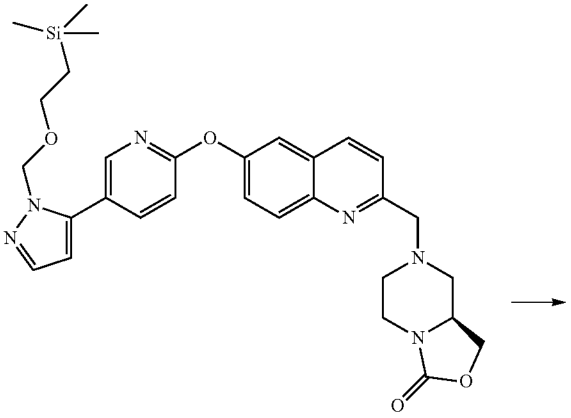

16-1

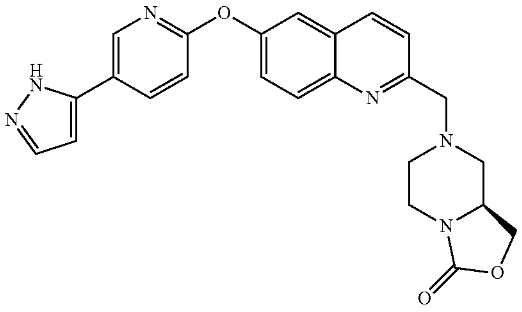

16

The title compound 16 is synthesized from intermediate D (0.100 g, 0.220 mmol) and (S)-hexahydro-oxazolo[3,4-a]pyrazin-3-one (48.0 mg, 0.269 mmol) according to the procedure described for the synthesis of compound 11.

Example 17

Preparation of 2-(2,2-Dioxo-2-λ-6-thia-5-aza-bicyclo[2.2.1]hept-5-ylmethyl)-6-[4-(2H-pyrazol-3-yl)-phenoxy]-quinoline (17)

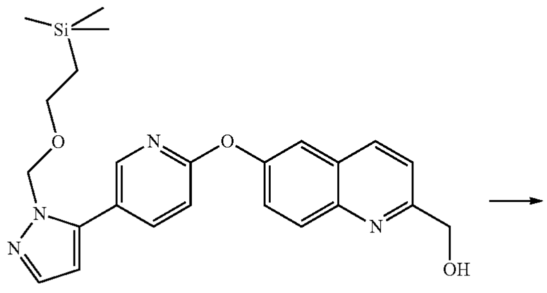

E

-continued

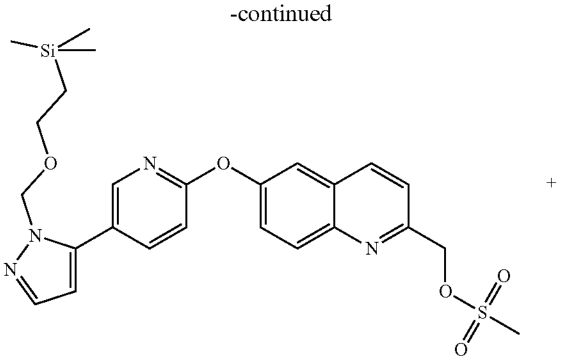

17-1

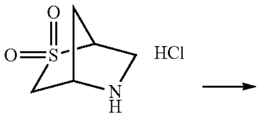

G

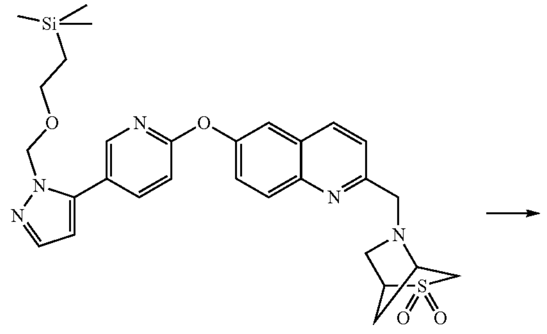

17-2

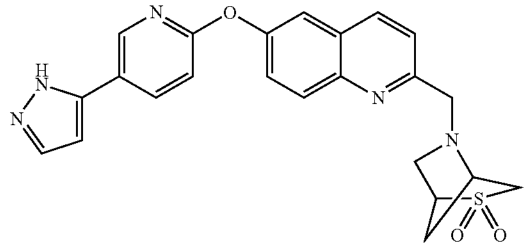

17

A stirred solution of E (0.100 g, 0.223 mmol) in DCM (2.00 mL) is treated with methanesulfonyl chloride (21 mL, 0.27 mmol), and triethylamine (37 mL, 0.27 mmol). After 2 h, the mixture is concentrated to afford the crude intermediate 17-1, which is redissolved in DCM (2.00 mL), and added to a mixture of intermediate G (49 mg, 0.27 mmol) in DCM (2.00 mL). The resultant mixture is treated with triethylamine (37 mL, 0.27 mmol) and stirred for 24 h. The volatiles are removed in vacuo and the resultant residue is purified using silica gel flash chromatography (25-75% EtOAc in Heptane) to afford 17-2.

Intermediate 17-2 (0.057 g, 0.10 mmol) is treated with HCl in dioxane (4N, 5.00 mL) and aged for 3 h. The mixture is concentrated, the resultant residue is re-suspended in DCM (20 mL) and poured into 10% aqueous $NaHCO_3$ (25 mL). The aqueous phase is separated and extracted with DCM (2×20 mL). The organic layers are combined, dried over $Na_2SO_4$, decanted and concentrated. The residue is purified using silica gel flash chromatography (1-5% MeOH-DCM gradient) to afford the title compound 17.

Example 18

Preparation of 2-{6-[5-(2H-pyrazol-3-yl)-pyridin-2-yloxy]-quinolin-2-ylmethyl}-hexahydro-pyrrolo[1,2-a]pyrazin-6-one (18)

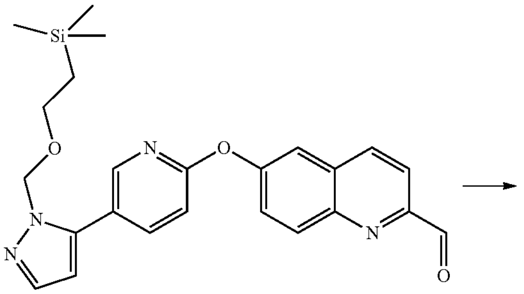

D

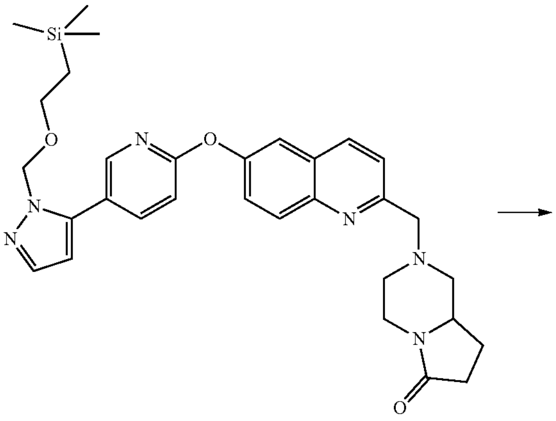

18-1

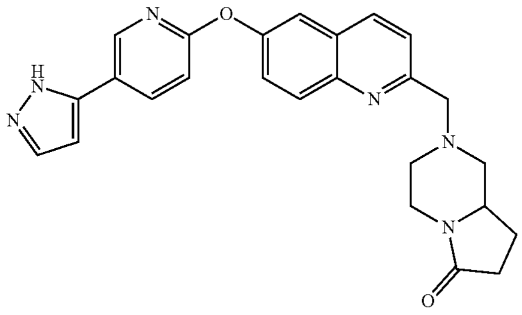

18

The title compound 18 is synthesized from intermediate D (0.100 g, 0.224 mmol) and hexahydro-pyrrolo[1,2-a]pyrazin- 6-one (78.5 mg, 0.560 mmol) according to the procedure described for the synthesis of compound 11.

Example 27

Preparation of 2-Hydroxy-1-(4-{6-[5-(2H-pyrazol-3-yl)-pyridin-2-yloxy]-quinolin-2-ylmethyl}-piperazin-1-yl)-ethanone (27)

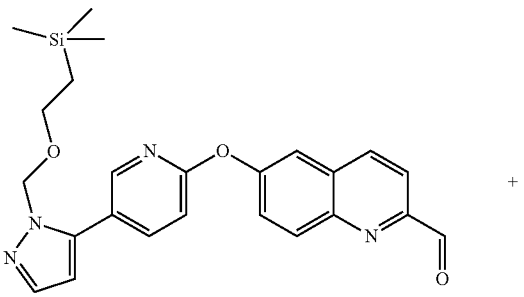

D

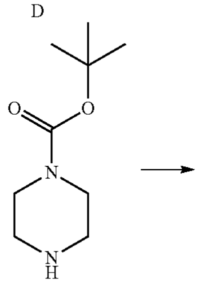

F-2

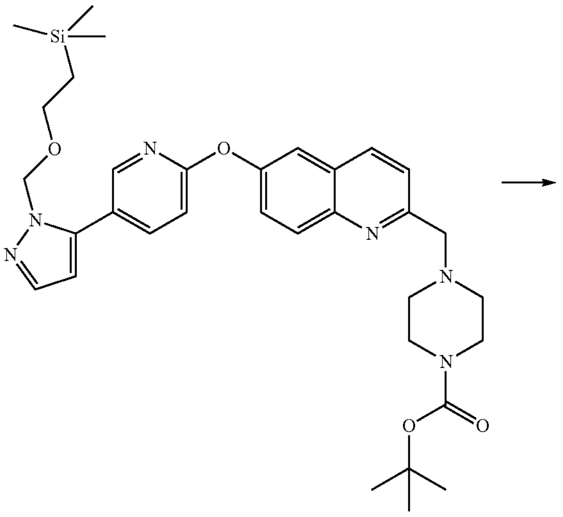

27-1

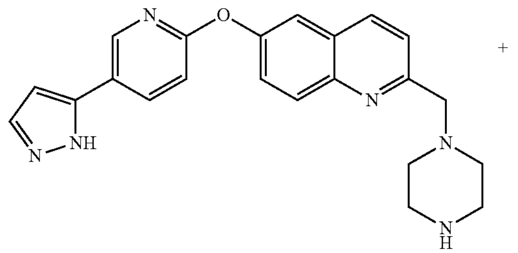

27-2

-continued

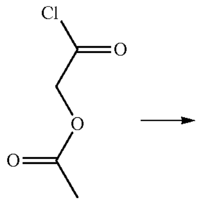

27-3

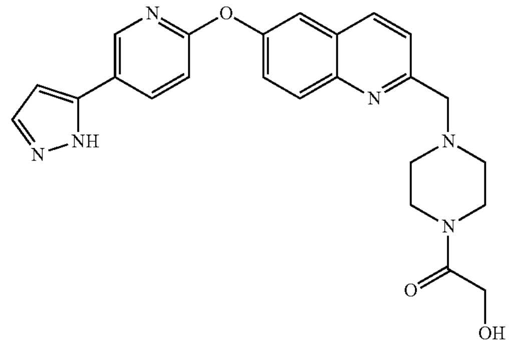

27

To a stirred solution of D (1.00 g, 2.24 mmol) and F-2 (0.830 g, 4.50 mmol) in DCM (25 mL) is added sodium triacetoxyborohydride (0.95 g, 4.5 mmol). After 16 hours, the reaction is quenched with MeOH and concentrated. The residue is treated with water (200 mL) and the aqueous layer is decanted. The residue is dissolved in DCM (200 mL), dried over $Na_2SO_4$, filtered and concentrated to afford the crude intermediate 27-1.

A solution of HCl in 1,4-dioxane (4 M, 10 mL) is added to a stirred solution of 27-1 (1.40 g, 2.00 mmol) in 1,4-dioxane (30 mL). After 72 hours, the mixture is filtered and the filter cake is washed with diethyl ether and dried under inert atmosphere to afford 27-2, as the hydrochloride salt.

A suspension of 27-2 (0.500 g, 0.540 mmol) in DCM (20 mL) is treated with 27-3 (0.170 mL, 1.60 mmol) and triethylamine (0.60 mL, 2.7 mmol). After 1 h, the reaction is concentrated and the residue is taken up in a 4:1 methanol/water mixture (25 mL). Lithium hydroxide monohydrate is added (0.050 g, 1.1 mmol) and the mixture is stirred at room temperature for 16 hours. The reaction is concentrated and the residue is purified by reverse phase prep HPLC eluting with 0-30% MeCN in water (+0.1% FA) over 20 minutes. The desired fractions are pooled and concentrated. The residue is dissolved in MeOH, passed through a PS—HCO3 cartridge, and lypholized to afford the title compound (27).

The following examples are synthesized using intermediate D and the appropriate amine reagent (free base or the salt form) according to the above-described procedure for the synthesis of Example 27. Generally, for the syntheses that utilize amine salts, an equivalent of triethylamine is added prior to addition of sodium triacetoxyborohydide.

| Ex. | Compound Name | Amine Reagent |
|---|---|---|
| 33 | 2-Hydroxy-N-methyl-N-(1-{6-[5-(2H-pyrazol-3-yl)-pyridin-2-yloxy]-quinolin-2-ylmethyl}-piperidin-4-yl)-acetamide | 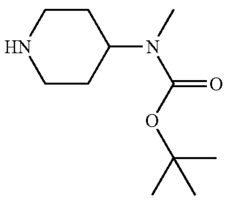 |
| 38 | 2-Hydroxy-1-((R)-3-methyl-4-{6-[5-(2H-pyrazol-3-yl)-pyridin-2-yloxy]-quinolin-2-ylmethyl}-piperazin-1-yl)-ethanone | 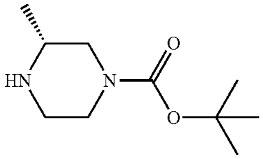 |
| 44 | 2-Hydroxy-1-(3-{6-[5-(2H-pyrazol-3-yl)-pyridin-2-yloxy]-quinolin-2-ylmethyl}-3,8-diaza-bicyclo[3.2.1]oct-8-yl)-ethanone | 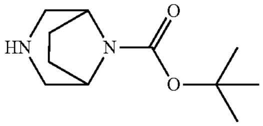 |
| 46 | 2-Hydroxy-N-(4-methyl-1-{6-[5-(2H-pyrazol-3-yl)-pyridin-2-yloxy]-quinolin-2-ylmethyl}-piperidin-4-yl)-acetamide | 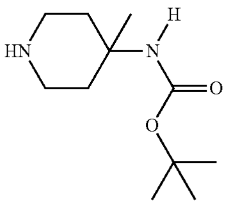 |
| 50 | 2-Hydroxy-1-(8-{6-[5-(2H-pyrazol-3-yl)-pyridin-2-yloxy]-quinolin-2-ylmethyl}-1,8-diaza-spiro[4.5]dec-1-yl)-ethanone | 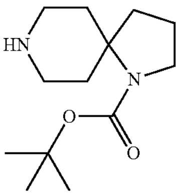 [SMILES: CC(C)(C)OC(=O)N1CCCC12CCNCC2] |

Alternative Preparation of Compound 27 (2-Hydroxy-1-(4-{6-[5-(2H-pyrazol-3-yl)-pyridin-2-yloxy]-quinolin-2-ylmethyl}-piperazin-1-yl)-ethanone)

Compound 27 can also be prepared by the method described below.

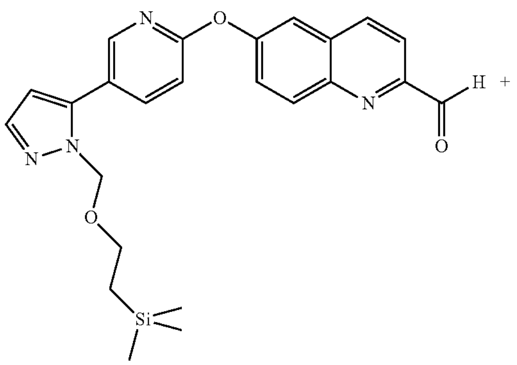

D

-continued

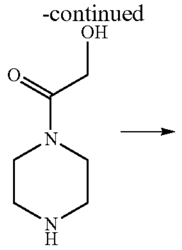

AY

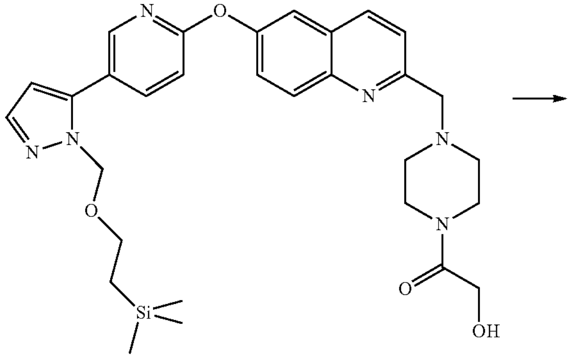

27-1

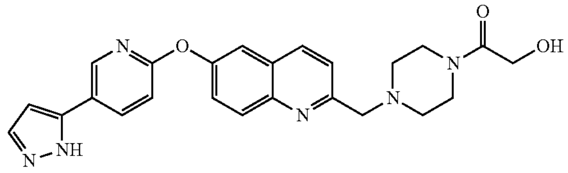

27

To a stirred solution of intermediates D (10.0 g, 22.4 mmol) and AY (3.55 g, 24.6 mmol) in DCM (200 mL) is added sodium triacetoxyborohydride (7.12 g, 33.6 mmol). After 24 h at ambient temperature, the mixture is diluted with DCM (1 L) and extracted with saturated aqueous $NaHCO_3$ (500 mL), and brine (500 mL). The organic layer is dried over anhydrous $Na_2SO_4$, filtered and concentrated. The residue is purified by silica gel chromatography eluting with 100% EtOAc, followed by a gradient of 0-10% MeOH in DCM to give compound 27-1.

To compound 27-1 (18.0 g, 31.3 mmol) is added a mixture of TFA and DCM (150 mL, 1:2). The resultant mixture is stirred at ambient temperature for 3 h, diluted with DCM (1 L) and carefully quenched with saturated aqueous $NaHCO_3$ (500 mL) and solid $Na_2CO_3$. The organic layer is dried over anhydrous $Na_2SO_4$, filtered and concentrated. The residue is purified by silica gel chromatography eluting with 0-10%

MeOH in DCM. The resultant solid is re-crystallized from MeOH to give the title product (27).

Example 28

Preparation of 2-methoxy-1-(4-{6-[5-(2H-pyrazol-3-yl)-pyridin-2-yloxy]-quinolin-2-ylmethyl}-piperazin-1-yl)-ethanone (28)

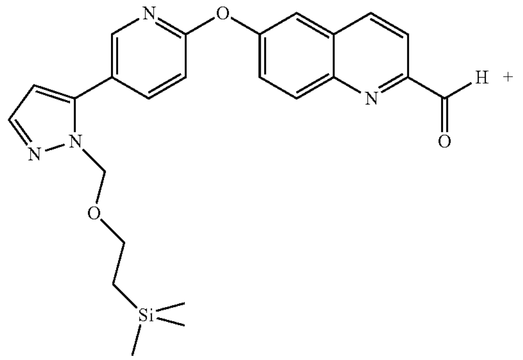

D

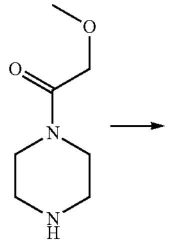

H

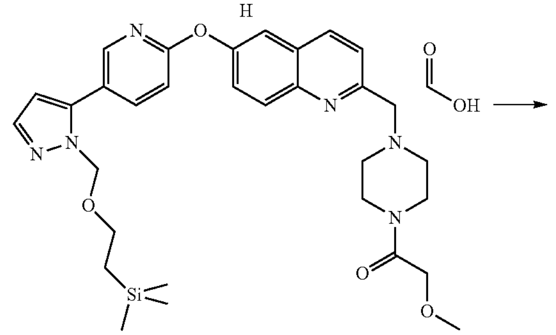

28-1

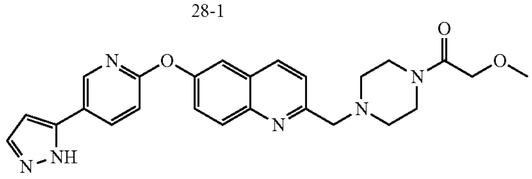

28

To a stirred solution of D (0.100 g, 0.220 mmol) and H (0.060 g, 0.370 mmol) in DCM (2 mL) is added sodium triacetoxyborohydride (95.0 mg, 0.450 mmol). After 16 h, the reaction is quenched with MeOH and purified by reverse phase HPLC eluting with 0-60% MeCN in water (+0.1% FA) over 20 minutes to afford 28-1.

A mixture of 28-1 (0.060 g, 0.10 mmol) in water (2 mL) is treated with aqueous 1N HCl and heated to 80° C. for 3 hours. Upon cooling to ambient temperature, the reaction is purified by reverse phase prep HPLC eluting with 0-30% MeCN in water (+0.1% FA) over 20 minutes. The desired fractions are pooled and concentrated. The residue is dissolved in MeOH, passed through a PS—HCO3 cartridge, and lypholized to afford the title compound (28).

The following examples are synthesized using Intermediate D and the appropriate amine reagent (free base or the salt form) according to the above-described procedure for the synthesis of Example 28. Generally, for the syntheses that utilize amine salts, an equivalent of triethylamine is added prior to addition of sodium triacetoxyborohydride.

| Ex. | Compound Name | Amine Reagent |
|---|---|---|
| 19 | 6-[5-(2H-Pyrazol-3-yl)-pyridin-2-yloxy]-2-pyrrolidin-1-ylmethyl-quinoline | 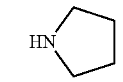 |
| 20 | 2-(2-Oxa-6-aza-spiro[3.4]oct-6-ylmethyl)-6-[5-(2H-pyrazol-3-yl)-pyridin-2-yloxy]-quinoline | 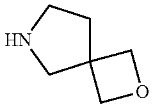 |
| 21 | 2-Azetidin-1-ylmethyl-6-[5-(2H-pyrazol-3-yl)-pyridin-2-yloxy]-quinoline | 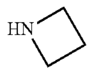 |
| 22 | 2-Azepan-1-ylmethyl-6-[5-(2H-pyrazol-3-yl)-pyridin-2-yloxy]-quinoline | 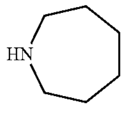 |
| 23 | 2-Piperidin-1-ylmethyl-6-[5-(2H-pyrazol-3-yl)-pyridin-2-yloxy]-quinoline | 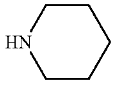 |
| 24 | 1-(8-{6-[5-(2H-Pyrazol-3-yl)-pyridin-2-yloxy]-quinolin-2-ylmethyl}-3,8-diaza-bicyclo[3.2.1]oct-3-yl)-ethanone | 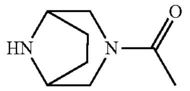 |
| 25 | Methyl -{6-[5-(2H-pyrazol-3-yl)-pyridin-2-yloxy]-quinolin-2-ylmethyl}-amine | 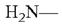 |
| 26 | 2-Methyl-1-(4-{6-[5-(2H-pyrazol-3-yl)-pyridin-2-yloxy]-quinolin-2-ylmethyl}-piperazin-1-yl)-propan-1-one | 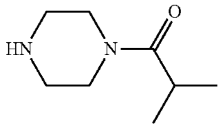 |
| 30 | 8-{6-[5-(2H-Pyrazol-3-yl)-pyridin-2-yloxy]-quinolin-2-ylmethyl}-1,8-diaza-spiro[4.5]decan-2-one | 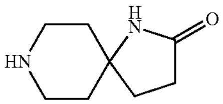 [SMILES: O=C1CCC2(CCNCC2)N1] |
| 31 | 3-Oxa-3-(4-{6-[5-(2H-pyrazol-3-yl)-pyridin-2-yloxy]-quinolin-2-ylmethyl}-piperazin-1-yl)-propionitrile | 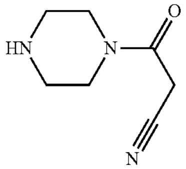 |
| 34 | (R)-2-({6-[5-(2H-Pyrazol-3-yl)-pyridin-2-yloxy]-quinolin-2-ylmethyl}-amino)-propionamide | 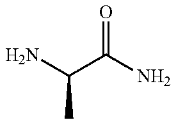 |

-continued

| Ex. | Compound Name | Amine Reagent |
|---|---|---|
| 36 | 1-{3-[(Methyl-{6-[5-(2H-pyrazol-3-yl)-pyridin-2-yloxy]-quinolin-2-ylmethyl}-amino)-methyl]-azetidin-1-yl}-ethanone | 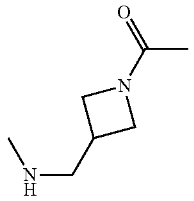 |
| 39 | 2-Methanesulfonyl-1-(4-{6-[5-(2H-pyrazol-3-yl)-pyridin-2-yloxy]-quinolin-2-ylmethyl}-piperazin-1-yl)-ethanone | 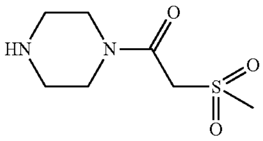 |
| 43 | 4-{6-[5-(2H-Pyrazol-3-yl)-pyridin-2-yloxy]-quinolin-2-ylmethyl}-piperazine-1-carboxylic acid amide | 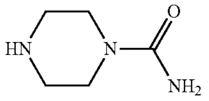 |
| 45 | 2-({6-[5-(2H-Pyrazol-3-yl)-pyridin-2-yloxy]-quinolin-2-ylmethyl}-amino)-1-pyrrolidin-1-yl-ethanone | 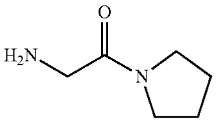 |
| 47 | 2-(Methyl-{6-[5-(2H-pyrazol-3-yl)-pyridin-2-yloxy]-quinolin-2-ylmethyl}-amino)-acetamide | 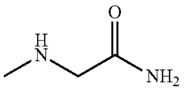 |
| 48 | 2-(2-Oxa-6-aza-spiro[3.5]non-6-ylmethyl)-6-[5-(2H-pyrazol-3-yl)-pyridin-2-yloxy]-quinoline | 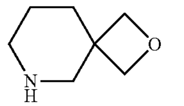 |
| 49 | (S)-3-({6-[5-(2H-Pyrazol-3-yl)-pyridin-2-yloxy]-quinolin-2-ylmethyl}-amino)-pyrrolidin-2-one | 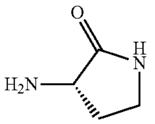 |
| 51 | (S)-2-Phenyl-2-({6-[5-(2H-pyrazol-3-yl)-pyridin-2-yloxy]-quinolin-2-ylmethyl}-amino)-acetamide | 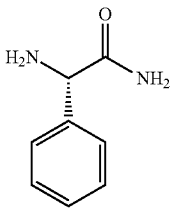 [SMILES: NC(=O)[C@@H](N)c1ccccc1] |

Alternative Preparation of Compound 28 (2-methoxy-1-(4-{6-[5-(2H-pyrazol-3-yl)-pyridin-2-yloxy]-quinolin-2-ylmethyl}-piperazin-1-yl)-ethanone)

Compound 28 can also be prepared by the method described below.

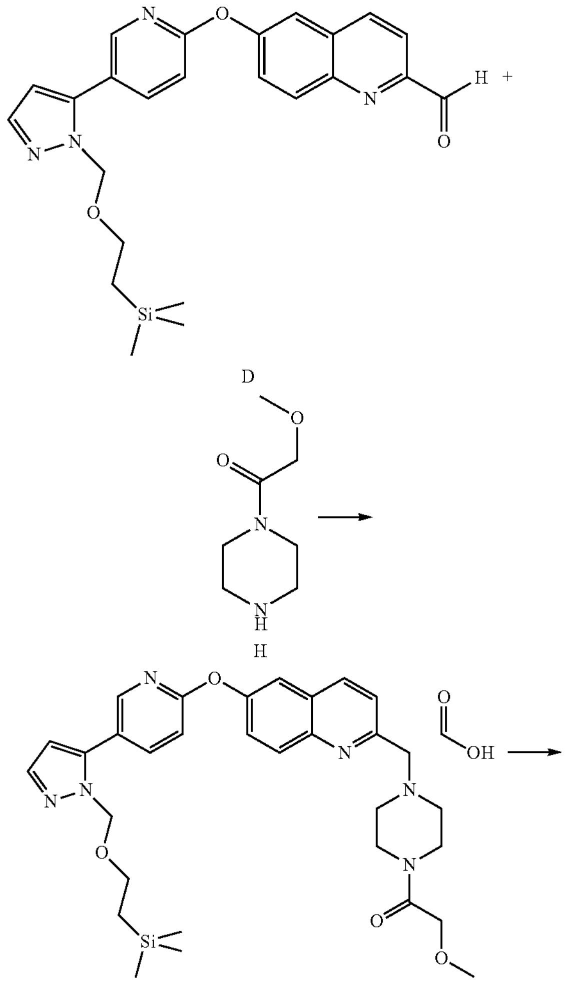

28-1

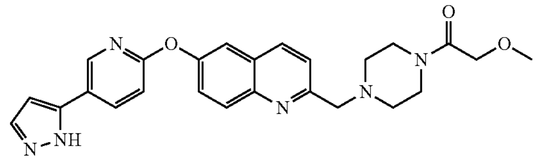

28

To a solution of intermediates D (5.00 g, 11.2 mmol) and H (2.13 g, 13.4 mmol) in DCM (100 mL) is added sodium triacetoxyborohydride (4.75 g, 22.4 mmol). The resultant mixture is stirred at ambient temperature for 5 h, diluted with DCM (500 mL) and washed with saturated aqueous $NaHCO_3$ (300 mL). The organic layer is dried over anhydrous $Na_2SO_4$, filtered and concentrated. The residue is purified by silica gel chromatography eluting with 100% EtOAc, followed by a gradient of 0-10% MeOH in DCM to give compound 28-1.

To compound 28-1 (3.40 g, 5.78 mmol) is added a mixture of TFA in DCM (30 mL, 1:1). The resultant mixture is stirred for 3 h, and concentrated. The residue is dissolved in DCM (500 mL) and extracted with saturated aqueous $NaHCO_3$ (300 mL). Phases are separated, the organic layer is dried over anhydrous $Na_2SO_4$, filtered and concentrated. The residue is purified by silica gel chromatography eluting with a gradient of 0-10% MeOH in DCM. The resultant solid is triturated with MeOH to afford the title product (28).

Example 29

Preparation of 1-(4-{6-[5-(2H-Pyrazol-3-yl)-pyridin-2-yloxy]-quinolin-2-ylmethyl}-piperazin-1-yl)-propan-1-one (29)

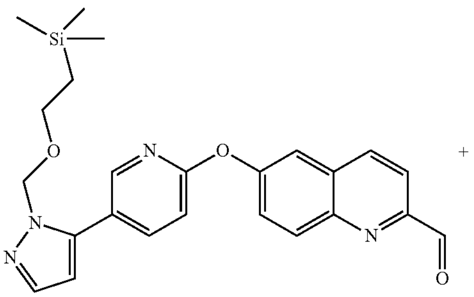

D

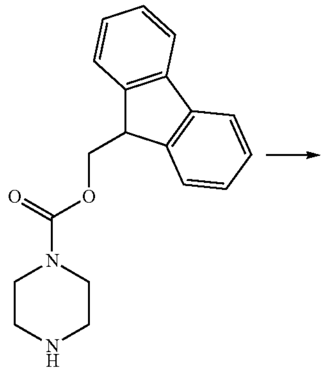

29-1

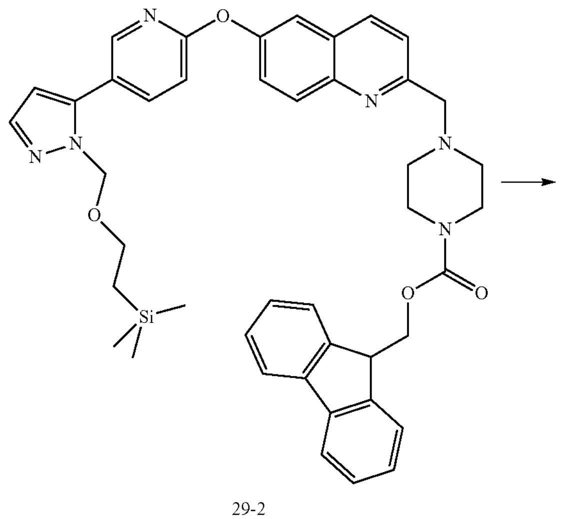

29-2

-continued

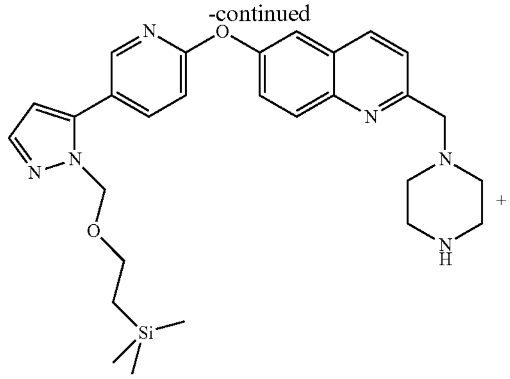

29-3

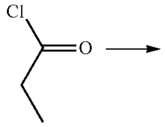

29-4

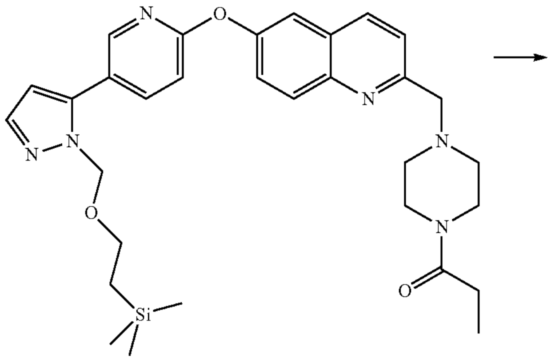

29-5

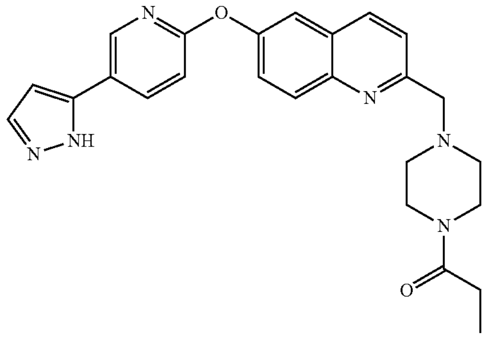

29

Compound 29-2 is synthesized from D (1.00 g, 2.24 mmol) and 29-1 (0.930 g, 2.70 mmol) according to the procedure described for the synthesis of 28-1.

A solution of 29-2 (0.900 g, 1.04 mmol) in dimethylformamide (20 mL) is treated with piperidine (0.31 mL, 3.1 mmol) and the reaction is stirred for 16 hours. The mixture is diluted with water (200 mL) and extracted with EtOAc (3×75 mL). The combined extracts are washed with water (4×50 mL), brine (50 mL), dried over $Na_2SO_4$, filtered and concentrated. The residue is purified by flash chromatography (0-8% MeOH in DCM, followed by 0.5% $NH_4OH$, 10% MeOH in DCM) to afford 29-3.

A solution of 29-3 (0.115 g, 0.190 mmol) in DCM (2 mL) is added 29-4 (0.020 mL, 0.23 mmol) and triethylamine (0.045 mL, 0.28 mmol). The reaction is stirred for 16 hours and then concentrated to afford 29-5.

The title product (29) is synthesized from intermediate 29-5 (0.11 g, 0.19 mmol) according to the method described for the synthesis of compound 28 from intermediate 28-1.

Example 32

Preparation of 1-(5-{6-[5-(2H-Pyrazol-3-yl)-pyridin-2-yloxy]-quinolin-2-ylmethyl}-hexahydro-pyrrolo[3,4-c]pyrrol-2-yl)-ethanone (32)

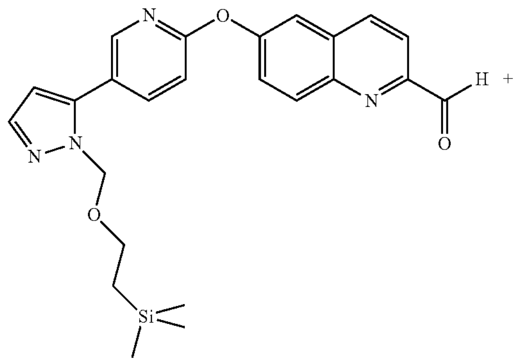

D

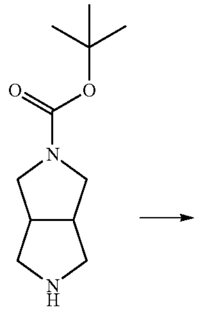

32-1

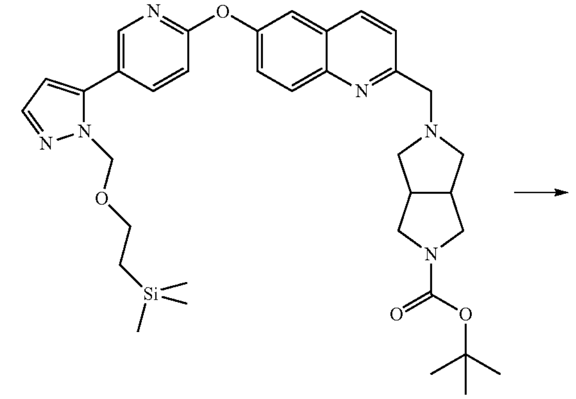

32-2

-continued

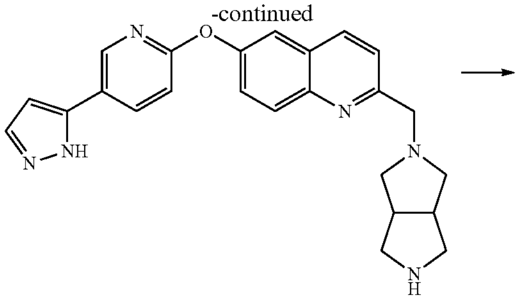

32-3

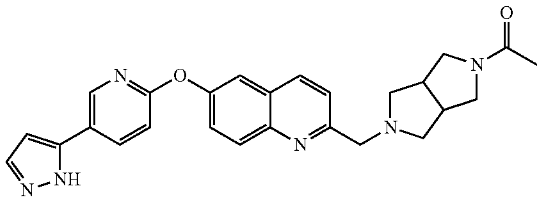

32

Intermediate 32-3 is synthesized from D (0.10 g, 0.22 mmol) and 32-1 (0.095 g, 0.45 mmol) according to the procedure described for the synthesis of 27-2.

A suspension of 32-3 (0.22 g, 0.22 mmol) in DCM (5 mL) is treated with acetic anhydride (0.053 mL, 0.56 mmol) and triethylamine (0.13 mL, 0.90 mmol). After 16 hours, the reaction is concentrated and the residue is purified by reverse phase prep HPLC eluting with 0-30% MeCN in water (+0.1% FA) over 20 minutes. The desired fractions are pooled and concentrated. The residue is dissolved in MeOH, passed through a PS—$HCO_3$ cartridge, and lypholized to afford the title compound (32).

The following examples are synthesized using Intermediate D and the appropriate amine reagent (free base or the salt form) according to the procedure described for the synthesis of Example 32.

| Ex, | Compound Name | Amine Reagent |
|---|---|---|
| 37 | N-Methyl-N-(1-{6-[5-(2H-pyrazol-3-yl)-pyridin-2-yloxy]-quinolin-2-ylmethyl}-piperidin-4-yl)-acetamide | 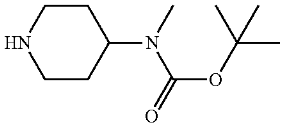 |
| 41 | N-((1α,5α,6α)-3-{6-[5-(2H-Pyrazol-3-yl)-pyridin-2-yloxy]-quinolin-2-ylmethyl}-3-aza-bicyclo[3.1.0]hex-6-ylmethyl)-acetamide | 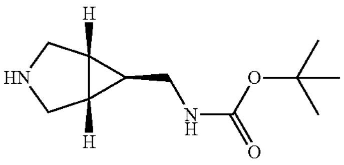 |
| 42 | 1-((S)-3-Hydroxymethyl-4-{6-[5-(2H-pyrazol-3-yl)-pyridin-2-yloxy]-quinolin-2-ylmethyl}-piperazin-1-yl)-ethanone | 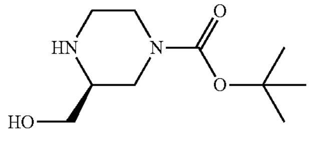 |

Example 40
Preparation of (1α,5α,6α)-3-{6-[5-(2H-Pyrazol-3-yl)-pyridin-2-yloxy]-quinolin-2-ylmethyl}-3-aza-bicyclo[3.1.0]hexane-6-carboxylic acid (2-hydroxy-2-methyl-propyl)-amide (40)
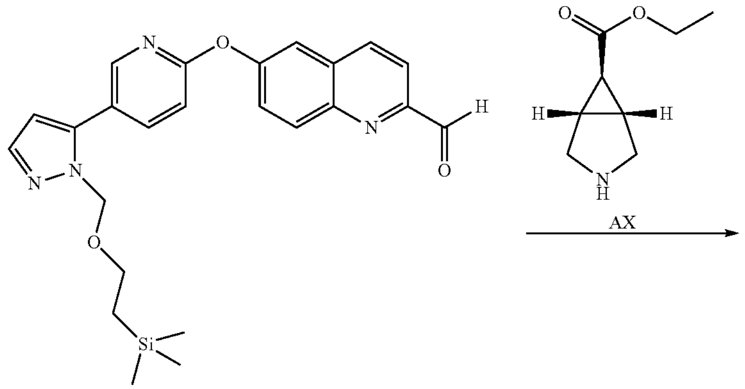
D
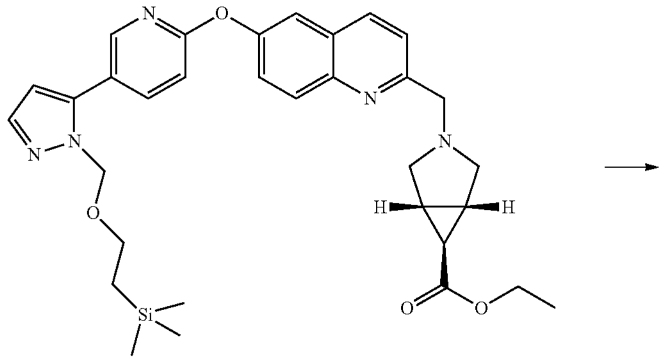
40-2
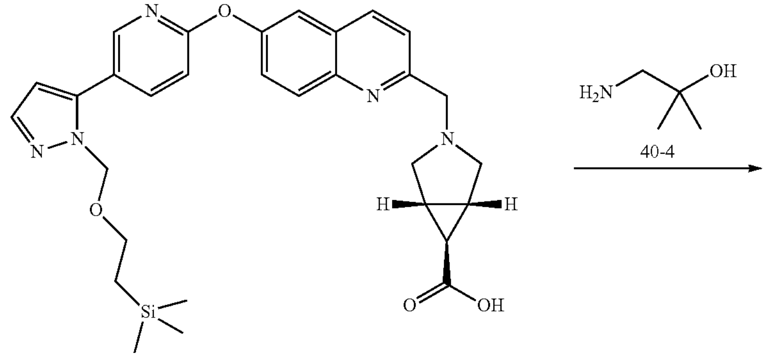
40-3

-continued

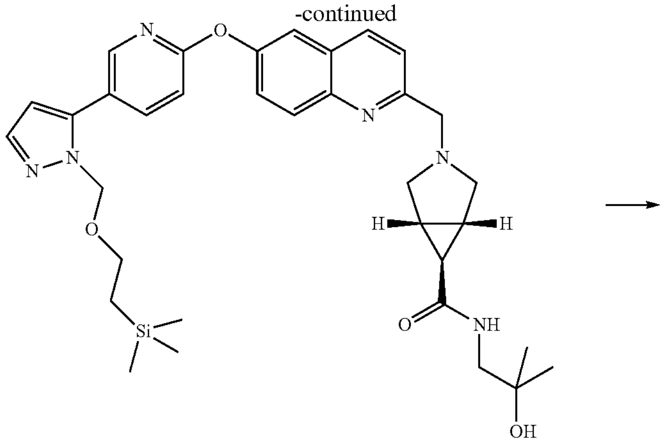

40-5

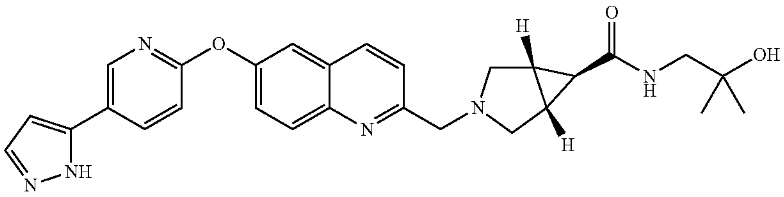

40

Intermediate 40-2 was synthesized from intermediates D (0.700 g, 1.60 mmol) and AX (0.360 g, 2.40 mmol) according to the procedure described for the synthesis of 28-1.

To a solution of 40-2 (0.61 g, 1.04 mmol) in a 4:1 mixture of methanol/water (16 mL) is added lithium hydroxide monohydrate (0.100 g, 2.2 mmol) and the reaction is stirred at room temperature for 16 hours. The reaction is diluted with water (50 mL), acidified with aqueous 1N HCl and extracted with EtOAc (3×15 mL). The combined extracts are dried over $Na_2SO_4$, filtered and concentrated to afford 40-3.

A solution of 40-3 (0.060 g, 0.11 mmol) in THF (1 mL) is treated with TBTU (0.040 g, 0.13 mmol). After 30 minutes, 40-4 (0.030 mL, 0.32 mmol) is added and the reaction is stirred at room temperature for 48 hours. The reaction is purified by reverse phase prep HPLC eluting with 0-60% MeCN in water (+0.1% FA) over 20 minutes. The desired fractions are pooled and lypholized to afford 40-5 as the formate salt.

The title product (40) is synthesized from 40-5 (0.060 g, 0.10 mmol) according to the procedure described for the synthesis of Example 28 from 28-1.

The following example is synthesized from the intermediate 40-3 and ammonia according to the amide coupling and deprotection procedures described for the synthesis of Example 40 from 40-3.

| Ex. | Compound Name |
|---|---|
| 35 | (1α,5α,6α)-3-{6-[5-(2H-Pyrazol-3-yl)-pyridin-2-yloxy]-quinolin-2-ylmethyl}-3-aza-bicyclo[3.1.0]hexane-6-carboxylic acid amide |

Example 52

Preparation of 5-[4-(2H-Pyrazol-3-yl)-phenoxy]-2-pyrrolidin-1-ylmethyl-1H-benzoimidazole (52)

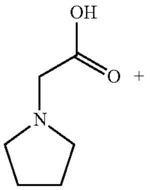

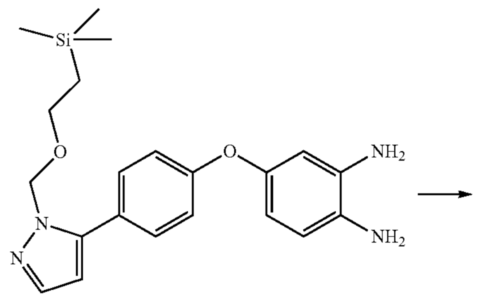

L

-continued

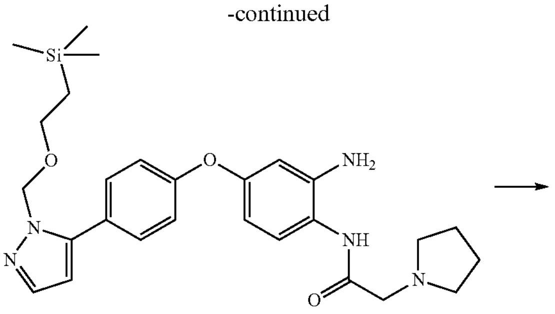

52-1

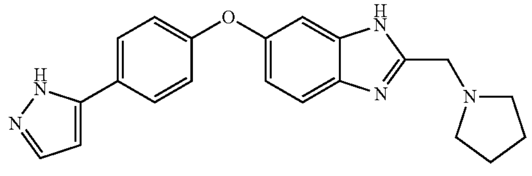

52

A solution of 2-pyrrolidin-1-ylacetic acid (40.0 mg, 0.310 mmol) and DIPEA (100 mg, 0.770 mmol) in DCM (1 mL) is treated with PyBrop (173 mg, 0.370 mmol) at ambient temperature. After 20 min, intermediate L (123 mg, 0.31 mmol) is added and the mixture is stirred at ambient temperature for 16 h. The mixture is concentrated, diluted with EtOAc (10 mL), and washed with saturated aqueous $NaHCO_3$ (3 mL). The organic layer is dried over $Na_2SO_4$, filtered and concentrated. The residue is purified by flash chromatography (1-6% MeOH in DCM with 7 N ammonia) to give 52-1.

A solution of 52-1 (162 mg, 0.320 mmol) in acetic acid (3 mL) is stirred at 110° C. for 20 min. The mixture is cooled to ambient temperature and concentrated. The residue is treated with HCl in dioxane (4M, 2 mL). The mixture is stirred at 50° C. for 1 h, cooled to ambient temperature, and concentrated.

The residue is purified by reverse phase HPLC eluting with 10-90% MeCN in water (+0.1% TFA). Fractions containing the desired product are combined and concentrated. The residue is dissolved in saturated aqueous $NaHCO_3$ and extracted with EtOAc (3×10 mL). The combined organic layer are dried over $Na_2SO_4$, filtered and concentrated to give the title product (52).

The following examples are synthesized using Intermediates L or M and the appropriate carboxylic acid reagent according to the procedure described for the synthesis of Example 52.

| Ex. | Compound Name | Intermediate | Acid Reagent |
|---|---|---|---|
| 53 | 2-((2R,6S)-2,6-Dimethyl-morpholin-4-ylmethyl)-5-[4-(2H-pyrazol-3-yl)-phenoxy]-1H-benzoimidazole | L | 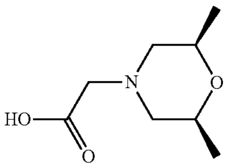 |
| 54 | 6-[4-(2H-Pyrazol-3-yl)-benzyl]-2-pyrrolidin-1-ylmethyl-1H-benzoimidazole | M | 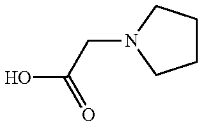 |

-continued

| Ex. | Compound Name | Intermediate | Acid Reagent |
|---|---|---|---|
| 55 | 2-((3S,5S)-3,5-Dimethyl-morpholin-4-ylmethyl)-5-[4-(2H-pyrazol-3-yl)-phenoxy]-1H-benzoimidazole | L | 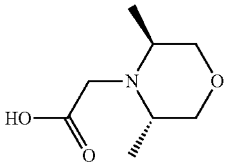 |
| 56 | 2-((2S,6S)-2,6-Dimethyl-morpholin-4-ylmethyl)-6-[4-(2H-pyrazol-3-yl)-benzyl]-1H-benzoimidazole | M | 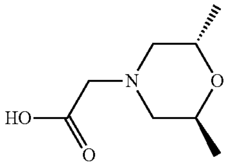 |
| 60 | 2-Morpholin-4-ylmethyl-6-[4-(2H-pyrazol-3-yl)-benzyl]-1H-benzoimidazole | M | 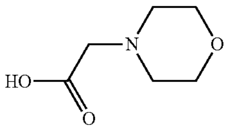 |
| 62 | 2-((S)-3-Methyl-morpholin-4-ylmethyl)-5-[4-(2H-pyrazol-3-yl)-phenoxy]-1H-benzoimidazole | L | 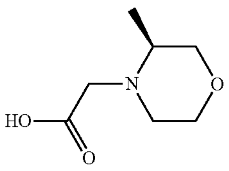 |
| 66 | (S)-1-{6-[4-(2H-Pyrazol-3-yl)-phenoxy]-1H-benzoimidazol-2-ylmethyl}-pyrrolidin-3-ol | L | 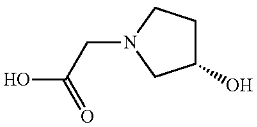 |
| 73 | 5-[4-(2H-Pyrazol-3-yl)-phenoxy]-2-pyridin-3-ylmethyl-1H-benzoimidazole | L | 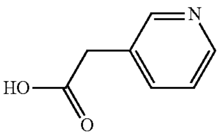 |

Example 57

Preparation of 2,2,2-Trifluoro-1-(4-[5-[4-(2H-pyrazol-3-yl)-phenoxy]-1H-benzoimidazol-2-ylmethyl]-piperazin-1-yl)-ethanone (57)

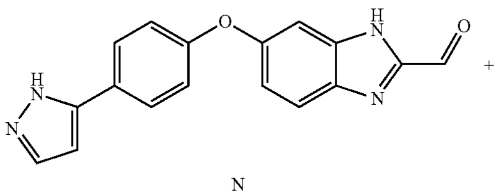

-continued

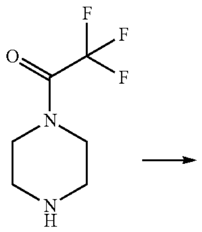

57-1

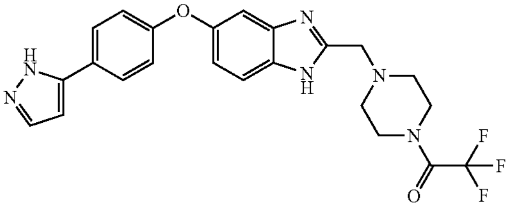

57

A mixture of Intermediate N (100 mg, 0.330 mmol) and 57-1 (120 mg, 0.660 mmol) in MeOH (6 mL) is stirred at 50° C. for 15 min Sodium cyanoborohydride (130 mg, 0.660 mmol) and acetic acid (30 μL) are added and the mixture is stirred at 50° C. for 15 h. The mixture is concentrated, diluted with EtOAc (10 mL) and washed with saturated aqueous $NaHCO_3$. The organic layer is dried over $Na_2SO_4$, filtered and concentrated. The residue is purified by flash chromatography (2-10% MeOH containing 10% $NH_4OH$/DCM) to give the title product (57).

The following examples are synthesized using Intermediates N and the appropriate amine reagent (free base or the salt form) according to the procedure described for the synthesis of Example 57. Generally, for the syntheses that utilize amine salts, an equivalent of triethylamine is added prior to addition of sodium triacetoxyborohydide.

| Ex. | Compound Name | Amine Reagent |
|---|---|---|
| 58 | (1S,5S)-3-{5-[4-(2H-Pyrazol-3-yl)-phenoxy]-1H-benzoimidazol-2-ylmethyl}-8-oxa-3-aza-bicyclo[3.2.1]octane | 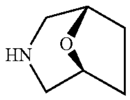 |
| 61 | 2-[4-(2-Methoxy-ethyl)-piperazin-1-ylmethyl]-5-[4-(2H-pyrazol-3-yl)-phenoxy]-1H-benzoimidazole | 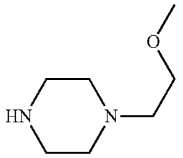 |
| 63 | 5-[4-(2H-Pyrazol-3-yl)-phenoxy]-2-[4-(2,2,2-trifluoro-ethyl)-piperazin-1-ylmethyl]-1H-benzoimidazole | 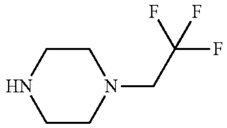 [SMILES: FC(F)(F)CN1CCNCC1] |
| 64 | 2-(4-Isopropyl-piperazin-1-ylmethyl)-5-[4-(2H-pyrazol-3-yl)-phenoxy]-1H-benzoimidazole | 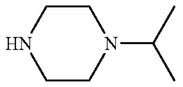 |

-continued

| Ex. | Compound Name | Amine Reagent |
|---|---|---|
| 65 | 2-[4-(3-Methyl-[1,2,4]oxadiazol-5-yl)-piperidin-1-ylmethyl]-5-[4-(2H-pyrazol-3-yl)-phenoxy]-1H-benzoimidazole | 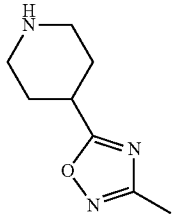 |
| 70 | 2,2-Dimethyl-1-(4-{5-[4-(2H-pyrazol-3-yl)-phenoxy]-1H-benzoimidazol-2-ylmethyl}-piperazin-1-yl)-propan-1-one | 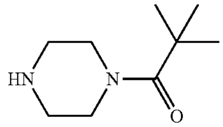 |
| 71 | 2,2,2-Trifluoro-1-(1-{5-[4-(2H-pyrazol-3-yl)-phenoxy]-1H-benzoimidazol-2-ylmethyl}-piperidin-4-yl)-ethanol | 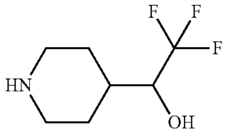 [SMILES: OC(C1CCNCC1)C(F)(F)F] |
| 72 | 2-(2-Oxa-6-aza-spiro[3.3]hept-6-ylmethyl)-5-[4-(2H-pyrazol-3-yl)-phenoxy]-1H-benzoimidazole | 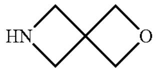 |
| 91 | (2-Methoxy-ethyl)-{5-[4-(2H-pyrazol-3-yl)-phenoxy]-1H-benzoimidazol-2-ylmethyl}-amine | 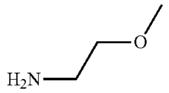 |
| 97 | {5-[4-(2H-Pyrazol-3-yl)-phenoxy]-1H-benzoimidazol-2-ylmethyl}-(tetrahydro-furan-2-ylmethyl)-amine | 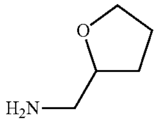 |
| 98 | 5-[4-(2H-Pyrazol-3-yl)-phenoxy]-2-thiomorpholin-4-ylmethyl-1H-benzoimidazole | 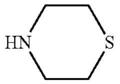 |
| 100 | {5-[4-(2H-Pyrazol-3-yl)-phenoxy]-1H-benzoimidazol-2-ylmethyl}-[(S)-1-(tetrahydro-furan-2-yl)methyl]-amine | 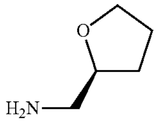 |
| 101 | {5-[4-(2H-Pyrazol-3-yl)-phenoxy]-1H-benzoimidazol-2-ylmethyl}-[(R)-1-(tetrahydro-furan-2-yl)methyl]-amine | 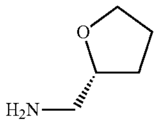 |
| 106 | {5-[4-(2H-Pyrazol-3-yl)-phenoxy]-1H-benzoimidazol-2-ylmethyl}-(tetrahydro-pyran-4-ylmethyl)-amine | 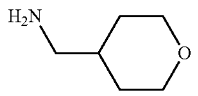 |

Example 59

Preparation of 2-(1-Morpholin-4-yl-cyclopropyl)-5-[4-(2H-pyrazol-3-yl)-phenoxy]-1H-benzoimidazole (59)

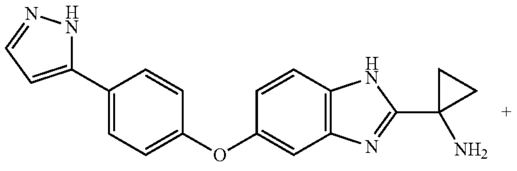

59-1

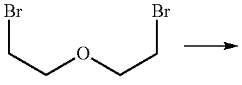

59-2

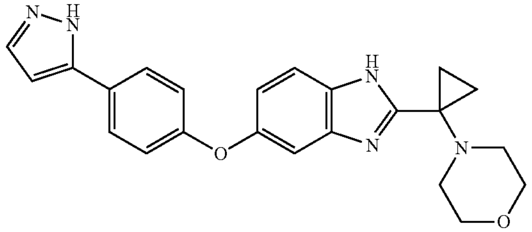

59

Compound 59-1 is synthesized from Intermediate L (1.00 g, 2.52 mmol), 1-(tert-butoxycarbonylamino)cyclopropanecarboxylic acid (558 mg, 2.77 mmol), and PyBrop (2.35 g, 5.04 mmol) according to the procedure described for the synthesis of Example 52, followed by Boc deprotection procedure described for the synthesis of intermediate K.

To a solution of compound 59-1 (1.00 g, 3.01 mmol) and DIPEA (2.63 mL, 15.1 mmol) in MeCN (20 mL) is added 59-2 (910 mg, 3.92 mmol), and the mixture is stirred at 70° C. for 7 days. The mixture is concentrated and the residue is purified by flash chromatography (1-10% MeOH with ammonia in DCM) to give the title product 59.

Example 67

Preparation of 5-{6-[4-(2H-Pyrazol-3-yl)-phenoxy]-imidazo[1,2-a]pyridin-2-yl}-piperidin-2-one (67)

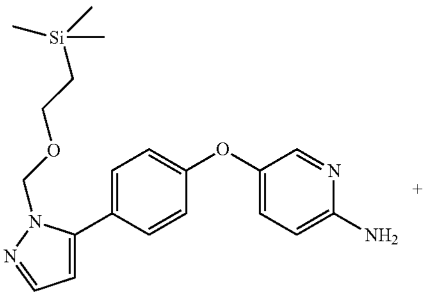

T

-continued

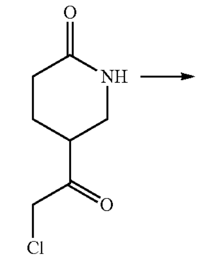

U

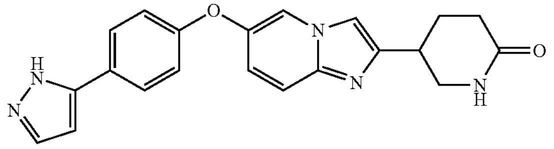

67

To a solution of T (100 mg, 0.260 mmol) in EtOH (2 mL) is added U (600 mg, 3.42 mmol) and triethylamine (0.1 mL). The mixture is heated to 120° C. for 1 h in a microwave. Solvent is removed and the residue is purified by reverse phase HPLC eluting with 10-80% MeCN in water (+0.1% TFA). Fractions containing the desired product are combined and concentrated. The residue is dissolved in dioxane (1 mL) and treated with a 4M HCl solution in dioxane (2 mL). The resultant mixture is stirred at 45° C. for 30 min. The solvent was decanted; the remaining solids are dissolved in MeOH, and neutralized with a saturated aqueous solution of $NaHCO_3$. The mixture is concentrated, and the residue is purified by flash chromatography (2-10% MeOH with 7N ammonia in DCM) to give the title product (67).

Example 68

Preparation of (S)-5-{6-[4-(2H-Pyrazol-3-yl)-phenoxy]-quinolin-2-yloxy}-piperidin-2-one (68)

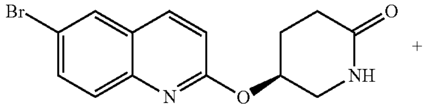

V

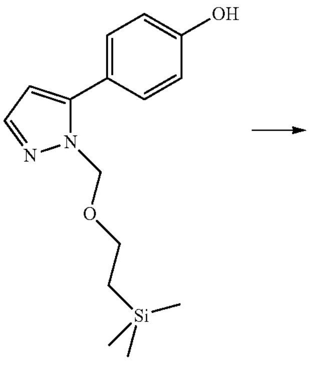

B

-continued

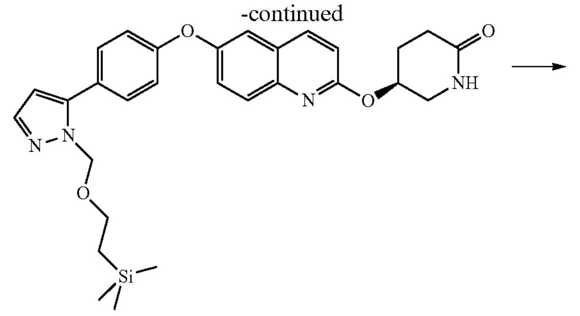

68-1

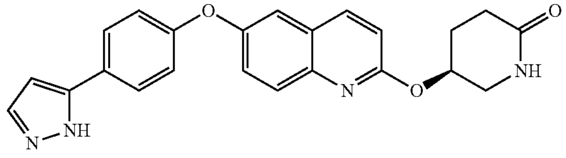

68

A mixture of B (115 mg, 0.410 mmol), V (130 mg, 0.410 mmol), CuI (8 mg, 0.04 mmol), 2-picolinic acid (10 mg, 0.080 mmol) and potassium phosphate (172 mg, 0.810 mmol) in DMSO (3 mL) is sparged with Ar and heated to 145° C. in a microwave for 5 h. The solution is cooled to ambient temperature, flittered, diluted with EtOAc (20 mL) and washed with water (2×5 mL). The organic layer is dried over $Na_2SO_4$, filtered and concentrated. The residue is purified by flash chromatography (100% EtOAc followed by 1-8% MeOH with 2N ammonia in DCM) to give 68-1.

To a solution of 68-1(381 mg, 0.720 mmol) in dioxane (2 mL) is added 4M HCl in dioxane (3 mL), and the mixture is stirred at ambient temperature for 1 h. The solvent is decant; the solids are neutralized with saturated aqueous $NaHCO_3$ (5 mL), and extracted with a mixture of 10% MeOH in DCM (2×20 mL). The combined organic layers are dried over $Na_2SO_4$, filtered and concentrated. The residue is purified by flash chromatography (1-8% MeOH with 2N ammonia in DCM) to give the title product 68.

Example 69

Preparation of 5-[4-(1H-Pyrazol-3-yl)-phenoxy]-1H-benzoimidazole-2-carboxylic acid (69)

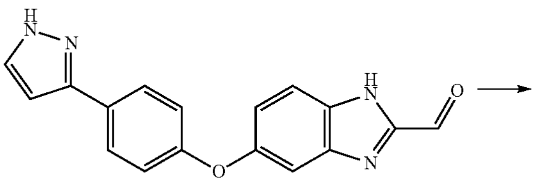

N

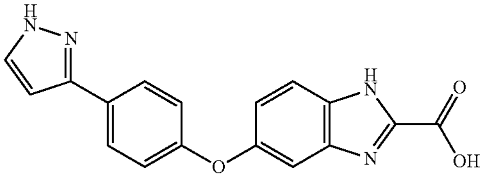

69

To a solution of N (50 mg, 0.16 mmol) in DMF (1.5 mL) is added oxone (101 mg, 0.160 mmol) and the mixture is stirred at ambient temperature for 1 h. The resultant mixture is diluted with water (2 mL) and filtered. The residue is purified by reverse phase HPLC eluting with 10-70% MeCN in water (+0.1% TFA). Fractions containing the desired product are combined and concentrated to give the title product (69) as a TFA salt.

Example 74

Preparation of ((S)-sec-butyl)-methyl-{5-[4-(2H-pyrazol-3-yl)-phenoxy]-1H-benzoimidazol-2-ylmethyl}-amine (74)

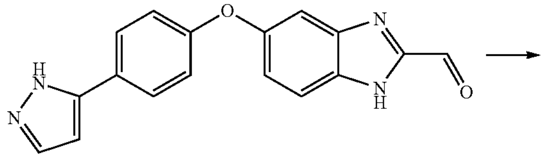

N

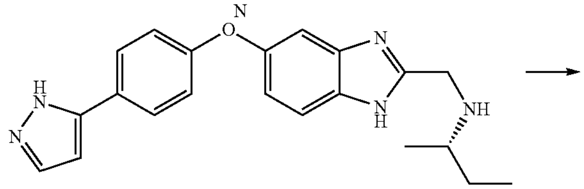

74-1

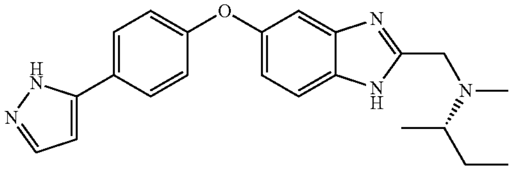

74

Compound 74-1 is synthesized from intermediate N and (S)-sec-butylamine according to the procedure described for the synthesis of Example 57.

A mixture of 74-1 (88 mg, 0.24 mmol), formaldehyde (100 mL; 37% wt. in $H_2O$) in MeOH (5.0 mL) is heated at 50° C. for 15 min Sodium cyanoborohydride (25 mg, 0.40 mmol) and acetic acid (3 drops) are added, and the reaction mixture is heated at 50° C. for 16 h. The mixture is cooled to ambient temperature and concentrated. The resultant residue is purified by flash chromatography (0-10% $NH_3$ in MeOH in DCM) to give the title product (74).

The following examples are synthesized from intermediate N and the appropriate amine reagent according to the procedure described for the synthesis of Example 74. For example 86, acetaldehyde was used instead of formaldehyde in the second step of the synthesis.

| Ex. | Compound Name | Amine Reagent |
|---|---|---|
| 76 | Methyl-{5-[4-(2H-pyrazol-3-yl)-phenoxy]-1H-benzoimidazol-2-ylmethyl}-[(S)-1-(tetrahydro-furan-2-yl)methyl]-amine | 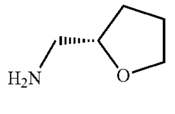 |
| 77 | Methyl-{5-[4-(2H-pyrazol-3-yl)-phenoxy]-1H-benzoimidazol-2-ylmethyl}-(S)-tetrahydro-furan-3-yl-amine | 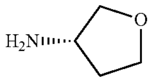 |

-continued

| Ex. | Compound Name | Amine Reagent |
|---|---|---|
| 78 | Methyl-{5-[4-(2H-pyrazol-3-yl)-phenoxy]-1H-benzoimidazol-2-ylmethyl}-(R)-tetrahydro-furan-3-yl-amine | 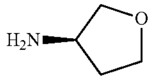 |
| 80 | ((R)-sec-Butyl)-methyl-{5-[4-(2H-pyrazol-3-yl)-phenoxy]-1H-benzoimidazol-2-ylmethyl}-amine | 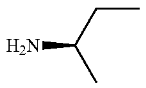 |
| 81 | Methyl-{5-[4-(2H-pyrazol-4-yl)-phenoxy]-1H-benzoimidazol-2-ylmethyl}-[(R)-1-(tetrahydro-furan-2-yl)methyl]-amine | 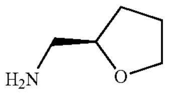 |
| 82 | ((S)-2-Methoxy-1-methyl-ethyl)-methyl-{5-[4-(2H-pyrazol-3-yl)-phenoxy]-1H-benzoimidazol-2-ylmethyl}-amine | 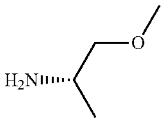 |
| 85 | Methyl-{5-[4-(2H-pyrazol-3-yl)-phenoxy]-1H-benzoimidazol-2-ylmethyl}-(tetrahydro-furan-2-ylmethyl)-amine | 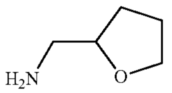 |
| 86 | Ethyl-((S)-2-methoxy-1-methyl-ethyl)-{5-[4-(2H-pyrazol-3-yl)-phenoxy]-1H-benzoimidazol-2-ylmethyl}-amine | 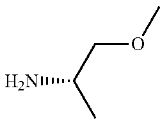 |
| 87 | [1,4]Dioxan-2-ylmethyl-methyl-{5-[4-(2H-pyrazol-3-yl)-phenoxy]-1H-benzoimidazol-2-ylmethyl}-amine | 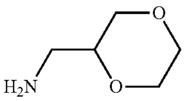 |
| 92 | Methyl-{5-[4-(2H-pyrazol-3-yl)-phenoxy]-1H-benzoimidazol-2-ylmethyl}-(tetrahydro-pyran-3-ylmethyl)-amine | 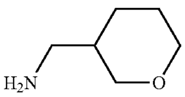 |
| 104 | Methyl-{5-[4-(2H-pyrazol-3-yl)-phenoxy]-1H-benzoimidazol-2-ylmethyl}-(tetrahydro-furan-3-ylmethyl)-amine | 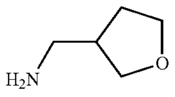 |

Example 75

Preparation of 5-[4-(2H-pyrazol-3-yl)-phenoxy]-1-(2-pyrrolidin-1-yl-ethyl)-1H-indazole (75)

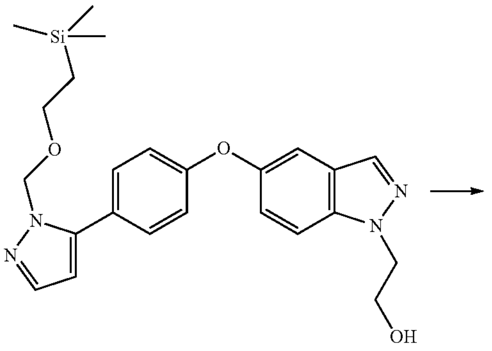

Y

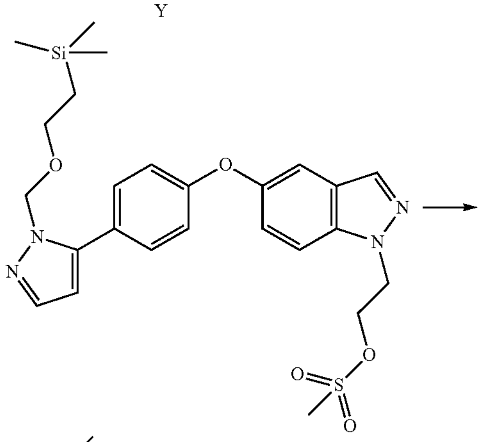

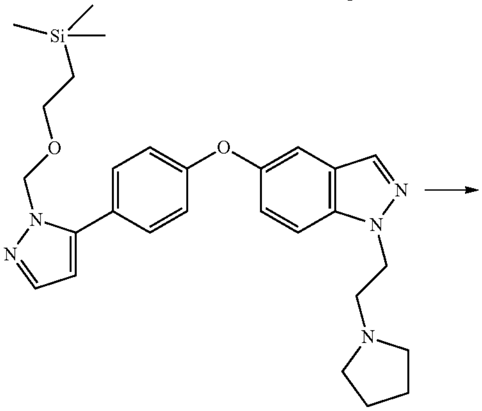

75-2

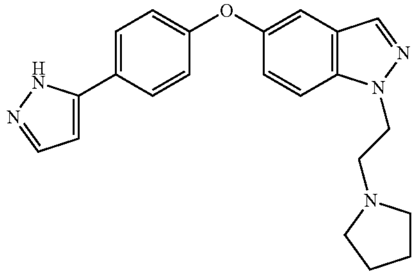

75

A mixture of Y (440 mg, 0.980 mmol), methanesulfonyl (100 mL, 1.29 mmol), and $Et_3N$ (200 μL, 1.43 mmol) in DCM (5.0 mL) is stirred at ambient temperature for 1 h. The reaction mixture is washed with saturated aqueous $Na_2SO_4$ (25 mL), dried over $Na_2SO_4$, filtered and concentrated to give 75-1.

A mixture of 75-1 (129 mg, 0.244 mmol), pyrrolidine (100 mL, 1.20 mmol), and $K_2CO_3$ (85 mg, 0.62 mmol) in DMF (2.5 mL) is heated at 80° C. for 16 h. The reaction mixture is cooled to ambient temperature, diluted with EtOAc (50 mL), washed with $H_2O$ (2×50 mL), dried over $Na_2SO_4$, filtered and concentrated. The residue is purified by flash chromatography (0-10% $NH_3$ in MeOH in DCM) to give 75-2.

A mixture of 75-2 (65 mg, 0.13 mmol) in a solution of HCl in dioxane (1M, 5.0 mL) is heated at 50° C. for 1 h, cool to ambient temperature and concentrated. The residue is purified by flash chromatography (0-10% $NH_3$ in MeOH in DCM) to give the title product (75).

The following examples are synthesized from the appropriate amine reagents and intermediates according to the procedure described for the synthesis of Example 75.

| Ex. | Compound Name | Intermediate | Amine Reagent |
|---|---|---|---|
| 79 | 5-[4-(2H-Pyrazol-3-yl)-phenoxy]-1-(3-pyrrolidin-1-yl-propyl)-1H-indazole | AA | 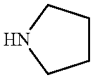 |
| 83 | 5-[5-(2H-Pyrazol-3-yl)-pyridin-2-yloxy]-1-(2-pyrrolidin-1-yl-ethyl)-1H-indazole | AC | 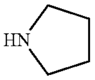 |
| 84 | 2-(3-Morpholin-4-yl-propyl)-5-[4-(2H-pyrazol-3-yl)-phenoxy]-2H-indazole | AB | 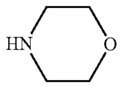 |
| 88 | N-[1-(2-{5-[4-(2H-Pyrazol-3-yl)-phenoxy]-indazol-1-yl}-ethyl)-piperidin-4-yl]-acetamide | Y | 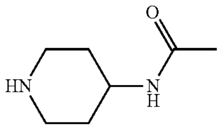 |
| 90 | 1-[4-(2-{5-[4-(2H-Pyrazol-3-yl)-phenoxy]-indazol-1-yl}-ethyl)-piperazin-1-yl]-ethanone | Y | 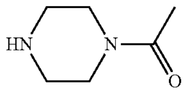 |
| 93 | 1-[4-(2-{5-[4-(2H-Pyrazol-3-yl)-phenoxy]-indazol-2-yl}-ethyl)-piperazin-1-yl]-ethanone | Z | 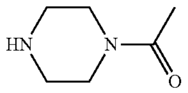 |
| 94 | 1-[4-(2-{5-[5-(2H-Pyrazol-3-yl)-pyridin-2-yloxy]-indazol-1-yl}-ethyl)-piperazin-1-yl]-ethanone | AC | 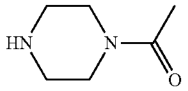 |
| 95 | 1-[4-(3-{5-[4-(2H-Pyrazol-3-yl)-phenoxy]-indazol-2-yl}-propyl)-piperazin-1-yl]-ethanone | AB | 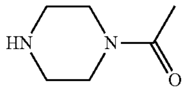 |
| 102 | 1-(2-Morpholin-4-yl-ethyl)-5-[4-(2H-pyrazol-3-yl)-phenoxy]-1H-indazole | Y | 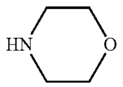 |
| 105 | 5-[4-(2H-Pyrazol-3-yl)-phenoxy]-2-(3-pyrrolidin-1-yl-propyl)-2H-indazole | AB | 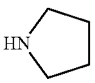 |
| 109 | N-[1-(3-{5-[4-(2H-Pyrazol-3-yl)-phenoxy]-indazol-1-yl}-propyl)-piperidin-4-yl]-acetamide | AA | 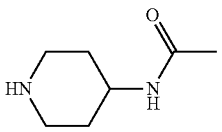 |
| 111 | 1-(2-Morpholin-4-yl-ethyl)-5-[5-(2H-pyrazol-3-yl)-pyridin-2-yloxy]-1H-indazole | AC | 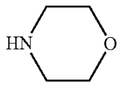 |

-continued

| Ex. | Compound Name | Intermediate | Amine Reagent |
|---|---|---|---|
| 112 | 2-Hydroxy-2-methyl-N-[1-(2-{5-[5-(2H-pyrazol-3-yl)-pyridin-2-yloxy]-indazol-2-yl}-ethyl)-piperidin-4-yl]-propionamide | AD | 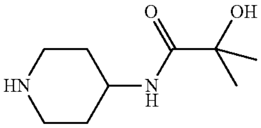 |
| 116 | N-[1-(3-{5-[4-(2H-Pyrazol-3-yl)-phenoxy]-indazol-2-yl}-propyl)-piperidin-4-yl]-acetamide | AB | 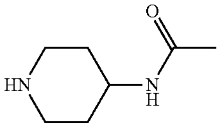 |
| 217 | 5-[4-(2H-Pyrazol-3-yl)-phenoxy]-2-(2-pyrrolidin-1-yl-ethyl)-2H-indazole | Z | 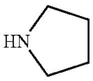 |

Example 89

Preparation of 2-((S)-1-Methyl-pyrrolidin-2-ylmethyl)-5-[4-(2H-pyrazol-3-yl)-phenoxy]-1H-benzoimidazole (89)

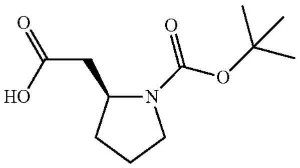

89-1

+

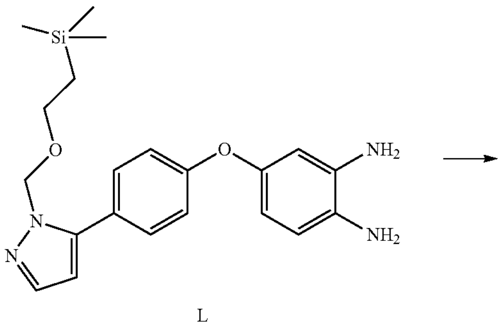

L

-continued

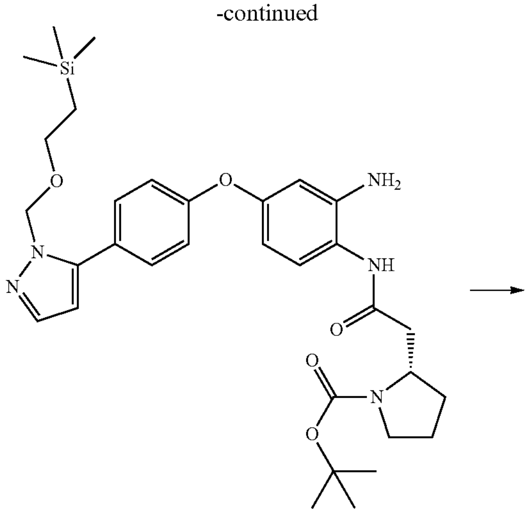

89-2

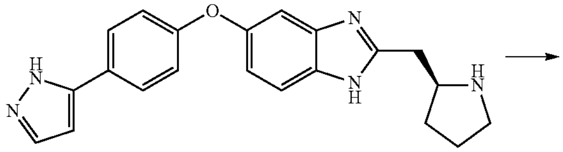

89-3

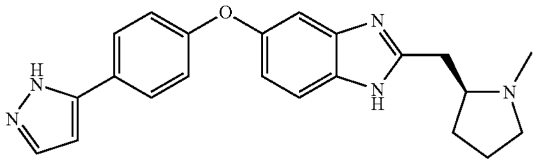

89

Compound 89-3 is synthesized from 89-1 and intermediate L according to the procedure described for the synthesis of Example 52.

The title product (89) is synthesized from 89-3 according to the procedure described for the synthesis of Example 74 from 74-1.

Example 99

Preparation of 1-{6-[5-(2H-pyrazol-3-yl)-pyridin-2-yloxy]-quinolin-2-ylmethyl}-piperidine-4-carbonitrile (99)

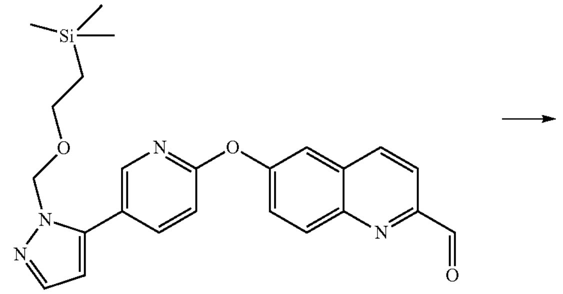

D

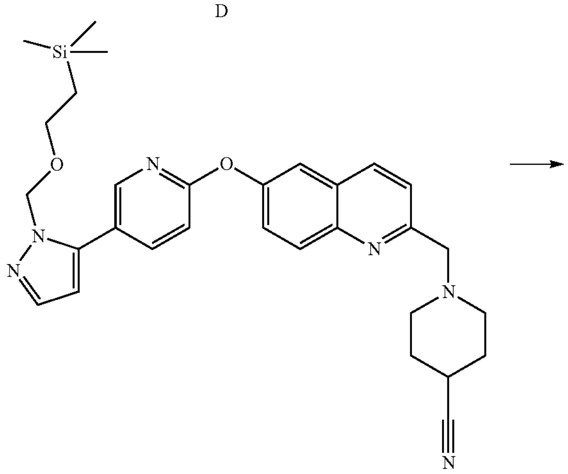

99-1

-continued

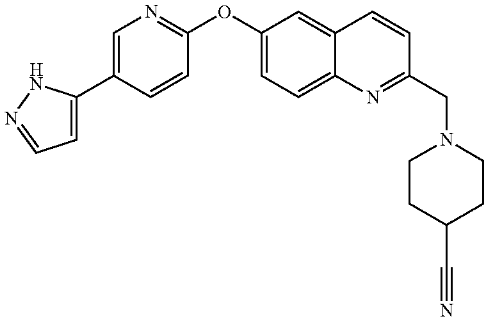

99

A reaction mixture of D (100 mg, 0.220 mmol), 4-cyanopiperidine (50.0 mg, 0.450 mmol), and sodium triacetoxyborohydride (100 mg, 0.470 mmol) in DCM (5.0 mL) is stirred at ambient temperature for 16 h. The reaction mixture is diluted with DCM (75 mL), washed with $H_2O$ (50 mL), dried over $Na_2SO_4$, filtered and concentrated. The residue is purified by flash chromatography (0-10% MeOH in DCM) to give 99-1.

A mixture of 99-1 (100 mg, 0.19 mmol) in 1M HCl in dioxane (2.5 mL) is stirred at ambient temperature for 1 h, and concentrated. The residue is purified by flash chromatography (0-10% $NH_3$ in MeOH in DCM) to give the title product (99).

The following examples are synthesized from the appropriate amine reagents and intermediate D according to the procedure described for the synthesis of Example 99.

| Ex. | Compound Name | Amine Reagent |
|---|---|---|
| 96 | (1-{6-[5-(2H-Pyrazol-3-yl)-pyridin-2-yloxy]-quinolin-2-ylmethyl}-piperidin-4-yl)-acetonitrile | 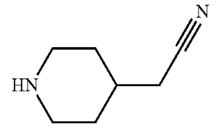 |
| 107 | (R)-1-{6-[5-(2H-Pyrazol-3-yl)-pyridin-2-yloxy]-quinolin-2-ylmethyl}-pyrrolidine-3-carbonitrile | 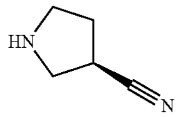 |
| 110 | 1-[4-(Methyl-{6-[5-(2H-pyrazol-3-yl)-pyridin-2-yloxy]-quinolin-2-ylmethyl}-amino)-piperidin-1-yl]-ethanone | 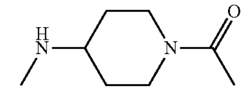 |
| 121 | N-[2-({6-[5-(2H-Pyrazol-3-yl)-pyridin-2-yloxy]-quinolin-2-ylmethyl}-amino)-ethyl]-acetamide | 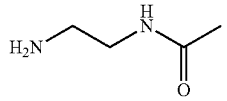 |

-continued

| Ex. | Compound Name | Amine Reagent |
|---|---|---|
| 122 | (2-Methoxy-ethyl)-methyl-{6-[5-(2H-pyrazol-3-yl)-pyridin-2-yloxy]-quinolin-2-ylmethyl}-amine | 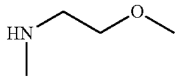 |

Example 103

Preparation of N—((S)-sec-butyl)-N-{5-[4-(2H-pyrazol-3-yl)-phenoxy]-1H-benzoimidazol-2-ylmethyl}-acetamide (103)

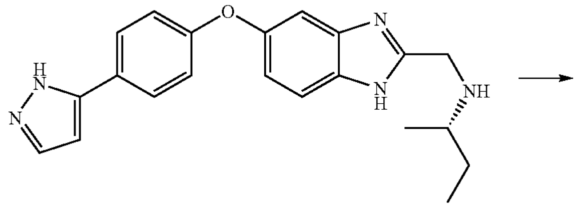

74-1

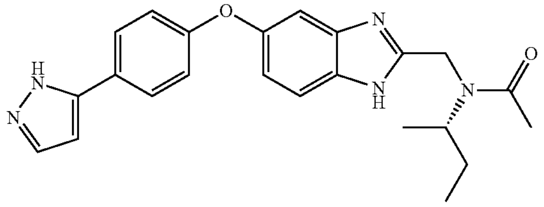

103

A mixture of 74-1 (45 mg, 0.13 mmol), acetyl chloride (10 mL, 0.14 mmol), $Et_3N$ (35 mL, 0.25 mmol) in DCM (5.0 mL) is stirred at ambient temperature for 16 h. The reaction mixture is diluted with EtOAc (50 mL), washed with $H_2O$ (2×25 mL), dried over $Na_2SO_4$, filtered and concentrated. The residue is purified by flash chromatography (0-10% $NH_3$ in MeOH-DCM) to give the title product (103).

Example 108

Preparation of 1-[4-(2-{6-[5-(2H-pyrazol-3-yl)-pyridin-2-yloxy]-quinolin-2-yl}-ethyl)-piperazin-1-yl]-ethanone (108)

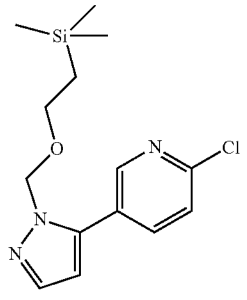

+

A

-continued

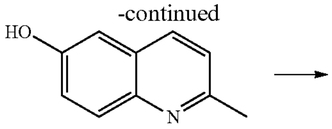

108-0

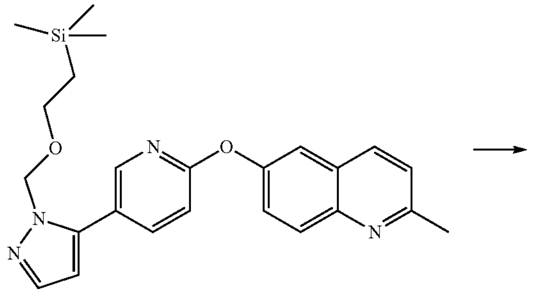

108-1

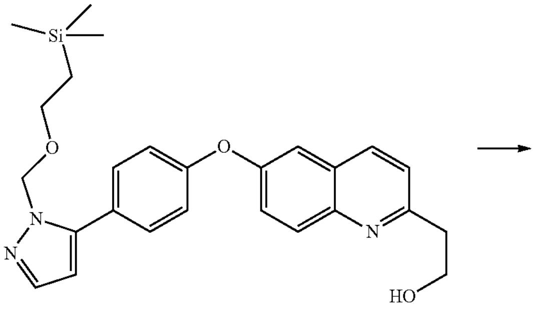

108-2

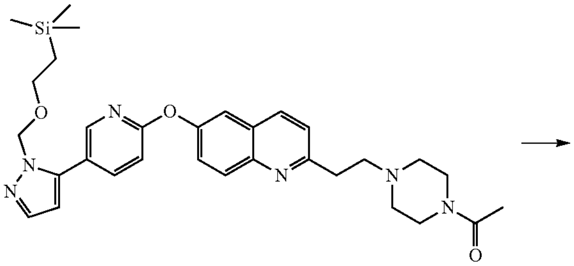

108-3

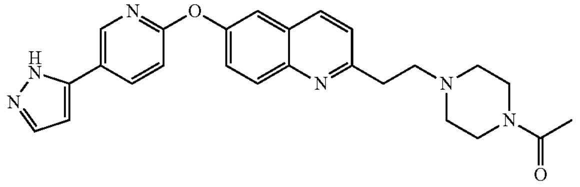

108

A mixture of A (1.80 g, 5.81 mmol), 108-0 (1.00 g, 6.28 mmol), and $K_2CO_3$ (4.00 g, 28.9 mmol) in DMSO (10.0 mL) is heated at 130° C. for 16 h. The reaction mixture is cooled to ambient temperature, diluted with EtOAc (50 mL), washed with $H_2O$ (2×50 mL), dried over $Na_2SO_4$, filtered and concentrated. The residue is purified by flash chromatography (0-100% EtOAc in heptane) to give 108-1.

To a stirred solution of LDA (2.0 M in THF, 7.0 mL) is added 108-1 (1.50 g, 3.50 mmol) in THF (15 mL) at −78° C. After 30 min at −78° C., ethyl chloroformate (420 μL, 4.41 mmol) is added; the mixture is stirred for an additional 30 min at −78° C., warmed to ambient temperature, and stirred for 16 h. The reaction mixture is quenched with $H_2O$ (25 mL), extracted with EtOAc (2×25 mL), dried over $Na_2SO_4$, filtered and concentrated.

The residue is purified by flash chromatography (0-10% MeOH in DCM). The residue is dissolved in THF (5 mL), cooled to 0° C., and treated with LAH (25.0 mg, 0.659 mmol). The mixture is stirred at 0° C. for 2 h and warmed to ambient temperature overnight. The reaction is quenched sequentially with water (25 μL), NaOH (1M, 25 μL) and water (75 μL), filtered through a pad of Diatomaceous earth, and concentrated to give 108-2.

A mixture of 108-2 (130 mg, 0.280 mmol), methanesulfonyl chloride (50.0 μL, 0.640 mmol), and $Et_3N$ (100 μL, 0.720 mmol) in DCM (5.0 mL) is stirred at ambient temperature for 1 h. 1-acetylpiperidine (50.0 mg, 0.390 mmol) is added, and the resultant mixture is stirred for 16 h. The reaction is diluted with DCM (50 mL), washed with $H_2O$ (2×50 mL), dried over $Na_2SO_4$, filtered and concentrated. The residue is purified by flash chromatography (0-10% MeOH in DCM) to give 108-3.

A mixture of 108-3 (119 mg, 0.210 mmol), in 4M HCl in dioxane (2.5 mL) is stirred at ambient temperature for 16 h, and concentrated. The residue is purified by flash chromatography (0-10% $NH_3$ in MeOH in DCM) to give the title product (108).

Example 113

Preparation of 3-Morpholin-4-ylmethyl-6-[5-(2H-pyrazol-3-yl)-pyridin-2-yloxy]-1H-indazole (113)

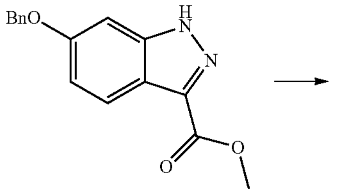

131-1

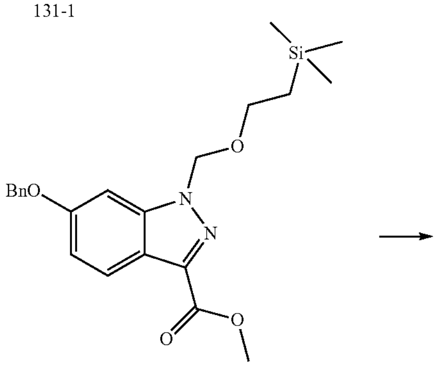

131-2

-continued

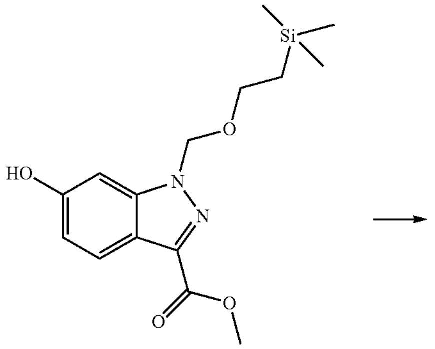

113-3

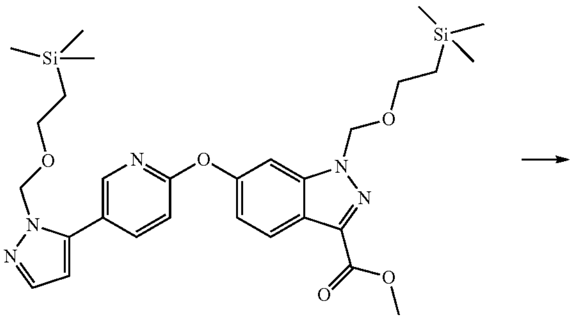

113-4

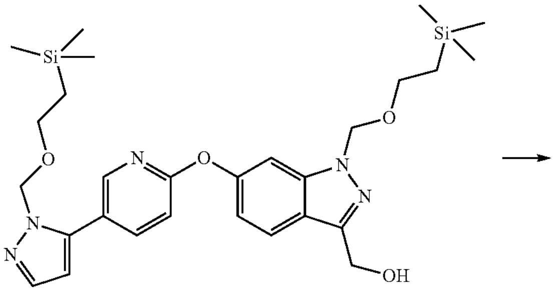

113-5

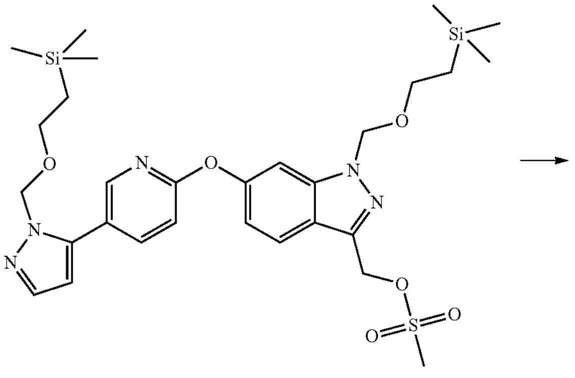

113-6

-continued

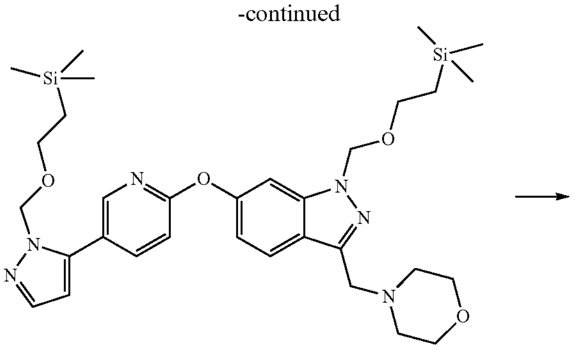

113-7

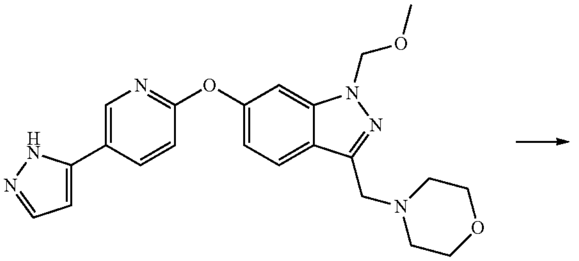

113-8

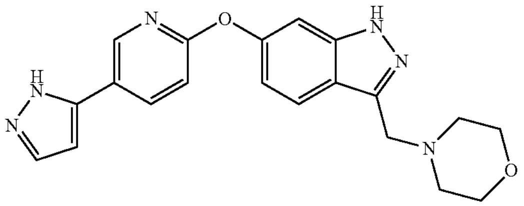

113

A solution of 113-1 (1.00 g, 3.54 mmol) in THF (5.0 mL) is added drop-wise to a mixture of NaH (275 mg, 4.53 mmol) in THF (25 mL) at 0° C. The mixture is stirred for 15 min, and treated with 2-(trimethylsilyl)ethoxy methyl chloride (800 μL, 4.53 mmol), warmed to ambient temperature, stirred for 1 h, cooled to 0° C., and quenched with $H_2O$ (50 mL). The mixture is diluted with EtOAc (50 mL), washed with $H_2O$ (2×50 mL), dried over $Na_2SO_4$, filtered and concentrated. The residue is purified by flash chromatography (0-50% EtOAc in heptane) to give 113-2.

A mixture of 113-2 (1.05 g, 2.54 mmol) and 10% Pd/C (150 mg) in EtOH (25 mL) is stirred under an atmosphere of $H_2$ at ambient temperature for 4 h. The reaction mixture is filtered though a pad of Diatomaceous earth, and concentrated to give 113-3.

A mixture of intermediate A (750 mg, 2.42 mmol), 113-3 (770 mg, 2.39 mmol), and $K_2CO_3$ (700 mg, 5.07 mmol) in DMF (10.0 mL) is heated at 110° C. for 16 h. The reaction mixture is cooled to ambient temperature, diluted with EtOAc (50 mL), washed with $H_2O$ (2×50 mL), dried over $Na_2SO_4$, filtered and concentrated. The residue is purified by flash chromatography (0-100% EtOAc in heptane) to give 113-4.

A solution of 113-4 (273 mg, 0.460 mmol) in THF (15.0 mL) is treated with $LiAlH_4$ (30 mg, 0.75 mmol) at 0° C. The mixture is stirred for 2 h at 0° C., and sequentially treated with $H_2O$ (30 μL), 1M NaOH (30 μL), and $H_2O$ (90 μL). The reaction mixture is filtered through a pad of Diatomaceous earth and concentrated to give 113-5.

A mixture of 113-5 (130 mg, 0.230 mmol), methanesulfonyl chloride (66.0 μL, 0.850 mmol), and $Et_3N$ (200 μL, 1.43 mmol) in DCM (5.0 mL) is stirred at ambient temperature for 3 h. Next, morpholine (1 mL) is added and the reaction is stirred at ambient temperature for 16 h. The mixture is diluted with DCM (25 mL), washed with $H_2O$ (2×25 mL), dried over $Na_2SO_4$, filtered and concentrated. The residue is purified by flash chromatography (0-10% $NH_3$ in MeOH in DCM) to give 113-7.

A mixture of 113-7 (63 mg, 0.10 mmol) in 4M HCl in dioxane (2.5 mL) is stirred at ambient temperature for 16 h. The mixture is concentrated, and the residue is purified by flash chromatography (0-10% $NH_3$ in MeOH in DCM) to give 113-8.

A mixture of 113-8 (12 mg) in 4M HCl in dioxane (2.5 mL) is treated with 3 drops of $H_2O$, and stirred at 65° C. for 1 h. The mixture is cooled to ambient temperature, and concentrated. The resultant residue is purified by flash chromatography (0-10% $NH_3$ in MeOH in DCM) to give the title compound (113).

Example 114

Preparation of 2-morpholin-4-ylmethyl-6-[4-(2H-pyrazol-3-yl)-phenoxy]-benzoxazole (114)

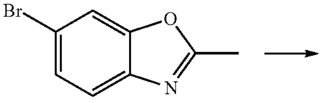

114-1

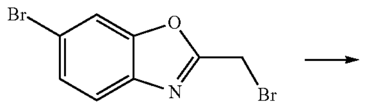

114-2

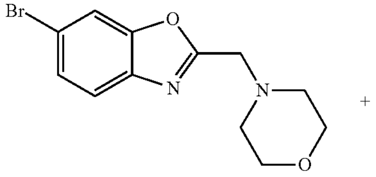

114-3

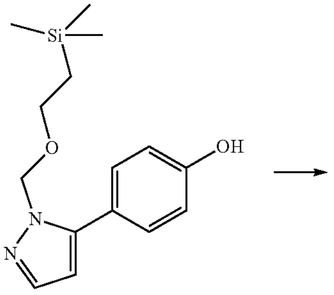

B

-continued

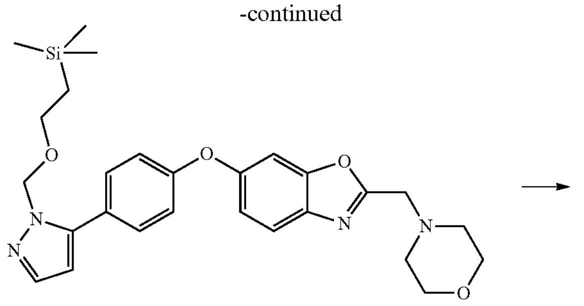

114-4

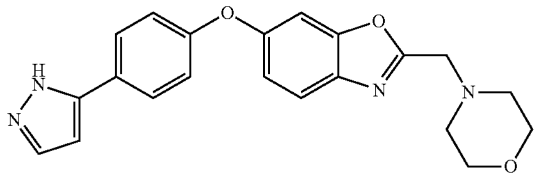

114

A mixture of 114-1 (1.00 g, 4.72 mmol), NBS (840 mg, 4.72 mmol), and AIBN (350 mg) in $CCl_4$ (20 mL) is heated at 90° C. for 16 h. The reaction is cooled to ambient temperature, diluted with DCM (100 mL), washed with $H_2O$ (2×75 mL), dried over $Na_2SO_4$, filtered and concentrated. The residue is purified by flash chromatography (0-50% EtOAc in heptane) to give 114-2.

A solution of 114-2 (260 mg, 0.890 mmol) and morpholine (200 μL, 2.30 mmol), in EtOH to (5.0 mL) is stirred for 16 h. The mixture is concentrated, and the resultant residue is purified by flash chromatography (0-50% EtOAc in heptane) to give 114-3.

A mixture of B (100 mg, 0.340 mmol), 114-3 (90.0 mg, 0.300 mmol), $Cs_2CO_3$ (225 mg, 0.690 mmol), CuI (13 mg, 0.07 mmol), and N,N-dimethylglycine.HCl (25 mg, 0.18 mmol) in toluene is heated at 110° C. for 16 h. The reaction mixture is cooled to ambient temperature, diluted with EtOAc (50 mL), washed with $H_2O$ (2×25 mL), dried over $Na_2SO_4$, filtered and concentrated. The residue is purified by flash chromatography (0-50% EtOAc in heptane) to give 114-4.

A mixture of 114-4 (80.0 mg, 0.16.0 mmol) and 4M HCl in dioxane (5.0 mL) is stirred at 50° C. for 30 min. The reaction is cooled to ambient temperature and concentrated. The residue is purified by flash chromatography (0-10% $NH_3$ in MeOH in DCM) to give the title product (114).

Example 115

Preparation of 1-(4-{6-[5-(2H-Pyrazol-3-yl)-pyridin-2-yloxy]-quinolin-2-yl}-piperazin-1-yl)-ethanone (115)

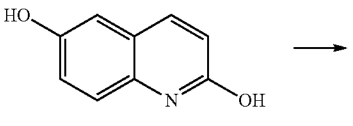

115-0

-continued

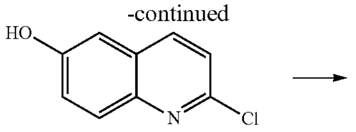

115-1

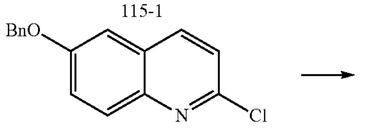

115-2

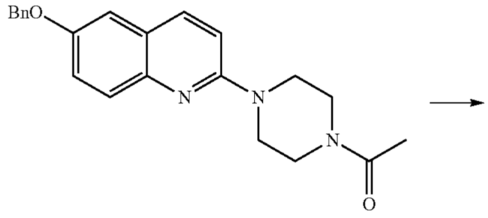

115-3

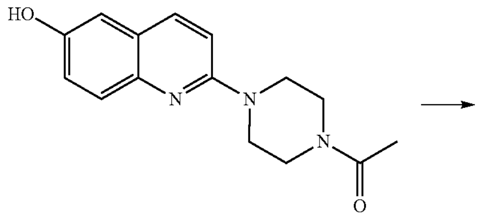

115-4

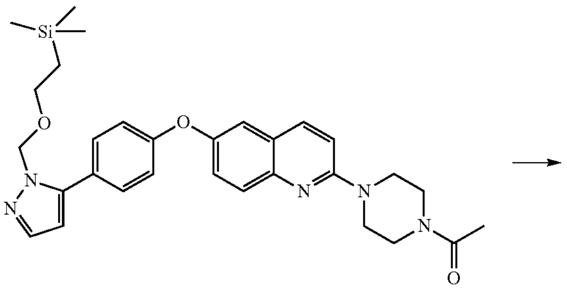

115-5

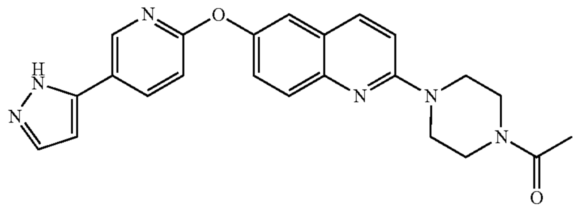

115

A solution of 115-0 (1.00 g, 6.21 mmol) and $POCl_3$ (1.5 mL) in DMF (5.0 mL) is stirred at ambient temperature. After 3 h, more $POCl_3$ (2.5 mL) is added and the reaction mixture is stirred for an additional 2 h. The mixture is diluted with EtOAc (100 mL), washed with $H_2O$ (3×100 mL), dried over $Na_2SO_4$, filtered and concentrated to give 115-1.

A mixture of 115-1 (450 mg, 2.51 mmol), benzyl bromide (600 μL, 5.05 mmol), and $Cs_2CO_3$ (1.60 g, 4.91 mmol) in DMF (7.5 mL) is stirred at ambient temperature for 4 h. The reaction mixture is diluted with EtOAc (100 mL), washed with $H_2O$ (2×75 mL), dried over $Na_2SO_4$, filtered and concentrated. The residue is purified by flash chromatography (0-100% EtOAc in heptane) to give 115-2.

A mixture of 115-2 (300 mg, 1.11 mmol), 1-acetyl-piperazine (300 mg, 2.34 mmol), $K_2CO_3$ (400 mg, 2.89 mmol) in DMF (5.0 mL) is stirred at 100° C. for 16 h. Additional 1-acetyl-piperazine (300 mg, 2.34 mmol) and $Cs_2CO_3$ (300 mg) are added and the mixture is heated at 130° C. After 72 h, the reaction mixture is cooled to ambient temperature, diluted with EtOAc (75 mL), washed with $H_2O$ (2×50 mL), dried over $Na_2SO_4$, filtered and concentrated. The residue is purified by flash chromatography (0-10% MeOH in DCM) to give 115-3.

A mixture of 115-3 (270 mg, 0.750 mmol), 10% Pd/C (54 mg) in EtOH (15 mL) is stirred under an atmosphere of $H_2$ at ambient temperature. After 16 h, the reaction mixture is filtered through a pad of Diatomaceous earth and concentrated to give 115-4.

A mixture of intermediate A (250 mg, 0.810 mmol), 115-4 (202 mg, 0.750 mmol), and $K_2CO_3$ (250 mg) in DMSO (10.0 mL) is heated at 130° C. After 16 h, the mixture is cooled to ambient temperature, diluted with EtOAc (50 mL), washed with $H_2O$ (2×50 mL), dried over $Na_2SO_4$, filtered and concentrated. The residue is purified by flash chromatography (0-10% MeOH in DCM) to give 115-5.

A mixture of 115-5 (133 mg, 0.244 mmol) and 4M HCl in dioxane (2.5 mL) is stirred at ambient temperature for 16 h, and concentrated. The residue is purified by flash chromatography (0-10% $NH_3$ in MeOH in DCM) to give the title product (115).

Example 117

Preparation of (S)-5-{5-[5-(2H-Pyrazol-3-yl)-pyridin-2-yloxy]-indazol-1-ylmethyl}-pyrrolidin-2-one (117)

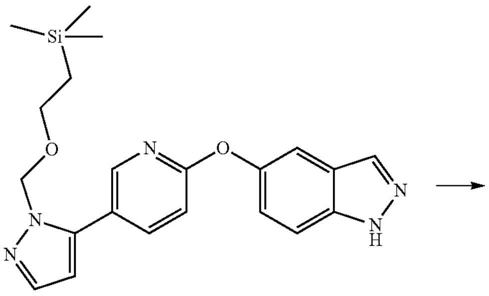

AC-2

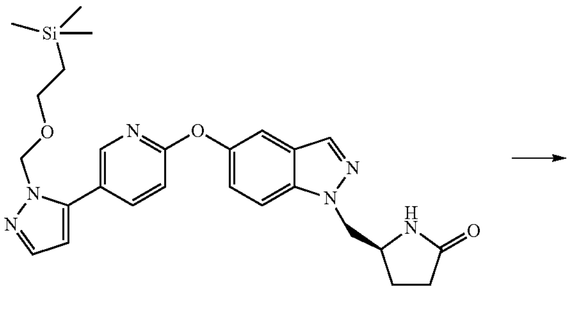

117-1

-continued

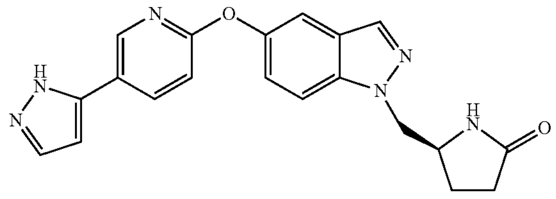

117

A reaction mixture of AC-2 (180 mg, 0.440 mmol), and NaH (35.0 mg, 0.880 mmol) in DMF (5.0 mL) is stirred for 15 min. Next, (S)-5-(bromomethyl)-2-pyrrolidinone (100 mg, 0.560 mmol) is added, and the mixture is heated at 120° C. After 16 h, the mixture is cooled to ambient temperature, diluted with EtOAc (50 mL), washed with $H_2O$ (2×50 mL), dried over $Na_2SO_4$, filtered and concentrated. The residue is purified by flash chromatography (0-10% EtOAc in heptane) to give 117-1.

A mixture of 117-1 (81 mg, 0.16 mmol) and 4M HCl in dioxane (2.5 mL) is stirred at ambient temperature. After 16 h, the reaction mixture is concentrated, and the resultant residue is purified by flash chromatography (0-10% $NH_3$ in MeOH in DCM) to give the title product (117).

Example 119

Preparation of (S)-5-{6-[4-(2H-Pyrazol-3-yl)-phenoxy]-isoquinolin-1-yloxymethyl}-pyrrolidin-2-one (119)

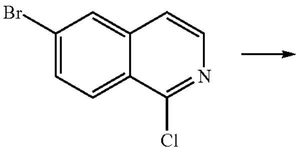

119-1

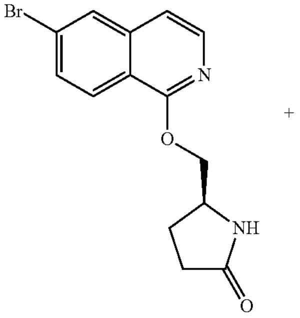

119-2

-continued

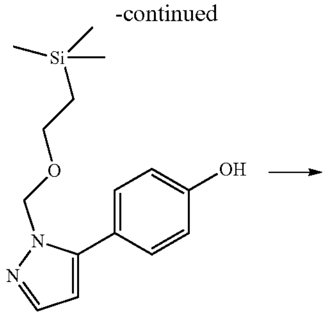

B

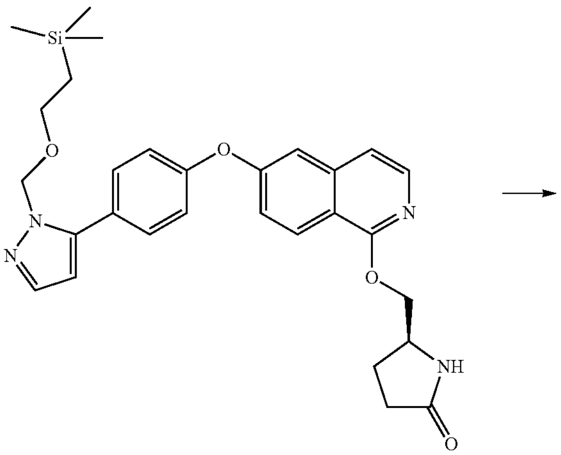

119-3

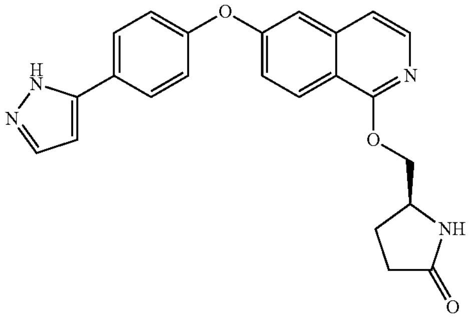

119

A mixture of (S)-(+)-5-hydroxymethyl-2-pyrrolidinone (60.0 mg, 0.520 mmol) and NaH (60.0 mg, 0.860 mmol) in DMF (5.0 mL) is stirred at 0° C. for 15 min. The mixture is treated with 119-1 (100 mg, 0.41) and heated at 80° C. for 1 h. The reaction is cooled to ambient temperature, diluted with EtOAc (50 mL), washed with $H_2O$ (2×50 mL), dried over $Na_2SO_4$ and concentrated. The residue is purified by flash chromatography (0-10% MeOH in DCM) to give 119-2.

A mixture of B (50.0 mg, 0.170 mmol), 119-2 (47.0 mg, 0.150 mmol), $Cs_2CO_3$ (120 mg, 0.37 mmol), CuI (10 mg, 0.05 mmol), and N,N-dimethylglycine.HCl (20.0 mg, 0.140 mmol) in toluene is heated at 110° C. for 16 h. The reaction mixture is cooled to ambient temperature, diluted with EtOAc (50 mL), washed with $H_2O$ (2×25 mL), dried over $Na_2SO_4$ and concentrated. The residue is purified by flash chromatography (0-10% MeOH in DCM) to give 119-3.

A mixture of 119-3 (20 mg, 0.040 mmol) in 4M HCl in dioxane (2.5 mL) is heated at 50° C. for 1 h. The reaction mixture is cooled to ambient temperature, and concentrated.

The residue is purified by flash chromatography (0-10% $NH_3$ in MeOH in DCM) to give the title compound (119).

Example 120

Preparation of 2-(2-morpholin-4-yl-ethoxy)-6-[5-(2H-pyrazol-3-yl)-pyridin-2-yloxy]-quinoline (120)

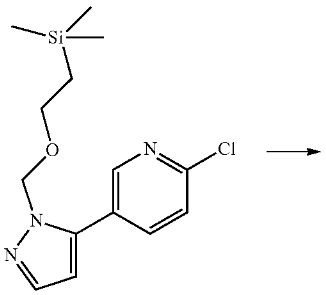

A

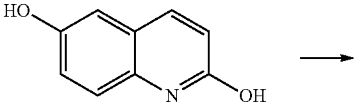

115-0

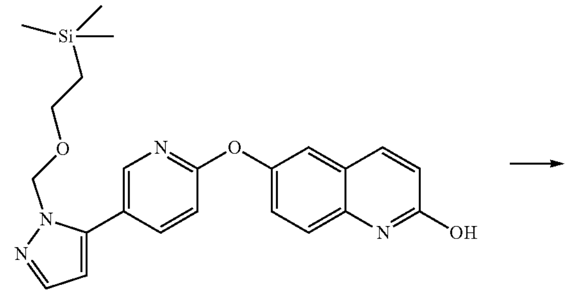

120-1

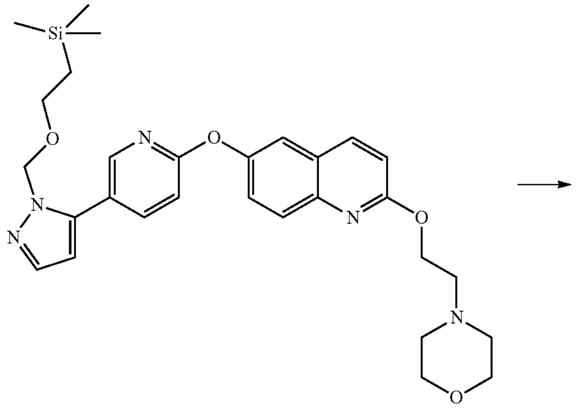

120-2

-continued

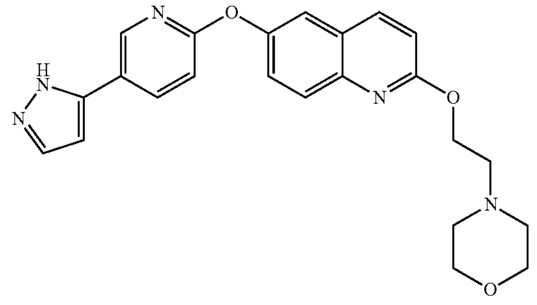

120

-continued

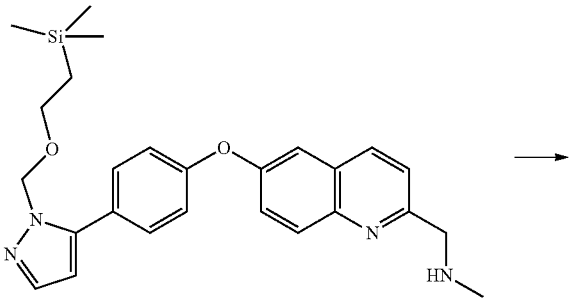

123-1

A mixture of A (2.00 g, 6.45 mmol), 115-0 (1.00 g, 6.21 mmol), and $K_2CO_3$ (2.70 g, 19.5 mmol) in DMSO (10.0 mL) is heated at 130° C. for 16 h. The reaction is cooled to ambient temperature, diluted with EtOAc (50 mL), washed with $H_2O$ (2×50 mL), dried over $Na_2SO_4$ and concentrated. The residue is purified by flash chromatography (0-10% MeOH in DCM) to give 120-1.

A mixture of 120-1 (200 mg, 0.460 mmol), (4-(2-chloro-ethyl)morpholine.HCl (200 mg, 1.08 mmol), and KOH (50.0 mg, 1.28 mmol) in EtOH (10.0 mL) is heated at 110° C. for 72 h. The reaction is cooled to ambient temperature, diluted with EtOAc (50 mL), washed with $H_2O$ (2×50 mL), dried over $Na_2SO_4$ and concentrated. The residue is purified by flash chromatography (0-10% MeOH in DCM) to give 120-2.

A mixture of 120-2 (30 mg, 0.060 mmol) and 4M HCl in dioxane (2.5 mL) is stirred at ambient temperature for 16 h. The reaction mixture is concentrated, and the resultant residue is purified by flash chromatography (0-10% $NH_3$ in MeOH in DCM) to give the title product (120).

Example 123

Preparation of Dimethyl-{6-[4-(2H-pyrazol-3-yl)-phenoxy]-quinolin-2-ylmethyl}-amine (123)

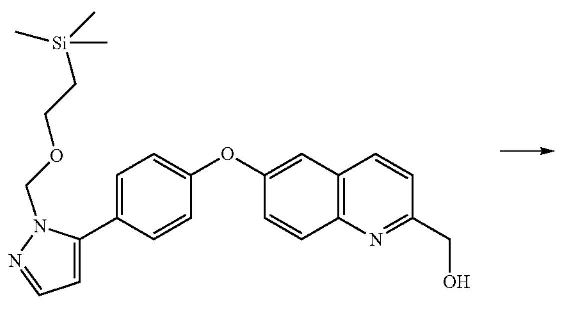

E

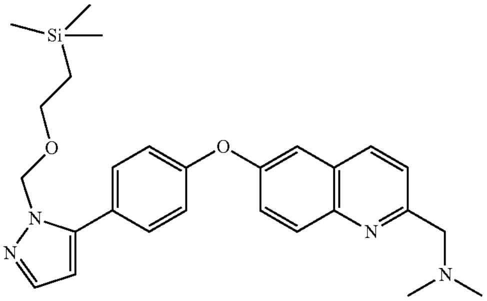

123

Compound 123-1 is synthesized from intermediate E (175 mg, 0.39 mmol) according to the procedure described for the synthesis of Example 250 from intermediate AU.

A solution of 123-1 (32 mg, 0.070 mmol) in EtOH (2 ml) is treated with formaldehyde (37% in water, 0.052 ml, 0.70 mmol), sodium cyanoborohydride (22 mg, 0.35 mmol), and 2 drops of acetic acid. The mixture is stirred at ambient temperature for 2 h, then diluted with water (5 ml), and extracted with EtOAc. The organic layer is dried over $Na_2SO_4$, filtered and concentrated. The residue is treated with HCl in dioxane (4M, 3 ml) and stirred overnight. The reaction mixture is concentrated and the resultant residue is purified by reversed phase HPLC eluting with 0-60% MeCN in water (+0.1% TFA) to give the title product (123).

Example 124

Preparation of 4-(1-{1-[4-(2H-pyrazol-3-yl)-benzyl]-1H-indol-5-ylmethyl}-piperidin-4-yl)-benzoic acid (124)

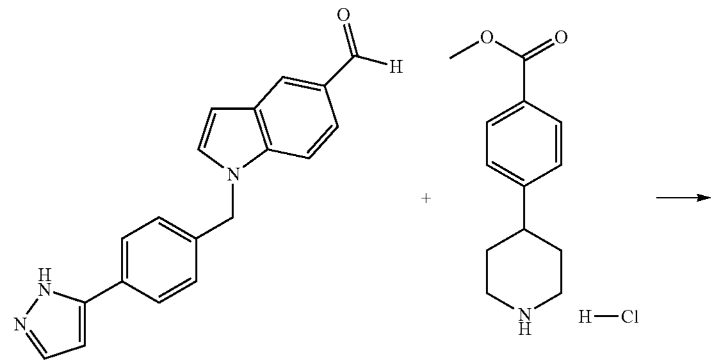

X 124-0

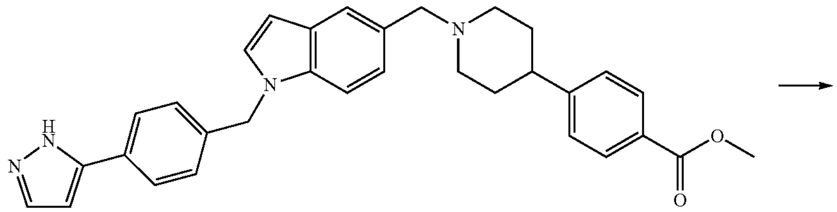

124-1

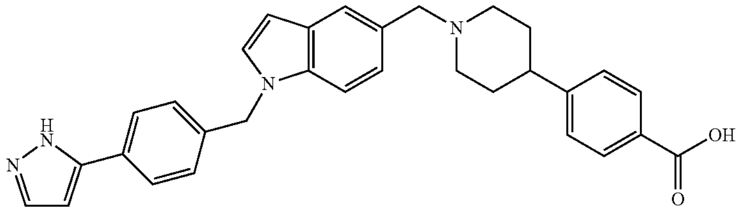

124

A mixture of X (100 mg, 0.332 mmol), 124-0 (115 mg, 0.450 mmol), and $Et_3N$ (75 μL, 0.54 mmol) in MeOH (5.0 mL) is stirred at ambient temperature for 15 min. The mixture is treated with $NaCNBH_3$ (35.0 mg, 0.550 mmol) and acetic acid (2 drops), and stirred for 16 h. The reaction mixture was concentrated and the resultant residue is purified by flash chromatography (0-10% $NH_3$ in MeOH in DCM) to give 124-1.

A mixture of 124-1 (96.0 mg, 0.190 mmol), and LiOH (50.0 mg, 1.19 mmol) in a solution of $H_2O$ (5.0 mL) and dioxane (5.0 mL) is heated at 50° C. for 3 h. The reaction mixture is cooled to ambient temperature, and concentrated.

The residue is diluted with $H_2O$ (10 mL) and adjusted to pH 6 with 1M aqueous HCl. The mixture is filtered to give the title product (124).

Example 125

Preparation of N-(1-{6-[5-(2H-Pyrazol-3-yl)-pyridin-2-yloxy]-2,3-dihydro-benzofuran-2-ylmethyl}-piperidin-4-yl)-acetamide (125)

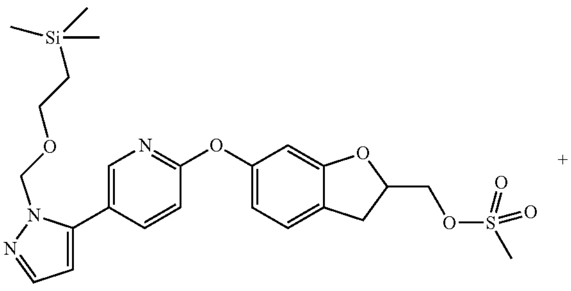

AE

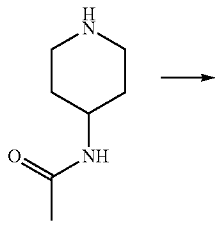

125-1

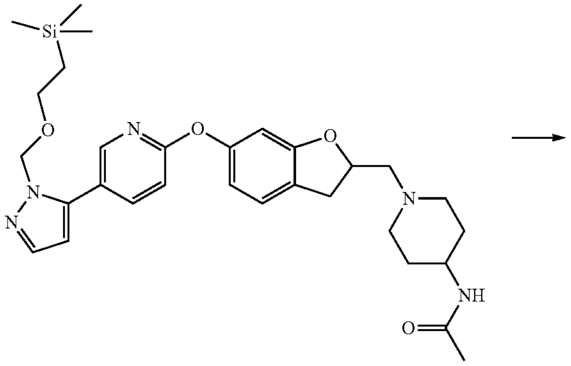

125-2

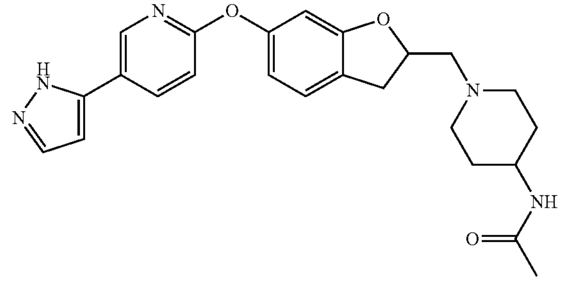

125

To a solution of AE (100 mg, 0.190 mmol) in DMSO (1 mL) is added 125-1 (284 mg, 2.00 mmol). The mixture is heated at 80° C. for 16 h. The mixture is diluted with DCM (50 mL), quenched with saturated aqueous $NH_4Cl$ (20 mL), washed with $H_2O$ (2×20 mL) and brine (20 mL), dried over $MgSO_4$, filtered and concentrated. The residue is purified on a $SiO_2$ prep plate eluting with 5% MeOH in DCM to give 125-2.

To a solution of 125-2 (108 mg. 0.190 mmol) in DCM (0.8 mL) is added TFA (0.2 mL). The mixture is stirred at ambient temperature. After 2 h, more TFA (0.2 mL) is added and the mixture is stirred for 30 min. The mixture is concentrated and purified by reversed phase HPLC eluting with 5-70% MeCN in water (+0.1% TFA). Fractions containing the desired product are combined and concentrated. The residue is dissolved in MeOH, passed through a PS—HCO3 cartridge, and concentrated to afford the title compound (125).

Example 126

Preparation of 5-(2H-Pyrazol-3-yl)-2-(2-pyrrolidin-1-ylmethyl-2,3-dihydro-benzofuran-6-yloxy)-pyridine (126)

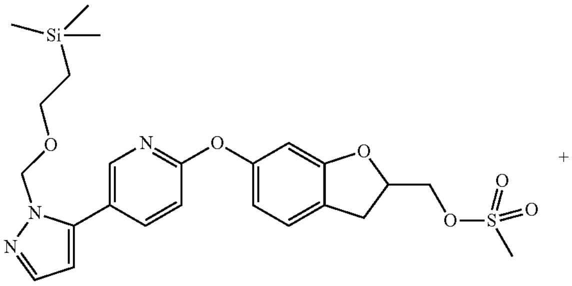

AE

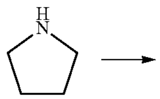

126-1

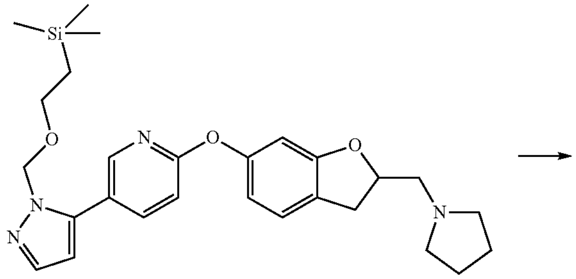

126-2

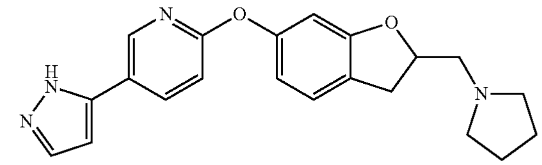

126

A solution of AE (100 mg, 0.190 mmol) 126-1 (1 mL) is heated at 80° C. for 16 h. The mixture is diluted with DCM (50 mL), quenched with saturated aqueous $NH_4Cl$ (20 mL), and washed with $H_2O$ (2×20 mL) and brine (20 mL). The organic phase is dried with $MgSO_4$, filtered and concentrated. The residue is purified on a $SiO_2$ prep plate eluting with 5% MeOH in DCM to give 126-2.

To a solution of 126-2 (101 mg. 0.190 mmol) in DCM (0.8 mL) is added TFA (0.2 mL). The mixture is stirred at ambient temperature for 2 h. The mixture is concentrated and purified by reversed phase HPLC eluting with 5-70% MeCN in water (+0.1% TFA). Fractions containing the desired product are combined and concentrated. The residue is dissolved in MeOH, passed through a PS—$HCO_3$ cartridge, and concentrated to afford the title compound (126).

Example 127

Preparation of 5-(2H-Pyrazol-3-yl)-2-(2-pyrrolidin-1-ylmethyl-benzofuran-6-yloxy)-pyridine (127)

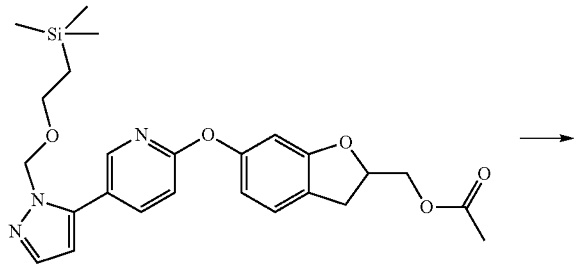

A-9

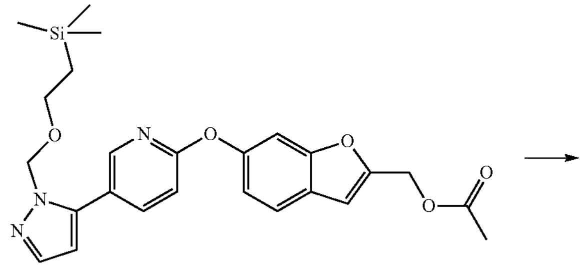

127-1

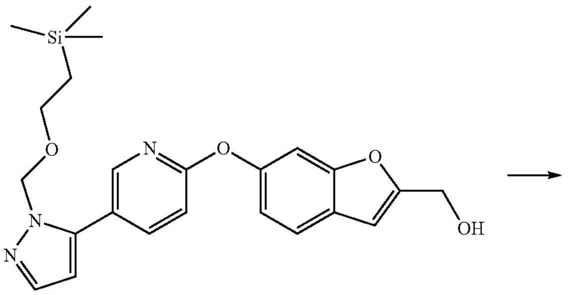

127-2

-continued

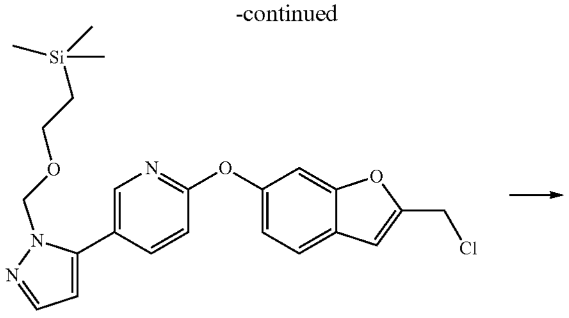

127-3

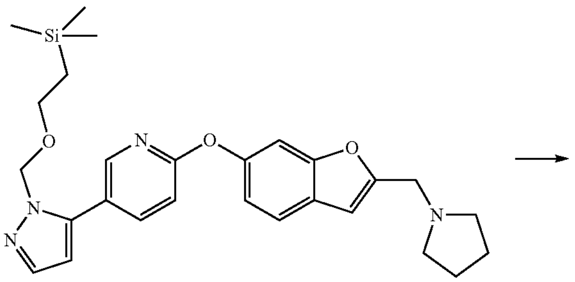

127-4

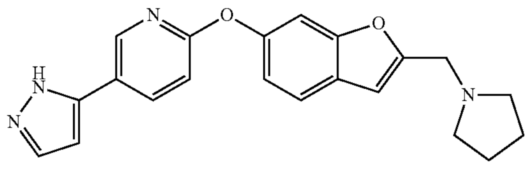

127

To a solution of A-9 (190 mg, 0.390 mmol) in dioxane (5 mL) is added DDQ (204 mg, 0.900 mmol). The mixture is heated at 120° C. for 3 h, diluted with EtOAc (50 mL), washed with saturated aqueous $NaHCO_3$ (2×50 mL) and brine (50 mL). The organic phase is dried over $MgSO_4$, filtered and concentrated to give 127-1.

To a solution of 127-1 (189 mg, 0.390 mmol) in a mixture of $H_2O$ and MeOH (30 mL; 1:5) is added $K_2CO_3$ (200 mg), and the resultant mixture is heated at 50° C. After 1 h, the mixture is treated with AcOH (2 mL) and concentrated. The residue is suspended in $H_2O$ (30 mL) and extracted with EtOAc (2×60 mL). The organic phase is washed with brine (50 mL), dried over $MgSO_4$, filtered and concentrated to give 127-2.

To a stirred solution of 127-2 (172 mg, 0.390 mmol) in DCM (10 mL) is added DIPEA (0.33 mL, 1.00 mmol) and methanesulfonyl chloride (0.060 mL, 0.80 mmol). After 2 h, more methanesulfonyl chloride (0.120 mL, 1.60 mmol) is added and the mixture is stirred for 72 h. The mixture is diluted with EtOAc (50 mL), quenched with saturated aqueous $NH_4Cl$ (20 mL), washed with saturated aqueous $K_2CO_3$ (2×20 mL) and brine (20 mL), dried over MgSO4, filtered and concentrated to give 127-3.

The title product 127 is synthesized from 127-3 (45.6 mg, 0.10 mmol) according to the procedure described for the synthesis of Example 126 from AE.

Example 128

Preparation of N-(1-{6-[5-(2H-Pyrazol-3-yl)-pyridin-2-yloxy]-2,3-dihydro-benzofuran-2-ylmethyl}-piperidin-4-ylmethyl)-acetamide (128)

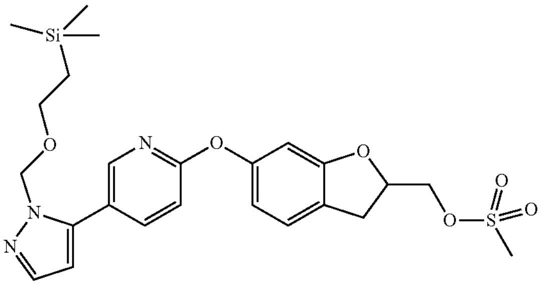

+

AE

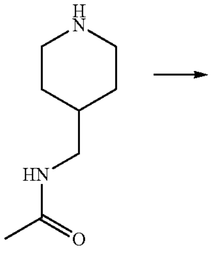

128-1

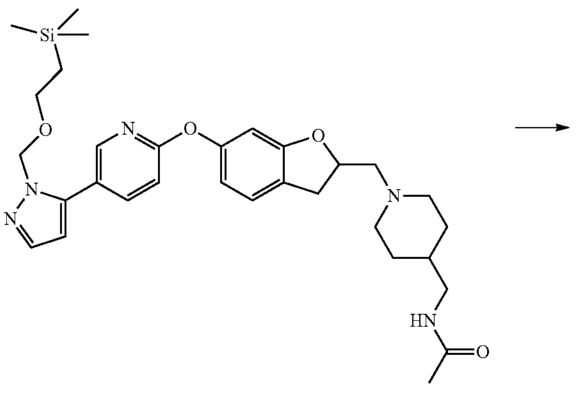

128-2

-continued

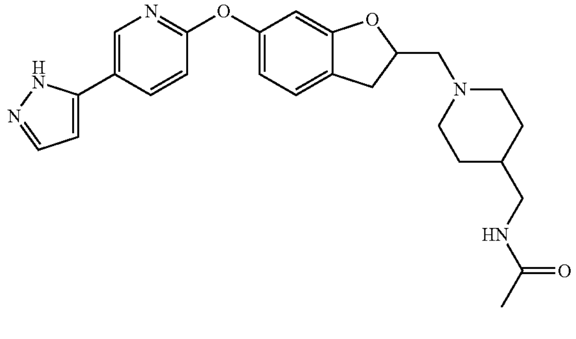

128

To a solution of AE (82.0 mg, 0.160 mmol) and 128-1 (156 mg, 1.00 mmol) in DMSO (1 mL) is added $K_2CO_3$ (200 mg). After 16 h at 80° C., the mixture is diluted with EtOAc (100 mL), washed with saturated aqueous $NaHCO_3$ (3×20 mL), $H_2O$ (2×50 mL) and brine (50 mL). The organic phase is dried over $MgSO_4$, filtered and concentrated. The residue is purified on a $SiO_2$ prep plate eluting with 5% MeOH in DCM to give 128-2.

The title product (128) is synthesized from 128-2 (101 mg. 0.19 mmol) according to the procedure described for the synthesis of Example 126 from 126-2.

The following example is synthesized from intermediate AE and the appropriate amine reagent according to the procedure described for the synthesis of Example 128.

| Ex. | Compound Name | Amine Reagent |
|---|---|---|
| 129 | 1-(1-{6-[5-(2H-Pyrazol-3-yl)-pyridin-2-yloxy]-2,3-dihydro-benzofuran-2-ylmethyl}-piperidin-4-yl)-pyrrolidin-2-one | 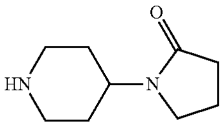 [SMILES: O=C1CCCN1C1CCNCC1] |

Example 130

Preparation of 3-[1-(2-{6-[5-(2H-Pyrazol-3-yl)-pyridin-2-yloxy]-benzofuran-3-yl}-ethyl)-piperidin-4-yl]-oxazolidin-2-one (130)

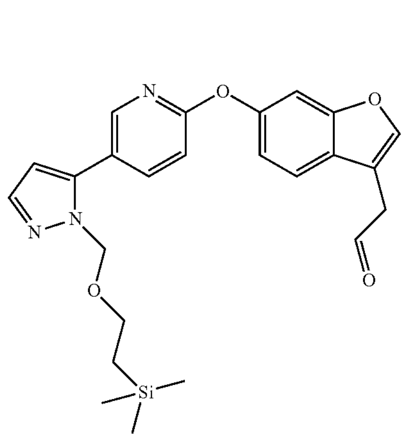

AS

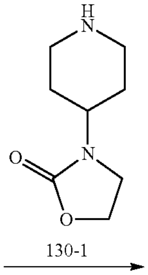

130-1

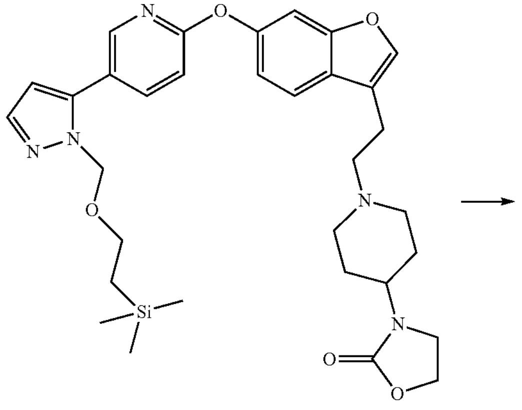

130-2

-continued

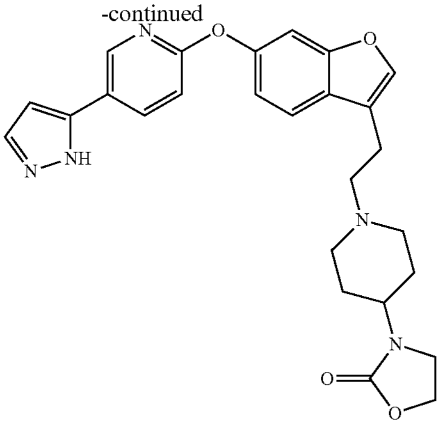

130

A mixture of intermediate AS (45.0 mg, 0.100 mmol) and 130-1 (34.1 mg, 0.200 mmol) in dry DCE (2 mL) is stirred for 20 min, sodium triacetoxyborohydride (42.4 mg, 0.200 mmol) is added, and the resultant mixture is stirred at ambient temperature. After 20 h, the mixture is diluted with DCM (10 mL). The organic layer is washed with saturated aqueous $NaHCO_3$ (10 mL), dried over $MgSO_4$, filtered and concentrated. The residue is purified on $SiO_2$ (0-10% MeOH in DCM) to give 130-2.

A solution of 130-2 (54.9 mg, 0.091 mmol) in DCM (1 mL) is treated with TFA (0.2 mL). The resultant mixture is stirred at ambient temperature for 2 h and concentrated. The residue is purified by reversed phase HPLC eluting with 10-100% MeCN in water (+0.1% TFA). Fractions containing the desired product are combined and lyophilized. The residue is dissolved in MeOH, passed through a PS—HCO3 cartridge, and concentrated to afford the title product (130).

The following examples are synthesized from intermediate AS or AT, and the appropriate amine reagents (free base or salt form) according to the procedure described for the synthesis of Example 130.

| Example No. | Compound Name | Intermediate | Amine Reagent |
|---|---|---|---|
| 133 | N-[1-(2-{6-[5-(2H-Pyrazol-3-yl)-pyridin-2-yloxy]-benzofuran-3-yl}-ethyl)-piperidin-4-yl]-acetamide | AS | 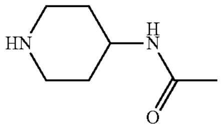 |
| 134 | 1-[4-(2-{6-[5-(2H-Pyrazol-3-yl)-pyridin-2-yloxy]-benzofuran-3-yl}-ethyl)-[1,4]diazepan-1-yl]-ethanone | AS | 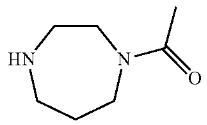 |
| 135 | 1-[4-(2-{6-[5-(2H-Pyrazol-3-yl)-pyridin-2-yloxy]-2,3-dihydro-benzofuran-3-yl}-ethyl)-[1,4]diazepan-1-yl]-ethanone | AT | 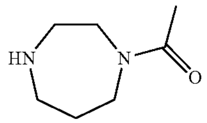 |

-continued

| Example No. | Compound Name | Intermediate | Amine Reagent |
|---|---|---|---|
| 136 | 1-[4-(2-{6-[5-(2H-Pyrazol-3-yl)-pyridin-2-yloxy]-benzofuran-3-yl}-ethyl)-piperazin-1-yl]-ethanone | AS | 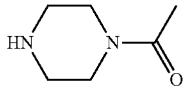 |
| 138 | 1-(2-{6-[5-(2H-Pyrazol-3-yl)-pyridin-2-yloxy]-benzofuran-3-yl}-ethyl)-piperidine-4-carboxylic acid methylamide | AS | 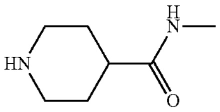 |
| 141 | N-[1-(2-{6-[5-(2H-Pyrazol-3-yl)-pyridin-2-yloxy]-benzofuran-3-yl}-ethyl)-piperidin-4-yl]-methanesulfonamide | AS | 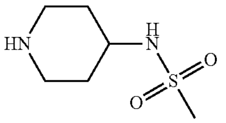 |
| 143 | 1-[4-(2-{6-[5-(2H-Pyrazol-3-yl)-pyridin-2-yloxy]-2,3-dihydro-benzofuran-3-yl}-ethyl)-piperazin-1-yl]-ethanone | AT | 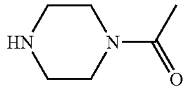 |

Example 131

Preparation of N-((endo)-8-{6-[4-(2H-Pyrazol-3-yl)-phenoxy]-2,3-dihydro-benzofuran-2-ylmethyl}-8-aza-bicyclo[3.2.1]oct-3-yl)-acetamide (131)

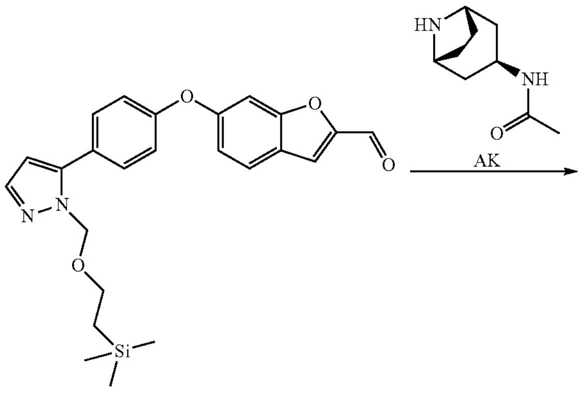

AG

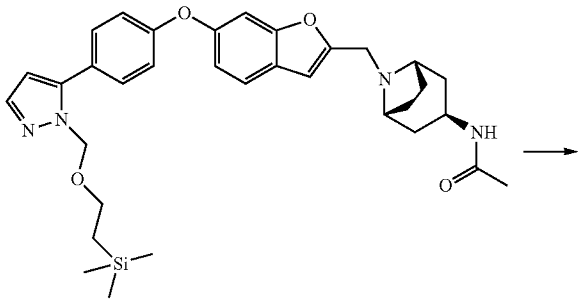

131-1

-continued

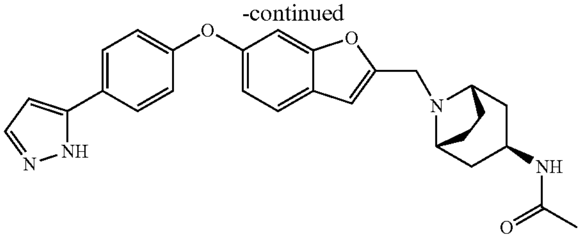

131

A stirred solution of AG (50.0 mg, 0.115 mmol) and AK (33.0 mg, 0.196 mmol) in dry DCE (6 mL) is treated with $Et_3N$ (27 mL, 0.20 mmol) and stirred for 10 minutes. To the mixture is added sodium triacetoxyborohydride (48.5 mg, 0.229 mmol), and the resultant mixture is stirred at ambient temperature. After 32 h, the mixture is diluted with DCM (25 mL) and extracted with saturated aqueous $NaHCO_3$ (25 mL). The organic layer is dried over $MgSO_4$, filtered and concentrated. The residue was purified on $SiO_2$ (0-10% methanol in DCM) to give 131-1.

To a solution of 131-1 (48.0 mg, 0.080 mmol) in DCM (1 mL) is added HCl in dioxane (4 M, 2 mL). The mixture is stirred at ambient temperature overnight, and concentrated. The residue is purified by reversed phase HPLC eluting with 5-95% MeCN in water (+0.1% TFA) to afford the title product (131).

The following example (142) is synthesized from AG and the appropriate amine reagent according to the procedure described for the synthesis of Example 131.

| Example No. | Compound Name | Amine Reagent |
|---|---|---|
| 142 | N-((exo)-8-{6-[4-(2H-Pyrazol-3-yl)-phenoxy]-2,3-dihydro-benzofuran-2-ylmethyl}-8-aza-bicyclo[3.2.1]oct-3-yl)-acetamide | 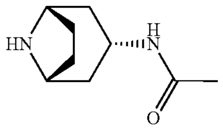 |

Example 132

Preparation of 2-Hydroxy-1-(8-{6-[5-(2H-pyrazol-3-yl)-pyridin-2-yloxy]-quinolin-2-ylmethyl}-3,8-diaza-bicyclo[3.2.1]oct-3-yl)-ethanone (132)

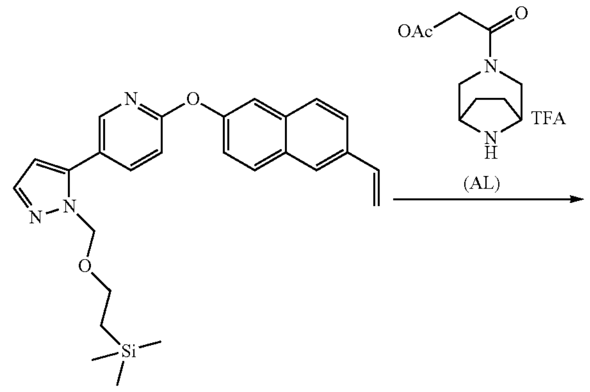

D

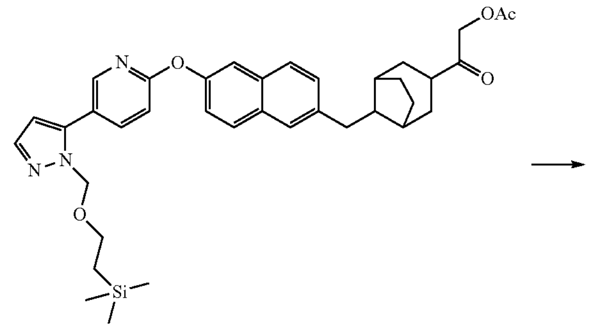

132-1

-continued

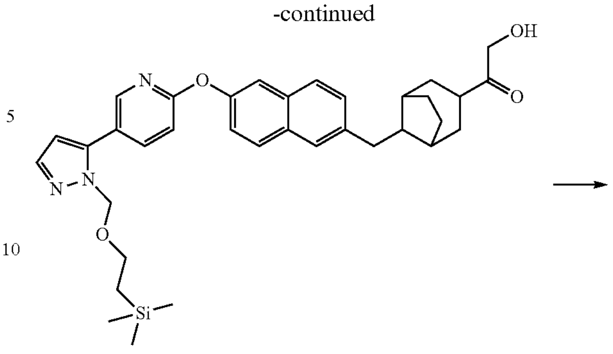

132-2

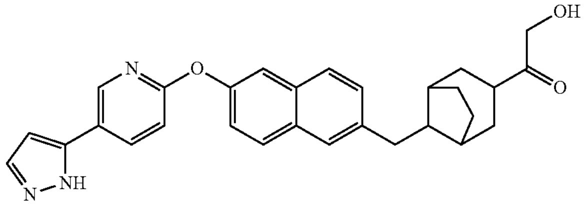

132

A mixture of D (300 mg, 0.672 mmol), AL (263 mg, 0.806 mmol), and DIPEA (0.176 mL, 1.01 mmol) in dry DCE (5.0 mL) is stirred for 20 min, and treated with sodium triacetoxyborohydride (213 mg, 1.01 mmol). After 22 h, the mixture is diluted with DCM (10 mL). The organic layer is washed with saturated aqueous $NaHCO_3$ (10 mL), dried over $MgSO_4$, filtered and concentrated. The residue is purified on $SiO_2$ (0-10% MeOH in DCM) to give 132-1.

A solution of 132-1 (313 mg, 0.487 mmol) in dry MeOH (3 mL) is treated with NaOMe (0.5M in MeOH, 49 μL). The mixture is stirred for 18 h, neutralized with AcOH, and concentrated to give 132-2.

To solution of 132-2 (290 mg, 0.49 mmol) in MeCN (3 mL) is added TFA (1 mL) and the mixture is stirred at ambient temperature for 82 h. The crude reaction mixture is purified by reversed phase HPLC eluting with 5-95% MeCN in water (+0.1% TFA). Fractions containing the desired product are combined and concentrated. The residue is dissolved in to MeOH, passed through a PS—$HCO_3$ cartridge, and concentrated to afford the title product (132).

The following examples are synthesized from intermediate D and the appropriate amine reagents (TFA salt) according to the procedure described for the synthesis of Example 132.

| Example No. | Compound Name | Amine Reagent |
|---|---|---|
| 139 | 2-Hydroxy-1-((1S,4S)-5-{6-[5-(2H-pyrazol-3-yl)-pyridin-2-yloxy]-quinolin-2-ylmethyl}-2,5-diaza-bicyclo[2.2.1]hept-2-yl)-ethanone | 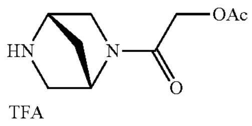 [SMILES: CC(=O)OCC(=O)N1C[C@@H]2C[C@H]1CN2] |
| 140 | 2-Hydroxy-1-(4-{6-[5-(2H-pyrazol-3-yl)-pyridin-2-yloxy]-quinolin-2-ylmethyl}-[1,4]diazepan-1-yl)-ethanone | 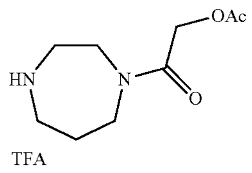 [SMILES: CC(=O)OCC(=O)N1CCCNCC1] |

-continued

| Example No. | Compound Name | Amine Reagent |
|---|---|---|
| 145 | 2-Hydroxy-1-((1R,4R)-5-{6-[5-(2H-pyrazol-3-yl)-pyridin-2-yloxy]-quinolin-2-ylmethyl}-2,5-diaza-bicyclo[2.2.1]hept-2-yl)-ethanone | 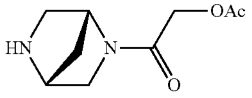 TFA |
| 146 | 2-Hydroxy-1-(5-{6-[5-(2H-pyrazol-3-yl)-pyridin-2-yloxy]-quinolin-2-ylmethyl}-2,5-diaza-bicyclo[2.2.2]oct-2-yl)-ethanone | 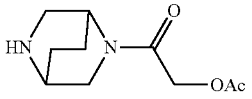 TFA |

Example 137

Preparation of 1-{6-[4-(2H-Pyrazol-3-yl)-phenoxy]-2,3-dihydro-benzofuran-2-ylmethyl}-piperidine-4-carboxylic acid methylamide (137)

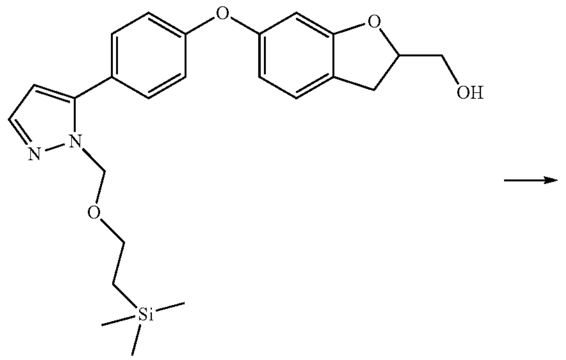

AG-3

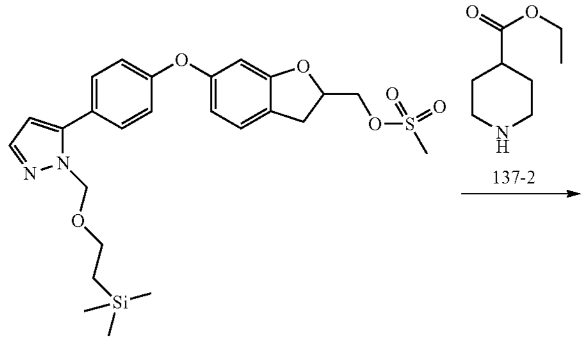

137-2

137-1

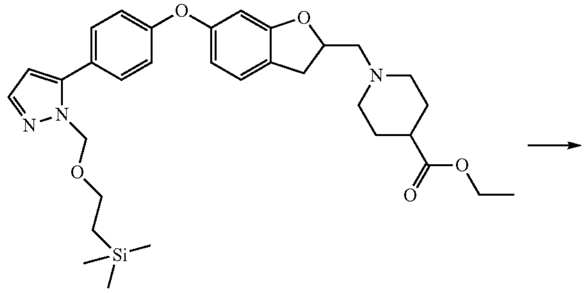

137-3

-continued

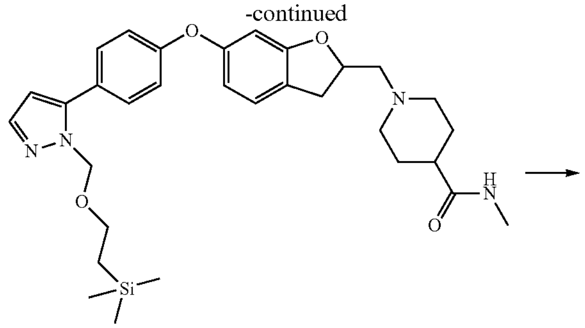

137-4

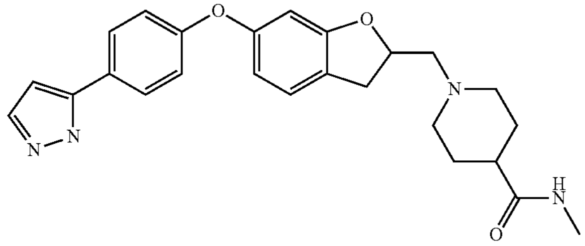

137

To a solution of AG-3 (140 mg, 0.319 mmol) in DCM (4 mL) is added $Et_3N$ (89.0 mL) and methanesulfonyl chloride (37.2 mL, 0.479 mmol). The mixture is stirred at ambient temperature for 1 h, diluted with DCM (20 mL), and washed with $NaHCO_3$ (20 mL). The organic layer is dried over $MgSO_4$, filtered and concentrated to give 137-1.

A mixture of 137-1 (162 mg, 0.314 mmol) and 137-2 (500 mL, 3.20 mmol) is heated at 60° C. After 20 h, the mixture is diluted with EtOAc (20 mL), washed with saturated aqueous $NH_4Cl$ (5x5 mL), dried over $MgSO_4$, filtered and concentrated. The residue is purified on $SiO_2$ (0-10% MeOH in DCM) to give 137-3.

A mixture of 137-3 (60.0 mg, 0.104 mmol) and $MeNH_2$ in ethanol (33%, 1.0 mL, 77 mmol) is stirred at 90° C. After 5 days, the mixture is cooled to ambient temperature, and concentrated to afford 137-4.

To a solution of 137-4 (59.0 mg, 0.105 mmol) in DCM (1 mL) is added HCl in dioxane (4 M, 2 mL). The mixture is stirred at ambient temperature for 18 h, and concentrated. The residue is purified by reversed phase HPLC eluting with 5-95% MeCN in water (+0.1% TFA) to afford the title product (137).

The following example (144) is synthesized from 137-3 and $NH_3$ (7M in MeOH) according to the procedure described for the synthesis of Example 137.

| Example No. | Compound Name |
|---|---|
| 144 | 1-{6-[4-(2H-Pyrazol-3-yl)-phenoxy]-2,3-dihydro-benzofuran-2-ylmethyl}-piperidine-4-carboxylic acid amide |

Example 147

Preparation of 1-((1R,4R)-5-{6-[5-(2H-Pyrazol-3-yl)-pyridin-2-yloxy]-quinolin-2-ylmethyl}-2,5-diaza-bicyclo[2.2.1]hept-2-yl)-ethanone (147)

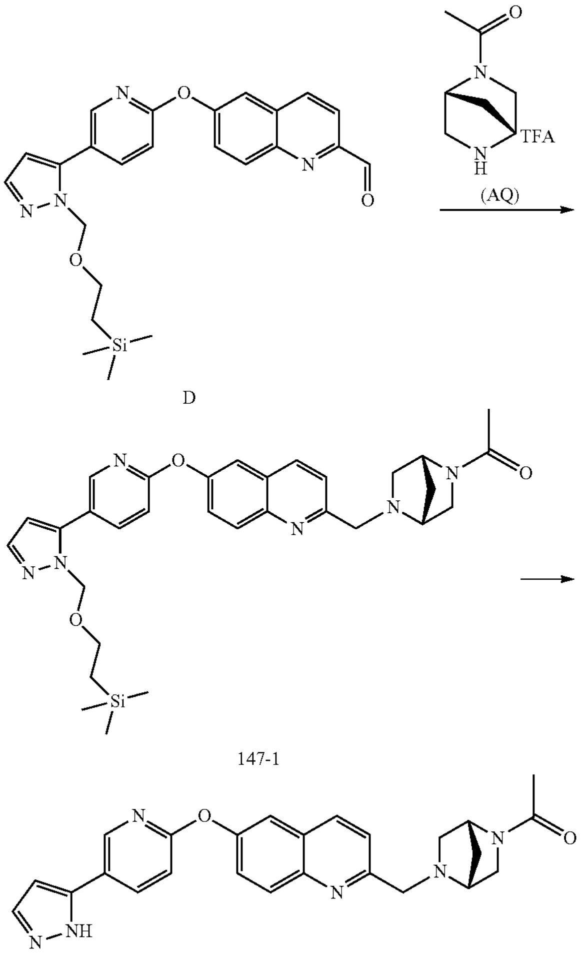

D 147-1

147

Compound 147-1 is synthesized from intermediates D and AQ according to the procedure described for the synthesis of 132-1.

The title compound (147) is synthesized from compound 147-1 according to the procedure described for the synthesis of Example 132 from 132-2.

The following example is synthesized from intermediate D and the appropriate amine reagent (TFA salt) according to the procedure described for the synthesis of Example 147.

| Example No. | Compound Name | Amine Reagent |
|---|---|---|
| 148 | 1-(5-{6-[5-(2H-Pyrazol-3-yl)-pyridin-2-yloxy]-quinolin-2-ylmethyl}-2,5-diaza-bicyclo[2.2.2]oct-2-yl)-ethanone | 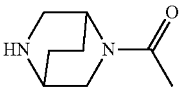 TFA |

Example 149

Preparation of 1-(4-{6-[5-(2H-Pyrazol-3-yl)-pyridin-2-yloxy]-benzofuran-3-ylmethyl}-piperazin-1-yl)-ethanone (149)

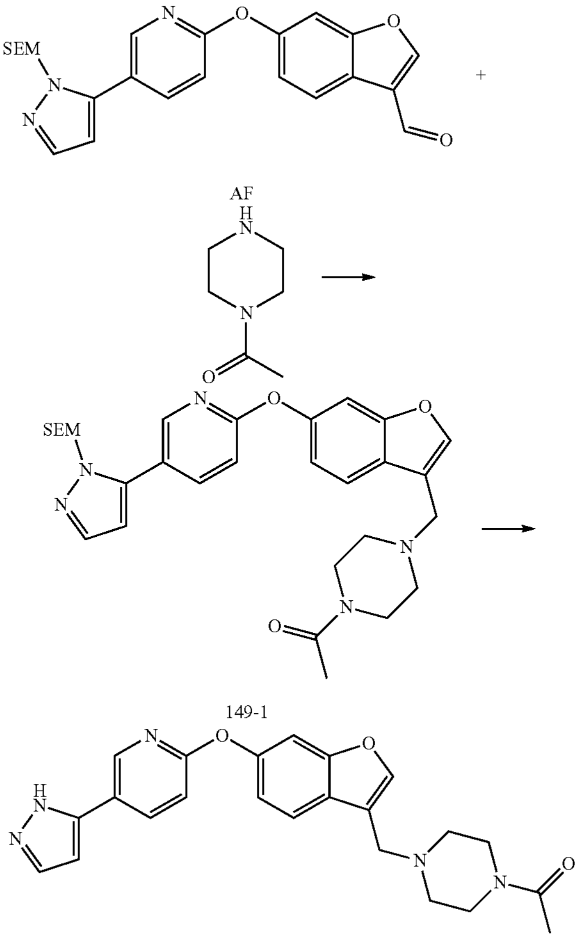

AF 149-1

149

To a solution of N-acetyl-piperazine (115 mg, 0.888 mmol) in a mixture of DCM (3 mL) and DMF (5 mL) is added glacial AcOH (0.012 mL, 0.21 mmol) and $ZnCl_2$ (1.0M in $Et_2O$, 5.0 mL). Next, AF (110 mg, 0.245 mmol) and sodium triacetoxy-borohydride (250 mg, 1.16 mmol) are added sequentially, and the resultant reaction is stirred at ambient temperature. After 18 h, more N-acetyl-piperazine (650 mg, 5.02 mmol) and sodium triacetoxyborohydride (500 mg, 2.31 mmol) are added. After 1 h, the reaction is diluted with EtOAc (125 mL), and washed with saturated aqueous $NaHCO_3$ (125 mL) and brine (40 mL). The aqueous layer is extracted with EtOAc (125 mL). The combined organic layers are dried over $Na_2SO_4$, filtered and concentrated to give 149-1.

To a solution of 149-1 (214 mg, 0.391 mmol) in DCM (5 mL) is added TFA (5 mL) and the reaction is stirred at ambient temperature for 2 h. The reaction is concentrated; the residue is treated with saturated aqueous $NaHCO_3$ (50 mL) and extracted with DCM (4×75 mL). The combined organic layers are dried over $Na_2SO_4$, filtered and concentrated. The residue is purified by silica gel chromatography (0-5% MeOH in DCM). The resultant residue is dissolved in EtOAc (20 mL) and treated with heptane (20 mL). The mixture is filtered to give the title product (149).

Example 150

Preparation of 4-((1S,4S)-5-{5-[4-(2H-Pyrazol-3-yl)-phenoxy]-1H-benzoimidazol-2-ylmethyl}-2,5-diaza-bicyclo[2.2.1]hept-2-ylmethyl)-benzoic acid methyl ester (150)

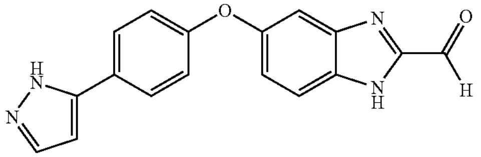

N

+

-continued

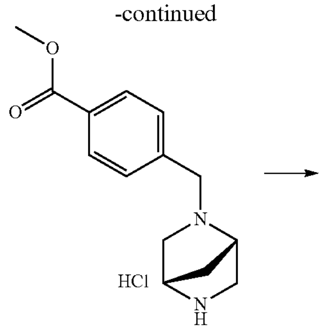

150-1

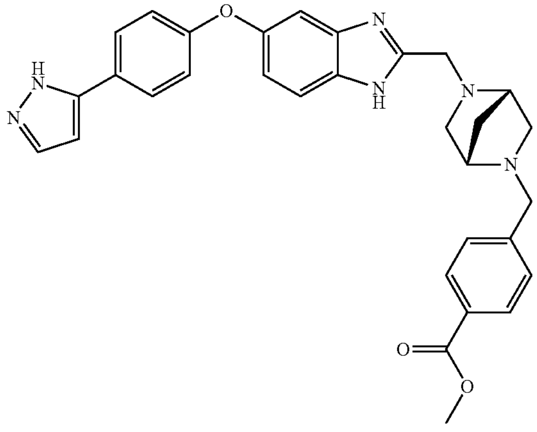

150

To a mixture of N (125 mg, 0.411 mmol) and 150-1 (150 mg, 0.515 mmol) in a mixture of DCM (1 mL) and MeOH (1 mL) is added triethylamine (0.100 mL, 0.717 mmol). The mixture is stirred at 35° C. for 1 h, treated with sodium cyanoborohydride (120 mg, 1.85 mmol) and acetic acid (0.100 mL, 1.75 mmol) and stirred for 2 h. The mixture is loaded onto a SiO2 column eluting with 0-20% MeOH in DCM to give the title compound 150.

The following example is synthesized from intermediate N and the appropriate amine reagent according to the procedure described for the synthesis of Example 150.

| Ex. | Compound Name | Amine reagent |
|---|---|---|
| 151 | 4-(1-{5-[4-(2H-Pyrazol-3-yl)-phenoxy]-1H-benzoimidazol-2-ylmethyl}-piperidin-4-yl)-benzoic acid methyl ester | 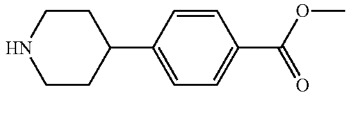 |

Example 152

Preparation of Diethyl-{5-[4-(2H-pyrazol-3-yl)-phenoxy]-1H-benzoimidazol-2-ylmethyl}-amine (152)

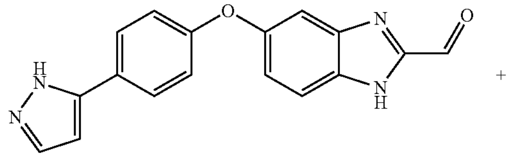

E

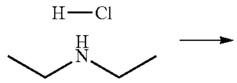

152-1

-continued

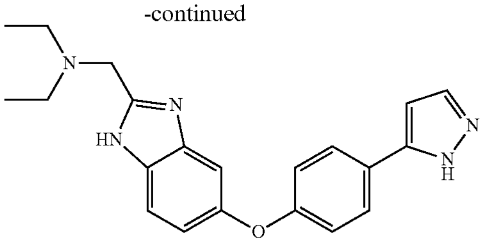

152

To a solution of Intermediate E (50.0 mg, 0.160 mmol) in N,N-dimethylacetamide (1.0 mL) is added 152-1 (26.7 mg, 0.330 mmol). The solution is shaken for 1 hour, a solution of sodium triacetoxyborohydride (69.7 mg, 0.330 mmol) in N,N-dimethylacetamide (0.50 mL) is added followed by the addition of acetic acid (50 mL). The reaction mixture is shaken overnight and concentrated. The residue is purified using a reverse phase HPLC to give the title product (152).

The following examples are synthesized using Intermediate E and the appropriate amine reagent (free base or the salt form) according to the procedure described for the synthesis of Example 152.

| Ex. | Compound Name | Amine Reagent |
|---|---|---|
| 155 | Ethyl-(2-methoxy-ethyl)-{5-[4-(2H-pyrazol-3-yl)-phenoxy]-1H-benzoimidazol-2-ylmethyl}-amine | 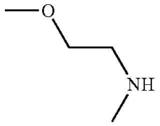 |
| 156 | 2-(3-Methoxymethyl-piperidin-1-ylmethyl)-5-[4-(2H-pyrazol-3-yl)-phenoxy]-1H-benzoimidazole | 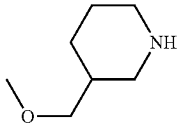 |
| 157 | 2-(3-Methoxy-pyrrolidin-1-ylmethyl)-5-[4-(2H-pyrazol-3-yl)-phenoxy]-1H-benzoimidazole | 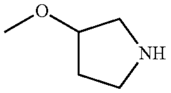 |
| 159 | Methyl-{5-[4-(2H-pyrazol-3-yl)-phenoxy]-1H-benzoimidazol-2-ylmethyl}-(tetrahydro-pyran-4-ylmethyl)-amine | 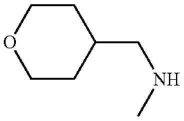 |
| 161 | ((S)-sec-Butyl)-{5-[4-(2H-pyrazol-3-yl)-phenoxy]-1H-benzoimidazol-2-ylmethyl}-amine | 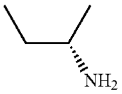 |
| 163 | 2-Azepan-1-ylmethyl-5-[4-(2H-pyrazol-3-yl)-phenoxy]-1H-benzoimidazole | 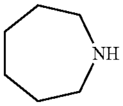 |
| 164 | Cyclopentyl-methyl-{5-[4-(2H-pyrazol-3-yl)-phenoxy]-1H-benzoimidazol-2-ylmethyl}-amine | 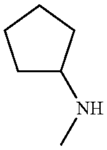 |

-continued

| Ex. | Compound Name | Amine Reagent |
|---|---|---|
| 165 | 2-((R)-2-Methyl-piperidin-1-ylmethyl)-5-[4-(2H-pyrazol-3-yl)-phenoxy]-1H-benzoimidazole | 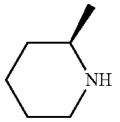 |
| 166 | 2-(3-Methoxymethyl-pyrrolidin-1-ylmethyl)-5-[4-(2H-pyrazol-3-yl)-phenoxy]-1H-benzoimidazole | 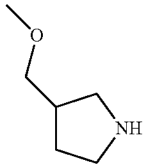 |
| 167 | 2-((R)-2-Methoxymethyl-pyrrolidin-1-ylmethyl)-5-[4-(2H-pyrazol-3-yl)-phenoxy]-1H-benzoimidazole | 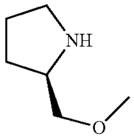 |
| 168 | 2-(2-Methoxymethyl-piperidin-1-ylmethyl)-5-[4-(2H-pyrazol-3-yl)-phenoxy]-1H-benzoimidazole | 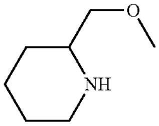 |
| 171 | 2-((S)-2-Methyl-piperidin-1-ylmethyl)-5-[4-(2H-pyrazol-3-yl)-phenoxy]-1H-benzoimidazole | 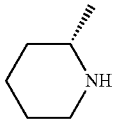 |
| 172 | 2-(3-Methoxy-piperidin-1-ylmethyl)-5-[4-(2H-pyrazol-3-yl)-phenoxy]-1H-benzoimidazole | 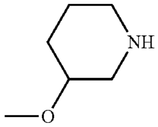 |
| 173 | 2-((S)-2-Methoxymethyl-pyrrolidin-1-ylmethyl)-5-[4-(2H-pyrazol-3-yl)-phenoxy]-1H-benzoimidazole | 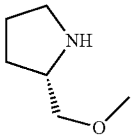 |
| 175 | 2-[1,4]Oxazepan-4-ylmethyl-5-[4-(2H-pyrazol-3-yl)-phenoxy]-1H-benzoimidazole | 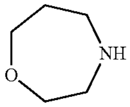 |
| 179 | Cyclopropyl-methyl-{5-[4-(2H-pyrazol-3-yl)-phenoxy]-1H-benzoimidazol-2-ylmethyl}-amine | 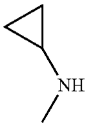 |
| 180 | ((R)-sec-Butyl)-{5-[4-(2H-pyrazol-3-yl)-phenoxy]-1H-benzoimidazol-2-ylmethyl}-amine | 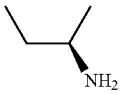 |
| 181 | {5-[4-(2H-Pyrazol-3-yl)-phenoxy]-1H-benzoimidazol-2-ylmethyl}-(tetrahydro-pyran-3-yl)-amine | 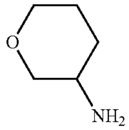 |

-continued

| Ex. | Compound Name | Amine Reagent |
|---|---|---|
| 182 | 2-(3,3-Dimethyl-moprholin-4-ylmethyl)-5-[4-(2H-pyrazol-3-yl)-phenoxy]-1H-benzoimidazole | 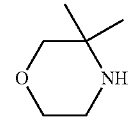 |
| 183 | Isopropyl-(2-methoxy-ethyl)-{5-[4-(2H-pyrazol-3-yl)-phenoxy]-1H-benzoimidazol-2-ylmethyl}-amine | 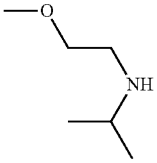 |
| 184 | (2-Methoxy-ethyl)-propyl-{5-[4-(2H-pyrazol-3-yl)-phenoxy]-1H-benzoimidazol-2-ylmethyl}-amine | 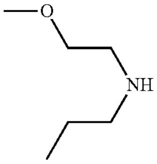 |
| 186 | Bis-(2-methoxy-ethyl)-{5-[4-(2H-pyrazol-3-yl)-phenoxy]-1H-benzoimidazol-2-ylmethyl}-amine | 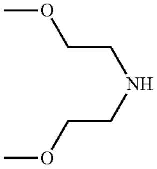 |
| 188 | Cyclopentyl-{5-[4-(2H-pyrazol-3-yl)-phenoxy]-1H-benzoimidazol-2-ylmethyl}-amine | 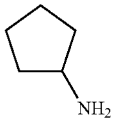 |
| 189 | ((S)-2-Methoxy-1-methyl-ethyl)-{5-[4-(2H-pyrazol-3-yl)-phenoxy]-1H-benzoimidazol-2-ylmethyl}-amine | 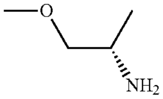 |
| 191 | Ethyl-{5-[4-(2H-pyrazol-3-yl)-phenoxy]-1H-benzoimidazol-2-ylmethyl}-amine | 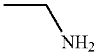 |
| 192 | 2-(Ethyl-{5-[4-(2H-pyrazol-3-yl)-phenoxy]-1H-benzoimidazol-2-ylmethyl}-amino)-ethanol | 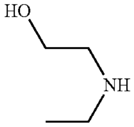 |
| 193 | 2-(4-Ethoxymethyl-piperidin-1-ylmethyl)-5-[4-(2H-pyrazol-3-yl)-phenoxy]-1H-benzoimidazole | 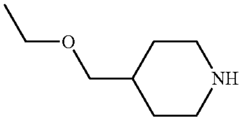 |
| 194 | {5-[4-(2H-Pyrazol-3-yl)-phenoxy]-1H-benzoimidazol-2-ylmethyl}-(S)-tetrahydro-furan-3-yl-amine | 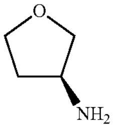 |
| 195 | (1-{5-[4-(2H-Pyrazol-3-yl)-phenoxy]-1H-benzoimidazol-2-ylmethyl}-piperidin-2-yl)-methanol | 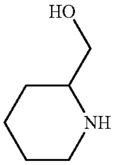 |

-continued

| Ex. | Compound Name | Amine Reagent |
|---|---|---|
| 196 | 5-[4-(2H-Pyrazol-3-yl)-phenoxy]-2-(3-trifluoromethyl-pyrrolidin-1-ylmethyl}-1H-benzoimidazole | 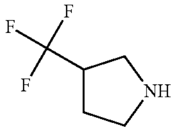 |
| 199 | 2-(Propyl-{5-[4-(2H-pyrazol-3-yl)-phenoxy]-1H-benzoimidazol-2-ylmethyl}-amino)-ethanol | 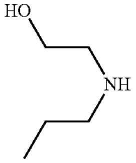 |
| 225 | 2-(4-Morpholin-4-ylmethyl-piperidin-1-ylmethyl)-5-[4-(2H-pyrazol-3-yl)-phenoxy]-1H-benzoimidazole | 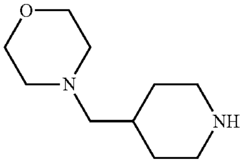 [SMILES: C1CC(CN2CCOCC2)CCN1] |
| 226 | 2-((S)-3-Methoxy-pyrrolidin-1-ylmethyl)-5-[4-(2H-pyrazol-3-yl)-phenoxy]-1H-benzoimidazole | 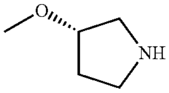 |
| 227 | 3-{5-[4-(2H-Pyrazol-3-yl)-phenoxy]-1H-benzoimidazol-2-ylmethyl}-8-oxa-3-aza-bicyclo[3.2.1]octane | 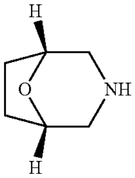 |
| 228 | 2-(4-Methoxy-piperidin-1-ylmethyl)-5-[4-(2H-pyrazol-3-yl)-phenoxy]-1H-benzoimidazole | 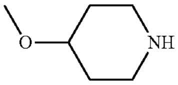 |
| 229 | (1S,2S)-2-(Methyl-{5-[4-(2H-pyrazol-3-yl)-phenoxy]-1H-benzoimidazol-2-ylmethyl}-amino)-cyclohexanol | 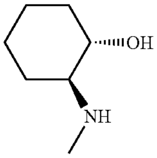 |
| 230 | Methyl-{5-[4-(2H-pyrazol-3-yl)-phenoxy]-1H-benzoimidazol-2-ylmethyl}-(tetrahydro-pyran-4-yl)-amine | 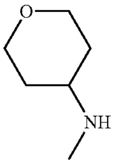 |

Example 153

Preparation of 2-(4-Methyl-piperidin-1-ylmethyl)-5-[4-(2H-pyrazol-3-yl)-phenoxy]-1H-benzoimidazole

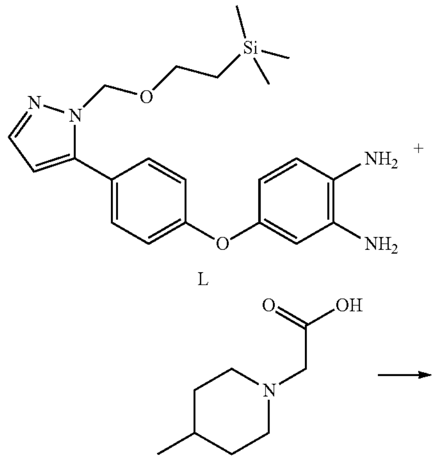

L 153-1

-continued

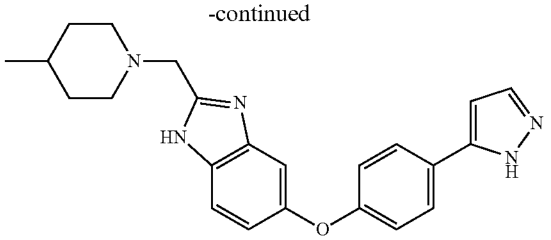

153

A solution of DIPEA (99 mL, 0.57 mmol) and PyBrop (185 mg, 0.400 mmol) in DCM (0.5 mL) is added to 153.1 (39.0 mg, 0.250 mmol) and the mixture is shaken for 20 min Next, a solution of L (90.0 mg, 0.227 mmol) in DCM (0.5 mL) is added, and the resultant mixture is stirred at ambient temperature overnight. The mixture is concentrated and purified by reverse phase HPLC. The desired fractions are concentrated; the residue is dissolve in acetic acid (2.0 mL), and heat at 110° C. After 5 h, the mixture is concentrated, taken up in MeOH (1.0 mL) and treated with 4N HCl in Dioxane (0.5 mL). The resultant mixture is heated at 50° C. for 5 h, concentrated, and purified by reverse phase HPLC to give the title product (153).

The following examples are synthesized using Intermediate L and the appropriate carboxylic acid reagent according to the procedure described for the synthesis of Example 153

| Ex. | Compound Name | Acid Reagent |
|---|---|---|
| 202 | 5-[4-(2H-Pyrazol-3-yl)-phenoxy]-2-(tetrahydro-pyran-4-ylmethyl)-1H-benzoimidazole | 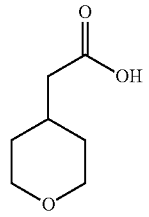 |
| 207 | 5-[4-(2H-Pyrazol-3-yl)-phenoxy]-2-(S)-1-pyrrolidin-2-ylmethyl-1H-benzoimidazole | 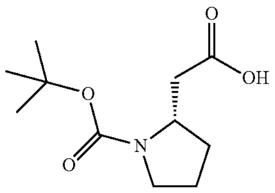 [SMILES: CC(C)(C)OC(=O)N1CCC[C@H]1CC(=O)O] |

Example 154

Preparation of Ethyl-methyl-(2-{5-[4-(2H-pyrazol-3-yl)-phenoxy]-indazol-2-yl}-ethyl)-amine (154)

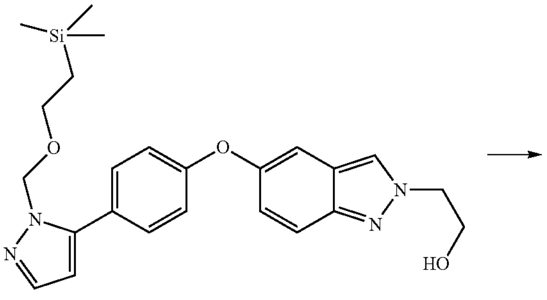

Z

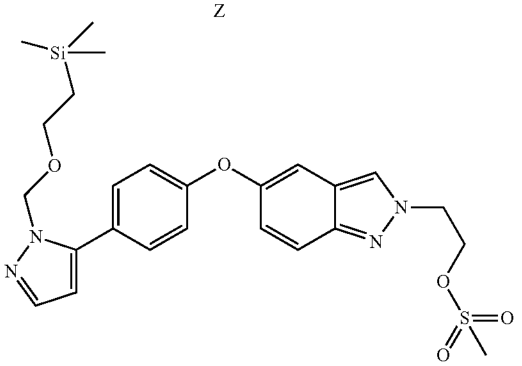

154-1

+

-continued

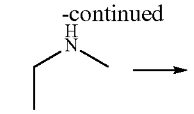

154-2

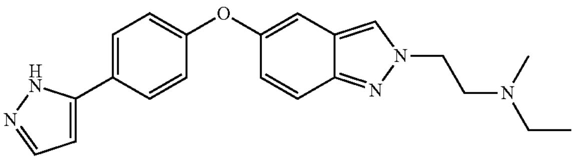

154

To a solution of intermediate Z (1.20 g, 2.66 mmol) in DCM (25 mL) is added methanesulfonyl chloride (0.280 mL, 3.60 mmol) and triethylamine (0.560 mL, 4.00 mmol). The mixture is stirred for 30 min, extracted with saturated aqueous $NaHCO_3$, dried over $Na_2SO_4$, filtered and concentrated to give 154-1.

To a solution of 154-1 (58 mg, 0.11 mmol) and 154-2 (13 mg, 0.22 mmol) in DMF (1.0 mL) is added $K_2CO_3$ (40 mg, 0.29 mmol). The mixture is heated at 80° C. overnight, cooled to ambient temperature, filtered and concentrated. The residue is dissolved in 1,2-dichloroethane (1.0 mL) and treated with 4.0 M HCl in dioxane (0.5 mL). The mixture is shaken at ambient temperature overnight, concentrated, and purified by reverse phase HPLC to give the title product (154).

The following examples are synthesized from the appropriate amine reagents and intermediates according to the procedure described for the synthesis of Example 154.

| Ex. | Compound Name | Intermediates | Amine Reagents |
|---|---|---|---|
| 158 | Dimethyl-(2-{5-[4-(2H-pyrazol-3-yl)-phenoxy]-indazol-2-yl}-ethyl)-amine | Z | 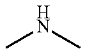 |
| 160 | N-[(R)-1-(2-{5-[4-(2H-Pyrazol-3-yl)-phenoxy]-indazol-1-yl}-ethyl)-pyrrolidin-3-yl]-acetamide | Y | 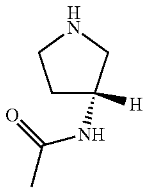 |
| 162 | Dimethyl-(2-{5-[4-(2H-pyrazol-3-yl)-phenoxy]-indazol-1-yl}-ethyl)-amine | Y | 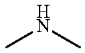 |
| 176 | 2-[2-(1,1-Dioxo-1-λ-6-thiomorpholin-4-yl)-ethyl]-5-[4-(2H-pyrazol-3-yl)-phenoxy]-2H-indazole | Z | 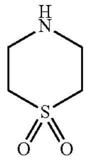 |

-continued

| Ex. | Compound Name | Intermediates | Amine Reagents |
|---|---|---|---|
| 177 | 1-[1-(2-{5-[4-(2H-Pyrazol-3-yl)-phenoxy]-indazol-1-yl}-ethyl)-piperidin-4-yl]-pyrrolidin-2-one | Y | 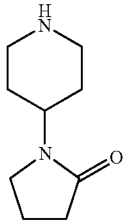 [SMILES: O=C1CCCN1C1CCNCC1] |
| 200 | N-[(R)-1-(2-{5-[4-(2H-Pyrazol-3-yl)-phenoxy]-indazol-2-yl}-ethyl)-pyrrolidin-3-yl]-acetamide | Z | 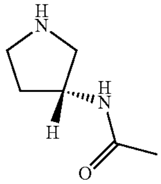 |
| 201 | 2-Methoxy-N-[1-(2-{5-[4-(2H-pyrazol-3-yl)-phenoxy]-indazol-1-yl}-ethyl)-piperidin-4-yl]-acetamide | Y | 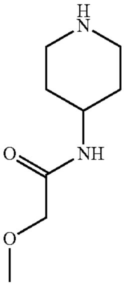 |
| 206 | (2-{5-[4-(2H-Pyrazol-3-yl)-phenoxy]-indazol-2-yl}-ethyl)-(tetrahydro-pyran-4-ylmethyl)-amine | Z | 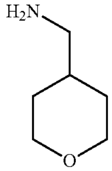 |

Example 185

Preparation of {6-[4-(2H-Pyrazol-3-yl)-phenoxy]-2,3-dihydro-benzofuran-2-ylmethyl}-(tetrahydro-pyran-4-ylmethyl)-amine (185)

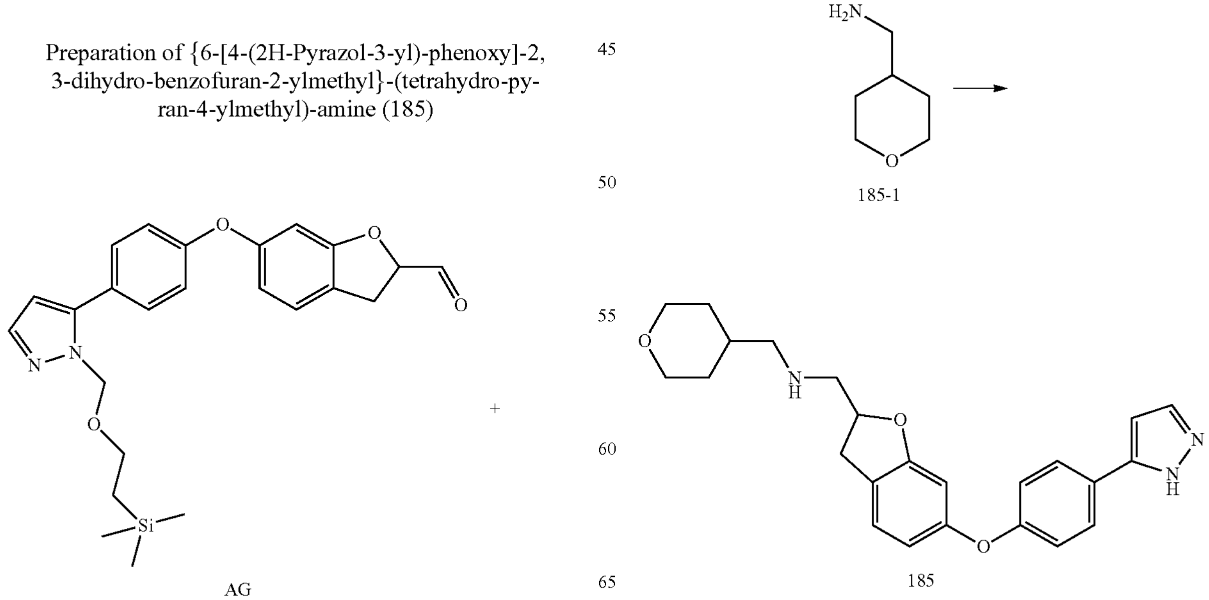

AG

+

-continued 185-1

185

A solution of AG (50.0 mg, 0.120 mmol) in 1,2-dichloroethane (1.0 mL) is added to 185-1 (26.5 mg, 0.230 mmol). The mixture is shaken for 1 h, treated with a solution of sodium triacetoxyborohydride (49.0 mg, 0.230 mmol) in N,N-dimethylacetamide (0.5 mL), and shaken over the weekend. The reaction mixture is concentrated; the resultant residue is dissolved in dichloroethane (1.0 mL) and treated with 4N HCl in Dioxane (0.5 mL). The mixture is shaken at ambient temperature overnight, concentrated, and purified by reverse phase HPLC to give the title product (185).

The following examples are synthesized from Intermediate AG and the appropriate amine reagents according to the procedure described for the synthesis of Example 185.

| Ex. | Compound Name | Amine Reagent |
|---|---|---|
| 169 | N,N-Dimethyl-2-(1-{6-[4-(2H-pyrazol-3-yl)-phenoxy]-2,3-dihydro-benzofuran-2-ylmethyl}-piperidin-4-yl)-acetamide | 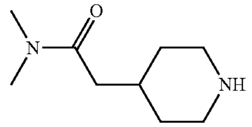 |
| 170 | 2-Methoxy-N-(1-{6-[4-(2H-pyrazol-3-yl)-phenoxy]-2,3-dihydro-benzofuran-2-ylmethyl}-piperidin-4-yl)-acetamide | 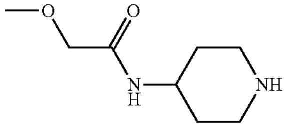 |
| 187 | Morpholin-4-yl-(1-{6-[4-(2H-pyrazol-3-yl)-phenoxy]-2,3-dihydro-benzofuran-2-ylmethyl}-piperidin-4-yl)-methanone | 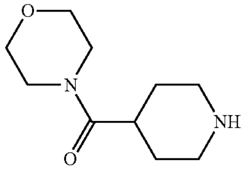 [SMILES: O=C(C1CCNCC1)N1CCOCC1] |
| 197 | 1-{6-[4-(2H-Pyrazol-3-yl)-phenoxy]-2,3-dihydro-benzofuran-2-ylmethyl}-piperidine-4-carboxylic acid dimethylamide | 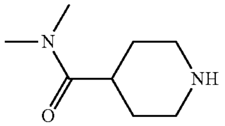 |
| 198 | 1-(1-{6-[4-(2H-Pyrazol-3-yl)-phenoxy]-2,3-dihydro-benzofuran-2-ylmethyl}-piperidin-4-yl)-pyrrolidin-2-one | 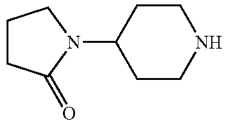 [SMILES: O=C1CCCN1C1CCNCC1] |
| 203 | 3-(1-{6-[4-(2H-Pyrazol-3-yl)-phenoxy]-2,3-dihydro-benzofuran-2-ylmethyl}-piperidin-4-yl)-oxazolidin-2-one | 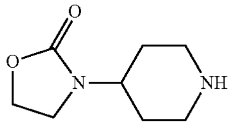 [SMILES: O=C1OCCN1C1CCNCC1] |

Example 214

Preparation of {6-[5-(2H-Pyrazol-3-yl)-pyridin-2-yloxy]-quinolin-2-ylmethyl}-[2-(tetrahydro-pyran-4-yl)-ethyl]-amine (214)

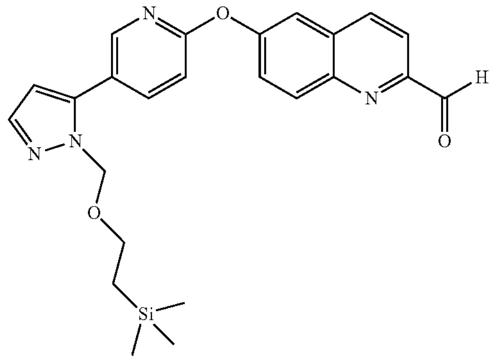

D

+

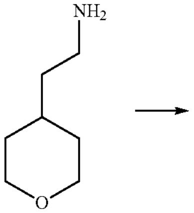

214-1

-continued

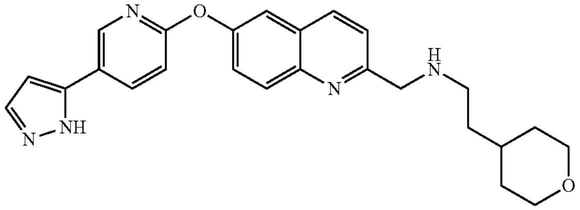

214

A solution of D (98 mg, 0.22 mmol) in 1,2-dichloroethane (2.0 mL) is added to 214-1 (28 mg, 0.22 mmol). The mixture is shaken overnight. A solution of sodium triacetoxyborohydride (93 mg, 0.44 mmol) in N,N-dimethylacetamide (1.0 mL) is added and the resulting reaction mixture is shaken for 4 hours. Next, the mixture is concentrated and purified by reverse phase HPLC. The desired fractions are pooled and concentrated. The residue is treated with water (1.0 mL) and 1N HCl in Dioxane (58 mL), shaken at 80° C. for 2 h, and concentrated. The resultant residue is purified by reverse phase HPLC to give the title product (214).

The following examples are synthesized from Intermediate D and the appropriate amine reagents according to the procedure described for the synthesis of Example 214.

| Ex. | Compound Name | Amine Reagent |
|---|---|---|
| 174 | 3-Methyl-1-{6-[5-(2H-pyrazol-3-yl)-pyridin-2-yloxy]-quinolin-2-ylmethyl}-azetidin-3-ol | 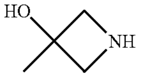 |
| 178 | 2-[(1S,4S)-1-(2-Oxa-5-aza-bicyclo[2.2.1]hept-5-yl)methyl]-6-[5-(2H-pyrazol-3-yl)-pyridin-2-yloxy]-quinoline | 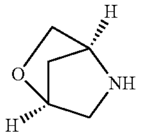 |
| 190 | 3-(1-{6-[5-(2H-Pyrazol-3-yl)-pyridin-2-yloxy]-quinolin-2-ylmethyl}-piperidin-4-yl)-[1,3]oxazinan-2-one | 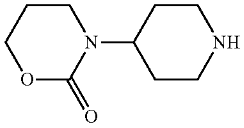 [SMILES: O=C1OCCCN1C1CCNCC1] |
| 204 | 1-{6-[5-(2H-Pyrazol-3-yl)-pyridin-2-yloxy]-quinolin-2-ylmethyl}-piperidin-4-ol | 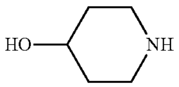 |
| 205 | 2-((R)-3-Methoxy-pyrrolidin-1-ylmethyl)-6-[5-(2H-pyrazol-3-yl)-pyridin-2-yloxy]-quinoline | 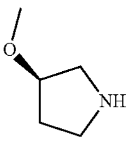 |

-continued

| Ex. | Compound Name | Amine Reagent |
|---|---|---|
| 208 | 2-((S)-3-Methoxy-pyrrolidin-1-ylmethyl)-6-[5-(2H-pyrazol-3-yl)-pyridin-2-yloxy]-quinoline | 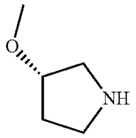 |
| 209 | 1'-{6-[5-(2H-Pyrazol-3-yl)-pyridin-2-yloxy]-quinolin-2-ylmethyl}-[1,4']bipiperidinyl-2-one | 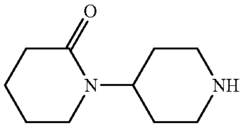 [SMILES: O=C1CCCCN1C1CCNCC1] |
| 210 | (S)-1-{6-[5-(2H-Pyrazol-3-yl)-pyridin-2-yloxy]-quinolin-2-ylmethyl}-pyrrolidin-3-ol | 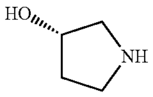 |
| 211 | 4-(1-{6-[5-(2H-Pyrazol-3-yl)-pyridin-2-yloxy]-quinolin-2-ylmethyl}-piperidin-4-yl)-morpholin-3-one | 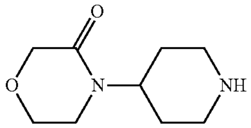 [SMILES: O=C1COCCN1C1CCNCC1] |
| 212 | 2-(4-Methoxy-piperidin-1-ylmethyl)-6-[5-(2H-pyrazol-3-yl)-pyridin-2-yloxy]-quinoline | 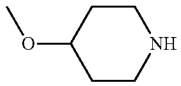 |
| 213 | (1R,5S)-3-{6-[5-(2H-Pyrazol-3-yl)-pyridin-2-yloxy]-quinolin-2-ylmethyl}-1,2,3,4,5,6-hexahydro-1,5-methano-pyrido[1,2-a][1,5]diazocin-8-one | 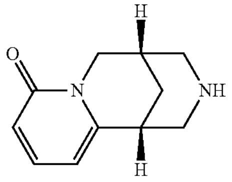 [SMILES: O=c1cccc2n1C[C@@H]1CNC[C@H]2C1] |
| 215 | 6-[5-(2H-Pyrazol-3-yl)-pyridin-2-yloxy]-2-[4-(pyridin-2-yloxy)-piperidin-1-ylmethyl]-quinoline | 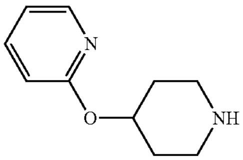 [SMILES: c1ccc(OC2CCNCC2)nc1] |

Example 216

Preparation of 1-{1-[4-(2H-Pyrazol-3-yl)-benzyl]-1H-indol-5-ylmethyl}-azetidin-3-ol (216)

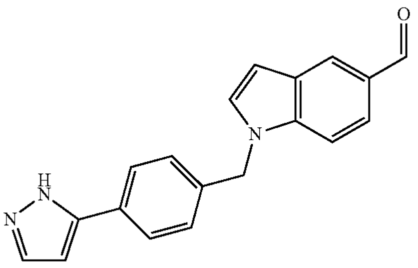

X

+

-continued

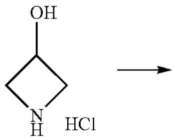

216-1

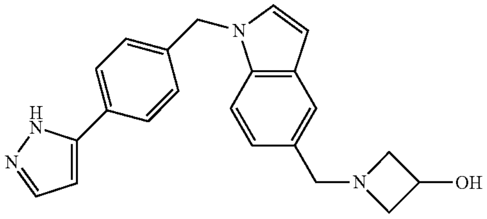

216

A solution of X (30 mg, 0.1 mmol) in MeOH (1.5 mL) is added to 216-1 (13 mg, 0.12 mmol). Next, a solution of sodium cyanoborohydride (14 mg, 0.22 mmol) in methanol (0.5 mL) and acetic acid (5 μL) are added, and the resultant mixture is shaken at 40° C. over the weekend. The reaction mixture is concentrated and purified by reverse phase HPLC to give the title product (216).

Example 219

Preparation of N-(1-[6-[4-(2H-Pyrazol-3-yl)-phenoxy]-2,3-dihydro-benzofuran-2-ylmethyl]-piperidin-4-yl)-acetamide (219)

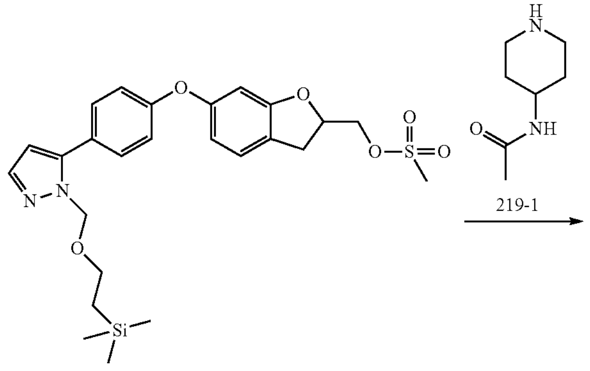

137-1

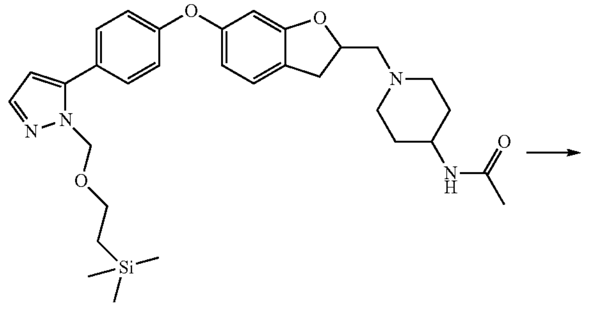

319-2

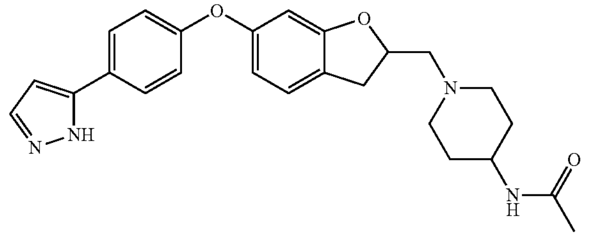

219

A mixture of 137-1 (83.0 mg, 0.161 mmol), $K_2CO_3$ (44.3 mg, 0.321 mmol) and 219-1 (114 mg, 0.803 mmol) in DMF (2 mL) is heated at 80° C. for 18 h followed by 4 h at 100° C. The cooled mixture is diluted with EtOAc, washed with aqueous $Na_2CO_3$, water and brine. The organic layer is dried over $MgSO_4$, filtered and concentrated to give 219-2.

To a solution of 219-2 (87.0 mg, 0.155 mmol) in DCM (1 mL) is added HCl in dioxane (4 M, 2 ml). The mixture is stirred at ambient temperature for 16 h, concentrated, dissolved in MeOH, and neutralized with $NH_3$ (7M in methanol). The mixture is concentrated, and the resultant residue is purified on $SiO_2$ (2-20% MeOH containing 5% $NH_4OH$/DCM) to give the title product (219).

The following example is synthesized from 137-1 and the appropriate amine reagent according to the procedure described for the synthesis of Example 219.

| Example | Compound Name | Amine Reagent |
|---|---|---|
| 218 | 5-[4-(2-Pyrrolidin-1-ylmethyl-2,3-dihydro-benzofuran-6-yloxy)-phenyl]-1H-pyrazole | 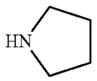 |

Example 220

Preparation of 6-[5-(2H-Pyrazol-3-yl)-pyrimidin-2-yloxy]-2-pyrrolidin-1-ylmethyl-quinoline (220)

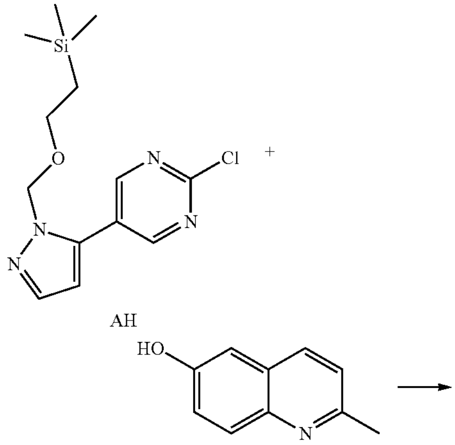

D-2

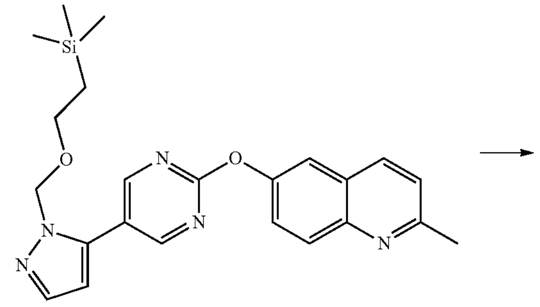

220-1

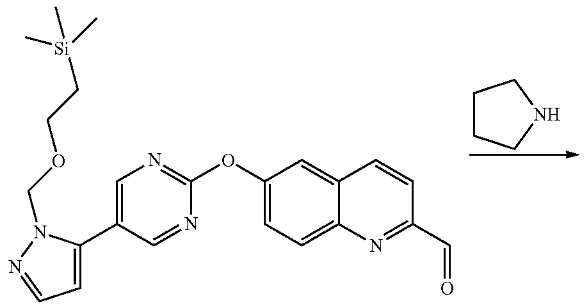

220-2

-continued

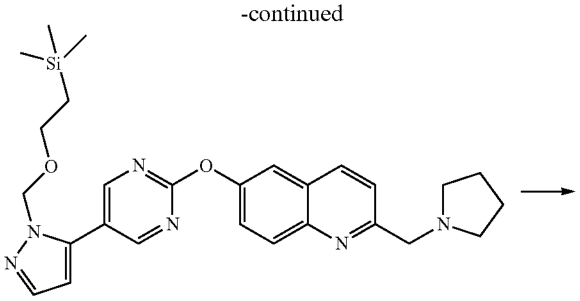

220-3

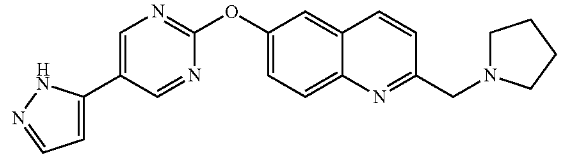

220

A mixture of AH (1.50 g, 4.82 mmol), D-2 (768 mg, 4.82 mmol) and $K_2CO_3$ (1.33 g, 9.65 mmol) in DMSO (7.5 mL) is purged with $N_2$ for 5 minutes and heated for 2 h at 130°. The mixture is diluted with $H_2O$, extracted thrice with EtOAc. The combined organic layers are washed with thrice with $H_2O$, dried over $Na_2SO_4$, filtered and concentrated to give 220-1.

A solution of 220-1 (2.00 g, 4.61 mmol) and selenium dioxide (614 mg, 5.54 mmol) in dioxane (20 mL) is heated to reflux for 4 h. The mixture is cooled to ambient temperature, filtered through a pad of Diatomaceous earth, and concentrated. The residue is dissolved in EtOH (12 mL), treated with an aqueous solution of sodium metabisulfite (4 g in 12 mL of $H_2O$) and stirred overnight. The mixture is filtered, and the solids are washed with EtOAc. The filtrate is concentrated, dissolved in $H_2O$, and washed thrice with ether. The aqueous phase is treated with aqueous $Na_2CO_3$, extracted four times with EtOAc, washed with $H_2O$, dried over $Na_2SO_4$, filtered and concentrated to give 220-2.

A solution of 220-2 (50.0 mg, 0.112 mmol), pyrrolidine (27.7 μL, 0.335 mmol), AcOH (25 μL) and sodium cyanoborohydride (14.0 mg, 0.223 mmol) in DCM (1 mL) is stirred overnight. The mixture is purified by reverse phase HPLC eluting with 10-90% MeCN in water (+0.1% TFA) over 20 minutes. The desired fractions are pooled and concentrated to give 220-3 as TFA salt.

A solution of 220-5 (25.4 mg) in a mixture of 50% TFA in DCM (0.5 mL) is stirred for 2 hr. The mixture is concentrated and purified by reverse phase HPLC eluting with 10-60% MeCN in water (+0.1% TFA) over 20 minutes. The desired fractions are pooled and concentrated; the residue dissolved in MeOH and passed through a PS—$HCO_3$ cartridge to give the title product (220).

Example 221

Preparation of 1-(4-{6-[5-(2H-Pyrazol-3-yl)-pyridin-2-yloxy]-1H-indol-2-ylmethyl}-piperazin-1-yl)-ethanone (221)

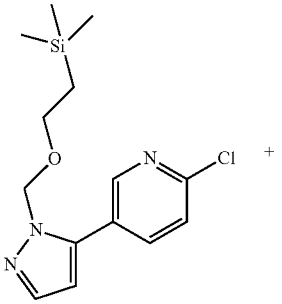

A

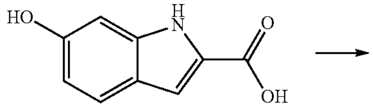

221-1

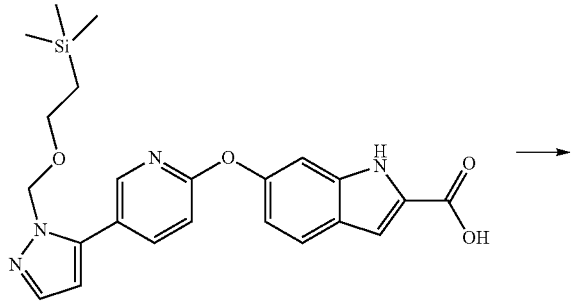

221-2

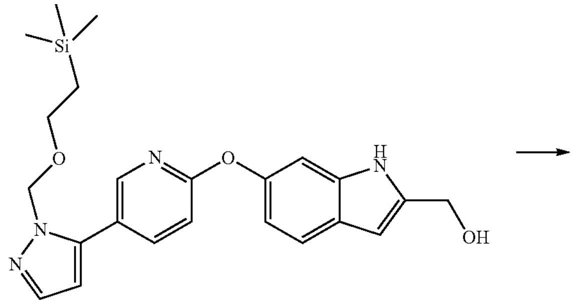

221-3

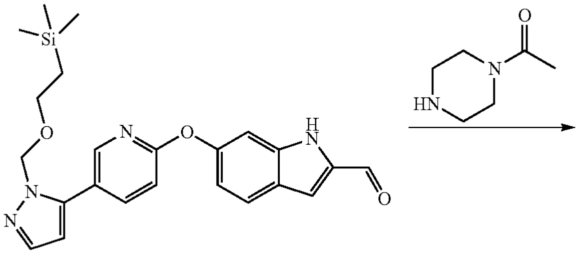

221-4

-continued

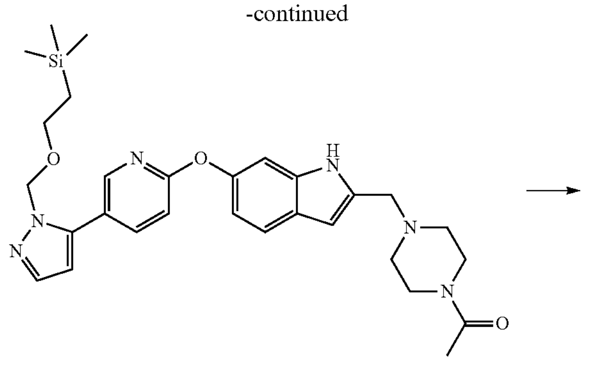

221-5

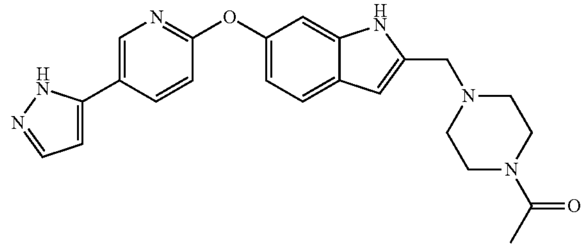

221

A solution of A (500 mg, 1.61 mmol) and 221-1 (286 mg, 1.61 mmol) and $K_2CO_3$ (446 g, 3.23 mmol) in DMSO (4 mL) is heated for 2 h at 140° C. and 10 h at 150° C. The reaction is poured into $H_2O$, extracted thrice with EtOAc, washed thrice with saturated aqueous $NaHCO_3$, dried over $Na_2SO_4$, filtered and concentrated to give 221-2. The aqueous phase is acidified with concentrated HCl and extracted four times with EtOAc, washed with $H_2O$, dried over $Na_2SO_4$, filtered and concentrated to provide additional 221-2.

Lithium aluminum hydride (67.4 mg, 1.78 mmol) is added to a solution of 221-2 (400 mg, 68%) in dry THF (8.0 mL), and the resultant reaction is stirred for 1 h at ambient temperature under Ar. The reaction is diluted with THF (8.0 mL), and heated for 2 h at 60° C. Next, additional LAH is added (twice, each time 67.4 mg, 1.78 mmol) and the mixture is stirred at ambient temperature (2 h and 96 h, respectively). The mixture is quenched with EtOAc followed by MeOH and 2N NaOH, and filtered through Diatomaceous earth eluting with EtOAc. The filtrate is washed successively with 2N NaOH and saturated aqueous $NH_4Cl$, dried over $Na_2SO_4$, filtered and concentrated. The residue is purified on a $SiO_2$ Prep plate (4% MeOH in DCM) to give 221-3.

A solution of 221-3 (101 mg, 0.231 mmol) and manganese (IV) oxide (201 mg, 2.31 mmol) in EtOH (2 mL) is stirred overnight. The mixture is filtered through Diatomaceous earth, and concentrated in vacuo. The residue is purified on a $SiO_2$ Prep plate (4% MeOH in DCM) to give 221-4.

A mixture of 221-4 (70.0 mg, 0.161 mmol), 1-acetylpiperazine (61.9 mg, 0.483 mmol), AcOH (50 μL) and sodium cyanoborohydride (20.2 mg, 0.322 mmol) in 20% MeOH in DCM (1 mL) is stirred for 90 min. The reaction is concentrated, treated with aqueous $Na_2CO_3$, and extracted thrice with EtOAc. The combined organic layers are washed with aqueous $Na_2CO_3$ and $H_2O$, dried over $Na_2SO_4$, filtered and concentrated. The residue is purified on a $SiO_2$ Prep plate (7% MeOH in DCM) to give 221-5.

A solution of 221-5 (66.0 mg, 0.121 mmol) and pyridinium p-toluenesulfonate (152 mg, 0.605 mmol) in EtOH (3 mL) is heated in a microwaved at 130° C. for 15 min. The mixture is concentrated, and treated with $H_2O$, and extracted with EtOAc (4 times). The aqueous phase is made basic with aqueous $Na_2CO_3$, and extracted with EtOAc (4 times). The combined organic layers are washed with aqueous $Na_2CO_3$, dried over $Na_2SO_4$, filtered and concentrated. The residue is purified on $SiO_2$ Prep plates (10% MeOH in DCM) to give the title product (221).

Example 222

Preparation of 1-(4-{5-[5-(2H-Pyrazol-3-yl)-pyridin-2-yloxy]-1H-indol-2-ylmethyl}-piperazin-1-yl)-ethanone (222)

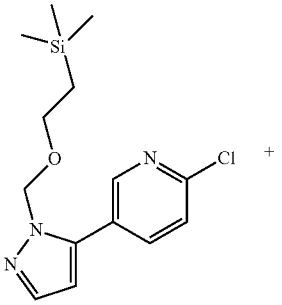

A

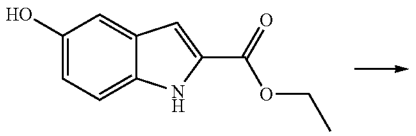

222-1

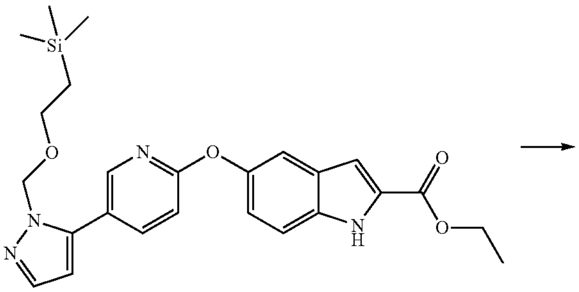

222-2

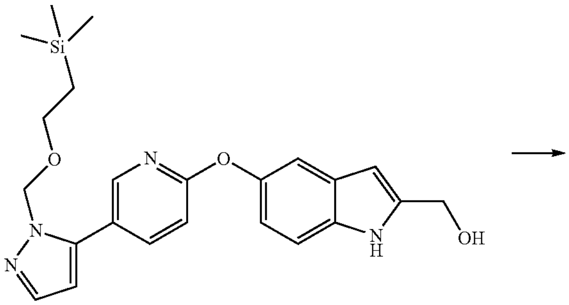

222-3

-continued

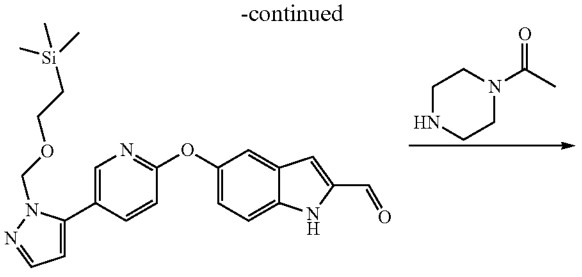

222-4

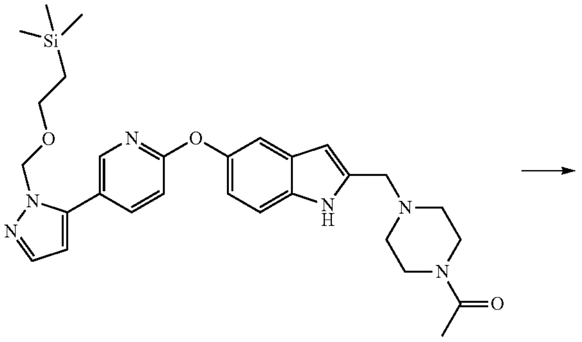

222-5

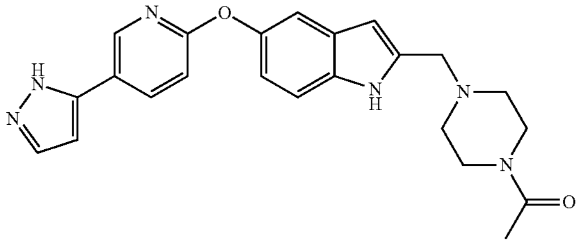

221

A mixture of A (500 mg, 1.61 mmol), 222-1 (331 mg, 1.61 mmol), $Cs(CO_3)_2$ (1.58 g, 4.84 mmol) and CuI (307 mg, 1.61 mmol) in DMSO (4 mL) is sparged with $N_2$ and heated at 150° C. for 3 h. The reaction is diluted with a mixture of EtOAc and $H_2O$, treated with activated charcoal, and filtered through Diatomaceous earth. Phases are separated and the organic layer is washed $H_2O$ (5 times), dried over $Na_2SO_4$, filtered and concentrated. The residue is purified on a $SiO_2$ Prep plate (3% MeOH in DCM) to give 222-2.

Lithium aluminum hydride (88.3 mg, 0.233 mmol) is added to a solution of 222-2 (556.8 mg, 1.16 mmol) in dry THF (10 mL) at 0° C. The mixture is stirred at 0° C. for 5 min, warmed to ambient temperature and stirred for 1 h. The reaction is quenched with EtOAc, followed by MeOH and 2N NaOH. The resultant mixture is filtered through a pad of Diatomaceous earth eluting with EtOAc. The filtrate is washed successively with 2N NaOH, water, saturated aqueous $NH_4Cl$, dried over $Na_2SO_4$, filtered and concentrated. The residue is purified on a $SiO_2$ Prep plate (4% MeOH in DCM) to give 222-3.

A solution of 222-3 (246 mg, 0.563 mmol) and manganese (IV) oxide (489 mg, 5.63 mmol) in EtOH (5 mL) is stirred overnight, filtered through a pad of Diatomaceous earth, and concentrated. The residue is purified on a $SiO_2$ Prep plate (4% MeOH in DCM) to give 222-4.

A solution of 222-4 (70 mg, 0.161 mmol), 1-acetylpiperazine (61.9 mg, 0.483 mmol), AcOH (50 μL) and sodium cyanoborohydride (20.2 mg, 0.322 mmol) in 20% MeOH in DCM (1 mL) is stirred for 2 h at ambient temperature. The reaction is concentrated, treated with aqueous $Na_2CO_3$, and extracted thrice with EtOAc. The combined organic layers are washed with aqueous $Na_2CO_3$ and $H_2O$, dried over $Na_2SO_4$, filtered and concentrated. The residue is purified on a $SiO_2$ Prep plate (7% MeOH in DCM) to give 222-5.

A solution of 222-5 (65.0 mg, 0.119 mmol) and pyridinium p-toluenesulfonate (89.7 mg, 0.357 mmol) in EtOH (3 mL) is heated in a microwave at 130° C. for 25 min. The reaction is diluted with EtOAc, washed twice with aqueous $Na_2CO_3$ and $H_2O$, dried over $Na_2SO_4$, filtered and concentrated. The residue is purified on a $SiO_2$ Prep plate (10% MeOH in DCM) to give the title product (222).

Example 223

Preparation of 1-(4-{6-[5-(2H-Pyrazol-3-yl)-pyridin-2-yloxy]-isoquinolin-3-ylmethyl}-piperazin-1-yl)-ethanone (223)

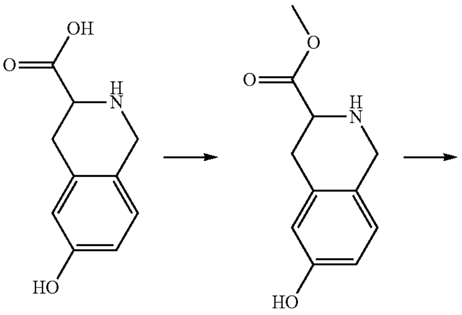

223-1 223-2

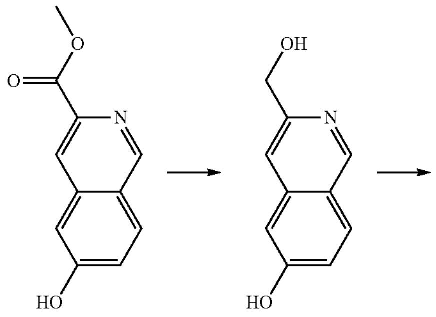

223-3 223-4

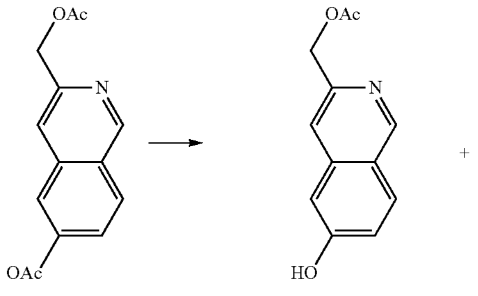

223-5 223-6

-continued

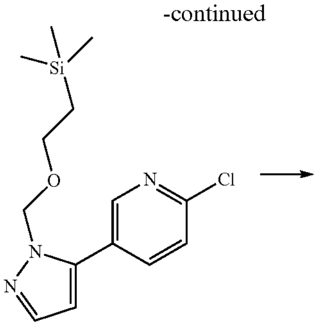

A

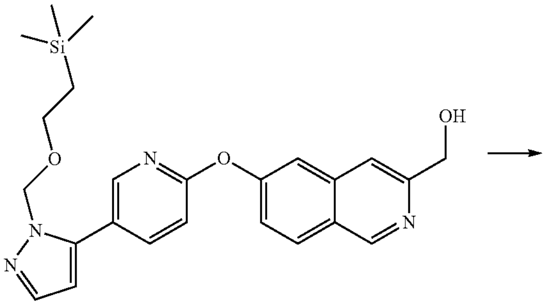

223-7

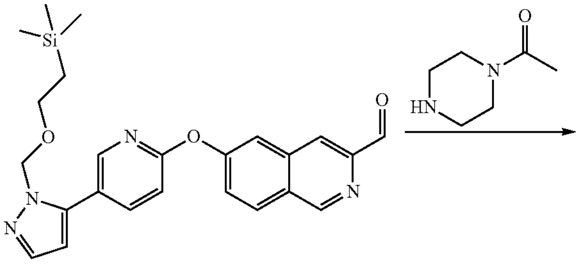

223-8

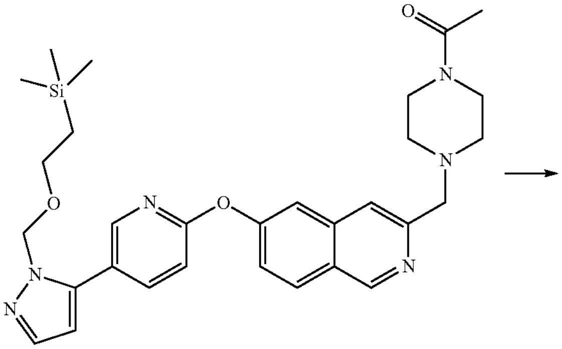

223-9

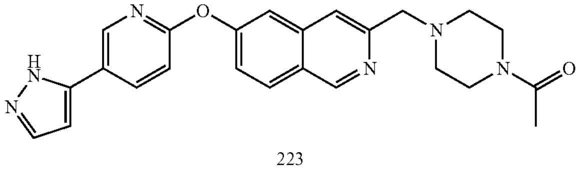

223

To an ice-cold suspension of 223-1 (1.10 g, 5.21 mmol) in MeOH (10 mL) is added con. $H_2SO_4$ (0.5 mL), and the solution is stirred overnight. The reaction is poured into ice-water, neutralized with aqueous NaOH (8.9 mL, 2N), and extracted with 50% n-butanol in EtOAc (4 times). The combined organic layers are dried over $Na_2SO_4$, filtered and concentrated to give 223-2.

A solution of 223-2 (380 mg, 1.83 mmol) and DDQ (500 mg, 2.20 mmol) in a 50% MeOH/DCM (15 mL) is stirred at ambient temperature overnight. Next, more DDQ (200 mg, 0.880 mmol) is added and the stirring is continued overnight. The reaction is chromatographed on $SiO_2$ (3-5% MeOH in DCM). The residue is dissolved in EtOAc, aged for 72 h, filtered, and washed with EtOAc. The filtrate is extracted with saturated aqueous $NaHCO_3$ (once) and $H_2O$ (4 times). The combined aqueous layers are neutralized with saturated aqueous $NH_4Cl$, and extracted with EtOAc (4 times). The organic layers are combined and washed with $H_2O$ (4 times). Next, the filter cake is dissolved in saturated aqueous $NaHCO_3$, and extracted with EtOAc (4 times), neutralized with saturated aqueous $NH_4Cl$, and extracted with EtOAc (4 times). The EtOAc phases are washed with $H_2O$ (4 times), combined with the EtOAc layers from the filtrate extraction, dried over $Na_2SO_4$, to filtered and concentrated to give 223-3.

A suspension of sodium borohydride (114 mg, 3.00 mmol) and calcium chloride (182 mg, 1.64 mmol) in 50% THF/EtOH (5 mL) is stirred at −10° C. for 20 min A solution of 223-3 (111 mg, 0.546 mmol) in 50% THF/EtOH (2 mL) is added and the mixture is stirred for 1 h. The reaction is quenched with saturated aqueous $NH_4Cl$, and extracted with EtOAc (2 mL). The combined organic layers are washed with $H_2O$ (2 times). The aqueous layer is re-extracted thrice with 50% n-butanol/EtOAc. The combined organic layers are concentrated and purified on a $SiO_2$ Prep plate (15% MeOH in DCM) to give 223-4.

Acetyl chloride (55.6 μL, 0.779 mmol) is added to an ice-cold suspension of 223-4 (62.0 mg, 0.354 mmol) and DIPEA (136 μL, 0.779 mmol) in DCM (1 mL). After 1.5 h at ambient temperature, more acetyl chloride (55.6 μL, 0.779 mmol) and DIPEA (136 μL, 0.779 mmol) are added. After 1 h, the mixture is concentrated, diluted with EtOAc, washed water and saturated aqueous $NH_4Cl$ (3 times), dried over $Na_2SO_4$, filtered and concentrated to give 223-5.

A mixture of 223-5 (83.4 mg, 0.322 mmol) and ammonium acetate (496 mg, 6.43 mmol) in 20% H2O/MeOH (0.3 mL) is stirred overnight. The reaction is diluted with water, extracted with EtOAc (4 times), washed with water, dried over $Na_2SO_4$, filtered and concentrated to give 223-6.

A mixture of A (103 mg, 0.332 mmol), 223-6 (60.0 mg, 0.276 mmol) and $K_2CO_3$ (91.6 g, 0.663 mmol) in DMSO (0.5 mL) is sparged with $N_2$ and heated at 160° C. for 2 h and at ambient temperature overnight. Methanol (1 mL) is added and the reaction is stirred for 1 h, poured into $H_2O$, extracted 4 times with EtOAc, washed with H2O (5 times), dried over $Na_2SO_4$, filtered and concentrated. The residue is purified on a $SiO_2$ Prep plate (8% MeOH in DCM) to give 223-7.

A mixture of 223-7 (97 mg, 0.216 mmol) and manganese (IV) oxide (376 mg, 4.32 mmol) in EtOH (2 mL) is stirred overnight, filtered through a pad of Diatomaceous earth eluting MeOH, and concentrated. The residue is purified on a $SiO_2$ Prep plate (5% MeOH in DCM) to give 223-8.

A solution of 223-8 (26.8 mg, 0.060 mmol), 1-acetylpiperazine (23.1 mg, 0.180 mmol), AcOH (25 μL) and sodium cyanoborohydride (7.5 mg, 0.12 mmol) in DCM (1 mL) is stirred for 4 h. The reaction is concentrated, treated with aqueous $Na_2CO_3$, and extracted thrice with EtOAc. The combined organic layers are washed with aqueous $Na_2CO_3$ and water, dried over $Na_2SO_4$, filtered, and concentrated. The residue is purified on a $SiO_2$ Prep plate (1% $NH_4OH$+10% MeOH in DCM) to give 223-9.

A solution of 223-9 (28 mg, 0.050 mmol) and pyridinium p-toluenesulfonate (37.8 mg, 0.150 mmol) in EtOH (2 mL) is heated at 130° C. in a microwave for 20 min. The reaction is diluted with EtOAc, washed with aqueous $Na_2CO_3$ (2 times)

and water, dried over $Na_2SO_4$, filtered and concentrated. The residue is purified on a $SiO_2$ Prep plate (1% $NH_4OH$+15% MeOH in DCM) to give the title product (223).

Example 224

Preparation of 1-[4-(2-{5-[5-(2H-Pyrazol-3-yl)-pyridin-2-yloxy]-indol-1-yl}-ethyl)-piperazin-1-yl]-ethanone (224)

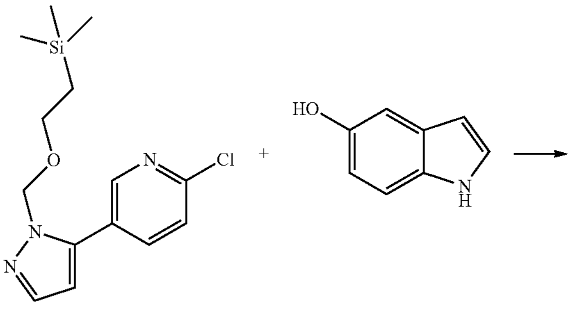

A 224-1

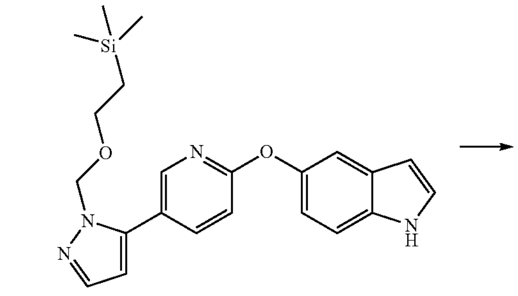

224-2

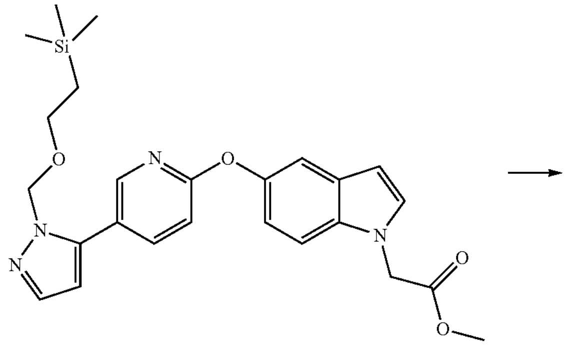

222-3

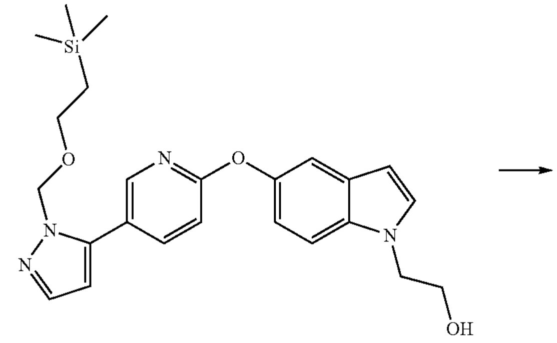

222-4

-continued

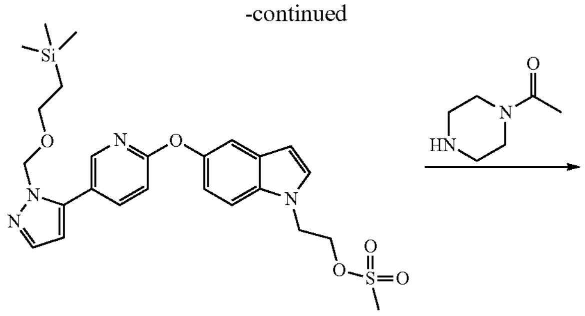

222-5

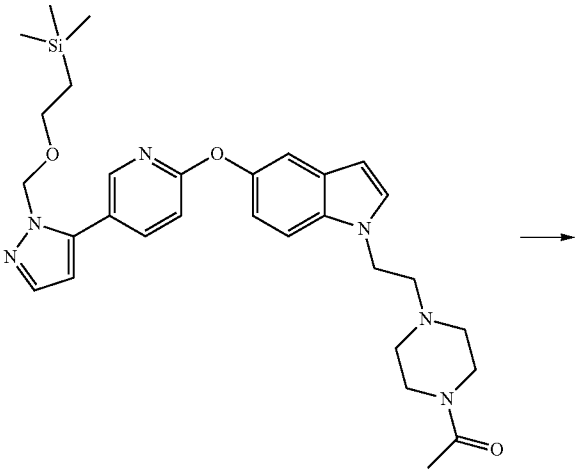

224-6

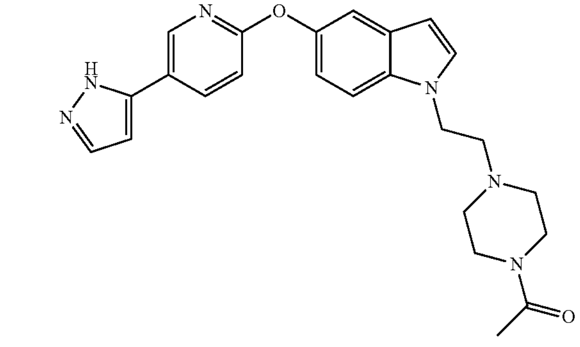

224

A mixture of A (500 mg, 1.61 mmol), 224-1 (215 mg, 1.61 mmol) and $K_2CO_3$ (446 mg, 3.23 mmol) in DMSO (4 mL) is sparged with $N_2$, and heated at 140° C. for 2 h. The reaction is poured into a mixture of $H_2O$ and EtOAc, filtered through a pad of Diatomaceous earth eluting with EtOAc. The aqueous phase is extracted with EtOAc (3 times), washed with H2O (5 times), dried over $Na_2SO_4$, filtered, and concentrated. The residue is purified on a $SiO_2$ Prep plate (3% MeOH in DCM) to give 224-2.

Methyl bromoacetate (77.9 μL, 0.819 mmol) is added to a suspension of 224-2 (256 mg, 0.630 mmol) and $K_2CO_3$ (174 mg, 1.26 mmol) in DMF (2 mL). After stiffing overnight, more methyl bromoacetate (77.9 μL, 0.819 mmol) is added and the mixture is stirred for 4 days. The reaction is poured into water, and extracted with EtOAc (4 times). The combined organic layers are washed with water (4 times), dried over $Na_2SO_4$, filtered, and concentrated. The residue is purified on a $SiO_2$ Prep plate (1% MeOH in DCM) to give 224-3.

Lithium aluminum hydride (31.3 mg, 0.824 mmol) is added to a solution of 224-3 (197 mg, 0.412 mmol) in dry THF (4.0 mL). The reaction is stirred for 1 h at ambient temperature, and quenched with EtOAc followed by MeOH and 2N NaOH. The mixture is filtered through a pad of Diatomaceous earth eluting with EtOAc. The filtrate is washed successively with 2N NaOH and aqueous $NH_4Cl$, dried over $Na_2SO_4$, filtered, and concentrated. The residue is purified on a $SiO_2$ Prep plate (4% MeOH in DCM) to give 224-4.

Methanesulfonyl chloride (31.9 μl, 0.413 mmol) is added to a solution of 224-4 (124 mg, 0.275 mmol) and DIPEA (95.8 μl, 0.550 mmol) in DCM (3 mL). After stirring overnight, more DIPEA (192 μl, 1.10 mmol) and methanesulfonyl chloride (63.8 μl, 0.826 mmol) are added and the reaction is stirred for 2.5 h. The mixture is concentrated, dissolved in EtOAc, washed aqueous $Na_2CO_3$ and water (3 times), dried over $Na_2SO_4$, filtered, and concentrated to give 224-5.

A solution of 224-5 (88 mg, 0.138 mmol), 1-acetylpiperazine (88.4 mg, 0.690 mmol), sodium iodide (41.4 mg, 0.276 mmol) and potassium carbonate (38.1 mg, 0.276 mmol) in DMF (0.5 mL) is heated at 60° C. overnight. The reaction is poured into $H_2O$, and extracted EtOAc (4 times). The combined organic layers are washed with water (4 times), dried over $Na_2SO_4$, filtered, and concentrated. The residue is purified on a $SiO_2$ Prep plate (7% MeOH in DCM) to give 224-6.

A solution of 224-6 (47.5 mg, 0.0847 mmol) and pyridinium p-toluenesulfonate (64.6 mg, 0.257 mmol) in EtOH (3 mL) is heated at 130° C. in a microwave for 20 min. The reaction is diluted with EtOAc, washed with aqueous $Na_2CO_3$ (2 times) and $H_2O$, dried over $Na_2SO_4$, filtered, and concentrated. The residue is purified on a $SiO_2$ Prep plate (10% MeOH in DCM) to give the title product (224).

Example 231

Preparation of 1-(4-{6-[5-(1H-Pyrazol-3-yl)-pyridin-2-yloxy]-quinolin-2-ylmethyl}-piperazin-1-yl)-ethanone (231)

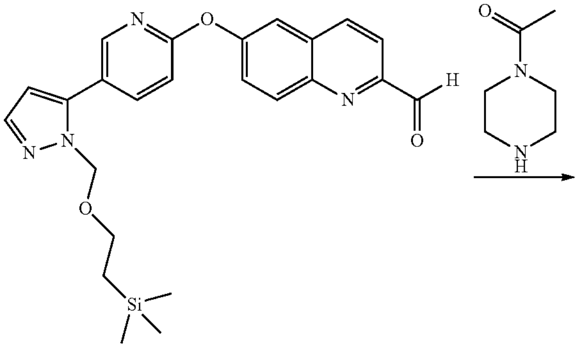

D

-continued

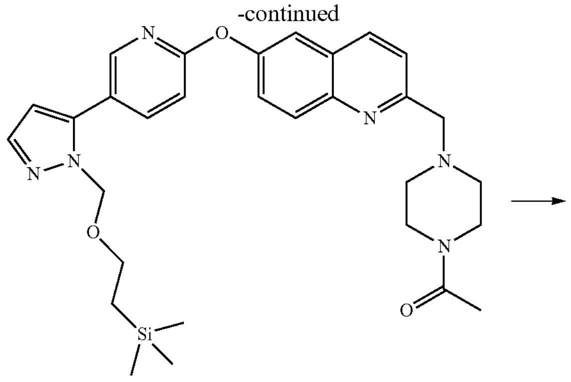

231-1

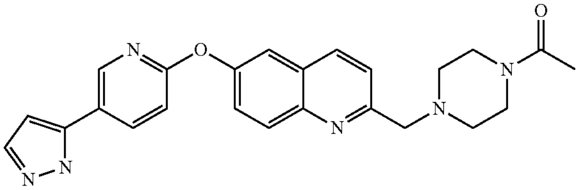

231-1

To a solution D (0.100 g, 0.224 mmol) in DMF (5 ml) is added N-acetylpiperazine (29.0 mg, 0.224 mmol), 1 drop of acetic acid, and sodium borohydride (43.0 g, 1.87 mmol). The reaction is stirred overnight, and the crude mixture is purified by reverse phase HPLC eluting with 10-60% MeCN in water (+0.1% TFA) over 20 minutes. The desired fractions are pooled and concentrated to give 231-1 as a TFA salt.

To a solution of 231-1 (50.0 mg, 0.116 mmol) in MeOH (5 mL) is added HCl in Dioxane (4 M, 100 μL). The reaction is stirred for 2 h and concentrated. The crude is purified by reverse phase HPLC eluting with 10-90% MeCN in water (+0.1% TFA) over 20 minutes. The desired fractions are pooled and concentrated. The residue is dissolved in MeOH and passed through a PS—$HCO_3$ cartridge to give the title product (231).

The following examples are synthesized from the appropriate amine reagents and intermediate D according to the procedure described for the synthesis of Example 231.

| Ex. | Compound Name | Amine Reagent |
|---|---|---|
| 236 | 2-Methoxy-N-(1-{6-[5-(1H-pyrazol-3-yl)-pyridin-2-yloxy]-quinolin-2-ylmethyl}-piperidin-4-yl)-acetamide | 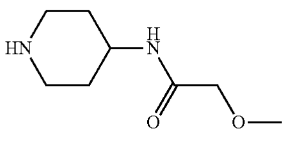 |

-continued

| Ex. | Compound Name | Amine Reagent |
|---|---|---|
| 237 | N-(1-{6-[5-(1H-Pyrazol-3-yl)-pyridin-2-yloxy]-quinolin-2-ylmethyl}-piperidin-4-yl)-acetamide | 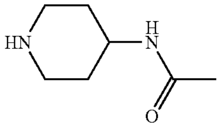 |
| 238 | N-((endo)-8-{6-[5-(1H-Pyrazol-3-yl)-pyridin-2-yloxy]-quinolin-2-ylmethyl}-8-aza-bicyclo[3.2.1]oct-3-yl)-acetamide | 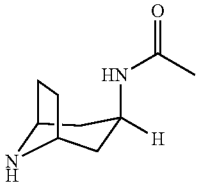 |
| 239 | N-((exo)-8-{6-[5-(1H-Pyrazol-3-yl)-pyridin-2-yloxy]-quinolin-2-ylmethyl}-8-aza-bicyclo[3.2.1]oct-3-yl)-acetamide | 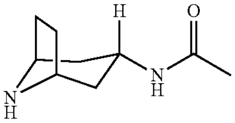 |
| 240 | 1-((S)-5-{6-[5-(1H-Pyrazol-3-yl)-pyridin-2-yloxy]-quinolin-2-ylmethyl}-2,5-diaza-bicyclo[2.2.1]hept-2-yl)-ethanone | 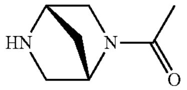 |
| 242 | 2-(1,1-Dioxo-1-λ-6-thiomorpholin-4-ylmethyl)-6-[5-(1H-pyrazol-3-yl)-pyridin-2-yloxy]-quinoline | 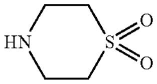 |

Example 232

Preparation of 2-(2-Morpholin-4-yl-ethoxy)-6-[4-(1H-pyrazol-3-yl)-phenoxy]-benzothiazole (232)

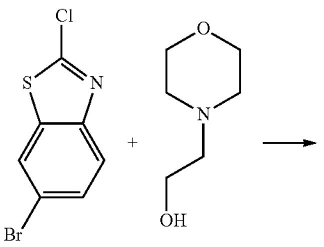

232-1 232-2

-continued

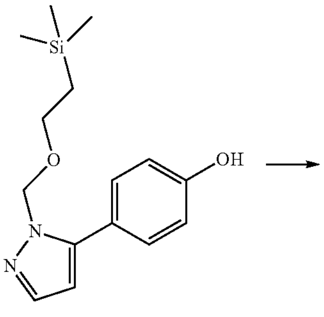

B

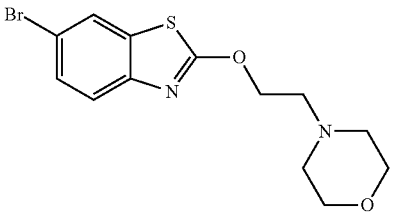

232-3

+

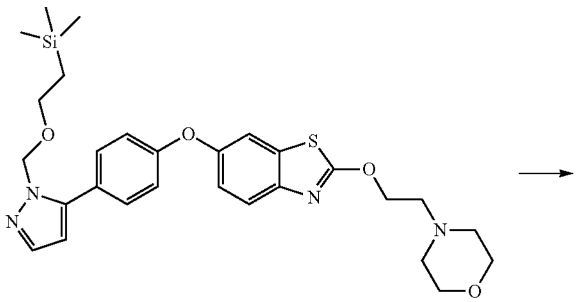

232-4

-continued

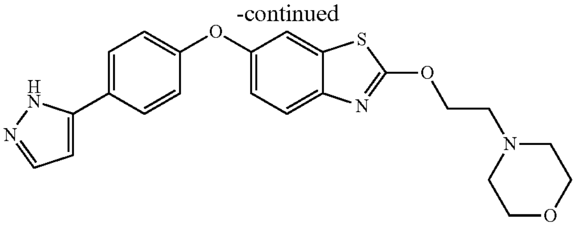

232

A mixture of 232-1 (0.500 g, 2.01 mmol), 232-2 (0.230 g, 2.00 mmol) and potassium tert-butoxide (0.384 g, 4.00 mmol) in DMF (2 mL) is heated at 100° C. for 10 min in a microwave. The crude mixture is filtered and purified by reverse phase HPLC eluting with 10-90% MeCN in water (+0.1% TFA) over 20 minutes. The desired fractions are pooled and concentrated to give 232-3.

A mixture of B (0.22 g, 0.064 mmol) and 232-3 (0.022 g, 0.064 mmol) in DMSO (1 mL) is sparged with Ar. Next, CuI (2.0 mg, 0.013 mmol), picolinic acid (3.0 mg, 0.026 mmol), and potassium phosphate (26.0 g, 0.124 mmol) are added, and the mixture is purged with Ar and heated at 140° C. for 78 h. The crude mixture is filtered and purified by reverse phase HPLC eluting with 10-90% MeCN in water (+0.1% TFA) over 20 minutes. The desired fractions are pooled and concentrated to give 232-4.

The title product 232 is synthesized from 232-4 according to the procedure described for the synthesis of Example 231 from 231-1.

Example 234

Preparation of 3,3-Dimethyl-1-{5-[4-(2H-pyrazol-3-yl)-phenoxy]-1H-benzoimidazol-2-ylmethyl}-pyrrolidin-2-one (234)

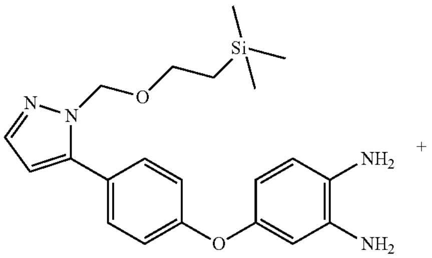

L

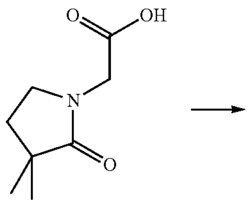

AJ

-continued

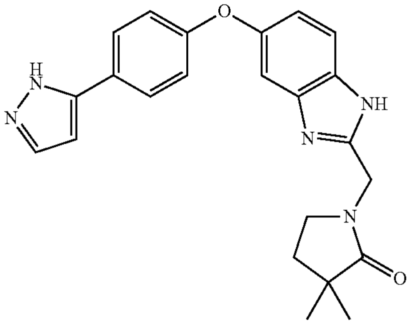

234

To a solution of intermediate AJ (0.130 g, 0.759 mmol) in DMA (1 mL) is added PyBrop (0.653 g, 1.40 mmol) and DIPEA (99 μL, 0.567 mmol). The mixture is stirred at ambient temperature for 1 h, intermediate L (0.300 g, 0.757 mmol) is added, and the resultant mixture is stirred at 45° C. overnight. The crude mixture is filtered and purified by reverse phase HPLC eluting with 10-90% MeCN in water (+0.1% TFA) over 20 minutes. The desired fractions are pooled and concentrated. To the resultant residue is added acetic acid (2 mL) and the mixture is heated for 18 hours, and concentrated. To the residue is added DCM (3 ml) and HCl/Dioxane (4 N, 1 mL). The reaction is stirred overnight and concentrated. The crude is purified by reverse phase HPLC eluting with 10-90% MeCN in water (+0.1% TFA) over 20 minutes. The desired fractions are pooled and concentrated to give the title product (234).

The following examples are synthesized using intermediate L and the appropriate carboxylic acid reagent according to the procedure described for the synthesis of Example (234).

| Ex. | Compound Name | Acid Reagent |
|---|---|---|
| 233 | Cyclopropanecarboxylic acid methyl-{5-[4-(2H-pyrazol-3-yl)-phenoxy]-1H-benzoimidazol-2-ylmethyl}-amide | 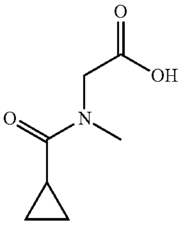 |
| 235 | Cyclopropanecarboxylic acid ethyl-{5-[4-(2H-pyrazol-3-yl)-phenoxy}-1H-benzoimidazol-2-ylmethyl}-amide | 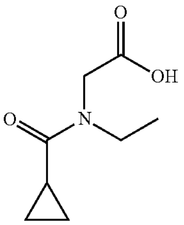 |

Example 241

Preparation of 1-(4-{6-[4-(2H-Pyrazol-3-yl)-phenoxy]-quinoxalin-2-ylmethyl}-piperazin-1-yl)-ethanone (241)

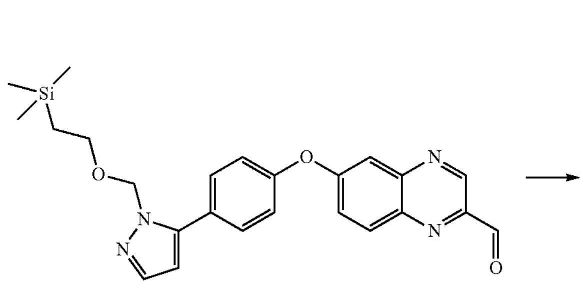

AI

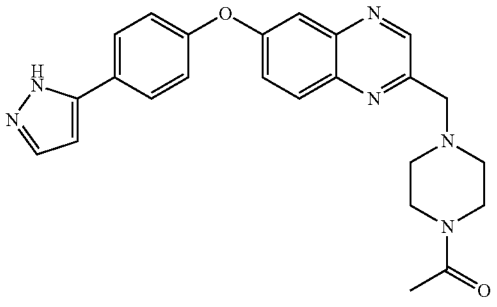

241

The title product (241) is synthesized from intermediate AI according to the procedure described for the synthesis of Example 231 from intermediate D.

Example 243

Preparation of 6-[4-(2H-Pyrazol-3-yl)-phenoxy]-2-pyrrolidin-1-ylmethyl-quinoline (243)

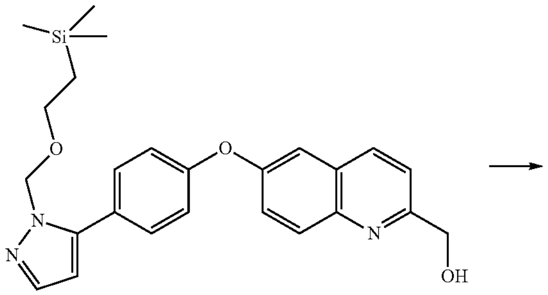

E

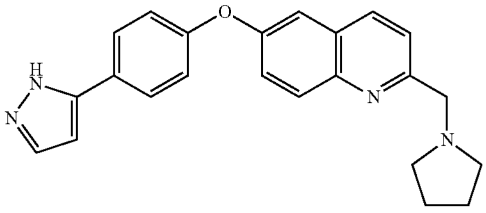

243

The title product (243) is synthesized from intermediate E (75 mg, 0.17 mmol) and pyrrolidine according to procedure described for the synthesis of Example 250 from intermediate AU.

The following Examples are synthesized from intermediate E and the appropriate amine reagent according to the procedure described for the synthesis of Example 243.

| Ex. | Compound Name | Amine Reagent |
|---|---|---|
| 244 | 2-Azetidin-1-ylmethyl-6-[4-(2H-pyrazol-3-yl)-phenoxy]-quinoline | 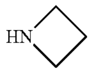 |
| 245 | 1-(8-{6-[4-(2H-Pyrazol-3-yl)-phenoxy]-quinolin-2-ylmethyl}-3,8-diaza-bicyclo[3.2.1]oct-3-yl)-ethanone | 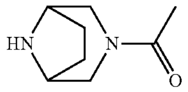 |
| 247 | 1-(4-{6-[4-(2H-Pyrazol-3-yl)-phenoxy]-quinolin-2-ylmethyl}-piperazin-1-yl)-ethanone | 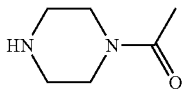 |
| 248 | N-((exo)-8-{6-[4-(2H-Pyrazol-3-yl)-phenoxy]-quinolin-2-ylmethyl}-8-aza-bicyclo[3.2.1]oct-3-yl)-acetamide | 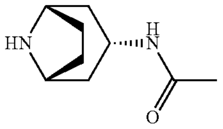 |
| 254 | 2-Morpholin-4-ylmethyl-6-[4-(2H-pyrazol-3-yl)-phenoxy]-quinoline | 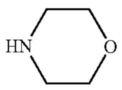 |

Example 250

Preparation of 2-Morpholin-4-ylmethyl-6-[4-(2H-pyrazol-3-yl)-phenoxy]-imidazo[1,2-a]pyridine (250)

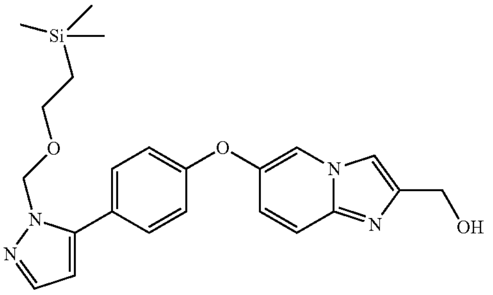

AU

+

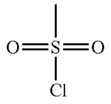

250-1

+

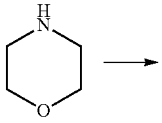

250-2

-continued

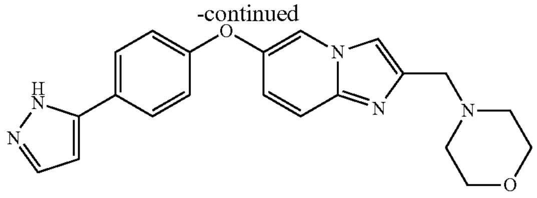

250

To a stirred solution of intermediate AU (52 mg, 0.12 mmol) in DCM (3 ml) is added 250-1 (21 mg, 0.18 mmol), and TEA (2 drops). After 3 h at ambient temperature, 250-2 (52 mg, 0.60 mmol) is added, and the mixture is stirred for 3 h. The mixture is concentrated and treated with HCl in dioxane (4M, 4 ml), and stirred overnight. The reaction mixture is concentrated, and the resultant residue is purified by reverse phase HPLC eluting with 0-60% MeCN in water (+0.1% TFA) to give the title product (250) as a TFA salt.

The following Examples are synthesized from intermediate AU and the appropriate nucleophile (amine, amide, or alcohol) according to the procedure described for the synthesis of Example 250. In general, the carbamate and alcohol nucleophiles are activated with NaH (2 eq.) in DMF prior to the addition to the reaction mixture. For the synthesis of Example 259, aqueous HCl (1M) is used, instead of HCl in dioxane, to facilitate the tandem SEM deprotection, as well as ester hydrolysis.

| Ex. | Compound Name | Nucleophile |
|---|---|---|
| 246 | 6-[4-(2H-Pyrazol-3-yl)-phenoxy]-2-pyrrolidin-1-ylmethyl-imidazo[1,2-a]pyridine | 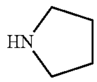 |
| 252 | 2-Morpholin-4-ylmethyl-6-[4-(2H-pyrazol-3-yl)-benzyl]-imidazo[1,2-a]pyridine | 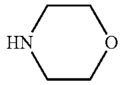 |
| 255 | 3-{6-[4-(2H-Pyrazol-3-yl)-phenoxy]-imidazo[1,2-a]pyridin-2-ylmethyl}-oxazolidin-2-one | 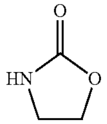 |
| 259 | 1-{6-[4-(2H-Pyrazol-3-yl)-phenoxy]-imidazo[1,2-a]pyridin-2-ylmethyl}-piperidine-4-carboxylic acid | 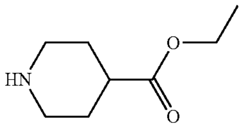 |
| 260 | (R)-5-{6-[4-(2H-Pyrazol-3-yl)-phenoxy]-imidazo[1,2-a]pyridin-2-ylmethoxy}-piperidin-2-one | 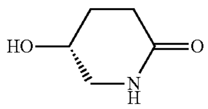 |

Example 253

Preparation of (S)-5-{5-[4-(2H-Pyrazol-3-yl)-phenoxy]-indazol-1-ylmethyl}-pyrrolidin-2-one (253)

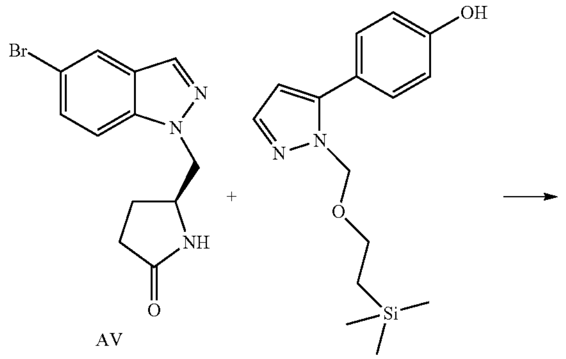

AV

B

-continued

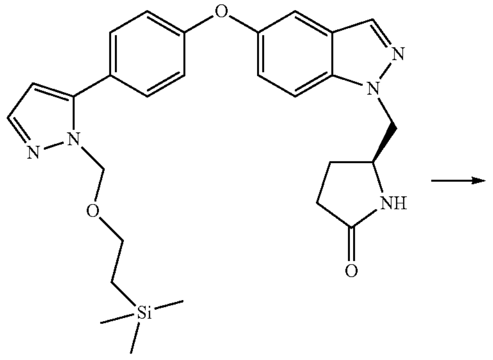

253-1

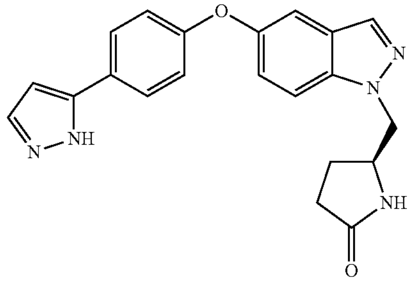

253

Compound 253-1 is synthesized from intermediates AV (153 mg, 0.520 mmol) and B (151 mg, 0.520 mmol) according to procedure described for the synthesis of 258-3.

A solution of compound 253-1 (107 mg, 0.210 mmol) is treated with HCl in dioxane (4M, 4 ml). The mixture is stirred at ambient temperature for 4 h and concentrated. The residue is reversed phase HPLC eluting with 5-50% MeCN in water (+0.1% TFA). Fractions containing the desired product are combined and concentrated. The residue is dissolved in MeOH, passed through a PS—HCO3 cartridge, and concentrated to afford the title compound (253).

The following example is synthesized from intermediates AW and B according to the procedure described for the synthesis of Example 253.

| Ex. | Compound Name | Intermediate (AW) |
|---|---|---|
| 251 | (S)-5-{5-[4-(2H-Pyrazol-3-yl)-phenoxy]-indazol-2-ylmethyl}-pyrrolidin-2-one | 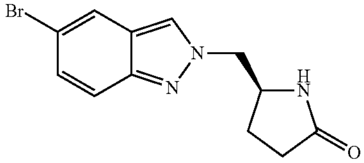 [SMILES: O=C1CC[C@@H](Cn2cc3cc(Br)ccc3n2)N1] |

Example 256

Preparation of 2-Methyl-6-[4-(2H-pyrazol-3-yl)-phenoxy]-3-pyrrolidin-1-ylmethyl-quinoline (256)

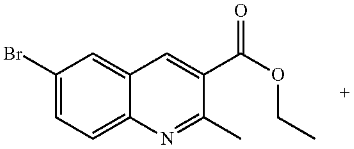

256-1

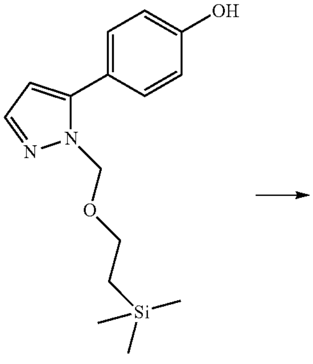

B

-continued

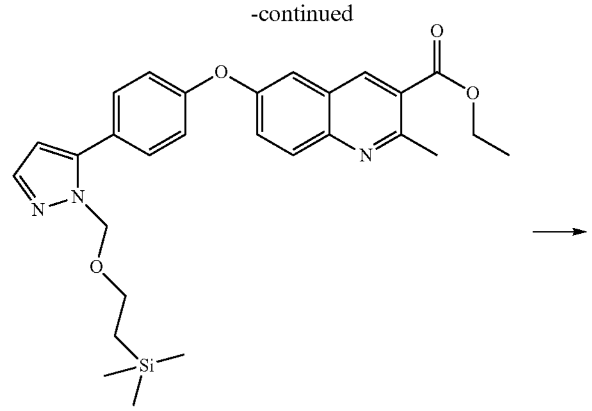

256-2

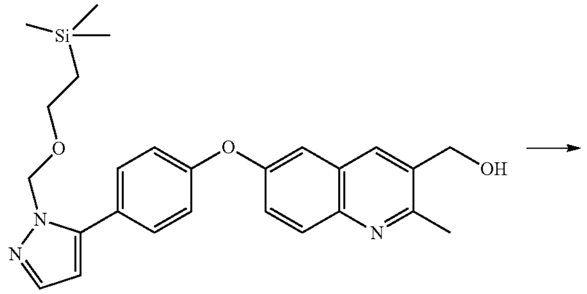

256-3

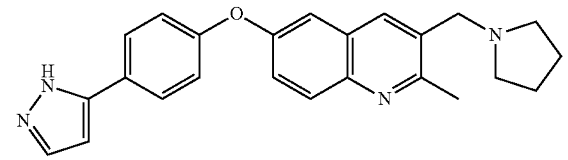

256

Compound 256-2 is synthesized from intermediate 256-1 (372 mg, 1.27 mmol) and B (367 mg, 1.27 mmol) according to procedure described for the synthesis of 258-3.

Compound 256-3 is synthesized from 256-2 (267 mg, 0.53 mmol) according to procedure described for the synthesis of intermediate AU from AU-3.

The title product (256) is synthesized from 256-3 (66 mg, 0.14 mmol) and pyrrolidine according to procedure described for the synthesis of example 250.

The following example is synthesized using the appropriate quinoline and amine reagent according to the method described for the synthesis of example 256.

| Ex. | Compound Name | Quinoline Reagent | Amine reagent |
|---|---|---|---|
| 249 | 3-Morpholin-4-ylmethyl-6-[4-(2H-pyrazol-3-yl)-phenoxy]-quinoline | 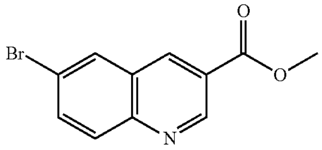 | 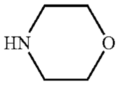 |

Example 257

Preparation of 2-Morpholin-4-ylmethyl-7-[4-(2H-pyrazol-3-yl)-phenoxy]-imidazo[1,2-a]pyridine (257)

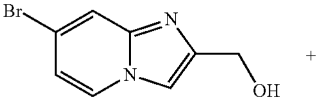

257-1

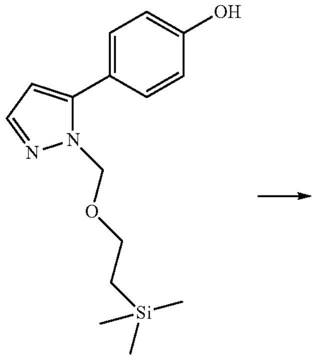

B

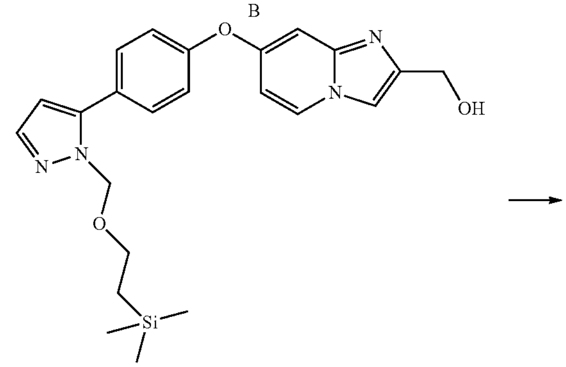

257-2

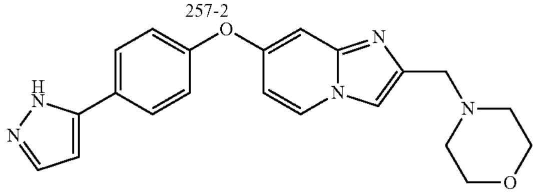

257

Compound 257-2 is prepared from 257-1 (60 mg, 0.26 mmol) and B (92 mg, 0.32 mmol) according to the procedure described for the synthesis of 258-3.

The title product (257) is synthesized from 257-2 (53 mg, 0.12 mmol) according to the procedure described for the synthesis of Example 250.

Example 258

Preparation of Morpholin-4-yl-{7-[4-(2H-pyrazol-3-yl)-phenoxy]-imidazo[1,2-a]pyridin-2-yl}-methanone (258)

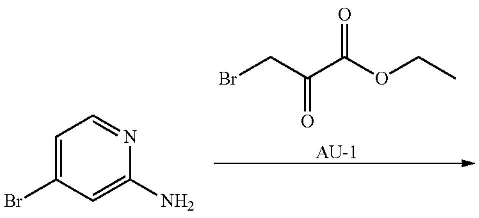

258-1

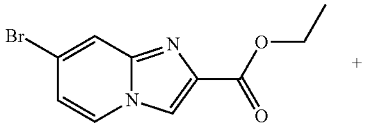

258-2

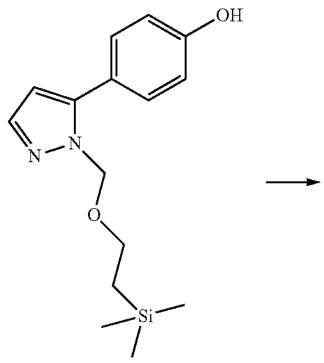

B

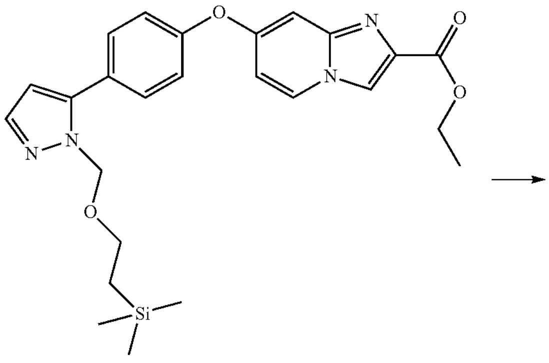

258-3

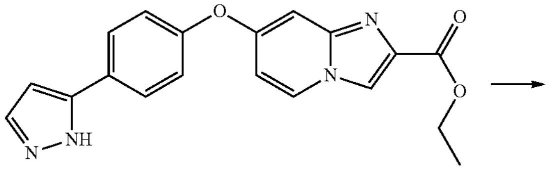

258-4

-continued

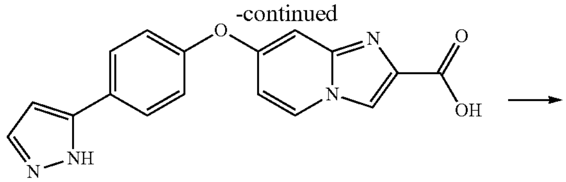

258-5

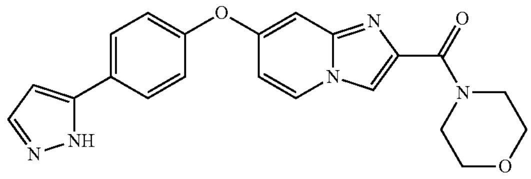

258

To a solution of 258-1 (2.477 g, 14.3 mmol) in THF (40 ml) is added AU-1 (2.20 ml, 15.8 mmol), and the mixture is heated at reflux for 2 h. A solution of TEA (5 ml) in ethanol (15 ml) is added. After stirring for 2 h at 80° C., the mixture is cooled to ambient temperature, and filtered. The residue is dissolved in EtOAc, washed with water, and concentrated. The residue is purified on $SiO_2$ (0-70% EtOAC in heptane) to give 258-2.

A mixture of 258-2 (300 mg, 1.12 mmol), B (356 mg, 1.23 mmol), CuI (21 mg, 0.11 mmol), $K_3PO_4$ (473 mg, 2.23 mmol), and picolinic acid (28 mg, 0.22 mmol) in DMSO (6 ml) is sparged with $N_2$ for 5 min, and heated at 90° C. overnight. The reaction mixture is cooled to ambient temperature, diluted with EtOAc and water, and filtered. The filtrate is washed with water and brine. The organic layer is dried, concentrated, and purified $SiO_2$ (0-6%, MeOH in DCM) to give 258-3.

A solution of 258-3 (102 mg, 0.210 mmol) in DCM (2 ml) is treated with HCl in dioxane (4M, 4 ml). The mixture is stirred at ambient temperature for 4 h and concentrated. The residue is treated with $NH_3$ in methanol (7M, 5 ml) and stirred for 1 h. The mixture is concentrated and the residue is purified on $SiO_2$ (0-10%, MeOH in DCM) to give 258-4.

A solution of reactant 258-4 (39 mg, 0.11 mmol) in a mixture of water/dioxane (1:1, 4 ml) is treated with $LiOH.H_2O$ (7.0 mg, 0.17 mmol). The reaction is stirred overnight and concentrated. The residue is dissolved in water (1 ml), and treated with HCl (1 M) until a precipitate formed. The mixture is filtered to give 258-5.

A mixture of 258-5 (29 mg, 0.09 mmol), TBTU (29 mg, 0.09 mmol), and morpholine (24 mg, 0.27 mmol) in DMF (2 ml) is stirred at ambient temperature overnight. The mixture is diluted with EtOAc and washed with water and brine. The organic layer is dried, concentrated, and purified on $SiO_2$ (0-3% MeOH/DCM) to give the title product (258).

TABLE 2

Mass spectral data for compounds 1-260.

| Ex. | Obs. Mass (m/z) | R.T. (min) |
|---|---|---|
| 1 | 458.4 | 2.65 |
| 2 | 428.3 | 2.65 |
| 3 | 371.3 | 2.73 |
| 4 | 401.3 | 2.65 |
| 5 | 428.3 | 2.64 |
| 6 | 442.3 | 2.65 |
| 7 | 484.3 | 2.63 |
| 8 | 350.3 | 2.74 |
| 9 | 434.4 | 2.62 |

TABLE 2-continued

Mass spectral data for compounds 1-260.

| Ex. | Obs. Mass (m/z) | R.T. (min) |
|---|---|---|
| 10 | 444.3 | 2.56 |
| 11 | 471.3 | 2.42 |
| 12 | 442.4 | 2.64 |
| 13 | 458.4 | 2.63 |
| 14 | 376.3 | 2.51 |
| 15 | 470.3 | 2.66 |
| 16 | 443.4 | 2.48 |
| 17 | 447.4 | 2.59 |
| 18 | 441.3 | 2.42 |
| 19 | 372.4 | 2.63 |
| 20 | 414.4 | 2.61 |
| 21 | 358.4 | 2.62 |
| 22 | 400.4 | 2.72 |
| 23 | 386.4 | 2.67 |
| 24 | 455.4 | 2.62 |
| 25 | 332.4 | 2.93 |
| 26 | 457.3 | 2.66 |
| 27 | 445.3 | 2.56 |
| 28 | 459.3 | 2.42 |
| 29 | 443.4 | 2.63 |
| 30 | 455.4 | 2.38 |
| 31 | 454.4 | 2.43 |
| 32 | 455.4 | 2.43 |
| 33 | 473.3 | 2.58 |
| 34 | 389.4 | 2.56 |
| 35 | 427.4 | 2.58 |
| 36 | 443.5 | 2.56 |
| 37 | 457.3 | 2.62 |
| 38 | 459.3 | 2.58 |
| 39 | 507.2 | 2.41 |
| 40 | 499.3 | 2.6 |
| 41 | 455.4 | 2.43 |
| 42 | 459.3 | 2.58 |
| 43 | 430.4 | 2.56 |
| 44 | 471.3 | 2.6 |
| 45 | 429.4 | 2.63 |
| 46 | 473.4 | 2.59 |
| 47 | 389.4 | 2.57 |
| 48 | 428.3 | 2.63 |
| 49 | 401.4 | 2.57 |
| 50 | 499.3 | 2.62 |
| 51 | 451.3 | 2.66 |
| 52 | 360.4 | 2.56 |
| 53 | 404.4 | 2.69 |
| 54 | 358.3 | 2.61 |
| 55 | 404.4 | 2.61 |
| 56 | 402.3 | 2.68 |
| 57 | 471.3 | 2.59 |
| 58 | 402.5 | 2.55 |
| 59 | 402.3 | 2.59 |
| 60 | 374.4 | 2.54 |
| 61 | 433.3 | 0.34 |
| 62 | 390.5 | 2.53 |
| 63 | 457.3 | 2.75 |
| 64 | 417.3 | 0.35 |
| 65 | 456.3 | 2.55 |
| 66 | 376.3 | 0.36 |
| 67 | 374.3 | 0.33 |
| 68 | 401.3 | 2.97 |
| 69 | 321.2 | 2.6 |
| 70 | 459.3 | 2.57 |
| 71 | 472.4 | 2.62 |
| 72 | 388.3 | 2.6 |
| 73 | 368.3 | 2.43 |
| 74 | 376.3 | 2.68 |
| 75 | 374.4 | 2.69 |
| 76 | 404.4 | 2.64 |
| 77 | 390.3 | 2.62 |
| 78 | 390.3 | 2.63 |
| 79 | 388.4 | 2.64 |
| 80 | 376.3 | 2.53 |
| 81 | 404.4 | 2.64 |
| 82 | 392.4 | 2.65 |
| 83 | 375.4 | 2.5 |
| 84 | 404.4 | 2.59 |

TABLE 2-continued

Mass spectral data for compounds 1-260.

| Ex. | Obs. Mass (m/z) | R.T. (min) |
|---|---|---|
| 85 | 404.4 | 2.46 |
| 86 | 406.4 | 2.54 |
| 87 | 420.4 | 2.61 |
| 88 | 445.4 | 2.62 |
| 89 | 374.4 | 2.58 |
| 90 | 431.5 | 2.64 |
| 91 | 364.3 | 0.32 |
| 92 | 418.3 | 2.46 |
| 93 | 431.3 | 2.63 |
| 94 | 432.4 | 2.56 |
| 95 | 445.3 | 2.54 |
| 96 | 425.3 | 2.51 |
| 97 | 390.3 | 2.43 |
| 98 | 392.4 | 2.65 |
| 99 | 411.3 | 2.64 |
| 100 | 390.3 | 2.43 |
| 101 | 390.3 | 2.43 |
| 102 | 390.5 | 2.65 |
| 103 | 404.4 | 2.7 |
| 104 | 404.4 | 2.61 |
| 105 | 388.4 | 2.61 |
| 106 | 404.3 | 2.4 |
| 107 | 397.3 | 2.63 |
| 108 | 443.4 | 2.78 |
| 109 | 459.3 | 2.59 |
| 110 | 457.4 | 2.63 |
| 111 | 391.3 | 2.4 |
| 112 | 490.3 | 2.39 |
| 113 | 377.2 | 2.32 |
| 114 | 377.3 | 2.64 |
| 115 | 415.4 | 2.59 |
| 116 | 459.4 | 2.57 |
| 117 | 375.4 | 2.74 |
| 118 | 335.4 | 2.83 |
| 119 | 401.4 | 3.02 |
| 120 | 418.3 | 2.49 |
| 121 | 403.4 | 2.59 |
| 122 | 390.4 | 2.68 |
| 123 | 345.4 | 2.62 |
| 124 | 491.1 | 2.73 |
| 125 | 434.3 | 2.71 |
| 126 | 363.3 | 2.6 |
| 127 | 361.4 | 2.63 |
| 128 | 448.3 | 2.42 |
| 129 | 460.4 | 2.44 |
| 130 | 474.3 | 2.46 |
| 131 | 459.4 | 2.65 |
| 132 | 471.2 | 2.59 |
| 133 | 446.3 | 2.61 |
| 134 | 446.3 | 2.44 |
| 135 | 448.3 | 2.62 |
| 136 | 432.4 | 2.43 |
| 137 | 433.4 | 2.6 |
| 138 | 446.3 | 2.44 |
| 139 | 457.3 | 2.57 |
| 140 | 459.3 | 2.58 |
| 141 | 482.2 | 2.45 |
| 142 | 459.4 | 2.66 |
| 143 | 434.4 | 2.61 |
| 144 | 419.5 | 2.58 |
| 145 | 457.4 | 2.58 |
| 146 | 471.3 | 2.6 |
| 147 | 441.3 | 2.61 |
| 148 | 455.3 | 2.64 |
| 149 | 418.3 | 2.62 |
| 150 | 535.3 | 2.53 |
| 151 | 508.3 | 2.74 |
| 152 | 362.4 | 2.54 |
| 153 | 388.3 | 2.71 |
| 154 | 337.3 | 0.23 |
| 155 | 392.4 | 2.64 |
| 156 | 418.4 | 2.52 |
| 157 | 390.5 | 2.54 |
| 158 | 348.4 | 2.57 |
| 159 | 418.4 | 2.5 |

TABLE 2-continued

| Mass spectral data for compounds 1-260. | | |
|---|---|---|
| Ex. | Obs. Mass (m/z) | R.T. (min) |
| 160 | 431.5 | 2.57 |
| 161 | 362.4 | 2.55 |
| 162 | 348.4 | 2.59 |
| 163 | 388.3 | 2.65 |
| 164 | 388.3 | 2.9 |
| 165 | 388.3 | 2.91 |
| 166 | 404.4 | 2.51 |
| 167 | 404.4 | 2.64 |
| 168 | 418.4 | 2.53 |
| 169 | 461.4 | 2.65 |
| 170 | 463.4 | 2.61 |
| 171 | 388.3 | 2.9 |
| 172 | 404.4 | 2.51 |
| 173 | 404.4 | 2.9 |
| 174 | 388.3 | 3.73 |
| 175 | 390.5 | 2.59 |
| 176 | 438.4 | 2.8 |
| 177 | 471.3 | 2.61 |
| 178 | 400.3 | 2.62 |
| 179 | 360.4 | 2.55 |
| 180 | 362.4 | 2.55 |
| 181 | 390.5 | 2.48 |
| 182 | 404.4 | 2.57 |
| 183 | 406.4 | 2.68 |
| 184 | 406.4 | 2.69 |
| 185 | 406.4 | 2.62 |
| 186 | 422.4 | 2.68 |
| 187 | 489.3 | 2.63 |
| 188 | 374.4 | 2.63 |
| 189 | 378.4 | 2.6 |
| 190 | 485.2 | 3.76 |
| 191 | 334.3 | 2.51 |
| 192 | 378.4 | 2.57 |
| 193 | 432.4 | 2.71 |
| 194 | 376.3 | 2.51 |
| 195 | 404.4 | 2.5 |
| 196 | 428.3 | 2.57 |
| 197 | 447.4 | 2.64 |
| 198 | 459.4 | 2.63 |
| 199 | 392.4 | 2.6 |
| 200 | 431.4 | 2.57 |
| 201 | 475.4 | 2.59 |
| 202 | 375.3 | 2.58 |
| 203 | 461.4 | 2.62 |
| 204 | 402.2 | 3.74 |
| 205 | 402.2 | 2.66 |
| 206 | 418.4 | 2.61 |
| 207 | 360.4 | 2.43 |
| 208 | 402.2 | 2.66 |
| 209 | 483.3 | 3.81 |
| 210 | 388.3 | 2.58 |
| 211 | 485.2 | 3.74 |
| 212 | 416.4 | 2.65 |
| 213 | 491.3 | 3.8 |
| 214 | 430.4 | 2.48 |
| 215 | 479.3 | 2.78 |
| 216 | 359.3 | 2.42 |
| 217 | 374.5 | 2.52 |
| 218 | 362.4 | 2.66 |
| 219 | 433.4 | 2.63 |
| 220 | 373.3 | 2.36 |
| 221 | 417.4 | 2.56 |
| 222 | 417.4 | 2.57 |
| 223 | 429.4 | 2.58 |
| 224 | 431.5 | 2.59 |
| 225 | 473.4 | 0.34 |
| 226 | 390.3 | 2.5 |
| 227 | 402.3 | 2.53 |
| 228 | 404.4 | 2.61 |
| 229 | 418.4 | 2.64 |
| 230 | 404.4 | 2.59 |
| 231 | 429.3 | 2.43 |
| 232 | 423.4 | 2.62 |
| 233 | 388.3 | 2.63 |
| 234 | 402.4 | 2.66 |

TABLE 2-continued

| Mass spectral data for compounds 1-260. | | |
|---|---|---|
| Ex. | Obs. Mass (m/z) | R.T. (min) |
| 235 | 402.5 | 2.7 |
| 236 | 473.2 | 2.59 |
| 237 | 443.3 | 2.47 |
| 238 | 469.3 | 2.57 |
| 239 | 469.3 | 2.58 |
| 240 | 441.4 | 2.53 |
| 241 | 429.5 | 2.62 |
| 242 | 436.2 | 2.65 |
| 243 | 371.4 | 2.62 |
| 244 | 357.3 | 2.56 |
| 245 | 454.4 | 2.67 |
| 246 | 360.3 | 2.56 |
| 247 | 428.3 | 2.66 |
| 248 | 468.4 | 2.68 |
| 249 | 387.3 | 2.93 |
| 250 | 376.3 | 2.55 |
| 251 | 374.4 | 2.68 |
| 252 | 374.4 | 0.34 |
| 253 | 374.4 | 2.74 |
| 254 | 387.3 | 2.82 |
| 255 | 376.3 | 0.34 |
| 256 | 385.3 | 2.5 |
| 257 | 376.3 | 0.33 |
| 258 | 390.4 | 2.59 |
| 259 | 418.3 | 2.55 |
| 260 | 404.4 | 2.82 |

Assessment of Biological Properties

The compounds of the invention are assessed for the ability to interact with human $LTA_4$ hydrolase in an enzymatic assay that measures the ability of the enzyme to cleave the peptide bond of arginyl-aminomethylcoumarin (Arg-AMC). $LTA_4H$ Enzyme (1 nM final), Arg-AMC substrate (50 μM final), and compound are combined in a reaction buffer (50 mM Tris-HCl (pH 7.5), 100 mM KCl, 0.5% bovine serum albumin) at room temperature for 1 h. The formation of product is assessed by measuring the fluorescence of aminomethylcoumarin product (excitation wavelength 380 nm/emission wavelength 460 nm). In general, the preferred potency range ($IC_{50}$) of compounds in the $LTA_4H$ Enzyme assay is between 0.1 nM to 10 μM, the more preferred potency range is 0.1 nM to 0.1 μM, and the most preferred potency range is 0.1 nM to 10 nM.

TABLE 3

| $IC_{50}$ values of $LTA_4H$ Enzyme assay. | |
|---|---|
| Ex. | Peptidase IC50 (nM) |
| 1 | 0.63 |
| 2 | 0.39 |
| 3 | 0.34 |
| 4 | 0.54 |
| 5 | 0.46 |
| 6 | 0.37 |
| 7 | 0.68 |
| 8 | 0.35 |
| 9 | 4.2 |
| 10 | 0.53 |
| 11 | 0.65 |
| 12 | 0.45 |
| 13 | 0.59 |
| 14 | 1.2 |
| 15 | 2.4 |
| 16 | 1.1 |
| 17 | 1.1 |
| 18 | 2.0 |

TABLE 3-continued

IC$_{50}$ values of LTA$_4$H Enzyme assay.

| Ex. | Peptidase IC50 (nM) |
|---|---|
| 19 | 0.24 |
| 20 | 0.3 |
| 21 | 0.22 |
| 22 | 0.36 |
| 23 | 0.48 |
| 24 | 0.33 |
| 25 | 0.5 |
| 26 | 0.57 |
| 27 | 0.72 |
| 28 | 0.87 |
| 29 | 0.66 |
| 30 | 1.1 |
| 31 | 1.0 |
| 32 | 0.85 |
| 33 | 0.77 |
| 34 | 5.7 |
| 35 | 0.49 |
| 36 | 0.98 |
| 37 | 0.86 |
| 38 | 0.76 |
| 39 | 2.0 |
| 40 | 0.47 |
| 41 | 0.99 |
| 42 | 0.88 |
| 43 | 3.9 |
| 44 | 0.71 |
| 45 | 2.8 |
| 46 | 1.6 |
| 47 | 1.3 |
| 48 | 2.1 |
| 49 | 8.9 |
| 50 | 2.8 |
| 51 | 8.1 |
| 52 | 0.12 |
| 53 | 0.096 |
| 54 | 0.13 |
| 55 | 0.13 |
| 56 | 0.18 |
| 57 | 0.13 |
| 58 | 0.13 |
| 59 | 0.13 |
| 60 | 0.23 |
| 61 | 0.21 |
| 62 | 0.13 |
| 63 | 0.11 |
| 64 | 0.14 |
| 65 | 0.15 |
| 66 | 0.14 |
| 67 | 1.4 |
| 68 | 4.2 |
| 69 | 3.9 |
| 70 | 0.16 |
| 71 | 0.14 |
| 72 | 0.14 |
| 73 | 0.36 |
| 74 | 0.099 |
| 75 | 0.24 |
| 76 | 0.2 |
| 77 | 0.099 |
| 78 | 0.089 |
| 79 | 0.3 |
| 80 | 0.09 |
| 81 | 0.27 |
| 82 | 0.077 |
| 83 | 0.88 |
| 84 | 0.36 |
| 85 | 0.24 |
| 86 | 0.056 |
| 87 | 0.36 |
| 88 | 0.23 |
| 89 | 0.086 |
| 90 | 0.45 |
| 91 | 0.21 |
| 92 | 0.11 |
| 93 | 0.58 |

TABLE 3-continued

IC$_{50}$ values of LTA$_4$H Enzyme assay.

| Ex. | Peptidase IC50 (nM) |
|---|---|
| 94 | 1.3 |
| 95 | 0.83 |
| 96 | 0.79 |
| 97 | 0.54 |
| 98 | 0.18 |
| 99 | 0.93 |
| 100 | 0.42 |
| 101 | 0.55 |
| 102 | 0.91 |
| 103 | 0.27 |
| 104 | 0.27 |
| 105 | 0.53 |
| 106 | 0.17 |
| 107 | 2.0 |
| 108 | 0.54 |
| 109 | 0.47 |
| 110 | 0.7 |
| 111 | 2.0 |
| 112 | 2.1 |
| 113 | 2.6 |
| 114 | 0.75 |
| 115 | 1.7 |
| 116 | 0.95 |
| 117 | 4.4 |
| 118 | 7.0 |
| 119 | 20 |
| 120 | 25 |
| 121 | 1.5 |
| 122 | 0.97 |
| 123 | 0.44 |
| 124 | 0.061 |
| 125 | 0.29 |
| 126 | 0.51 |
| 127 | 0.68 |
| 128 | 0.74 |
| 129 | 0.92 |
| 130 | 0.26 |
| 131 | 0.17 |
| 132 | 0.28 |
| 133 | 0.35 |
| 134 | 0.28 |
| 135 | 0.56 |
| 136 | 0.63 |
| 137 | 0.57 |
| 138 | 0.39 |
| 139 | 0.39 |
| 140 | 0.93 |
| 141 | 0.35 |
| 142 | 0.25 |
| 143 | 0.85 |
| 144 | 0.64 |
| 145 | 0.4 |
| 146 | 0.37 |
| 147 | 0.48 |
| 148 | 0.46 |
| 149 | 1.2 |
| 150 | 0.32 |
| 151 | 0.4 |
| 152 | 0.1 |
| 153 | 0.17 |
| 154 | 0.19 |
| 155 | 0.18 |
| 156 | 0.22 |
| 157 | 0.11 |
| 158 | 0.28 |
| 159 | 0.19 |
| 160 | 0.38 |
| 161 | 0.14 |
| 162 | 0.61 |
| 163 | 0.065 |
| 164 | 0.14 |
| 165 | 0.075 |
| 166 | 0.21 |
| 167 | 0.14 |
| 168 | 0.13 |

TABLE 3-continued

| IC$_{50}$ values of LTA$_4$H Enzyme assay. | |
|---|---|
| Ex. | Peptidase IC50 (nM) |
| 169 | 0.25 |
| 170 | 0.35 |
| 171 | 0.11 |
| 172 | 0.07 |
| 173 | 0.16 |
| 174 | 0.65 |
| 175 | 0.17 |
| 176 | 0.32 |
| 177 | 0.33 |
| 178 | 0.74 |
| 179 | 0.2 |
| 180 | 0.13 |
| 181 | 0.21 |
| 182 | 0.062 |
| 183 | 0.17 |
| 184 | 0.2 |
| 185 | 0.45 |
| 186 | 0.23 |
| 187 | 0.31 |
| 188 | 0.13 |
| 189 | 0.23 |
| 190 | 0.53 |
| 191 | 0.18 |
| 192 | 0.17 |
| 193 | 0.13 |
| 194 | 0.18 |
| 195 | 0.14 |
| 196 | 0.17 |
| 197 | 0.46 |
| 198 | 0.35 |
| 199 | 0.13 |
| 200 | 0.47 |
| 201 | 0.61 |
| 202 | 0.32 |
| 203 | 0.77 |
| 204 | 0.98 |
| 205 | 1.2 |
| 206 | 0.42 |
| 207 | 0.17 |
| 208 | 1.2 |
| 209 | 0.66 |
| 210 | 0.82 |
| 211 | 0.8 |
| 212 | 1.2 |
| 213 | 0.77 |
| 214 | 2.5 |
| 215 | 5.0 |
| 216 | 0.2 |
| 217 | 0.12 |
| 218 | 0.097 |
| 219 | 0.22 |
| 220 | 1.7 |
| 221 | 0.27 |
| 222 | 0.73 |
| 223 | 0.94 |
| 224 | 2.3 |
| 225 | 0.13 |
| 226 | 0.3 |
| 227 | 0.054 |
| 228 | 0.16 |
| 229 | 0.22 |
| 230 | 0.19 |
| 231 | 0.55 |
| 232 | 1.4 |
| 233 | 0.24 |
| 234 | 0.26 |
| 235 | 0.43 |
| 236 | 0.96 |
| 237 | 0.84 |
| 238 | 0.61 |
| 239 | 0.43 |
| 240 | 0.94 |
| 241 | 3.5 |
| 242 | 1.6 |
| 243 | 0.065 |

TABLE 3-continued

| IC$_{50}$ values of LTA$_4$H Enzyme assay. | |
|---|---|
| Ex. | Peptidase IC50 (nM) |
| 244 | 0.048 |
| 245 | 0.18 |
| 246 | 0.17 |
| 247 | 0.21 |
| 248 | 0.083 |
| 249 | 0.37 |
| 250 | 0.57 |
| 251 | 0.87 |
| 252 | 0.93 |
| 253 | 1.4 |
| 254 | 0.7 |
| 255 | 1.7 |
| 256 | 1.6 |
| 257 | 2.5 |
| 258 | 10 |
| 259 | 0.12 |
| 260 | 5.3 |

The compounds of the invention are additionally tested in a human whole blood (HWB) assay to determine their ability to inhibit the synthesis of LTB4 in a cellular system. Compounds are combined with heparinized human whole blood and incubated for 15 minutes at 37° C. Calcimycin (20 μM final, prepared in phosphate-buffered saline, pH 7.4) is then added and the mixture is incubated for another 30 minutes at 37° C. The samples are centrifuged for 5 min at low speed (1500×g) and the plasma layer is removed. Plasma LTB4 concentrations are then measured using an antibody-based homogenous time-resolved fluorescence method (CisBio, Bedford, Mass.). In general, the preferred potency range (IC50) of compounds in the HWB assay is between 10 nM to 10 μM, the more preferred potency range is 10 nM to 1 μM, and the most preferred potency range is 10 nM to 100 nM. The potencies of representative compounds of the invention in the WHB assays are shown in Table 4.

TABLE 4

| IC50 values of LTB4 production inhibition assay in human whole blood. | |
|---|---|
| Ex. | 1050 (nM)Ex. |
| 1 | 180 |
| 2 | 130 |
| 3 | 120 |
| 4 | 190 |
| 5 | 220 |
| 6 | 210 |
| 7 | 180 |
| 8 | 99 |
| 9 | 1300 |
| 10 | 150 |
| 11 | 180 |
| 12 | 190 |
| 13 | 200 |
| 14 | 310 |
| 15 | 810 |
| 16 | 250 |
| 17 | 430 |
| 18 | 580 |
| 19 | 70 |
| 20 | 82 |
| 21 | 86 |
| 22 | 89 |
| 23 | 90 |
| 24 | 99 |
| 25 | 110 |
| 26 | 130 |

TABLE 4-continued

IC50 values of LTB4 production inhibition assay in human whole blood.

| Ex. | 1050 (nM)Ex. |
|---|---|
| 27 | 150 |
| 28 | 150 |
| 29 | 190 |
| 30 | 190 |
| 31 | 200 |
| 32 | 210 |
| 33 | 230 |
| 34 | 800 |
| 35 | 220 |
| 36 | 240 |
| 37 | 270 |
| 38 | 280 |
| 39 | 280 |
| 40 | 300 |
| 41 | 320 |
| 42 | 360 |
| 43 | 380 |
| 44 | 410 |
| 45 | 420 |
| 46 | 540 |
| 47 | 570 |
| 48 | 740 |
| 49 | 860 |
| 50 | 1100 |
| 51 | 2200 |
| 52 | 66 |
| 53 | 67 |
| 54 | 94 |
| 55 | 100 |
| 56 | 110 |
| 57 | 110 |
| 58 | 120 |
| 59 | 130 |
| 60 | 140 |
| 61 | 140 |
| 62 | 150 |
| 63 | 150 |
| 64 | 180 |
| 65 | 180 |
| 66 | 240 |
| 67 | 480 |
| 68 | 590 |
| 69 | 650 |
| 70 | 230 |
| 71 | 260 |
| 72 | 320 |
| 73 | 330 |
| 74 | 67 |
| 75 | 84 |
| 76 | 87 |
| 77 | 88 |
| 78 | 95 |
| 79 | 98 |
| 80 | 98 |
| 81 | 100 |
| 82 | 110 |
| 83 | 120 |
| 84 | 120 |
| 85 | 120 |
| 86 | 120 |
| 87 | 120 |
| 88 | 130 |
| 89 | 130 |
| 90 | 130 |
| 91 | 140 |
| 92 | 140 |
| 93 | 150 |
| 94 | 150 |
| 95 | 150 |
| 96 | 160 |
| 97 | 160 |
| 98 | 160 |
| 99 | 170 |
| 100 | 170 |
| 101 | 190 |

TABLE 4-continued

IC50 values of LTB4 production inhibition assay in human whole blood.

| Ex. | 1050 (nM)Ex. |
|---|---|
| 102 | 190 |
| 103 | 190 |
| 104 | 190 |
| 105 | 200 |
| 106 | 200 |
| 107 | 220 |
| 108 | 230 |
| 109 | 230 |
| 110 | 240 |
| 111 | 280 |
| 112 | 280 |
| 113 | 470 |
| 114 | 500 |
| 115 | 550 |
| 116 | 580 |
| 117 | 650 |
| 118 | 760 |
| 119 | 2000 |
| 120 | 3100 |
| 121 | 390 |
| 122 | 200 |
| 123 | 240 |
| 124 | 130 |
| 125 | 100 |
| 126 | 110 |
| 127 | 130 |
| 128 | 170 |
| 129 | 190 |
| 130 | 99 |
| 131 | 120 |
| 132 | 140 |
| 133 | 150 |
| 134 | 150 |
| 135 | 180 |
| 136 | 190 |
| 137 | 190 |
| 138 | 190 |
| 139 | 200 |
| 140 | 200 |
| 141 | 200 |
| 142 | 210 |
| 143 | 230 |
| 144 | 260 |
| 145 | 210 |
| 146 | 160 |
| 147 | 160 |
| 148 | 150 |
| 149 | 250 |
| 150 | 300 |
| 151 | 310 |
| 152 | 71 |
| 153 | 89 |
| 154 | 95 |
| 155 | 95 |
| 156 | 95 |
| 157 | 98 |
| 158 | 110 |
| 159 | 110 |
| 160 | 110 |
| 161 | 120 |
| 162 | 120 |
| 163 | 120 |
| 164 | 120 |
| 165 | 120 |
| 166 | 120 |
| 167 | 120 |
| 168 | 120 |
| 169 | 120 |
| 170 | 120 |
| 171 | 130 |
| 172 | 130 |
| 173 | 130 |
| 174 | 140 |
| 175 | 140 |
| 176 | 140 |

TABLE 4-continued

| IC50 values of LTB4 production inhibition assay in human whole blood. | |
|---|---|
| Ex. | 1050 (nM)Ex. |
| 177 | 140 |
| 178 | 150 |
| 179 | 150 |
| 180 | 150 |
| 181 | 150 |
| 182 | 150 |
| 183 | 150 |
| 184 | 150 |
| 185 | 150 |
| 186 | 150 |
| 187 | 150 |
| 188 | 160 |
| 189 | 160 |
| 190 | 170 |
| 191 | 170 |
| 192 | 170 |
| 193 | 170 |
| 194 | 180 |
| 195 | 180 |
| 196 | 180 |
| 197 | 180 |
| 198 | 180 |
| 199 | 190 |
| 200 | 190 |
| 201 | 190 |
| 202 | 200 |
| 203 | 200 |
| 204 | 210 |
| 205 | 210 |
| 206 | 210 |
| 207 | 220 |
| 208 | 220 |
| 209 | 220 |
| 210 | 230 |
| 211 | 230 |
| 212 | 250 |
| 213 | 390 |
| 214 | 400 |
| 215 | 680 |
| 216 | 110 |
| 217 | 81 |
| 218 | 110 |
| 219 | 110 |
| 220 | 160 |
| 221 | 170 |
| 222 | 230 |
| 223 | 230 |
| 224 | 540 |
| 225 | 130 |
| 226 | 170 |
| 227 | 170 |
| 228 | 180 |
| 229 | 190 |
| 230 | 200 |
| 231 | 150 |
| 232 | 160 |
| 233 | 170 |
| 234 | 180 |
| 235 | 180 |
| 236 | 200 |
| 237 | 210 |
| 238 | 250 |
| 239 | 260 |
| 240 | 340 |
| 241 | 980 |
| 242 | 210 |
| 243 | 66 |
| 244 | 120 |
| 245 | 170 |
| 246 | 180 |
| 247 | 190 |
| 248 | 200 |
| 249 | 200 |
| 250 | 210 |
| 251 | 220 |

TABLE 4-continued

| IC50 values of LTB4 production inhibition assay in human whole blood. | |
|---|---|
| Ex. | 1050 (nM)Ex. |
| 252 | 250 |
| 253 | 300 |
| 254 | 330 |
| 255 | 360 |
| 256 | 480 |
| 257 | 650 |
| 258 | 2000 |
| 259 | 2100 |
| 260 | 2200 |

Methods of Use

The compounds of the invention are effective inhibitors of leukotriene $A_4$ hydrolase ($LTA_4H$) and thus inhibit leukotriene production. Therefore, in one embodiment of the invention, there is provided methods of treating leukotriene-mediated disorders using compounds of the invention. In another embodiment, there is provided methods of treating cardiovascular, inflammatory, allergic, pulmonary and fibrotic diseases, renal diseases and cancer using compounds of the invention.

In one embodiment, the invention relates to a compound of the invention for use as a medicament for the treatment leukotriene-mediated disorders. In another embodiment, the invention relates to a compound of the invention for use in a method of treating cardiovascular, inflammatory, allergic, pulmonary and fibrotic diseases, renal diseases and cancer.

In one embodiment, the invention relates to the use of a compound of the invention for the preparation of a medicament for the treatment leukotriene-mediated disorders. In another embodiment, the invention relates to the use of a compound of the invention, for the preparation of a medicament for treating cardiovascular, inflammatory, allergic, pulmonary and fibrotic diseases, renal diseases and cancer.

In one embodiment, the invention relates to a compound of the invention for use as a medicament for the treatment leukotriene-mediated disorders. In another embodiment, the invention relates to a compound of the invention for use in a method of treating cardiovascular, inflammatory, allergic, pulmonary and fibrotic diseases, renal diseases and cancer.

Without wishing to be bound by theory, by inhibiting the activity of $LTA_4H$, the compounds of the invention block the production of $LTB_4$ resulting from the oxidation of arachidonic acid by 5-LO and subsequent metabolism. Thus, the inhibition of $LTA_4H$ activity is an attractive means for preventing and treating a variety of diseases mediated by $LTB_4$. These include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease systemic lupus erythematosus, transplant rejection, inflammatory and allergic ocular diseases;

Cancer including solid tumors, leukemias and lymphomas; and Renal diseases such as glomerulonephritis.

For treatment of the above-described diseases and conditions, a therapeutically effective dose will generally be in the range from about 0.01 mg to about 100 mg/kg of body weight to per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

Combination Therapy

The compounds of the invention may be administered alone or in combination with at least one additional active agent. Thus, in one embodiment, the invention relates to a pharmaceutical composition comprising one or more compounds of the invention in combination with at least one additional agent. In another embodiment, the invention relates a method of treating diseases mediated by $LTB_4$, the method comprising administering a therapeutically effective amount of one or more compounds of the invention in combination with a pharmaceutically effective amount of at least one additional agent.

Nonlimiting examples of additional active agents include statins (or HMG-CoA reductase inhibitors); cholesterol ester transfer protein (CETP) inhibitors (or antagonists); fibrates, niacin derivatives, Lp-PLA2-inhibitors (e.g., darapladib, varespladib), antiplatelets and anticoagulants.

In one embodiment, the additional active agent is a statin. In another embodiment, the additional active agent is a statin selected from the group consisting of atorvastatin, fluvastatin, lovastatin, pitavastatin, pravastatin, rosuvastatin, and simvastatin.

In one embodiment, the additional active agent is a CETP inhibitor. In another embodiment, the additional active agent is a CETP inhibitor selected from the group consisting of anacetrapib, dalcetrapib, evacetrapib, TA-8995 (Mitsubishi Tanabe Pharma), ATH-03 (Affris), DRL-17822 (Dr. Reddy's). In yet another embodiment, the additional active is selected from the group consisting of dalcetrapib and anacetrapib.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound of formula (I):

(I)

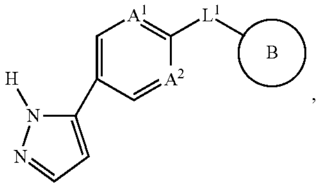

or a pharmaceutically acceptable salt thereof, wherein:

$A^1$ and $A^2$ are each independently selected from the group consisting of CH and N;

$L^1$ is a linker selected from the group consisting of —O— and —$CH_2$—;

B is a 9- or 10-membered ring selected from the group consisting of:
B-1
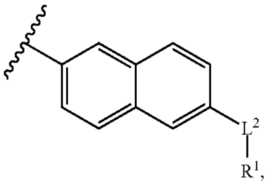
B-2
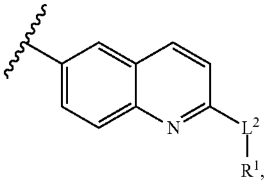
B-3
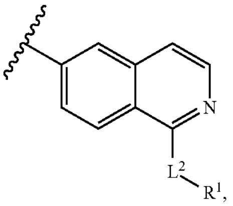
B-4
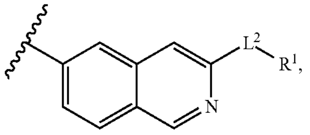
B-5
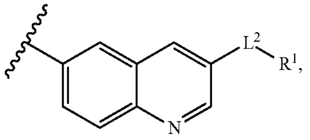
B-6
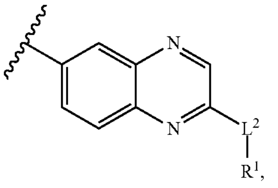
B-7
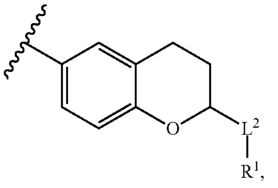
B-8
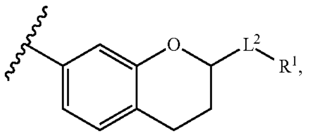
-continued
B-9
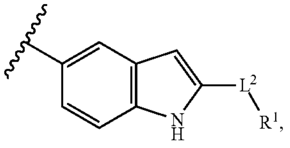
B-10
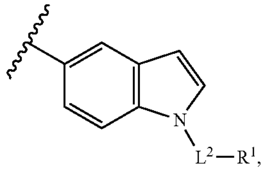
B-11
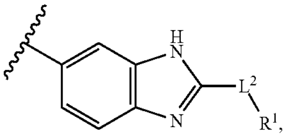
B-12
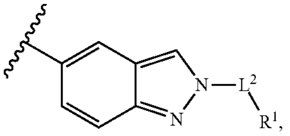
B-13
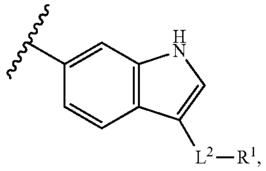
B-14
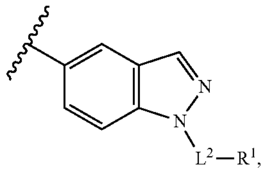
B-15
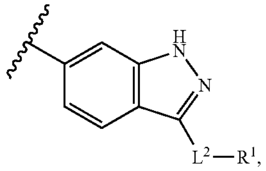
B-16
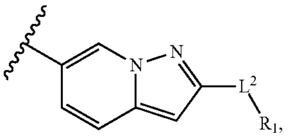
B-17
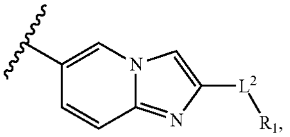
B-18
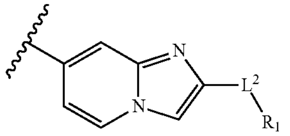

-continued

B-19

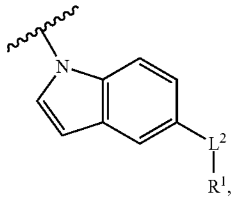

B-20

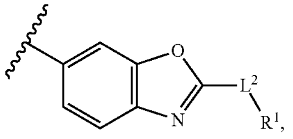

B-21

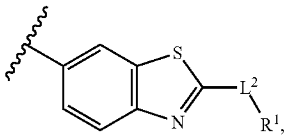

B-22

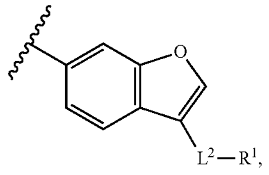

B-23

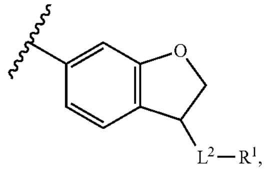

B-24

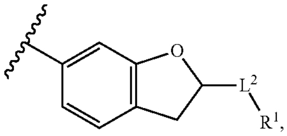

and

B-25

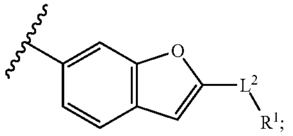

wherein each B ring may optionally be further substituted by —$(C_1\text{-}C_6)$alkyl;

$L^2$ is absent or a —$(CH_2)_n$— linker, wherein n is an integer selected from 1, 2 and 3, and wherein one —$(CH_2)$— moiety of said $L^2$ linker may optionally be replaced, where possible, by —O— and wherein each —$(CH_2)$— of said $L^2$ linker may be substituted with one to two groups selected from the group consisting of —OH, -halo, =O, —$(C_1\text{-}C_6)$alkyl, —$(C_3\text{-}C_6)$cycloalkyl, -(4- to 7-membered)heterocyclyl, and phenyl; wherein two —$(C_1\text{-}C_6)$alkyls groups, when attached to the same carbon atom of said $L^2$ linker moiety may join to form a —$(C_3\text{-}C_6)$cycloalkyl;

$R^1$ is selected from the group consisting of:

(a) a group of formula —$N(R^2)(R^3)$, wherein $R^2$ and $R^3$ are each independently selected from the group consisting of —H, —$(C_1\text{-}C_6)$alkyl, —$(C_3\text{-}C_6)$cycloalkyl, and -(4- to 7-membered)heterocyclyl, wherein each of said —$(C_1\text{-}C_6)$alkyl, —$(C_3\text{-}C_6)$cycloalkyl, and -(4- to 7-membered)heterocyclyl of said $R^2$ and $R^3$ may optionally be independently substituted by 1 to 3 $R^4$ groups;

$R^4$ is selected from the group consisting of halo, —OH, =O, —$(C_1\text{-}C_6)$alkyl, —$O(C_1\text{-}C_6)$alkyl, —$N(R^5)_2$, —C(O)—$R^5$, —$N(R^5)$—C(O)—$R^5$, —C(O)—$N(R^5)_2$, —$(C_3\text{-}C_6)$cycloalkyl optionally substituted by —C(O)—$(C_1\text{-}C_6)$alkyl, -(4- to 7-membered)heterocyclyl optionally substituted by —C(O)—$(C_1\text{-}C_6)$alkyl, and phenyl; and each $R^5$ is independently selected from the group consisting of —H, —$(C_1\text{-}C_6)$alkyl, —$(C_3\text{-}C_6)$cycloalkyl, and -(4- to 7-membered)heterocyclyl;

(b) a 4- to 9-membered N-heterocyclic ring, wherein said 4- to 9-membered N-heterocyclic ring is optionally independently substituted with one or more substituents selected from the group consisting of (i) 1 $G^1$ group or (ii) 1 to 3 $G^2$ groups; wherein $G^1$ is selected from the group consisting of -$L^4$-$(C_1\text{-}C_6)$alkyl, -$L^4$-$(C_3\text{-}C_6)$cycloalkyl, -$L^4$-$(C_3\text{-}C_6)$heterocyclyl, and -$L^4$-phenyl; wherein each of said —$(C_1\text{-}C_6)$alkyl, —$(C_3\text{-}C_6)$cycloalkyl, -(4- to 7-membered)heterocyclyl, and phenyl substituents may optionally be individually substituted by 1 to 4 $R^6$ groups;

$L^4$ is absent or selected from the group consisting of —O—, —C(O)—, —$N(R^7)$—, —C(O)—$N(R^7)$—, —$N(R^7)$—C(O)—, and —$N(R^7)$—$S(O)_j$—;

—$R^6$ is selected from the group consisting of halo, —OH, =O, —CN, —$(C_1\text{-}C_6)$alkyl, —$O(C_1\text{-}C_6)$alkyl, —$N(R^7)_2$, —C(O)—$R^7$, —C(O)—O—$R^7$, —$N(R^7)$—C(O)—$R^7$, —C(O)—$N(R^7)_2$, —$S(O)_j$—$R^7$, —$(C_3\text{-}C_6)$cycloalkyl, -(4- to 7-membered)heterocyclyl, and phenyl optionally substituted with —C(O)—O—$R^7$;

each $R^7$ is independently selected from the group consisting of —H, —$(C_1\text{-}C_6)$alkyl, —$(C_3\text{-}C_6)$cycloalkyl, and -(4- to 7-membered)heterocyclyl; and $G^2$ is independently selected from the group consisting of -halo, —OH, =O, —CN, —$O(C_1\text{-}C_6)$alkyl and —$(C_1\text{-}C_6)$alkyl optionally substituted with —$O(C_1\text{-}C_6)$alkyl; or (c) a group selected from the group consisting of a tetrahydro-2H-pyranyl, —C(O)—OH and OH;

wherein j is an integer selected from 0, 1 and 2.

2. The compound of claim 1, or a pharmaceutically acceptable salt thereof, wherein one of $A^1$ and $A^2$ is N and the other is CH.

3. The compound of claim 1, or a pharmaceutically acceptable salt thereof, wherein $A^2$ is N.

4. The compound of claim 1, or a pharmaceutically acceptable salt thereof, wherein $A^1$ and $A^2$ are each CH.

5. The compound of claim 1, or a pharmaceutically acceptable salt thereof, wherein $A^1$ and $A^2$ are each N.

6. The compound of claim 1, or a pharmaceutically acceptable salt thereof, wherein ring B is selected from the group consisting of B-1, B-2, B-3, B-4, B-5 and B-6.

7. The compound of claim 1, or a pharmaceutically acceptable salt thereof, wherein $R^1$ is a group of formula —$N(R^2)(R^3)$, wherein $R^2$ and $R^3$ are each independently selected from the group consisting of —H, —$(C_1\text{-}C_6)$alkyl, —$(C_3\text{-}C_6)$cycloalkyl, and -(4- to 7-membered)heterocyclyl, wherein each of said —$(C_1\text{-}C_6)$alkyl, —$(C_3\text{-}C_6)$cycloalkyl, and -(4- to 7-membered)heterocyclyl of said $R^2$ and $R^3$ may optionally be independently substituted by 1 to 3 $R^4$ groups;

$R^4$ is selected from the group consisting of halo, —OH, =O, —$(C_1$-$C_6)$alkyl), —$O(C_1$-$C_6)$alkyl), —$N(R^5)_2$, —C(O)—$R^5$, —$N(R^5)$—C(O)—$R^5$, —C(O)—$N(R^5)_2$, —$(C_3$-$C_6)$cycloalkyl optionally substituted by —C(O)—$(C_1$-$C_6)$alkyl), -(4- to 7-membered)heterocyclyl optionally substituted by —C(O)—$(C_1$-$C_6)$alkyl), and phenyl; and each $R^5$ is independently selected from the group consisting of —H, —$(C_1$-$C_6)$alkyl, —$(C_3$-$C_6)$cycloalkyl, and -(4- to 7-membered)heterocyclyl.

8. The compound of claim 1, or a pharmaceutically acceptable salt thereof, wherein $R^1$ is selected from the group consisting of —$N(H)((C_1$-$C_6)$alkyl), —$N((C_1$-$C_6)$alkyl$)_2$, —N(H)((4- to 7-membered)heterocyclyl) and —$N((C_1$-$C_6)$ alkyl)((4- to 7-membered)heterocyclyl); wherein each of said —$(C_1$-$C_6)$alkyl groups may optionally be independently substituted by one to three groups independently selected from the group consisting of —OH, =O, —$O(C_1$-$C_6)$alkyl), —$NH_2$, -(4- to 7-membered)heterocyclyl, and phenyl.

9. The compound of claim 1, or a pharmaceutically acceptable salt thereof, wherein $R^1$ is a 4- to 9-membered N-heterocyclic ring optionally independently substituted by (a) 1 $G^1$ group as defined in claim 1 or (b) 1 to 3 $G^2$ groups as defined in claim 1.

10. The compound of claim 9, or a pharmaceutically acceptable salt thereof, wherein said 4- to 9-membered N-heterocyclic ring is a nonaromatic 4- to 7-membered monocyclic heterocyclic radical selected from the group consisting of azetidinyl, pyrrolidinyl, oxazolidinyl, piperazinyl, piperidinyl, morpholinyl, thiomorpholinyl, azepanyl, 1,4-diazepanyl and 1,4-oxazepanyl; wherein each of said nonaromatic 4- to 7-membered monocyclic heterocyclic radicals is optionally substituted by (a) 1 $G^1$ group or (b) 1 to 3 $G^2$ groups.

11. A compound selected from the group consisting of:

2-Methoxy-1-(4-{6-[5-(2H-pyrazol-3-yl)-pyridin-2-yloxy]-naphthalen-2-ylmethyl}-piperazin-1-yl)-ethanone;

1-(4-{6-[5-(2H-Pyrazol-3-yl)-pyridin-2-yloxy]-naphthalen-2-ylmethyl}-piperazin-1-yl)-ethanone;

5-(2H-Pyrazol-3-yl)-2-(6-pyrrolidin-1-ylmethyl-naphthalen-2-yloxy)-pyridine;

1-{6-[5-(2H-Pyrazol-3-yl)-pyridin-2-yloxy]-naphthalen-2-ylmethyl}-piperidin-4-ol;

1-{6-[5-(2H-Pyrazol-3-yl)-pyridin-2-yloxy]-naphthalen-2-ylmethyl}-piperidine-4-carboxylic acid amide;

N-(1-{6-[5-(2H-Pyrazol-3-yl)-pyridin-2-yloxy]-naphthalen-2-ylmethyl}-piperidin-4-yl)-acetamide;

(S)-3-Hydroxy-1-(1-{6-[5-(2H-pyrazol-3-yl)-pyridin-2-yloxy]-naphthalen-2-ylmethyl}-piperidin-4-yl)-pyrrolidin-2-one;

Dimethyl-{6-[4-(2H-pyrazol-3-yl)-phenoxy]-chroman-2-ylmethyl}-amine;

1-{7-[5-(2H-Pyrazol-3-yl)-pyridin-2-yloxy]-chroman-2-ylmethyl}-piperidine-4-carboxylic acid amide;

2-Hydroxy-1-(4-{6-[4-(2H-pyrazol-3-yl)-phenoxy]-quinolin-2-ylmethyl}-piperazin-1-yl)-ethanone;

3-(1-{6-[5-(2H-Pyrazol-3-yl)-pyridin-2-yloxy]-quinolin-2-ylmethyl}-piperidin-4-yl)-oxazolidin-2-one;

1-(4-{6-[4-(2H-Pyrazol-3-yl)-phenoxy]-quinolin-2-ylmethyl}-piperazin-1-yl)-propan-1-one;

(S)-2-Hydroxy-1-(4-{6-[4-(2H-pyrazol-3-yl)-phenoxy]-quinolin-2-ylmethyl}-piperazin-1-yl)-propan-1-one;

2-Morpholin-4-ylmethyl-6-[4-(2H-pyrazol-3-yl)-phenoxy]-pyrazolo[1,5-a]pyridine;

(1-Hydroxy-cyclopropyl)-(4-{6-[4-(2H-pyrazol-3-yl)-phenoxy]-quinolin-2-ylmethyl}-piperazin-1-yl)-methanone;

(S)-7-{6-[5-(2H-Pyrazol-3-yl)-pyridin-2-yloxy]-quinolin-2-ylmethyl}-hexahydro-oxazolo[3,4-a]pyrazin-3-one;

2-(2,2-Dioxo-2-λ-6-thia-5-aza-bicyclo[2.2.1]hept-5-ylmethyl)-6-[4-(2H-pyrazol-3-yl)-phenoxy]-quinoline;

2-{6-[5-(2H-Pyrazol-3-yl)-pyridin-2-yloxy]-quinolin-2-ylmethyl}-hexahydro-pyrrolo[1,2-a]pyrazin-6-one;

6-[5-(2H-Pyrazol-3-yl)-pyridin-2-yloxy]-2-pyrrolidin-1-ylmethyl-quinoline;

2-(2-Oxa-6-aza-spiro[3.4]oct-6-ylmethyl)-6-[5-(2H-pyrazol-3-yl)-pyridin-2-yloxy]-quinoline;

2-Azetidin-1-ylmethyl-6-[5-(2H-pyrazol-3-yl)-pyridin-2-yloxy]-quinoline;

2-Azepan-1-ylmethyl-6-[5-(2H-pyrazol-3-yl)-pyridin-2-yloxy]-quinoline;

2-Piperidin-1-ylmethyl-6-[5-(2H-pyrazol-3-yl)-pyridin-2-yloxy]-quinoline;

1-(8-{6-[5-(2H-Pyrazol-3-yl)-pyridin-2-yloxy]-quinolin-2-ylmethyl}-3,8-diaza-bicyclo[3.2.1]oct-3-yl)-ethanone;

Methyl-{6-[5-(2H-pyrazol-3-yl)-pyridin-2-yloxy]-quinolin-2-ylmethyl}-amine;

2-Methyl-1-(4-{6-[5-(2H-pyrazol-3-yl)-pyridin-2-yloxy]-quinolin-2-ylmethyl}-piperazin-1-yl)-propan-1-one;

2-Hydroxy-1-(4-{6-[5-(2H-pyrazol-3-yl)-pyridin-2-yloxy]-quinolin-2-ylmethyl}-piperazin-1-yl)-ethanone;

2-Methoxy-1-(4-{6-[5-(2H-pyrazol-3-yl)-pyridin-2-yloxy]-quinolin-2-ylmethyl}-piperazin-1-yl)-ethanone;

1-(4-{6-[5-(2H-Pyrazol-3-yl)-pyridin-2-yloxy]-quinolin-2-ylmethyl}-piperazin-1-yl)-propan-1-one;

8-{6-[5-(2H-Pyrazol-3-yl)-pyridin-2-yloxy]-quinolin-2-ylmethyl}-1,8-diaza-spiro[4.5]decan-2-one;

3-Oxo-3-(4-{6-[5-(2H-pyrazol-3-yl)-pyridin-2-yloxy]-quinolin-2-ylmethyl}-piperazin-1-yl)-propionitrile;

1-(5-{6-[5-(2H-Pyrazol-3-yl)-pyridin-2-yloxy]-quinolin-2-ylmethyl}-hexahydro-pyrrolo[3,4-c]pyrrol-2-yl)-ethanone;

2-Hydroxy-N-methyl-N-(1-{6-[5-(2H-pyrazol-3-yl)-pyridin-2-yloxy]-quinolin-2-ylmethyl}-piperidin-4-yl)-acetamide;

(R)-2-({6-[5-(2H-Pyrazol-3-yl)-pyridin-2-yloxy]-quinolin-2-ylmethyl}-amino)-propionamide;

(1α,5α,6α)-3-{6-[5-(2H-Pyrazol-3-yl)-pyridin-2-yloxy]-quinolin-2-ylmethyl}-3-aza-bicyclo[3.1.0]hexane-6-carboxylic acid amide;

1-{3-[(Methyl-{6-[5-(2H-pyrazol-3-yl)-pyridin-2-yloxy]-quinolin-2-ylmethyl}-amino)-methyl]-azetidin-1-yl}-ethanone;

N-Methyl-N-(1-{6-[5-(2H-pyrazol-3-yl)-pyridin-2-yloxy]-quinolin-2-ylmethyl}-piperidin-4-yl)-acetamide;

2-Hydroxy-1-((R)-3-methyl-4-{6-[5-(2H-pyrazol-3-yl)-pyridin-2-yloxy]-quinolin-2-ylmethyl}-piperazin-1-yl)-ethanone;

2-Methanesulfonyl-1-(4-{6-[5-(2H-pyrazol-3-yl)-pyridin-2-yloxy]-quinolin-2-ylmethyl}-piperazin-1-yl)-ethanone;

(1α,5α,6α)-3-{6-[5-(2H-Pyrazol-3-yl)-pyridin-2-yloxy]-quinolin-2-ylmethyl}-3-aza-bicyclo[3.1.0]hexane-6-carboxylic acid (2-hydroxy-2-methyl-propyl)-amide;

N-((1α,5α,6α)-3-{6-[5-(2H-Pyrazol-3-yl)-pyridin-2-yloxy]-quinolin-2-ylmethyl}-3-aza-bicyclo[3.1.0]hex-6-ylmethyl)-acetamide;

1-((S)-3-Hydroxymethyl-4-{6-[5-(2H-pyrazol-3-yl)-pyridin-2-yloxy]-quinolin-2-ylmethyl}-piperazin-1-yl)-ethanone;

4-{6-[5-(2H-Pyrazol-3-yl)-pyridin-2-yloxy]-quinolin-2-ylmethyl}-piperazine-1-carboxylic acid amide;

2-Hydroxy-1-(3-{6-[5-(2H-pyrazol-3-yl)-pyridin-2-yloxy]-quinolin-2-ylmethyl}-3,8-diaza-bicyclo[3.2.1]oct-8-yl)-ethanone;

2-({6-[5-(2H-Pyrazol-3-yl)-pyridin-2-yloxy]-quinolin-2-ylmethyl}-amino)-1-pyrrolidin-1-yl-ethanone;

2-Hydroxy-N-(4-methyl-1-{6-[5-(2H-pyrazol-3-yl)-pyridin-2-yloxy]-quinolin-2-ylmethyl}-piperidin-4-yl)-acetamide;

2-(Methyl-{6-[5-(2H-pyrazol-3-yl)-pyridin-2-yloxy]-quinolin-2-ylmethyl}-amino)-acetamide;

2-(2-Oxa-6-aza-spiro[3.5]non-6-ylmethyl)-6-[5-(2H-pyrazol-3-yl)-pyridin-2-yloxy]-quinoline;

(S)-3-({6-[5-(2H-Pyrazol-3-yl)-pyridin-2-yloxy]-quinolin-2-ylmethyl}-amino)-pyrrolidin-2-one;

2-Hydroxy-1-(8-{6-[5-(2H-pyrazol-3-yl)-pyridin-2-yloxy]-quinolin-2-ylmethyl}-1,8-diaza-spiro[4.5]dec-1-yl)-ethanone;

(S)-2-Phenyl-2-({6-[5-(2H-pyrazol-3-yl)-pyridin-2-yloxy]-quinolin-2-ylmethyl}-amino)-acetamide;

5-[4-(2H-Pyrazol-3-yl)-phenoxy]-2-pyrrolidin-1-ylmethyl-1H-benzoimidazole;

2-((2R,6S)-2,6-Dimethyl-morpholin-4-ylmethyl)-5-[4-(2H-pyrazol-3-yl)-phenoxy]-1H-benzoimidazole;

6-[4-(2H-Pyrazol-3-yl)-benzyl]-2-pyrrolidin-1-ylmethyl-1H-benzoimidazole;

2-((3S,5S)-3,5-Dimethyl-morpholin-4-ylmethyl)-5-[4-(2H-pyrazol-3-yl)-phenoxy]-1H-benzoimidazole;

2-((2S,6S)-2,6-Dimethyl-morpholin-4-ylmethyl)-6-[4-(2H-pyrazol-3-yl)-benzyl]-1H-benzoimidazole;

2,2,2-Trifluoro-1-(4-{5-[4-(2H-pyrazol-3-yl)-phenoxy]-1H-benzoimidazol-2-ylmethyl}-piperazin-1-yl)-ethanone;

(1S,5S)-3-{5-[4-(2H-Pyrazol-3-yl)-phenoxy]-1H-benzoimidazol-2-ylmethyl}-8-oxa-3-aza-bicyclo[3.2.1]octane;

2-(1-Morpholin-4-yl-cyclopropyl)-5-[4-(2H-pyrazol-3-yl)-phenoxy]-1H-benzoimidazole;

2-Morpholin-4-ylmethyl-6-[4-(2H-pyrazol-3-yl)-benzyl]-1H-benzoimidazole;

2-[4-(2-Methoxy-ethyl)-piperazin-1-ylmethyl]-5-[4-(2H-pyrazol-3-yl)-phenoxy]-1H-benzoimidazole;

2-((S)-3-Methyl-morpholin-4-ylmethyl)-5-[4-(2H-pyrazol-3-yl)-phenoxy]-1H-benzoimidazole;

5-[4-(2H-Pyrazol-3-yl)-phenoxy]-2-[4-(2,2,2-trifluoro-ethyl)-piperazin-1-ylmethyl]-1H-benzoimidazole;

2-(4-Isopropyl-piperazin-1-ylmethyl)-5-[4-(2H-pyrazol-3-yl)-phenoxy]-1H-benzoimidazole;

2-[4-(3-Methyl-[1,2,4]oxadiazol-5-yl)-piperidin-1-ylmethyl]-5-[4-(2H-pyrazol-3-yl)-phenoxy]-1H-benzoimidazole;

(S)-1-{6-[4-(2H-Pyrazol-3-yl)-phenoxy]-1H-benzoimidazol-2-ylmethyl}-pyrrolidin-3-ol;

5-{6-[4-(2H-Pyrazol-3-yl)-phenoxy]-imidazo[1,2-a]pyridin-2-yl}-piperidin-2-one;

(S)-5-{6-[4-(2H-Pyrazol-3-yl)-phenoxy]-quinolin-2-yloxy}-piperidin-2-one;

5-[4-(1H-Pyrazol-3-yl)-phenoxy]-1H-benzoimidazole-2-carboxylic acid;

2,2-Dimethyl-1-(4-{5-[4-(2H-pyrazol-3-yl)-phenoxy]-1H-benzoimidazol-2-ylmethyl}-piperazin-1-yl)-propan-1-one;

2,2,2-Trifluoro-1-(1-{5-[4-(2H-pyrazol-3-yl)-phenoxy]-1H-benzoimidazol-2-ylmethyl}-piperidin-4-yl)-ethanol;

2-(2-Oxa-6-aza-spiro[3.3]hept-6-ylmethyl)-5-[4-(2H-pyrazol-3-yl)-phenoxy]-1H-benzoimidazole;

5-[4-(2H-Pyrazol-3-yl)-phenoxy]-2-pyridin-3-ylmethyl-1H-benzoimidazole;

((S)-sec-Butyl)-methyl-{5-[4-(2H-pyrazol-3-yl)-phenoxy]-1H-benzoimidazol-2-ylmethyl}-amine;

5-[4-(2H-Pyrazol-3-yl)-phenoxy]-1-(2-pyrrolidin-1-yl-ethyl)-1H-indazole;

Methyl-{5-[4-(2H-pyrazol-3-yl)-phenoxy]-1H-benzoimidazol-2-ylmethyl}-[(S)-1-(tetrahydro-furan-2-yl)methyl]-amine;

Methyl-{5-[4-(2H-pyrazol-3-yl)-phenoxy]-1H-benzoimidazol-2-ylmethyl}-(S)-tetrahydro-furan-3-yl-amine;

Methyl-{5-[4-(2H-pyrazol-3-yl)-phenoxy]-1H-benzoimidazol-2-ylmethyl}-(R)-tetrahydro-furan-3-yl-amine;

5-[4-(2H-Pyrazol-3-yl)-phenoxy]-1-(3-pyrrolidin-1-yl-propyl)-1H-indazole;

((R)-sec-Butyl)-methyl-{5-[4-(2H-pyrazol-3-yl)-phenoxy]-1H-benzoimidazol-2-ylmethyl}-amine;

Methyl-{5-[4-(2H-pyrazol-3-yl)-phenoxy]-1H-benzoimidazol-2-ylmethyl}-[(R)-1-(tetrahydro-furan-2-yl)methyl]-amine;

((S)-2-Methoxy-1-methyl-ethyl)-methyl-{5-[4-(2H-pyrazol-3-yl)-phenoxy]-1H-benzoimidazol-2-ylmethyl}-amine;

5-[5-(2H-Pyrazol-3-yl)-pyridin-2-yloxy]-1-(2-pyrrolidin-1-yl-ethyl)-1H-indazole;

2-(3-Morpholin-4-yl-propyl)-5-[4-(2H-pyrazol-3-yl)-phenoxy]-2H-indazole;

Methyl-{5-[4-(2H-pyrazol-3-yl)-phenoxy]-1H-benzoimidazol-2-ylmethyl}-(tetrahydro-furan-2-ylmethyl)-amine;

Ethyl-((S)-2-methoxy-1-methyl-ethyl)-{5-[4-(2H-pyrazol-3-yl)-phenoxy]-1H-benzoimidazol-2-ylmethyl}-amine;

[1,4]Dioxan-2-ylmethyl-methyl-{5-[4-(2H-pyrazol-3-yl)-phenoxy]-1H-benzoimidazol-2-ylmethyl}-amine;

N-[1-(2-{5-[4-(2H-Pyrazol-3-yl)-phenoxy]-indazol-1-yl}-ethyl)-piperidin-4-yl]-acetamide;

2-((S)-1-Methyl-pyrrolidin-2-ylmethyl)-5-[4-(2H-pyrazol-3-yl)-phenoxy]-1H-benzoimidazole;

1-[4-(2-{5-[4-(2H-Pyrazol-3-yl)-phenoxy]-indazol-1-yl}-ethyl)-piperazin-1-yl]-ethanone;

(2-Methoxy-ethyl)-{5-[4-(2H-pyrazol-3-yl)-phenoxy]-1H-benzoimidazol-2-ylmethyl}-amine;

Methyl-{5-[4-(2H-pyrazol-3-yl)-phenoxy]-1H-benzoimidazol-2-ylmethyl}-(tetrahydro-pyran-3-ylmethyl)-amine;

1-[4-(2-{5-[4-(2H-Pyrazol-3-yl)-phenoxy]-indazol-2-yl}-ethyl)-piperazin-1-yl]-ethanone;

1-[4-(2-{5-[5-(2H-Pyrazol-3-yl)-pyridin-2-yloxy]-indazol-1-yl}-ethyl)-piperazin-1-yl]-ethanone;

1-[4-(3-{5-[4-(2H-Pyrazol-3-yl)-phenoxy]-indazol-2-yl}-propyl)-piperazin-1-yl]-ethanone;

(1-{6-[5-(2H-Pyrazol-3-yl)-pyridin-2-yloxy]-quinolin-2-ylmethyl}-piperidin-4-yl)-acetonitrile;

{5-[4-(2H-Pyrazol-3-yl)-phenoxy]-1H-benzoimidazol-2-ylmethyl}-(tetrahydro-furan-2-ylmethyl)-amine;

5-[4-(2H-Pyrazol-3-yl)-phenoxy]-2-thiomorpholin-4-ylmethyl-1H-benzoimidazole;

1-{6-[5-(2H-Pyrazol-3-yl)-pyridin-2-yloxy]-quinolin-2-ylmethyl}-piperidine-4-carbonitrile;

{5-[4-(2H-Pyrazol-3-yl)-phenoxy]-1H-benzoimidazol-2-ylmethyl}-[(S)-1-(tetrahydro-furan-2-yl)methyl]-amine;

{5-[4-(2H-Pyrazol-3-yl)-phenoxy]-1H-benzoimidazol-2-ylmethyl}-[(R)-1-(tetrahydro-furan-2-yl)methyl]-amine;

1-(2-Morpholin-4-yl-ethyl)-5-[4-(2H-pyrazol-3-yl)-phenoxy]-1H-indazole;

N—((S)-sec-Butyl)-N-{5-[4-(2H-pyrazol-3-yl)-phenoxy]-1H-benzoimidazol-2-ylmethyl}-acetamide;

Methyl-{5-[4-(2H-pyrazol-3-yl)-phenoxy]-1H-benzoimidazol-2-ylmethyl}-(tetrahydro-furan-3-ylmethyl)-amine;

5-[4-(2H-Pyrazol-3-yl)-phenoxy]-2-(3-pyrrolidin-1-yl-propyl)-2H-indazole;

{5-[4-(2H-Pyrazol-3-yl)-phenoxy]-1H-benzoimidazol-2-ylmethyl}-(tetrahydro-pyran-4-ylmethyl)-amine;

(R)-1-{6-[5-(2H-Pyrazol-3-yl)-pyridin-2-yloxy]-quinolin-2-ylmethyl}-pyrrolidine-3-carbonitrile;

1-[4-(2-{6-[5-(2H-Pyrazol-3-yl)-pyridin-2-yloxy]-quinolin-2-yl}-ethyl)-piperazin-1-yl]-ethanone;

N-[1-(3-{5-[4-(2H-Pyrazol-3-yl)-phenoxy]-indazol-1-yl}-propyl)-piperidin-4-yl]-acetamide;

1-[4-(Methyl-{6-[5-(2H-pyrazol-3-yl)-pyridin-2-yloxy]-quinolin-2-ylmethyl}-amino)-piperidin-1-yl]-ethanone;

1-(2-Morpholin-4-yl-ethyl)-5-[5-(2H-pyrazol-3-yl)-pyridin-2-yloxy]-1H-indazole;

2-Hydroxy-2-methyl-N-[1-(2-{5-[5-(2H-pyrazol-3-yl)-pyridin-2-yloxy]-indazol-2-yl}-ethyl)-piperidin-4-yl]-propionamide;

3-Morpholin-4-ylmethyl-6-[5-(2H-pyrazol-3-yl)-pyridin-2-yloxy]-1H-indazole;

2-Morpholin-4-ylmethyl-6-[4-(2H-pyrazol-3-yl)-phenoxy]-benzooxazole;

1-(4-{6-[5-(2H-Pyrazol-3-yl)-pyridin-2-yloxy]-quinolin-2-yl}-piperazin-1-yl)-ethanone;

N-[1-(3-{5-[4-(2H-Pyrazol-3-yl)-phenoxy]-indazol-2-yl}-propyl)-piperidin-4-yl]-acetamide;

(S)-5-{5-[5-(2H-Pyrazol-3-yl)-pyridin-2-yloxy]-indazol-1-ylmethyl}-pyrrolidin-2-one;

3-{5-[4-(2H-Pyrazol-3-yl)-phenoxy]-indazol-1-yl}-propan-1-ol;

(S)-5-{6-[4-(2H-Pyrazol-3-yl)-phenoxy]-isoquinolin-1-yloxymethyl}-pyrrolidin-2-one;

2-(2-Morpholin-4-yl-ethoxy)-6-[5-(2H-pyrazol-3-yl)-pyridin-2-yloxy]-quinoline;

N-[2-({6-[5-(2H-Pyrazol-3-yl)-pyridin-2-yloxy]-quinolin-2-ylmethyl}-amino)-ethyl]-acetamide;

(2-Methoxy-ethyl)-methyl-{6-[5-(2H-pyrazol-3-yl)-pyridin-2-yloxy]-quinolin-2-ylmethyl}-amine;

Dimethyl-{6-[4-(2H-pyrazol-3-yl)-phenoxy]-quinolin-2-ylmethyl}-amine;

4-(1-{1-[4-(2H-Pyrazol-3-yl)-benzyl]-1H-indol-5-ylmethyl}-piperidin-4-yl)-benzoic acid;

N-(1-{6-[5-(2H-Pyrazol-3-yl)-pyridin-2-yloxy]-2,3-dihydro-benzofuran-2-ylmethyl}-piperidin-4-yl)-acetamide;

5-(2H-Pyrazol-3-yl)-2-(2-pyrrolidin-1-ylmethyl-2, 3-dihydro-benzofuran-6-yloxy)-pyridine;

5-(2H-Pyrazol-3-yl)-2-(2-pyrrolidin-1-ylmethyl-benzofuran-6-yloxy)-pyridine;

N-(1-{6-[5-(2H-Pyrazol-3-yl)-pyridin-2-yloxy]-2,3-dihydro-benzofuran-2-ylmethyl}-piperidin-4-ylmethyl)-acetamide;

1-(1-{6-[5-(2H-Pyrazol-3-yl)-pyridin-2-yloxy]-2,3-dihydro-benzofuran-2-ylmethyl}-piperidin-4-yl)-pyrrolidin-2-one;

3-[1-(2-{6-[5-(2H-Pyrazol-3-yl)-pyridin-2-yloxy]-benzofuran-3-yl}-ethyl)-piperidin-4-yl]-oxazolidin-2-one;

N-((endo)-8-{6-[4-(2H-Pyrazol-3-yl)-phenoxy]-2, 3-dihydro-benzofuran-2-ylmethyl}-8-aza-bicyclo[3.2.1]oct-3-yl)-acetamide;

2-Hydroxy-1-(8-{6-[5-(2H-pyrazol-3-yl)-pyridin-2-yloxy]-quinolin-2-ylmethyl}-3,8-diaza-bicyclo[3.2.1]oct-3-yl)-ethanone;

N-[1-(2-{6-[5-(2H-Pyrazol-3-yl)-pyridin-2-yloxy]-benzofuran-3-yl}-ethyl)-piperidin-4-yl]-acetamide;

1-[4-(2-{6-[5-(2H-Pyrazol-3-yl)-pyridin-2-yloxy]-benzofuran-3-yl}-ethyl)-[1,4]diazepan-1-yl]-ethanone;

1-[4-(2-{6-[5-(2H-Pyrazol-3-yl)-pyridin-2-yloxy]-2,3-dihydro-benzofuran-3-yl}-ethyl)-[1,4]diazepan-1-yl]-ethanone;

1-[4-(2-{6-[5-(2H-Pyrazol-3-yl)-pyridin-2-yloxy]-benzofuran-3-yl}-ethyl)-piperazin-1-yl]-ethanone;

1-{6-[4-(2H-Pyrazol-3-yl)-phenoxy]-2,3-dihydro-benzofuran-2-ylmethyl}-piperidine-4-carboxylic acid methylamide;

1-(2-{6-[5-(2H-Pyrazol-3-yl)-pyridin-2-yloxy]-benzofuran-3-yl}-ethyl)-piperidine-4-carboxylic acid methylamide;

2-Hydroxy-1-((1S,4S)-5-{6-[5-(2H-pyrazol-3-yl)-pyridin-2-yloxy]-quinolin-2-ylmethyl}-2,5-diaza-bicyclo[2.2.1]hept-2-yl)-ethanone;

2-Hydroxy-1-(4-{6-[5-(2H-pyrazol-3-yl)-pyridin-2-yloxy]-quinolin-2-ylmethyl}-[1,4]diazepan-1-yl)-ethanone;

N-[1-(2-{6-[5-(2H-Pyrazol-3-yl)-pyridin-2-yloxy]-benzofuran-3-yl}-ethyl)-piperidin-4-yl]-methanesulfonamide;

N-((exo)-8-{6-[4-(2H-Pyrazol-3-yl)-phenoxy]-2,3-dihydro-benzofuran-2-ylmethyl}-8-aza-bicyclo[3.2.1]oct-3-yl)-acetamide;

1-[4-(2-{6-[5-(2H-Pyrazol-3-yl)-pyridin-2-yloxy]-2,3-dihydro-benzofuran-3-yl}-ethyl)-piperazin-1-yl]-ethanone;

1-{6-[4-(2H-Pyrazol-3-yl)-phenoxy]-2,3-dihydro-benzofuran-2-ylmethyl}-piperidine-4-carboxylic acid amide;

2-Hydroxy-1-((1R,4R)-5-{6-[5-(2H-pyrazol-3-yl)-pyridin-2-yloxy]-quinolin-2-ylmethyl}-2,5-diaza-bicyclo[2.2.1]hept-2-yl)-ethanone;

2-Hydroxy-1-(5-{6-[5-(2H-pyrazol-3-yl)-pyridin-2-yloxy]-quinolin-2-ylmethyl}-2,5-diaza-bicyclo[2.2.2]oct-2-yl)-ethanone;

1-((1R,4R)-5-{6-[5-(2H-Pyrazol-3-yl)-pyridin-2-yloxy]-quinolin-2-ylmethyl}-2,5-diaza-bicyclo[2.2.1]hept-2-yl)-ethanone;

1-(5-{6-[5-(2H-Pyrazol-3-yl)-pyridin-2-yloxy]-quinolin-2-ylmethyl}-2,5-diaza-bicyclo[2.2.2]oct-2-yl)-ethanone;

1-(4-{6-[5-(2H-Pyrazol-3-yl)-pyridin-2-yloxy]-benzofuran-3-ylmethyl}-piperazin-1-yl)-ethanone;

4-((1S,4S)-5-{5-[4-(2H-Pyrazol-3-yl)-phenoxy]-1H-benzoimidazol-2-ylmethyl}-2,5-diaza-bicyclo[2.2.1]hept-2-ylmethyl)-benzoic acid methyl ester;

4-(1-{5-[4-(2H-Pyrazol-3-yl)-phenoxy]-1H-benzoimidazol-2-ylmethyl}-piperidin-4-yl)-benzoic acid methyl ester;

Diethyl-{5-[4-(2H-pyrazol-3-yl)-phenoxy]-1H-benzoimidazol-2-ylmethyl}-amine;

2-(4-Methyl-piperidin-1-ylmethyl)-5-[4-(2H-pyrazol-3-yl)-phenoxy]-1H-benzoimidazole;

Ethyl-methyl-(2-{5-[4-(2H-pyrazol-3-yl)-phenoxy]-indazol-2-yl}-ethyl)-amine;

Ethyl-(2-methoxy-ethyl)-{5-[4-(2H-pyrazol-3-yl)-phenoxy]-1H-benzoimidazol-2-ylmethyl}-amine;

2-(3-Methoxymethyl-piperidin-1-ylmethyl)-5-[4-(2H-pyrazol-3-yl)-phenoxy]-1H-benzoimidazole;

2-(3-Methoxy-pyrrolidin-1-ylmethyl)-5-[4-(2H-pyrazol-3-yl)-phenoxy]-1H-benzoimidazole;

Dimethyl-(2-{5-[4-(2H-pyrazol-3-yl)-phenoxy]-indazol-2-yl}-ethyl)-amine;

Methyl-{5-[4-(2H-pyrazol-3-yl)-phenoxy]-1H-benzoimidazol-2-ylmethyl}-(tetrahydro-pyran-4-ylmethyl)-amine;

N—[(R)-1-(2-{5-[4-(2H-Pyrazol-3-yl)-phenoxy]-indazol-1-yl}-ethyl)-pyrrolidin-3-yl]-acetamide;

((S)-sec-Butyl)-{5-[4-(2H-pyrazol-3-yl)-phenoxy]-1H-benzoimidazol-2-ylmethyl}-amine;

Dimethyl-(2-{5-[4-(2H-pyrazol-3-yl)-phenoxy]-indazol-1-yl}-ethyl)-amine;

2-Azepan-1-ylmethyl-5-[4-(2H-pyrazol-3-yl)-phenoxy]-1H-benzoimidazole;

Cyclopentyl-methyl-{5-[4-(2H-pyrazol-3-yl)-phenoxy]-1H-benzoimidazol-2-ylmethyl}-amine;

2-((R)-2-Methyl-piperidin-1-ylmethyl)-5-[4-(2H-pyrazol-3-yl)-phenoxy]-1H-benzoimidazole;

2-(3-Methoxymethyl-pyrrolidin-1-ylmethyl)-5-[4-(2H-pyrazol-3-yl)-phenoxy]-1H-benzoimidazole;

2-((R)-2-Methoxymethyl-pyrrolidin-1-ylmethyl)-5-[4-(2H-pyrazol-3-yl)-phenoxy]-1H-benzoimidazole;

2-(2-Methoxymethyl-piperidin-1-ylmethyl)-5-[4-(2H-pyrazol-3-yl)-phenoxy]-1H-benzoimidazole;

N,N-Dimethyl-2-(1-{6-[4-(2H-pyrazol-3-yl)-phenoxy]-2,3-dihydro-benzofuran-2-ylmethyl}-piperidin-4-yl)-acetamide;

2-Methoxy-N-(1-{6-[4-(2H-pyrazol-3-yl)-phenoxy]-2,3-dihydro-benzofuran-2-ylmethyl}-piperidin-4-yl)-acetamide;

2-((S)-2-Methyl-piperidin-1-ylmethyl)-5-[4-(2H-pyrazol-3-yl)-phenoxy]-1H-benzoimidazole;

2-(3-Methoxy-piperidin-1-ylmethyl)-5-[4-(2H-pyrazol-3-yl)-phenoxy]-1H-benzoimidazole;

2-((S)-2-Methoxymethyl-pyrrolidin-1-ylmethyl)-5-[4-(2H-pyrazol-3-yl)-phenoxy]-1H-benzoimidazole;

3-Methyl-1-{6-[5-(2H-pyrazol-3-yl)-pyridin-2-yloxy]-quinolin-2-ylmethyl}-azetidin-3-ol;

2-[1,4]Oxazepan-4-ylmethyl-5-[4-(2H-pyrazol-3-yl)-phenoxy]-1H-benzoimidazole;

2-[2-(1,1-Dioxo-1-λ-6-thiomorpholin-4-yl)-ethyl]-5-[4-(2H-pyrazol-3-yl)-phenoxy]-2H-indazole;

1-[1-(2-{5-[4-(2H-Pyrazol-3-yl)-phenoxy]-indazol-1-yl}-ethyl)-piperidin-4-yl]-pyrrolidin-2-one;

2-[(1S,4S)-1-(2-Oxa-5-aza-bicyclo[2.2.1]hept-5-yl)methyl]-6-[5-(2H-pyrazol-3-yl)-pyridin-2-yloxy]-quinoline;

Cyclopropyl-methyl-{5-[4-(2H-pyrazol-3-yl)-phenoxy]-1H-benzoimidazol-2-ylmethyl}-amine;

((R)-sec-Butyl)-{5-[4-(2H-pyrazol-3-yl)-phenoxy]-1H-benzoimidazol-2-ylmethyl}-amine;

{5-[4-(2H-Pyrazol-3-yl)-phenoxy]-1H-benzoimidazol-2-ylmethyl}-(tetrahydro-pyran-3-yl)-amine;

2-(3,3-Dimethyl-morpholin-4-ylmethyl)-5-[4-(2H-pyrazol-3-yl)-phenoxy]-1H-benzoimidazole;

Isopropyl-(2-methoxy-ethyl)-{5-[4-(2H-pyrazol-3-yl)-phenoxy]-1H-benzoimidazol-2-ylmethyl}-amine;

(2-Methoxy-ethyl)-propyl-{5-[4-(2H-pyrazol-3-yl)-phenoxy]-1H-benzoimidazol-2-ylmethyl}-amine;

{6-[4-(2H-Pyrazol-3-yl)-phenoxy]-2,3-dihydro-benzofuran-2-ylmethyl}-(tetrahydro-pyran-4-ylmethyl)-amine;

Bis-(2-methoxy-ethyl)-{5-[4-(2H-pyrazol-3-yl)-phenoxy]-1H-benzoimidazol-2-ylmethyl}-amine;

Morpholin-4-yl-(1-{6-[4-(2H-pyrazol-3-yl)-phenoxy]-2,3-dihydro-benzofuran-2-ylmethyl}-piperidin-4-yl)-methanone;

Cyclopentyl-{5-[4-(2H-pyrazol-3-yl)-phenoxy]-1H-benzoimidazol-2-ylmethyl}-amine;

((S)-2-Methoxy-1-methyl-ethyl)-{5-[4-(2H-pyrazol-3-yl)-phenoxy]-1H-benzoimidazol-2-ylmethyl}-amine;

3-(1-{6-[5-(2H-Pyrazol-3-yl)-pyridin-2-yloxy]-quinolin-2-ylmethyl}-piperidin-4-yl)-[1,3]oxazinan-2-one;

Ethyl-{5-[4-(2H-pyrazol-3-yl)-phenoxy]-1H-benzoimidazol-2-ylmethyl}-amine;

2-(Ethyl-{5-[4-(2H-pyrazol-3-yl)-phenoxy]-1H-benzoimidazol-2-ylmethyl}-amino)-ethanol;

2-(4-Ethoxymethyl-piperidin-1-ylmethyl)-5-[4-(2H-pyrazol-3-yl)-phenoxy]-1H-benzoimidazole;

{5-[4-(2H-Pyrazol-3-yl)-phenoxy]-1H-benzoimidazol-2-ylmethyl}-(S)-tetrahydro-furan-3-yl-amine;

(1-{5-[4-(2H-Pyrazol-3-yl)-phenoxy]-1H-benzoimidazol-2-ylmethyl}-piperidin-2-yl)-methanol;

5-[4-(2H-Pyrazol-3-yl)-phenoxy]-2-(3-trifluoromethyl-pyrrolidin-1-ylmethyl)-1H-benzoimidazole;

1-{6-[4-(2H-Pyrazol-3-yl)-phenoxy]-2,3-dihydro-benzofuran-2-ylmethyl}-piperidine-4-carboxylic acid dimethylamide;

1-(1-{6-[4-(2H-Pyrazol-3-yl)-phenoxy]-2,3-dihydro-benzofuran-2-ylmethyl}-piperidin-4-yl)-pyrrolidin-2-one;

2-(Propyl-{5-[4-(2H-pyrazol-3-yl)-phenoxy]-1H-benzoimidazol-2-ylmethyl}-amino)-ethanol;

N—[(R)-1-(2-{5-[4-(2H-Pyrazol-3-yl)-phenoxy]-indazol-2-yl}-ethyl)-pyrrolidin-3-yl]-acetamide;

2-Methoxy-N-[1-(2-{5-[4-(2H-pyrazol-3-yl)-phenoxy]-indazol-1-yl}-ethyl)-piperidin-4-yl]-acetamide;

5-[4-(2H-Pyrazol-3-yl)-phenoxy]-2-(tetrahydro-pyran-4-ylmethyl)-1H-benzoimidazole;

3-(1-{6-[4-(2H-Pyrazol-3-yl)-phenoxy]-2,3-dihydro-benzofuran-2-ylmethyl}-piperidin-4-yl)-oxazolidin-2-one;

1-{6-[5-(2H-Pyrazol-3-yl)-pyridin-2-yloxy]-quinolin-2-ylmethyl}-piperidin-4-ol;

2-((R)-3-Methoxy-pyrrolidin-1-ylmethyl)-6-[5-(2H-pyrazol-3-yl)-pyridin-2-yloxy]-quinoline;

(2-{5-[4-(2H-Pyrazol-3-yl)-phenoxy]-indazol-2-yl}-ethyl)-(tetrahydro-pyran-4-ylmethyl)-amine;

5-[4-(2H-Pyrazol-3-yl)-phenoxy]-2-(S)-1-pyrrolidin-2-ylmethyl-1H-benzoimidazole;

2-((S)-3-Methoxy-pyrrolidin-1-ylmethyl)-6-[5-(2H-pyrazol-3-yl)-pyridin-2-yloxy]-quinoline;

1'-{6-[5-(2H-Pyrazol-3-yl)-pyridin-2-yloxy]-quinolin-2-ylmethyl}-[1,4']bipiperidinyl-2-one;

(S)-1-{6-[5-(2H-Pyrazol-3-yl)-pyridin-2-yloxy]-quinolin-2-ylmethyl}-pyrrolidin-3-ol;

4-(1-{6-[5-(2H-Pyrazol-3-yl)-pyridin-2-yloxy]-quinolin-2-ylmethyl}-piperidin-4-yl)-morpholin-3-one;

2-(4-Methoxy-piperidin-1-ylmethyl)-6-[5-(2H-pyrazol-3-yl)-pyridin-2-yloxy]-quinoline;

(1R,5S)-3-{6-[5-(2H-Pyrazol-3-yl)-pyridin-2-yloxy]-quinolin-2-ylmethyl}-1,2,3,4,5,6-hexahydro-1,5-methano-pyrido[1,2-a][1,5]diazocin-8-one;

{6-[5-(2H-Pyrazol-3-yl)-pyridin-2-yloxy]-quinolin-2-ylmethyl}-[2-(tetrahydro-pyran-4-yl)-ethyl]-amine;

6-[5-(2H-Pyrazol-3-yl)-pyridin-2-yloxy]-2-[4-(pyridin-2-yloxy)-piperidin-1-ylmethyl]-quinoline;

1-{1-[4-(2H-Pyrazol-3-yl)-benzyl]-1H-indol-5-ylmethyl}-azetidin-3-ol;

5-[4-(2H-Pyrazol-3-yl)-phenoxy]-2-(2-pyrrolidin-1-yl-ethyl)-2H-indazole;

5-[4-(2-Pyrrolidin-1-ylmethyl-2,3-dihydro-benzofuran-6-yloxy)-phenyl]-1H-pyrazole;

N-(1-{6-[4-(2H-Pyrazol-3-yl)-phenoxy]-2,3-dihydro-benzofuran-2-ylmethyl}-piperidin-4-yl)-acetamide;

6-[5-(2H-Pyrazol-3-yl)-pyrimidin-2-yloxy]-2-pyrrolidin-1-ylmethyl-quinoline;

1-(4-{6-[5-(2H-Pyrazol-3-yl)-pyridin-2-yloxy]-1H-indol-2-ylmethyl}-piperazin-1-yl)-ethanone;

1-(4-{5-[5-(2H-Pyrazol-3-yl)-pyridin-2-yloxy]-1H-indol-2-ylmethyl}-piperazin-1-yl)-ethanone;

1-(4-{6-[5-(2H-Pyrazol-3-yl)-pyridin-2-yloxy]-isoquinolin-3-ylmethyl}-piperazin-1-yl)-ethanone;

1-[4-(2-{5-[5-(2H-Pyrazol-3-yl)-pyridin-2-yloxy]-indol-1-yl}-ethyl)-piperazin-1-yl]-ethanone;

2-(4-Morpholin-4-ylmethyl-piperidin-1-ylmethyl)-5-[4-(2H-pyrazol-3-yl)-phenoxy]-1H-benzoimidazole;

2-((S)-3-Methoxy-pyrrolidin-1-ylmethyl)-5-[4-(2H-pyrazol-3-yl)-phenoxy]-1H-benzoimidazole;

3-{5-[4-(2H-Pyrazol-3-yl)-phenoxy]-1H-benzoimidazol-2-ylmethyl}-8-oxa-3-aza-bicyclo[3.2.1]octane;

2-(4-Methoxy-piperidin-1-ylmethyl)-5-[4-(2H-pyrazol-3-yl)-phenoxy]-1H-benzoimidazole;

(1S,2S)-2-(Methyl-{5-[4-(2H-pyrazol-3-yl)-phenoxy]-1H-benzoimidazol-2-ylmethyl}-amino)-cyclohexanol;

Methyl-{5-[4-(2H-pyrazol-3-yl)-phenoxy]-1H-benzoimidazol-2-ylmethyl}-(tetrahydro-pyran-4-yl)-amine;

1-(4-{6-[5-(1H-Pyrazol-3-yl)-pyridin-2-yloxy]-quinolin-2-ylmethyl}-piperazin-1-yl)-ethanone;

2-(2-Morpholin-4-yl-ethoxy)-6-[4-(1H-pyrazol-3-yl)-phenoxy]-benzothiazole;

Cyclopropanecarboxylic acid methyl-{5-[4-(2H-pyrazol-3-yl)-phenoxy]-1H-benzoimidazol-2-ylmethyl}-amide;

3,3-Dimethyl-1-{5-[4-(2H-pyrazol-3-yl)-phenoxy]-1H-benzoimidazol-2-ylmethyl}-pyrrolidin-2-one;

Cyclopropanecarboxylic acid ethyl-{5-[4-(2H-pyrazol-3-yl)-phenoxy]-1H-benzoimidazol-2-ylmethyl}-amide;

2-Methoxy-N-(1-{6-[5-(1H-pyrazol-3-yl)-pyridin-2-yloxy]-quinolin-2-ylmethyl}-piperidin-4-yl)-acetamide;

N-(1-{6-[5-(1H-Pyrazol-3-yl)-pyridin-2-yloxy]-quinolin-2-ylmethyl}-piperidin-4-yl)-acetamide;

N-((endo)-8-{6-[5-(1H-Pyrazol-3-yl)-pyridin-2-yloxy]-quinolin-2-ylmethyl}-8-aza-bicyclo[3.2.1]oct-3-yl)-acetamide;

N-((exo)-8-{6-[5-(1H-Pyrazol-3-yl)-pyridin-2-yloxy]-quinolin-2-ylmethyl}-8-aza-bicyclo[3.2.1]oct-3-yl)-acetamide;

1-((S)-5-{6-[5-(1H-Pyrazol-3-yl)-pyridin-2-yloxy]-quinolin-2-ylmethyl}-2,5-diaza-bicyclo[2.2.1]hept-2-yl)-ethanone;

1-(4-{6-[4-(2H-Pyrazol-3-yl)-phenoxy]-quinoxalin-2-ylmethyl}-piperazin-1-yl)-ethanone;

2-(1,1-Dioxo-1-λ-6-thiomorpholin-4-ylmethyl)-6-[5-(1H-pyrazol-3-yl)-pyridin-2-yloxy]-quinoline;

6-[4-(2H-Pyrazol-3-yl)-phenoxy]-2-pyrrolidin-1-ylmethyl-quinoline;

2-Azetidin-1-ylmethyl-6-[4-(2H-pyrazol-3-yl)-phenoxy]-quinoline;

1-(8-{6-[4-(2H-Pyrazol-3-yl)-phenoxy]-quinolin-2-ylmethyl}-3,8-diaza-bicyclo[3.2.1]oct-3-yl)-ethanone;

6-[4-(2H-Pyrazol-3-yl)-phenoxy]-2-pyrrolidin-1-ylmethyl-imidazo[1,2-a]pyridine;

1-(4-{6-[4-(2H-Pyrazol-3-yl)-phenoxy]-quinolin-2-ylmethyl}-piperazin-1-yl)-ethanone;

N-((exo)-8-{6-[4-(2H-Pyrazol-3-yl)-phenoxy]-quinolin-2-ylmethyl}-8-aza-bicyclo[3.2.1]oct-3-yl)-acetamide;

3-Morpholin-4-ylmethyl-6-[4-(2H-pyrazol-3-yl)-phenoxy]-quinoline;

2-Morpholin-4-ylmethyl-6-[4-(2H-pyrazol-3-yl)-phenoxy]-imidazo[1,2-a]pyridine;

(S)-5-{5-[4-(2H-Pyrazol-3-yl)-phenoxy]-indazol-2-ylmethyl}-pyrrolidin-2-one;

2-Morpholin-4-ylmethyl-6-[4-(2H-pyrazol-3-yl)-benzyl]-imidazo[1,2-a]pyridine;

(S)-5-{5-[4-(2H-Pyrazol-3-yl)-phenoxy]-indazol-1-ylmethyl}-pyrrolidin-2-one;

2-Morpholin-4-ylmethyl-6-[4-(2H-pyrazol-3-yl)-phenoxy]-quinoline;

3-{6-[4-(2H-Pyrazol-3-yl)-phenoxy]-imidazo[1,2-a]pyridin-2-ylmethyl}-oxazolidin-2-one;

2-Methyl-6-[4-(2H-pyrazol-3-yl)-phenoxy]-3-pyrrolidin-1-ylmethyl-quinoline;

2-Morpholin-4-ylmethyl-7-[4-(2H-pyrazol-3-yl)-phenoxy]-imidazo[1,2-a]pyridine;

Morpholin-4-yl-{7-[4-(2H-pyrazol-3-yl)-phenoxy]-imidazo[1,2-a]pyridin-2-yl}-methanone;

1-{6-[4-(2H-Pyrazol-3-yl)-phenoxy]-imidazo[1,2-a]pyridin-2-ylmethyl}-piperidine-4-carboxylic acid;

(R)-5-{6-[4-(2H-Pyrazol-3-yl)-phenoxy]-imidazo[1,2-a]pyridin-2-ylmethoxy}-piperidin-2-one;

or a pharmaceutically acceptable salt thereof.

12. A pharmaceutical composition comprising a compound of claim 1, or a pharmaceutically acceptable salt thereof, and a pharmaceutically acceptable carrier or excipient.

13. The pharmaceutical composition of claim 12, further comprising at least one additional pharmacologically active substance.

14. A method of treating a leukotriene-mediated disorder comprising administering a pharmaceutically effective amount of a compound of claim 1, or a pharmaceutically acceptable salt thereof, to a patient in need thereof; wherein the leukotriene-mediated disorder is a cardiovascular disease selected from the group consisting of atherosclerosis, myocardial infarction, stroke, aortic aneurysm, sickle cell crisis, ischemia-reperfusion injury, pulmonary arterial hypertension, and sepsis.

15. The method of claim 14, wherein the cardiovascular disease is atherosclerosis.

* * * * *